United States Patent
Bernard et al.

(10) Patent No.: US 11,410,770 B2
(45) Date of Patent: *Aug. 9, 2022

(54) MEDICAL SCAN DIAGNOSING SYSTEM

(71) Applicant: Enlitic, Inc., San Francisco, CA (US)

(72) Inventors: Devon Bernard, San Francisco, CA (US); Kevin Lyman, Fords, NJ (US); Li Yao, San Francisco, CA (US); Alan Liu, Palo Alto, CA (US)

(*) Notice: Subject to any disclaimer, the term of this patent is extended or adjusted under 35 U.S.C. 154(b) by 181 days.

This patent is subject to a terminal disclaimer.

(21) Appl. No.: 16/998,208

(22) Filed: Aug. 20, 2020

(65) Prior Publication Data

US 2020/0381105 A1     Dec. 3, 2020

Related U.S. Application Data

(63) Continuation of application No. 15/683,073, filed on Aug. 22, 2017, now Pat. No. 10,811,134.
(Continued)

(51) Int. Cl.
*G16H 30/40* (2018.01)
*G06F 3/048* (2013.01)
(Continued)

(52) U.S. Cl.
CPC ............ *G16H 30/40* (2018.01); *A61B 5/002* (2013.01); *A61B 5/0022* (2013.01); *A61B 6/032* (2013.01);
(Continued)

(58) Field of Classification Search
CPC ........ G16H 30/40; G16H 10/60; G16H 15/00; G16H 30/20; G16H 40/20; G16H 40/63;
(Continued)

(56) References Cited

U.S. PATENT DOCUMENTS

| | | |
|---|---|---|
| 6,466,687 B1 | 10/2002 | Uppaluri et al. |
| 6,524,246 B1 | 2/2003 | Kelly et al. |

(Continued)

FOREIGN PATENT DOCUMENTS

| | | |
|---|---|---|
| CN | 106295139 A | 1/2017 |
| CN | 106551704 A | 4/2017 |
| KR | 20100014065 A | 2/2010 |

OTHER PUBLICATIONS

Lu et al., A novel computer-aided diagnosis system for breast MRI based on feature selection and ensemble learning, Computers in Biology and Medicine 83 (2017) 157-165 (Year: 2017).*
(Continued)

*Primary Examiner* — Jason S Tiedeman
(74) *Attorney, Agent, or Firm* — William W. Cochran; Cochran Freund & Young, LLC

(57) ABSTRACT

A medical scan diagnosing system is operable to receive a medical scan. Diagnosis data of the medical scan is generated by performing a medical scan inference function on the medical scan. The first medical scan is transmitted to a first client device associated with a user of the medical scan diagnosing system in response to the diagnosis data indicating that the medical scan corresponds to a non-normal diagnosis. The medical scan is displayed to the user via an interactive interface displayed by a display device corresponding to the first client device. Review data is received from the first client device, where the review data is generated by the first client device in response to a prompt via the interactive interface. Updated diagnosis data is generated based on the review data. The updated diagnosis data is transmitted to a second client device associated with a requesting entity.

20 Claims, 83 Drawing Sheets

Related U.S. Application Data

(60) Provisional application No. 62/511,150, filed on May 25, 2017.

(51) Int. Cl.

| | | |
|---|---|---|
| *G06T 7/00* | (2017.01) | |
| *G06Q 50/22* | (2018.01) | |
| *G16H 50/20* | (2018.01) | |
| *A61B 6/00* | (2006.01) | |
| *A61B 8/00* | (2006.01) | |
| *A61B 8/08* | (2006.01) | |
| *G16H 50/70* | (2018.01) | |
| *G06N 3/04* | (2006.01) | |
| *G06F 40/30* | (2020.01) | |
| *G06F 40/56* | (2020.01) | |
| *G06F 40/169* | (2020.01) | |
| *G06F 40/197* | (2020.01) | |
| *G06F 40/247* | (2020.01) | |
| *G06F 40/279* | (2020.01) | |
| *G16H 30/20* | (2018.01) | |
| *G06T 7/11* | (2017.01) | |
| *G16H 40/20* | (2018.01) | |
| *G01T 1/24* | (2006.01) | |
| *G06V 10/98* | (2022.01) | |
| *G16H 10/60* | (2018.01) | |
| *G16H 15/00* | (2018.01) | |
| *G16H 50/30* | (2018.01) | |
| *A61B 6/03* | (2006.01) | |
| *G06F 3/16* | (2006.01) | |
| *G06K 9/62* | (2022.01) | |
| *A61B 5/00* | (2006.01) | |
| *G06N 3/08* | (2006.01) | |
| *G06Q 10/10* | (2012.01) | |
| *H04N 5/32* | (2006.01) | |
| *G16H 40/63* | (2018.01) | |
| *G06T 11/60* | (2006.01) | |
| *G06N 20/10* | (2019.01) | |
| *G06N 7/00* | (2006.01) | |
| *G16H 40/67* | (2018.01) | |
| *G06V 10/75* | (2022.01) | |
| *G16H 50/50* | (2018.01) | |
| *H04L 67/12* | (2022.01) | |
| *H04L 67/01* | (2022.01) | |
| *G06F 3/04842* | (2022.01) | |
| *G06F 3/0485* | (2022.01) | |
| *G06T 11/00* | (2006.01) | |

(52) U.S. Cl.
CPC ............ *A61B 6/4233* (2013.01); *A61B 6/463* (2013.01); *A61B 6/468* (2013.01); *A61B 6/50* (2013.01); *A61B 6/503* (2013.01); *A61B 6/5217* (2013.01); *A61B 6/5288* (2013.01); *A61B 6/5294* (2013.01); *A61B 6/563* (2013.01); *A61B 8/468* (2013.01); *A61B 8/5223* (2013.01); *A61B 8/565* (2013.01); *G01T 1/247* (2013.01); *G06F 3/048* (2013.01); *G06F 3/167* (2013.01); *G06F 40/169* (2020.01); *G06F 40/197* (2020.01); *G06F 40/247* (2020.01); *G06F 40/279* (2020.01); *G06F 40/30* (2020.01); *G06F 40/56* (2020.01); *G06K 9/6215* (2013.01); *G06K 9/6267* (2013.01); *G06N 3/04* (2013.01); *G06N 3/0454* (2013.01); *G06N 3/084* (2013.01); *G06Q 10/10* (2013.01); *G06Q 10/103* (2013.01); *G06Q 50/22* (2013.01); *G06T 7/0012* (2013.01); *G06T 7/0016* (2013.01); *G06T 7/11* (2017.01); *G06V 10/98* (2022.01); *G16H 10/60* (2018.01); *G16H 15/00* (2018.01); *G16H 30/20* (2018.01); *G16H 40/20* (2018.01); *G16H 40/63* (2018.01); *G16H 50/20* (2018.01); *G16H 50/30* (2018.01); *G16H 50/70* (2018.01); *H04N 5/32* (2013.01); *A61B 6/505* (2013.01); *G06F 3/0485* (2013.01); *G06F 3/04842* (2013.01); *G06K 9/6256* (2013.01); *G06N 7/005* (2013.01); *G06N 20/10* (2019.01); *G06T 11/003* (2013.01); *G06T 11/60* (2013.01); *G06T 2200/24* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20081* (2013.01); *G06T 2207/30004* (2013.01); *G06T 2207/30061* (2013.01); *G06T 2207/30068* (2013.01); *G06V 10/751* (2022.01); *G06V 2201/03* (2022.01); *G16H 40/67* (2018.01); *G16H 50/50* (2018.01); *H04L 67/12* (2013.01); *H04L 67/42* (2013.01)

(58) Field of Classification Search
CPC ........ G16H 50/20; G16H 50/30; G16H 50/70; G16H 40/67; G16H 50/50; A61B 5/002; A61B 5/0022; A61B 6/032; A61B 6/4233; A61B 6/463; A61B 6/468; A61B 6/50; A61B 6/503; A61B 6/5217; A61B 6/5288; A61B 6/5294; A61B 6/563; A61B 8/468; A61B 8/5223; A61B 8/565; A61B 6/505; G01T 1/247; G06F 3/048; G06F 3/167; G06F 40/169; G06F 40/197; G06F 40/247; G06F 40/279; G06F 40/30; G06F 40/56; G06F 3/04842; G06F 3/0485; G06K 9/6215; G06K 9/6267; G06K 9/6256; G06N 3/04; G06N 3/0454; G06N 3/084; G06N 7/005; G06N 20/10; G06Q 10/10; G06Q 10/103; G06Q 50/22; G06T 7/0012; G06T 7/0016; G06T 7/11; G06T 11/003; G06T 11/60; G06T 2200/24; G06T 2207/10081; G06T 2207/10088; G06T 2207/10104; G06T 2207/10116; G06T 2207/10132; G06T 2207/20081; G06T 2207/30004; G06T 2207/30061; G06T 2207/30068; G06V 10/98; G06V 10/751; G06V 2201/03; H04N 5/32; H04L 67/12; H04L 67/42

See application file for complete search history.

(56) References Cited

U.S. PATENT DOCUMENTS

| | | | |
|---|---|---|---|
| 6,760,715 B1 * | 7/2004 | Barnhill | G06N 20/00 706/45 |
| 6,819,790 B2 | 11/2004 | Suzuki et al. | |
| 6,937,776 B2 | 8/2005 | Li et al. | |
| 7,117,188 B2 * | 10/2006 | Guyon | G16B 40/30 706/19 |
| 7,123,762 B2 | 10/2006 | Giger et al. | |
| 7,418,123 B2 | 8/2008 | Giger et al. | |
| 7,813,822 B1 | 10/2010 | Hoffberg | |
| 8,121,362 B2 | 2/2012 | Zhan et al. | |
| 8,303,505 B2 | 11/2012 | Webler et al. | |
| 8,331,637 B2 | 12/2012 | Bar-Aviv et al. | |
| 8,379,950 B2 | 2/2013 | Ye et al. | |
| 8,600,133 B2 | 12/2013 | Buelow et al. | |
| 8,885,898 B2 | 11/2014 | Liu | |
| 9,165,360 B1 | 10/2015 | Bates et al. | |
| 9,349,178 B1 | 5/2016 | Itu | |

(56) References Cited

U.S. PATENT DOCUMENTS

| | | | |
|---|---|---|---|
| 9,501,863 B1 | 11/2016 | Fram et al. |
| 9,569,736 B1 | 2/2017 | Ghesu et al. |
| 9,579,518 B2 | 2/2017 | Gertner |
| 9,760,978 B1 | 9/2017 | Lu et al. |
| 10,140,421 B1 | 11/2018 | Bernard et al. |
| 10,304,198 B2 | 5/2019 | Yan et al. |
| 10,340,041 B2 | 7/2019 | Chan et al. |
| 2002/0186818 A1 | 12/2002 | Arnaud et al. |
| 2003/0016850 A1 | 1/2003 | Kaufman et al. |
| 2004/0064029 A1 | 4/2004 | Summers et al. |
| 2004/0147840 A1 | 7/2004 | Duggirala et al. |
| 2004/0181431 A1 | 9/2004 | Kuth et al. |
| 2004/0252870 A1 | 12/2004 | Reeves et al. |
| 2005/0027566 A1 | 2/2005 | Haskell |
| 2005/0207630 A1 | 9/2005 | Chan et al. |
| 2005/0283450 A1 | 12/2005 | Matsugu et al. |
| 2007/0004980 A1 | 1/2007 | Warner et al. |
| 2008/0004505 A1 | 1/2008 | Kapit et al. |
| 2008/0015418 A1 | 1/2008 | Jarrell et al. |
| 2008/0021834 A1 | 1/2008 | Holla et al. |
| 2008/0205717 A1 | 8/2008 | Reeves et al. |
| 2008/0243539 A1 | 10/2008 | Barish et al. |
| 2008/0267483 A1 | 10/2008 | Zhan et al. |
| 2009/0177495 A1 | 7/2009 | Abousy et al. |
| 2009/0222388 A1 | 9/2009 | Hua et al. |
| 2009/0228299 A1 | 9/2009 | Kangarloo et al. |
| 2010/0088117 A1 | 4/2010 | Belden et al. |
| 2010/0278405 A1 | 11/2010 | Kakadiaris et al. |
| 2012/0130734 A1 | 5/2012 | White |
| 2013/0124527 A1 | 5/2013 | Lee et al. |
| 2014/0219500 A1 | 8/2014 | Moehrle et al. |
| 2014/0328517 A1 | 11/2014 | Gluncic |
| 2014/0341471 A1 | 11/2014 | Ono et al. |
| 2015/0031979 A1 | 1/2015 | Rappaport et al. |
| 2015/0063667 A1 | 3/2015 | Sprencz et al. |
| 2015/0230773 A1 | 8/2015 | Cho et al. |
| 2015/0254843 A1 | 9/2015 | Brown et al. |
| 2015/0305706 A1 | 10/2015 | Kanik et al. |
| 2016/0019695 A1 | 1/2016 | Chukka et al. |
| 2016/0027175 A1 | 1/2016 | Kim et al. |
| 2016/0048972 A1 | 2/2016 | Kam et al. |
| 2016/0104281 A1 | 4/2016 | Grady et al. |
| 2016/0174902 A1 | 6/2016 | Georgescu et al. |
| 2016/0203281 A1 | 7/2016 | Zalis et al. |
| 2016/0260211 A1 | 9/2016 | Gillies et al. |
| 2016/0314588 A1 | 10/2016 | Harper |
| 2016/0343127 A1 | 11/2016 | Miller et al. |
| 2016/0350919 A1 | 12/2016 | Steigauf et al. |
| 2016/0364862 A1 | 12/2016 | Reicher et al. |
| 2017/0004619 A1 | 1/2017 | Liang et al. |
| 2017/0024517 A1 | 1/2017 | Biegert et al. |
| 2017/0068780 A1 | 3/2017 | Dobrean |
| 2017/0116497 A1 | 4/2017 | Georgescu et al. |
| 2017/0200268 A1* | 7/2017 | Podilchuk ............ G06K 9/6278 |
| 2017/0330320 A1 | 11/2017 | Lynch et al. |
| 2017/0337343 A1 | 11/2017 | Kakadiaris et al. |
| 2018/0025255 A1 | 1/2018 | Poole et al. |
| 2018/0033144 A1 | 2/2018 | Risman et al. |
| 2018/0060535 A1 | 3/2018 | Reicher |
| 2018/0060691 A1 | 3/2018 | Bernal et al. |
| 2018/0114595 A1 | 4/2018 | Stern |
| 2018/0204111 A1 | 7/2018 | Zadeh et al. |
| 2018/0315182 A1 | 11/2018 | Rapaka et al. |
| 2018/0342055 A1 | 11/2018 | Lyman et al. |
| 2019/0142519 A1 | 5/2019 | Siemionow et al. |

OTHER PUBLICATIONS

"What Not to Include in a Medical Record. (Jun. 6, 2012). Retrieved from https://www.texmed.org/Template.aspxid=1741. (Year: 2012)".

Andersch, Michael; Inference: The Next Step in GPU-Accelerated Deep Learning; https://devblogs.nvidia.com/parallelforall/inference-next-step-gpu-accelerated-deep-learning/; Nov. 11, 2015; 7 pages.

Choi, Y., Chiu, C. Y. I., Sontag, D. (2016). Learning low-dimensional representations of medical concepts. AM IA Summits on Translational Science Proceedings, 2016, 41. (Year: 2016).

International Searching Authority; International Search Report and Written Opinion; International Application No. PCT/US2018/032927; dated Sep. 14, 2018; 9 pgs.

Jamie A. Weydert, MD, Barry R. De Young, MD and Michael B. Cohen, MD, A preliminary Diagnosis Service Provides Prospective Blinded Dual-Review of All General Surgical Pathology Cases in an Academic Practice, 2005, Am J Surg Pathol, vol. 29, pp. 801-805 (Year: 2005).

Minnaar, Alex; Deep Learning Basics: Neural Networks, Backpropagation and Stochastic Gradient Descent; http://alexminnaar.com/deep-learning-basics-neural-networks-backpropagation-and-stochastic-gradient-descent.html; Feb. 14, 2015; 11 pages.

Olah, Christopher; Calculus on Computational Graphs: Backpropagation; http://colah.github.io/posts/2015-08-Backprop/; Aug. 31, 2015; 7 pages.

Pham, A.-D., Neveol, A., Lavergne, T., Yasunaga, D., Clement, 0., Meyer, G., . . . Burgun, A. (2014). Natural language processing of radiology reports for the detection of thromboembolic diseases and clinically relevant incidental findings. BMC Bioinformatics, 15(1). doi: 10.1186/1471-2105-15-266 (Year: 2014).

Pons, E., Braun, L. M. M., Hunink, M. G. M., Kors, J. A. (2016). Natural Language Processing in Radiology: A Systematic Review Radiology, 279(2), 329-343. doi: 10.1148/radiol.16142770.

Pre Conference Proceedings of the 7th MICCAI BraTS Challenge (2018); BraTS Multimodal Brain Tumor Segmentation Challenge; Granada, Spain; Sep. 16, 2018; 578 pages.

Reid, Stuart; 10 misconceptions about Neural Networks; http://www.turingfinance.com/misconceptions-about-neural-networks/; May 8, 2014; 24 pages.

S. Ted Sandler, Regularlized Learning with Feature Networks (Year: 2010).

Wikipedia: Backpropagation; https://en.wikipedia.org/wiki/Backpropagation#Assumptions_about_the_loss_function; downloaded from the internet on 18/15/18; 12 pages.

Wikipedia; Convolutional neural network; https://en.wikipedia.org/wiki/Convolutional_neural_network#Pooling_layer; downloaded from the internet on Jan. 15, 2018; 21 pages.

Yoo Jae Chern, Remote medical-diagnosis system and method. 2010. Translated by IP.com (Year 2010).

* cited by examiner

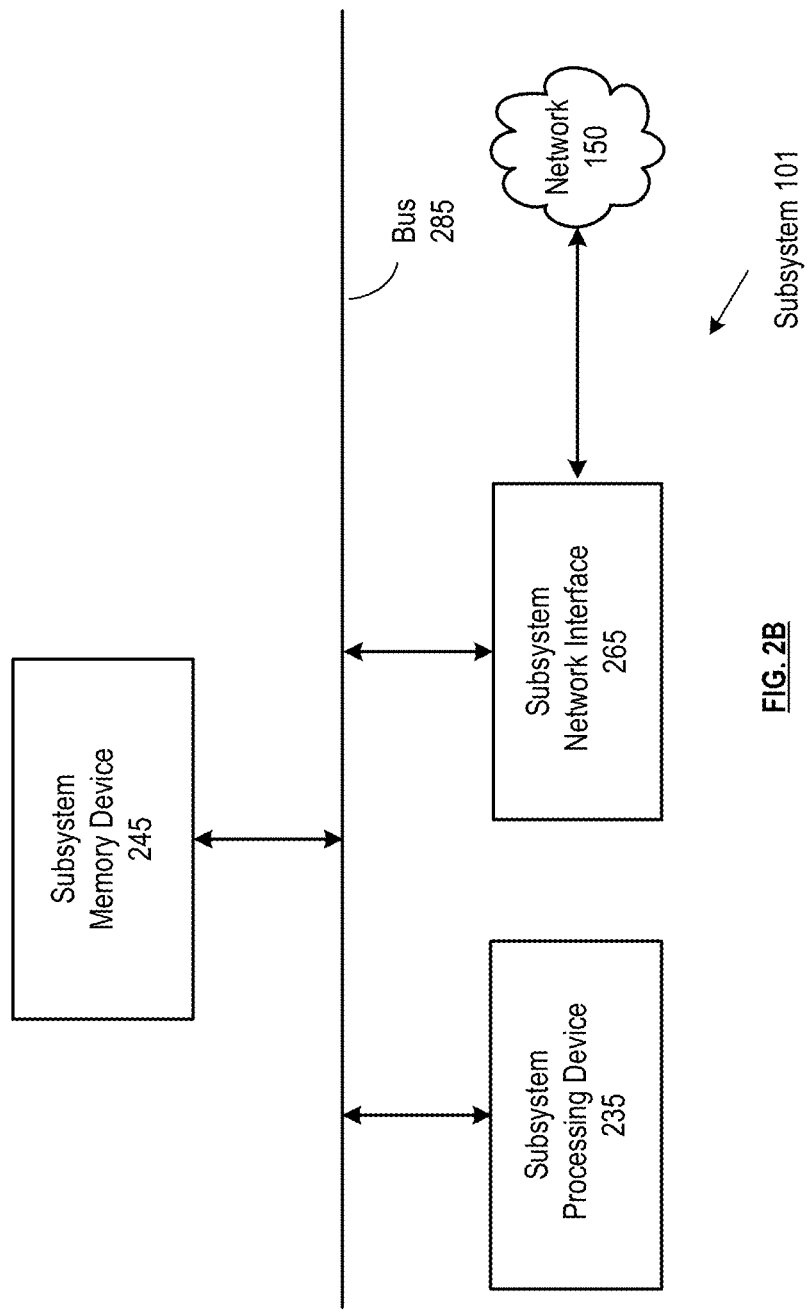

FIG. 8B

We detected 3 findings automatically, 2 of which were confirmed by the user. This case took 3:11 to complete.

PATIENT HISTORY

Patient is a 56 year old male with 35 pack years of smoking history, prior exposure to asbestos, and a father with lung cancer.

REPORT

1. There is a 10mm nodule with volume 13.5mm³ located in the lower left lobe on slice 35. It is lobulated, has popcorn calcification, shows ground glass texture, and consists of fat and fluid components. The nodule has a doubling time of 435 days. This nodule is suspicious for malignancy and has a LungRADs score of 4B. (generated automatically)

2. There is also a 14mm nodule with volume 21.5mm³ located in the lower left lobe on slice 100. It is spiculated, has laminated calcification, shows part solid texture, and consists of air components. The nodule has a doubling time of 214 days. This nodule is suspicious for malignancy and has a LungRADs score of 3. (generated automatically)

3. Lorem ipsum dolor sit amet, consectetur adipiscing elit, sed do eiusmod tempor incididunt ut labore et dolore magna aliqua. Ut enim ad minim veniam, quis nostrud exercitation ullamco laboris nisi ut aliquip ex ea commodo consequat. Duis aute irure dolor in reprehenderit in voluptate velit esse cillum dolore eu fugiat nulla pariatur. Excepteur sint occaecat cupidatat non proident, sunt in culpa qui officia deserunt mollit anim id est laborum. (user generated)

IMAGES OF FINDINGS

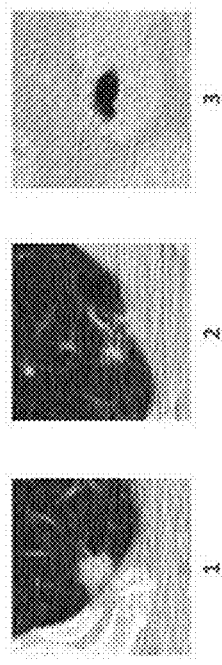

T4: Invasive bronchiolo-alveolar adenocarcinoma of the left lower lobe (stage IA)

T6: Invasive squamous cell carcinoma, NOS of the left lower lobe (stage IA)

Please characterize each nodule displayed below

Nodule Characterizations

AnswerID of referenced nodule

33341

☒ Does this nodule have spiculation?

☒ Does this nodule have lobulation?

Nodule Texture

Solid

Nodule Calcification absent

Nodule Sphericity round

Nodule Internal Structure
- ☒ soft
- ☐ fluid
- ☐ fat
- ☐ air

FIG. 10D

T4: Invasive bronchiolo-alveolar adenocarcinoma of the left lower lobe (stage IA)

T6: Invasive squamous cell carcinoma, NOS of the left lower lobe (stage IA)

Please characterize each nodule displayed below

Nodule Characterizations

AnswerID of referenced nodule

33341

☑ Does this nodule have spiculation?

☑ Does this nodule have lobulation?

Nodule Texture
- Please select an option
- Solid
- Part Solid/Mixed
- Non-Solid/Ground Glass Opacity Nodule Calcification absent Nodule Sphericity round Nodule Internal Structure
- ☑ soft
- ☐ fluid
- ☐ fat
- ☐ air

FIG. 10E

T4: Invasive bronchiolo-alveolar adenocarcinoma of the left lower lobe (stage IA)

T6: Invasive squamous cell carcinoma, NOS of the left lower lobe (stage IA)

Please characterize each nodule displayed below

Nodule Characterizations

AnswerID of referenced nodule

33341

☑ Does this nodule have spiculation?

☑ Does this nodule have lobulation?

Nodule Texture

Please select an option
popcorn
laminated
solid
non-central
central
▓▓▓▓▓▓
stippled Nodule Sphericity round Nodule Internal Structure
☑ soft
○ fluid
○ fat
○ air

FIG. 10F

T4: invasive bronchiolo-alveolar adenocarcinoma of the left lower lobe (stage IA)

T6: invasive squamous cell carcinoma, NOS of the left lower lobe (stage IA)

Please characterize each nodule displayed below

Nodule Characterizations

AnswerID of referenced nodule

33341

☒ Does this nodule have spiculation?

☒ Does this nodule have lobulation?

Nodule Texture

Solid

Nodule Calcification absent

Please select an option
linear
ovoid

Nodule Internal Structure
☒ soft
☐ fluid
☐ fat
☐ air

FIG. 10G

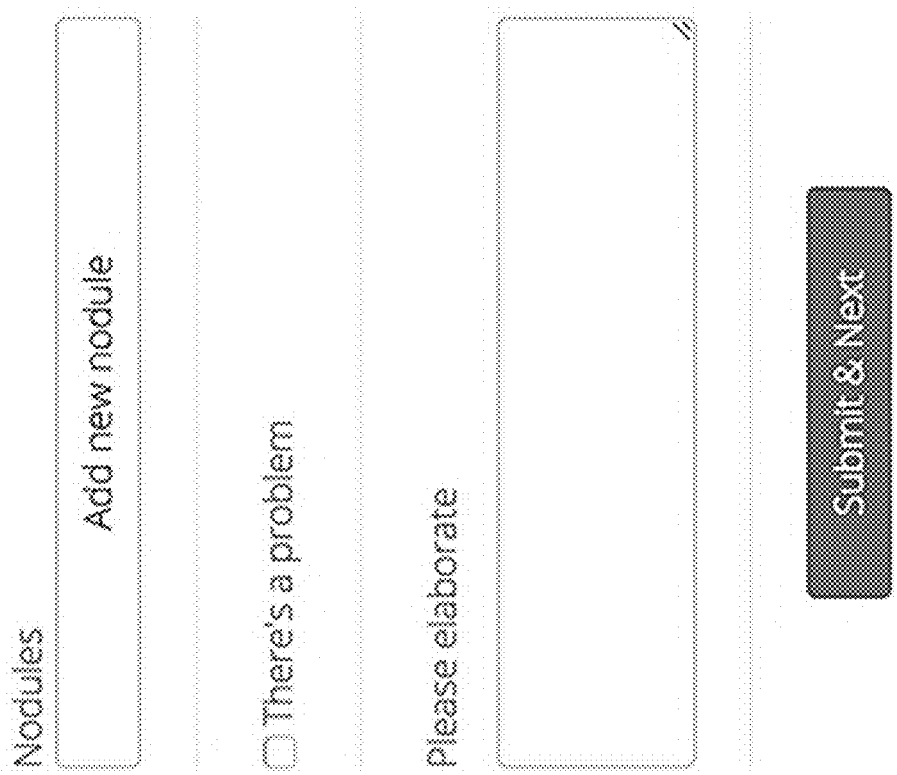

FIG. 10I

Nodules
Please identify this nodule in a scan from each year in which it is visible, and indicate its ultimate malignancy.
Contours
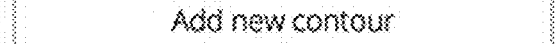
Did it become malignant?
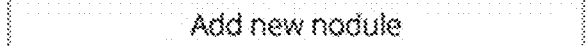
☐ There's a problem
Please elaborate
FIG. 10J

FIG. 10M

In the context of a screening program on a generally healthy population, with no clinical history available, would you use a normal template for this study?

No, this study is abnormal.

Please add all abnormalities that you can identify in this study which you would include in your radiology report.

Please put an ROI the abnormality in all locations on all views where it is visible.

Add new ROI

Please select the category if this abnormality.

Please select an option

Add an abnormality

Submit & Next

Assume patients A and B were part of a screening program on a healthy population, and no clinical history is available. If you had to give one patient a normal report, which would you choose?

○ I would give Patient A a normal report.
● I would give Patient B a normal report.

Submissions 1  2  3  4

In the context of a screening program on a generally healthy population, with no clinical history available, would you use a normal template for this study?

No, this study is abnormal.  ▲▼

Please add all abnormalities that you can identify in this study which you would include in your radiology report.

Please put an ROI the abnormality in all locations on all views where it is visible.

Please select the category if this abnormality.

Foreign Body (non-medical)  ▲▼

FIG. 10R

Please select all abnormalities

For each abnormality you identify in the study, please check the box below that best describes that abnormality.

- ☐ Pulmonary Parenchyma
- ☒ Pulmonary Vasculature
  - ☐ Plethora
  - ☐ Oligaemia
- ☐ Bronchial
- ☐ Abnormal Hilum
- ☐ Diaphragmatic Abnormality
- ☐ Pleural Abnormality
- ☐ Extra Pleural/Chest Wall
- ☐ Mediastinum
- ☐ Spine Abnormality
- ☐ Anatomic Variation
- ☐ Foreign Body
- ☐ Techincal/Imaging Issue
- ☐ Other

FIG. 10S

[Submit & Next]

Please select all abnormalities

For each abnormality you identify in the study, please check the box below that best describes that abnormality.

- ☐ Pulmonary Parenchyma
- ☒ Pulmonary Vasculature
    - ☒ Plethora
        - ☒ Diffuse
            - ☐ Left
            - ☐ Right
        - ☐ Focal/Multifocal
    - ☐ Oligaemia
- ☐ Bronchial
- ☐ Abnormal Hilum
- ☐ Diaphragmatic Abnormality
- ☐ Pleural Abnormality
- ☐ Extra Pleural/Chest Wall
- ☐ Mediastinum
- ☐ Spine Abnormality
- ☐ Anatomic Variation
- ☐ Foreign Body
- ☐ Techincal/Imaging Issue
- ☐ Other

FIG. 10T

[Submit & Next]

Please select all abnormalities

For each abnormality you identify in the study, please check the box below that best describes that abnormality.

○ Pulmonary Parenchyma
● Pulmonary Vasculature
   ● Plethora
      ● Diffuse
         ● Left
            ○ Zone - Left Upper
            ○ Zone - Left Mid
            ○ Zone - Left Lower
            ● Lobe - Left Upper
            ○ Lobe - Left Lingular
            ○ Lobe - Left Lower
         ○ Right
      ○ Focal/Multifocal
   ○ Oligaemia
○ Bronchial
○ Abnormal Hilum
○ Diaphragmatic Abnormality
○ Pleural Abnormality
○ Extra Pleural/Chest Wall
○ Mediastinum
○ Spine Abnormality
○ Anatomic Variation
○ Foreign Body
○ Techincal/Imaging Issue
○ Other

[Submit & Next]

FIG. 10U

Please select all abnormalities

For each abnormality you identify in the study, please check the box below that best describes that abnormality.

- ☐ Pulmonary Parenchyma
- ☒ Pulmonary Vasculature
  - ☒ Plethora
    - ☒ Diffuse
      - ☒ Left
        - ☐ Zone - Left Upper
        - ☐ Zone - Left Mid
        - ☐ Zone - Left Lower
        - ☒ Lobe - Left Upper
        - ☐ Lobe - Left Lingular
        - ☐ Lobe - Left Lower
      - ☐ Right
    - ☐ Focal/Multifocal
  - ☐ Oligaemia
  - ☐ Bronchial
  - ☐ Abnormal Hilum
  - ☐ Diaphragmatic Abnormality
  - ☐ Pleural Abnormality
  - ☐ Extra Pleural/Chest Wall
- ☒ Mediastinum
  - ☐ Mass
  - ☒ Compression of Structure
    - ☐ Superior
    - ☒ Inferior - Anterior
    - ☐ Inferior - Middle
    - ☐ Inferior - Posterior
    - ☐ Heart
    - ☐ Aorta
  - ☐ Enlargement of Structure
  - ☐ Ectasia
  - ☐ Other
- ☐ Spine Abnormality
- ☐ Anatomic Variation
- ☐ Foreign Body
- ☐ Techincal/Imaging Issue
- ☐ Other

[Submit & Next]

FIG. 10V

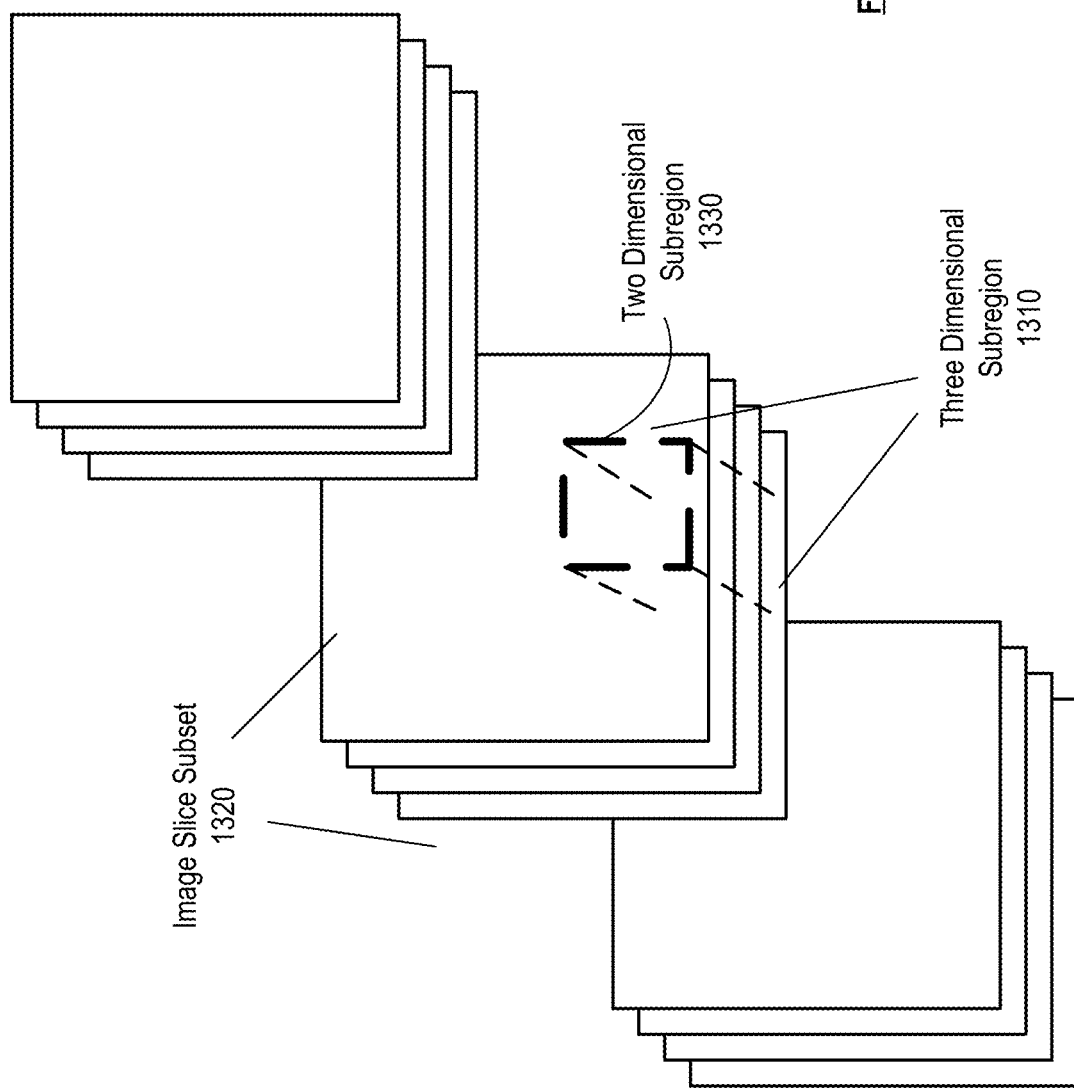

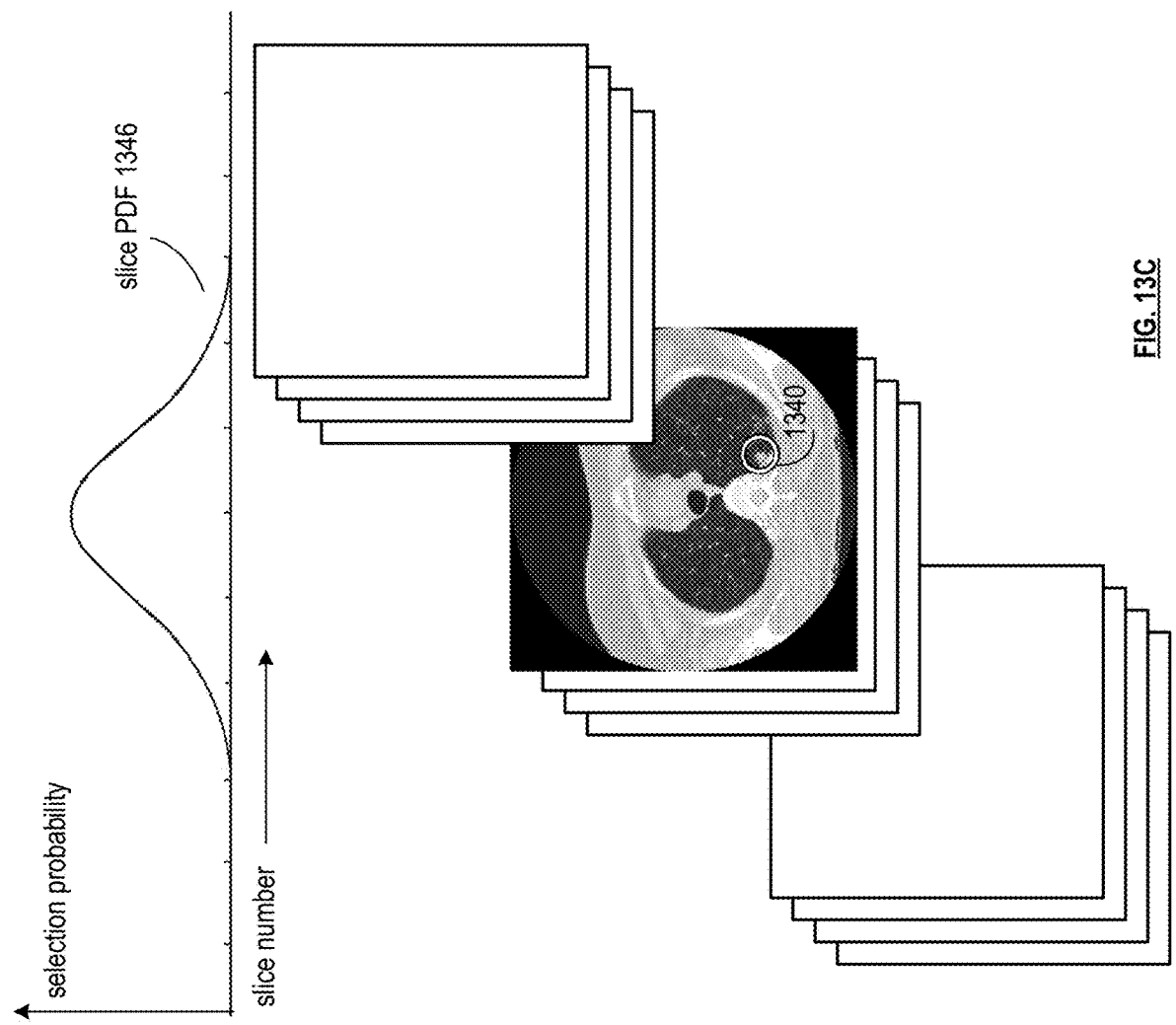

Report #1 Text:

CT ANGIOGRAM HEAD   INDICATION: DIZZINESS AND ATAXIA; H/O BROWN SEQUARD SYNDROME

COMPARISON: NONE AVAILABLE.

Technique: 3 MM CONTIGUOUS AXIAL IMAGES WERE OBTAINED FROM THE SKULL BASE TO THE VERTEX IN BOTH BONE AND SOFT TISSUE ALGORITHMS, BOTH BEFORE AND AFTER THE ADMINISTRATION OF 75 CC OF ISOVUE 300 INTRAVENOUS CONTRAST MATERIAL. ADDITIONAL 0.5 MM CONTIGUOUS AXIAL IMAGES WERE OBTAINED IN THE ARTERIAL PHASE AFTER THE ADMINISTRATION OF INTRAVENOUS CONTRAST MATERIAL. ADDITIONAL SAGITTAL AND CORONAL RECONSTRUCTIONS WERE ALSO PERFORMED. 3-D RECONSTRUCTIONS WERE OBTAINED AT AN INDEPENDENT WORKSTATION AND ARCHIVED.

FINDINGS: NO ABNORMAL ATTENUATION. NO ABNORMAL ENHANCEMENT. NO EVIDENCE OF INTRACRANIAL HEMORRHAGE. NO MASS EFFECT OR MIDLINE SHIFT. NO INTRA OR EXTRA-AXIAL FLUID COLLECTIONS ARE IDENTIFIED. VENTRICLES ARE NORMAL IN SIZE AND CONFIGURATION. GLOBES AND ORBITS ARE WITHIN NORMAL LIMITS. PARANASAL SINUSES AND MASTOID AIR CELLS ARE CLEAR. NO FRACTURES IDENTIFIED. CAROTIDS AND ANTERIOR CIRCULATION: NO HEMODYNAMICALLY SIGNIFICANT STENOSIS IS IDENTIFIED INVOLVING ANY OF THE INTRACRANIAL VESSELS. NO EVIDENCE OF ARTERIOVENOUS MALFORMATION OR ANEURYSM IS SEEN. NO DISSECTION IDENTIFIED. VERTEBROBASILAR AND POSTERIOR CIRCULATION: NO HEMODYNAMICALLY SIGNIFICANT STENOSIS IS IDENTIFIED INVOLVING ANY OF THE INTRACRANIAL VESSELS. NO EVIDENCE OF ARTERIOVENOUS MALFORMATION OR ANEURYSM IS SEEN. NO DISSECTION IDENTIFIED. DEVELOPMENTAL VENOUS ANOMALY LEFT CEREBELLUM. DOMINANT LEFT PICA.

Impression: NO EVIDENCE OF HEMODYNAMICALLY SIGNIFICANT STENOSIS, ANEURYSM, OR ARTERIOVENOUS MALFORMATION.

CT ANGIOGRAM NECK   INDICATION: DIZZINESS AND ATAXIA, H/O BROWN SEQUARD SYNDROME

COMPARISON: NONE AVAILABLE

Technique: 0.5 MM CONTIGUOUS AXIAL IMAGES WERE OBTAINED FROM THE THORACIC INLET THROUGH THE SKULL BASE IN THE ARTERIAL PHASE AFTER THE ADMINISTRATION OF 75 CC OF ISOVUE 300 INTRAVENOUS CONTRAST MATERIAL. ADDITIONAL SAGITTAL AND CORONAL REFORMATIONS WERE OBTAINED. ADDITIONAL OBLIQUE REFORMATIONS THROUGH THE CAROTID BIFURCATIONS WERE OBTAINED BILATERALLY. 3D REFORMATS OBTAINED.

FINDINGS: RIGHT CAROTID: NO EVIDENCE OF HEMODYNAMICALLY SIGNIFICANT STENOSIS. NO EVIDENCE OF DISSECTION. LEFT CAROTID: NO EVIDENCE OF HEMODYNAMICALLY SIGNIFICANT STENOSIS. NO EVIDENCE OF DISSECTION. VERTEBRAL: NO EVIDENCE OF HEMODYNAMICALLY SIGNIFICANT STENOSIS. NO EVIDENCE OF DISSECTION. AORTIC ARCH: NO EVIDENCE OF HEMODYNAMICALLY SIGNIFICANT STENOSIS. THE ORIGINS OF THE GREAT VESSELS ARE UNREMARKABLE. VISUALIZED NECK SOFT TISSUES ARE WITHIN NORMAL LIMITS. OSSEOUS FUSION ACROSS THE C5-C6 DISC SPACE AND FACET JOINTS. LUNG APICES ARE CLEAR.

Impression: NO EVIDENCE OF HEMODYNAMICALLY SIGNIFICANT STENOSIS OR DISSECTION IN ANY OF THE VESSELS OF THE NECK.

449

Output #1:

ICD-9 Code 780.4 -- Dizziness and giddiness
ICD-9 Code 781.3 -- Lack of coordination
Current Procedure Terminology (CPT) Code 70498 -- Under Diagnostic Radiology (Diagnostic Imaging) Procedures of the Head and Neck

Report #2 Text:

PATIENT NAME: JANE, DOE MEDICAL RECORD NUMBER: 2345678 CT DATED 1/01/2000 AT 0800 HOURS REASON FOR EXAM: CONCERN FOR VERTEBROBASILAR INSUFFICIENCY.

Technique: 0.6 MM AXIAL IMAGES WERE OBTAINED THROUGH THE NECK FOLLOWING THE ADMINISTRATION OF 65 ML ISOVUE-300. ADDITIONAL SAGITTAL, CORONAL AND BIFURCATION IMAGES WERE REFORMATTED.

COMPARISON: NONE AVAILABLE.

FINDINGS: MULTILEVEL CERVICAL SPONDYLOSIS AND FACET ARTHROSIS WITH GRADE 1 RETROLISTHESIS OF C5 ON C6. AT THE C6-C7 LEVEL THERE IS MILD LEFT VERTEBRAL ARTERY NARROWING OF LESS THAN 50% DUE TO FACET ARTHROSIS. MINIMAL SCATTERED ATHEROSCLEROSIS OF THE AORTIC ARCH AND BILATERAL COMMON CAROTID ARTERY BIFURCATIONS WITHOUT EVIDENCE FOR HEMODYNAMICALLY SIGNIFICANT NARROWING. INCIDENTAL NOTE MADE OF DOMINANT RIGHT VERTEBRAL SYSTEM. THERE IS NO EVIDENCE OF HEMODYNAMICALLY SIGNIFICANT STENOSIS INVOLVING THE VISUALIZED ARTERIOVASCULAR STRUCTURES OF THE NECK. THERE IS NO EVIDENCE DISSECTION OR BRANCH VESSEL OCCLUSION. CALCIFIED GRANULOMA IN THE LEFT LUNG APEX.

Impression: 1. MILD ATHEROSCLEROSIS OF THE AORTIC ARCH AND BILATERAL COMMON CAROTID ARTERY BIFURCATIONS WITHOUT EVIDENCE FOR HEMODYNAMICALLY SIGNIFICANT NARROWING AT THE SITES. 2. MULTILEVEL CERVICAL SPONDYLOSIS AND FACET ARTHROSIS. AT THE C6-C7 LEVEL THERE IS MILD LEFT VERTEBRAL ARTERY NARROWING OF LESS THAN 50% DUE TO ADJACENT FACET ARTHROSIS.

Output #2:

ICD-9 Code 433.3 – *Occlusion and stenosis of multiple and bilateral precerebral arteries*
Current Procedure Terminology (CPT) Code 70491 – *Under Diagnostic Radiology (Diagnostic Imaging) Procedures of the Head and Neck*

FIG. 14D

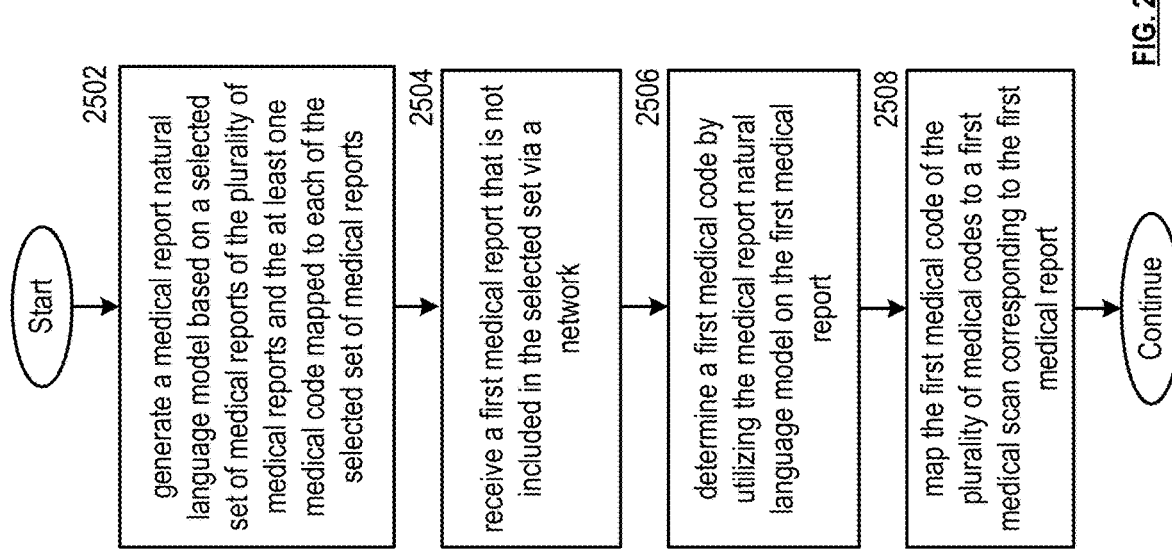

MEDICAL SCAN DIAGNOSING SYSTEM

CROSS-REFERENCE TO RELATED APPLICATIONS

The present U.S. Utility patent application is a continuation of U.S. Utility application Ser. No. 15/683,073, entitled "MEDICAL SCAN DIAGNOSING SYSTEM", filed Aug. 22, 2017, which claims priority pursuant to 35 U.S.C. § 119(e) to U.S. Provisional Application No. 62/511,150, entitled "MEDICAL SCAN ASSISTED REVIEW SYSTEM AND METHODS", filed May 25, 2017, both of which are hereby incorporated herein by reference in their entirety and made part of the present U.S. Utility patent application for all purposes.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND

Technical Field

This invention relates generally to medical imaging devices and knowledge-based systems used in conjunction with client/server network architectures.

BRIEF DESCRIPTION OF THE SEVERAL VIEWS OF THE DRAWING(S)

Description of Related Art

FIG. 2B is a schematic block diagram of one or more subsystems in accordance with various embodiments;

FIG. 13A is a graphical illustration of a three-dimensional subregion in accordance with various embodiments;

FIG. 13C is a graphical illustration a probability density function in accordance with various embodiments;

FIGS. 14C-14D are example input and output of a medical scan natural language analysis system in accordance with various embodiments.

FIG. 25 is a flowchart representation of a method in accordance with an embodiment.

DETAILED DESCRIPTION

Figure 1:
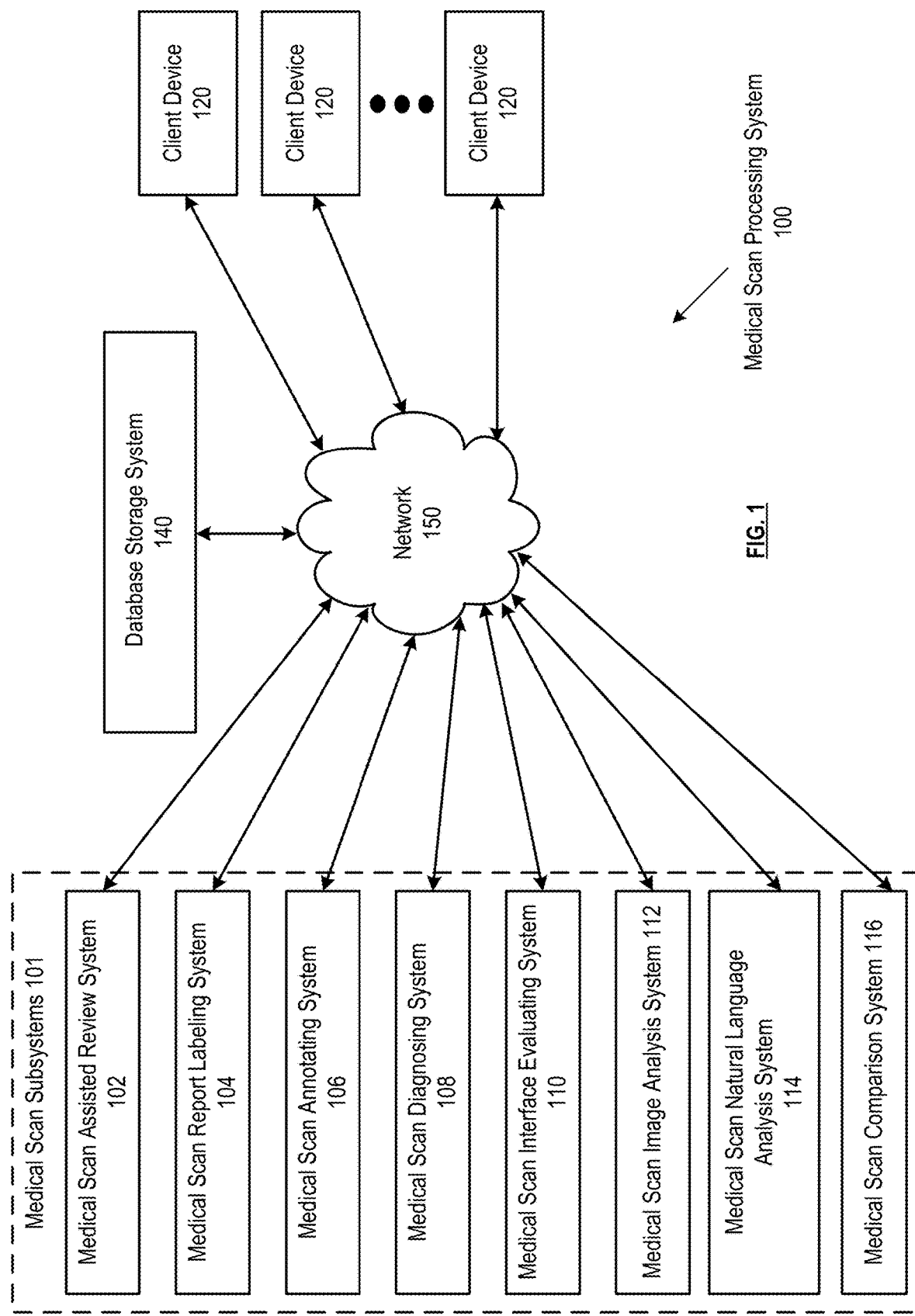
FIG. 1 is a schematic block diagram of an embodiment.

FIG. 1 presents a medical scan processing system 100, which can include one or more medical scan subsystems 101 that communicate bidirectionally with one or more client devices 120 via a wired and/or wireless network 150. The medical scan subsystems 101 can include a medical scan assisted review system 102, medical scan report labeling system 104, a medical scan annotator system 106, a medical scan diagnosing system 108, a medical scan interface feature evaluator system 110, a medical scan image analysis system 112, a medical scan natural language analysis system 114, and/or a medical scan comparison system 116. Some or all of the subsystems 101 can utilize the same processing devices, memory devices, and/or network interfaces, for example, running on a same set of shared servers connected to network 150. Alternatively or in addition, some or all of the subsystems 101 be assigned their own processing devices, memory devices, and/or network interfaces, for example, running separately on different sets of servers connected to network 150. Some or all of the subsystems 101 can interact directly with each other, for example, where one subsystem's output is transmitted directly as input to another subsystem via network 150. Network 150 can include one or more wireless and/or wired communication systems; one or more non-public intranet systems and/or public internet systems; and/or one or more local area networks (LAN) and/or wide area networks (WAN).

The medical scan processing system 100 can further include a database storage system 140, which can include one or more servers, one or more memory devices of one or more subsystems 101, and/or one or more other memory devices connected to network 150. The database storage system 140 can store one or more shared databases and/or one or more files stored on one or more memory devices that include database entries as described herein. The shared databases and/or files can each be utilized by some or all of the subsystems of the medical scan processing system, allowing some or all of the subsystems and/or client devices to retrieve, edit, add, or delete entries to the one or more databases and/or files.

The one or more client devices 120 can each be associated with one or more users of one or more subsystems of the medical scan processing system. Some or all of the client devices can be associated with hospitals or other medical institutions and/or associated with medical professionals, employees, or other individual users for example, located at one or more of the medical institutions. Some of the client devices 120 can correspond to one or more administrators of one or more subsystems of the medical scan processing system, allowing administrators to manage, supervise, or override functions of one or more subsystems for which they are responsible.

Some or all of the subsystems 101 of the medical scan processing system 100 can include a server that presents a website for operation via a browser of client devices 120. Alternatively or in addition, each client device can store application data corresponding to some or all subsystems, for example, a subset of the subsystems that are relevant to the user in a memory of the client device, and a processor of the client device can display the interactive interface based on instructions in the interface data stored in memory. For example, the website presented by a subsystem can operate via the application. Some or all of the web sites presented can correspond to multiple subsystems, for example, where the multiple subsystems share the server presenting the web site. Furthermore, the network 150 can be configured for secure and/or authenticated communications between the medical scan subsystems 101, the client devices 120 and the database storage system 140 to protect the data stored in the database storage system and the data communicated between the medical scan subsystems 101, the client devices 120 and the database storage system 140 from unauthorized access.

Figure 2A:
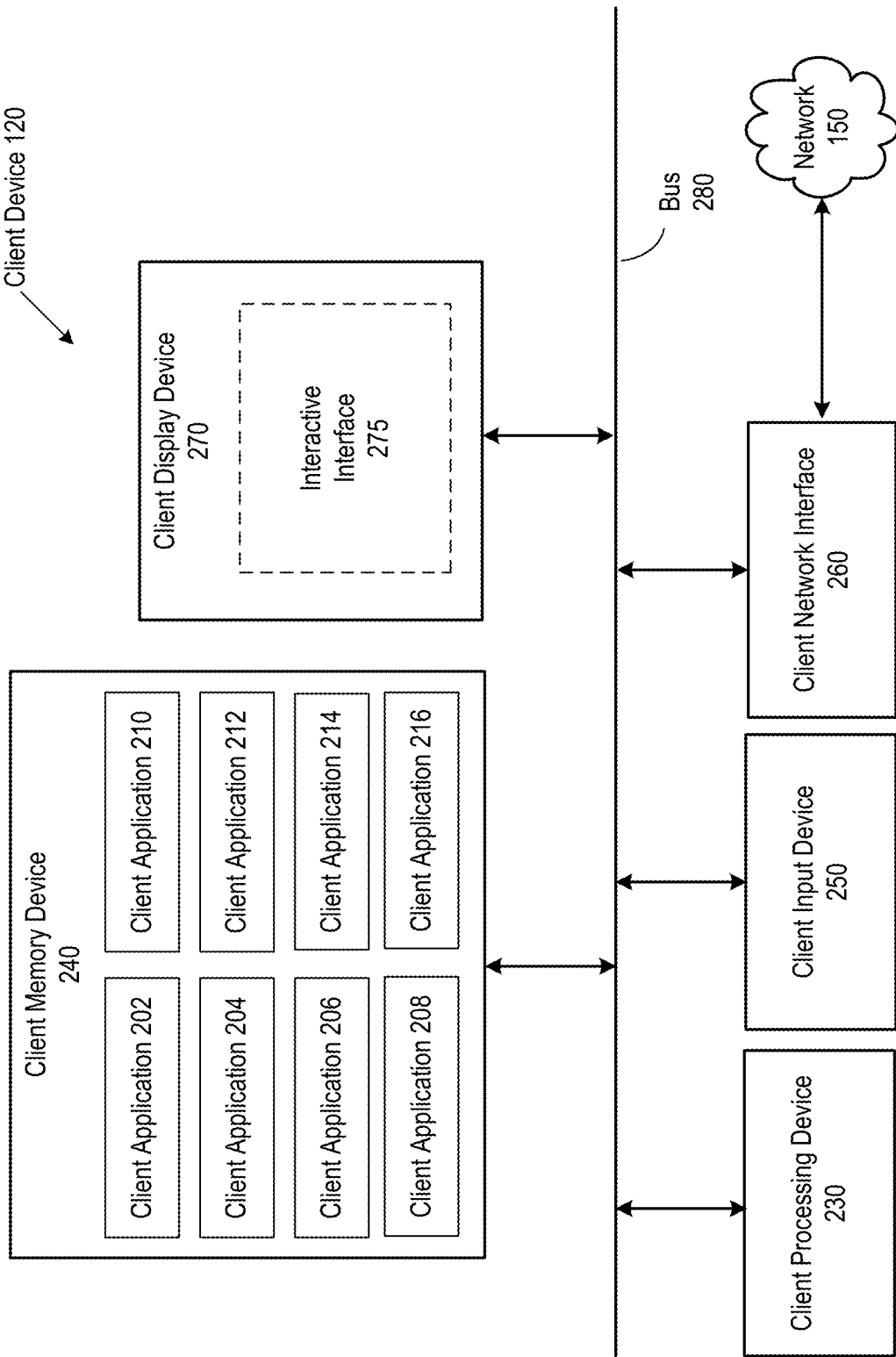
FIG. 2A is a schematic block diagram of a client device in accordance with various embodiments.

FIG. 2A presents an embodiment of client device 120. Each client device 120 can include one or more client processing devices 230, one or more client memory devices 240, one or more client input devices 250, one or more client network interfaces 260 operable to more support one or more communication links via the network 150 indirectly and/or directly, and/or one or more client display devices 270, connected via bus 280. Client applications 202, 204, 206, 208, 210, 212, 214, and/or 216 correspond to subsystems 102, 104, 106, 108, 110, 112, 114, and/or 116 of the medical scan processing system respectfully. Each client device 120 can receive the application data from the corresponding subsystem via network 150 by utilizing network interface 260, for storage in the one or more memory devices 240. In various embodiments, some or all client devices 120 can include a computing device associated with a radiologist, medical entity, or other user of one or more subsystems as described herein.

The one or more processing devices 230 can display interactive interface 275 on the one or more client display devices 270 in accordance with one or more of the client applications 202, 204, 206, 208, 210, 212, 214, and/or 216, for example, where a different interactive interface 275 is displayed for some or all of the client applications in accordance with the website presented by the corresponding subsystem 102, 104, 106, 108, 110, 112, 114 and/or 116. The user can provide input in response to menu data or other prompts presented by the interactive interface via the one or more client input devices 250, which can include a microphone, mouse, keyboard, touchscreen of display device 270 itself or other touchscreen, and/or other device allowing the user to interact with the interactive interface. The one or more processing devices 230 can process the input data and/or send raw or processed input data to the corresponding subsystem, and/or can receive and/or generate new data in response for presentation via the interactive interface 275 accordingly, by utilizing network interface 260 to communicate bidirectionally with one or more subsystems and/or databases of the medical scan processing system via network 150.

FIG. 2B presents an embodiment of a subsystem 101, which can be utilized in conjunction with subsystem 102, 104, 106, 108, 110, 112, 114 and/or 116. Each subsystem 101 can include one or more subsystem processing devices 235, one or more subsystem memory devices 245, and/or one or more subsystem network interfaces 265, connected via bus 285. The subsystem memory devices 245 can store executable instructions that, when executed by the one or more subsystem processing devices 235, facilitate performance of operations by the subsystem 101, as described for each subsystem herein.

Figure 3:
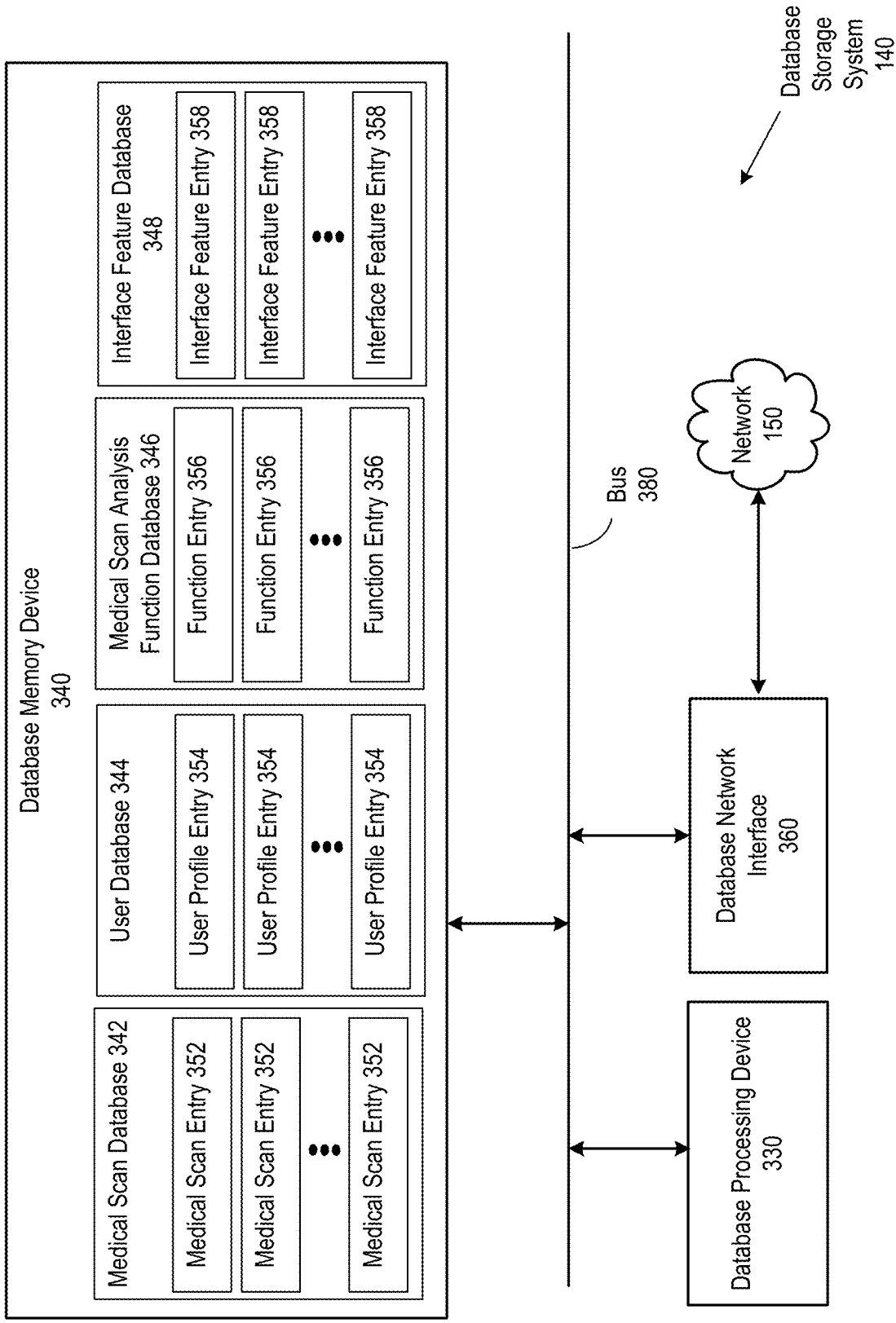
FIG. 3 is a schematic block diagram of a database storage system in accordance with various embodiments.

FIG. 3 presents an embodiment of the database storage system 140. Database storage system 140 can include at least one database processing device 330, at least one database memory device 340, and at least one database network interface 360, operable to more support one or more communication links via the network 150 indirectly and/or directly, all connected via bus 380. The database storage system 140 can store one or more databases the at least one memory 340, which can include a medical scan database 342 that includes a plurality medical scan entries 352, a user database 344 that includes a plurality of user profile entries 354, a medical scan analysis function database 346 that includes a plurality of medical scan analysis function entries 356, an interface feature database 348 can include a plurality of interface feature entries 358, and/or other databases that store data generated and/or utilized by the subsystems 101. Some or all of the databases 342, 344, 346 and/or 348 can consist of multiple databases, can be stored relationally or non-relationally, and can include different types of entries and different mappings than those described herein. A database entry can include an entry in a relational table or entry in a non-relational structure. Some or all of the data attributes of an entry 352, 354, 356, and/or 358 can refer to data included in the entry itself or that is otherwise mapped to an identifier included in the entry and can be retrieved from, added to, modified, or deleted from the database storage system 140 based on a given identifier of the entry. Some or all of the databases 342, 344, 346, and/or 348 can instead be stored locally by a corresponding subsystem, for example, if they are utilized by only one subsystem.

The processing device 330 can facilitate read/write requests received from subsystems and/or client devices via the network 150 based on read/write permissions for each database stored in the at least one memory device 340. Different subsystems can be assigned different read/write permissions for each database based on the functions of the subsystem, and different client devices 120 can be assigned different read/write permissions for each database. One or more client devices 120 can correspond to one or more administrators of one or more of the databases stored by the database storage system, and database administrator devices can manage one or more assigned databases, supervise assess and/or efficiency, edit permissions, or otherwise oversee database processes based on input to the client device via interactive interface 275.

Figure 4A:
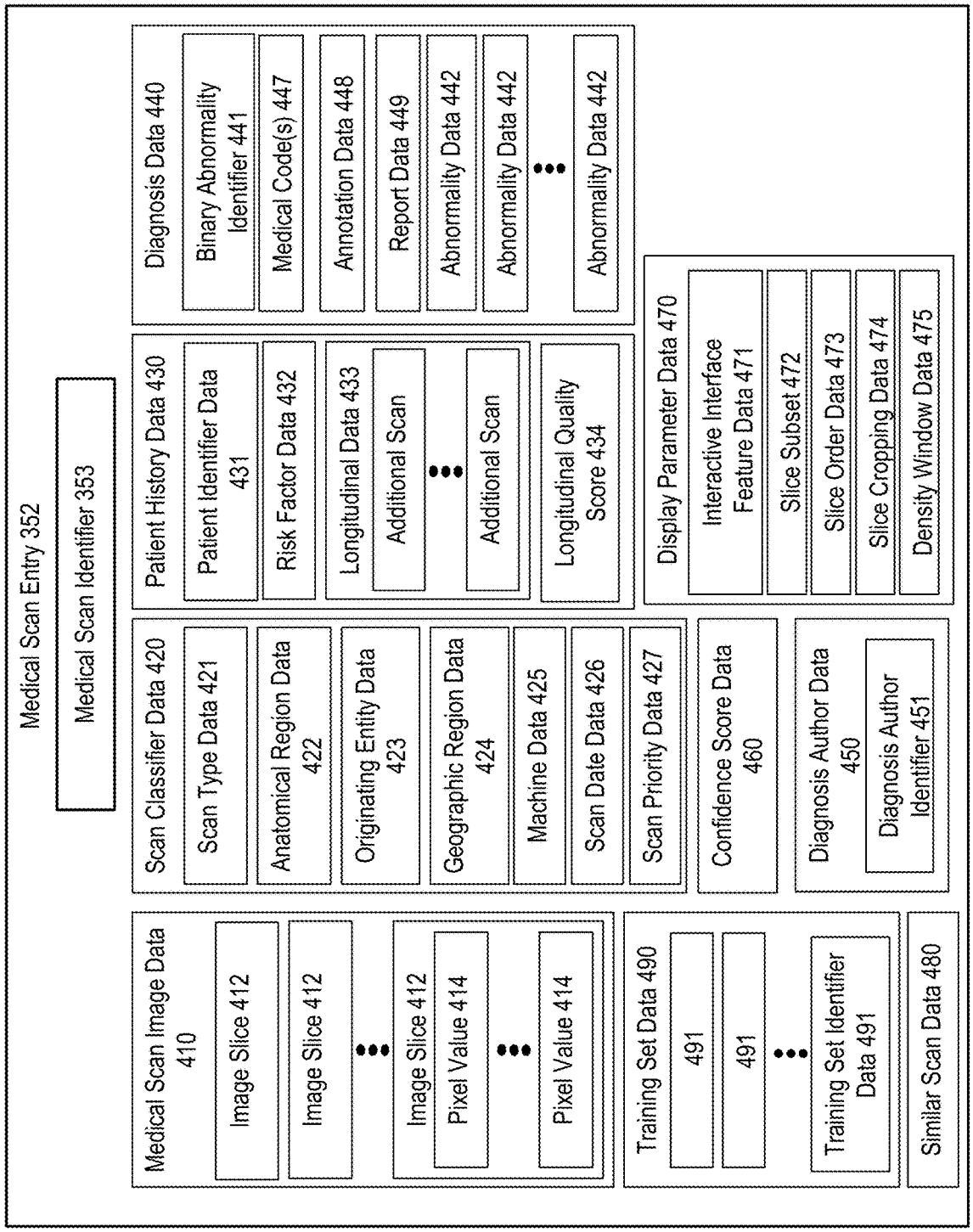
FIG. 4A is schematic block diagram of a medical scan entry in accordance with various embodiments.

FIG. 4A presents an embodiment of a medical scan entry 352, stored in medical scan database 342, included in metadata of a medical scan, and/or otherwise associated with a medical scan. A medical scan can include imaging data corresponding to a CT scan, x-ray, MM, PET scan, Ultrasound, EEG, mammogram, or other type of radiological scan or medical scan taken of an anatomical region of a human body, animal, organism, or object and further can include metadata corresponding to the imaging data. Medical scans can be awaiting review or can have already been reviewed by one or more users or automatic processes and can include tentative diagnosis data automatically generated by a subsystem, generated based on user input, and/or generated from another source. Some medical scans can include final, known diagnosis data generated by a subsystem and/or generated based on user input, and/or generated from another source, and can included in training sets used to train processes used by one or more subsystems such as the medical scan image analysis system 112 and/or the medical scan natural language analysis system 114.

Some medical scans can include one or more abnormalities, which can be identified by a user or identified automatically. Abnormalities can include nodules, for example malignant nodules identified in a chest CT scan. Abnormalities can also include and/or be characterized by one or more abnormality pattern categories such as such as cardiomegaly, consolidation, effusion, emphysema, and/or fracture, for example identified in a chest x-ray. Abnormalities can also include any other unknown, malignant or benign feature of a medical scan identified as not normal. Some scans can contain zero abnormalities, and can be identified as normal scans. Some scans identified as normal scans can include identified abnormalities that are classified as benign, and include zero abnormalities classified as either unknown or malignant. Scans identified as normal scans may include abnormalities that were not detected by one or more subsystems and/or by an originating entity. Thus, some scans may be improperly identified as normal. Similarly, scans identified to include at least one abnormality may include at least one abnormality that was improperly detected as an abnormality by one or more subsystems and/or by an originating entity. Thus, some scans may be improperly identified as containing abnormalities.

Each medical scan entry 352 can be identified by its own medical scan identifier 353, and can include or otherwise map to scan image data 410, and metadata such as scan classifier data 420, patient history data 430, diagnosis data 440, annotation author data 450, confidence score data 460, display parameter data 470, similar scan data 480, training set data 490, and/or other data relating to the medical scan. Some or all of the data included in a medical scan entry 352 can be used to aid a user in generating or editing diagnosis data 440, for example, in conjunction with the medical scan assisted review system 102, the medical scan report labeling system 104, and/or the medical scan annotator system 106. Some or all of the data included in a medical scan entry 352 can be used to allow one or more subsystems 101, such as automated portions of the medical scan report labeling system 104 and/or the medical scan diagnosing system 108, to automatically generate and/or edit diagnosis data 440 or other data the medical scan. Some or all of the data included in a medical scan entry 352 can be used to train some or all medical scan analysis functions of the medical scan analysis function database 346 such as one or more medical scan image analysis functions, one or more medical scan natural language analysis functions, one or more medical scan similarity analysis functions, one or more medical report generator functions, and/or one or more medical report analysis functions, for example, in conjunction with the medical scan image analysis system 112, the medical scan natural language analysis system 114, and/or the medical scan comparison system 116.

The medical scan entries 352 and the associated data as described herein can also refer to data associated with a medical scan that is not stored by the medical scan database, for example, that is uploaded by a client device for direct transmission to a subsystem, data generated by a subsystem and used as input to another subsystem or transmitted directly to a client device, or other data associated with a medical scan that is received and or generated without being stored in the medical scan database 342. For example, some or all of the structure and data attributes described with respect to a medical scan entry 352 can also correspond to structure and/or data attribute of data objects or other data generated by and/or transmitted between subsystems and/or client devices that correspond to a medical scan. Herein, any of the data attributes described with respect to a medical scan entry 352 can also correspond to data extracted from a data object generated by a subsystem or client device or data otherwise received from a subsystem, client device, or other source via network 150 that corresponds to a medical scan.

The medical scan image data 410 can include one or more images corresponding to a medical scan. The medical scan image data 410 can include one or more image slices 412, for example, corresponding to a single x-ray image, a plurality of cross-sectional, tomographic images of a scan such as a CT scan, or any plurality of images taken from the same or different point at the same or different angles. The medical scan image data 410 can also indicate an ordering of the one or more image slices 412. Herein, a "medical scan" can refer a full scan of any type represented by medical scan image data 410. Herein, an "image slice" can refer to one of a plurality of cross-sectional images of the medical scan image data 410, one of a plurality of images taken from different angles of the medical scan image data 410, and/or the single image of the medical scan image data 410 that includes only one image. Furthermore "plurality of image slices" can refer to all of the images of the associated medical scan, and refers to only a single image if the medical scan image data 410 includes only one image. Each image slice 412 can include a plurality of pixel values 414 mapped to each pixel of the image slice. Each pixel value can correspond to a density value, such as a Hounsfield value or other measure of density. Pixel values can also correspond to a grayscale value, a RGB (Red-Green-Blue) or other color value, or other data stored by each pixel of an image slice 412.

Scan classifier data 420 can indicate classifying data of the medical scan. Scan classifier data can include scan type data 421, for example, indicating that the scan is a CT scan, x-ray, MM, PET scan, Ultrasound, EEG, mammogram, or other type of scan. Scan classifier data 420 can also include anatomical region data 422, indicating for example, the scan is a scan of the chest, head, right knee, or other anatomical region. Scan classifier data can also include originating entity data 423, indicating the hospital where the scan was taken and/or a user that uploaded the scan to the system. If the originating entity data corresponds to a user of one or more subsystems 101, the originating entity data can include a corresponding user profile identifier 355 and/or include other data from the user profile entry 354 of the user. Scan classifier data 420 can include geographic region data 424, indicating a city, state, and/or country from which the scan originated, for example, based on the basic user data 510 retrieved from the user database 344 based on the originating entity. Scan classifier data can also include machine data 425, which can include machine identifier data, machine model data, machine calibration data, and/or contrast agent data, for example based on imaging machine data 514 retrieved from the user database 344 based on the originating entity data 423. The scan classifier data 420 can include scan date data 426 indicating when the scan was taken. The scan classifier data 420 can include scan priority data 427, which can indicate a priority score, ranking, number in a queue, or other priority data with regard to triaging and/or review. A priority score, ranking, or queue number of the scan priority data 427 can be generated by automatically by a subsystem based on the scan priority data 427, based on a severity of patient symptoms or other indicators in the risk factor data 432, based on a priority corresponding to the originating entity, based on previously generated diagnosis data 440 for the scan, and/or can be assigned by the originating entity and/or a user of the system.

The patient history data 430 can include patient identifier data 431 which can include basic patient information such as name or an identifier that may be anonymized to protect the confidentiality of the patient, age, and/or gender. The patient identifier data 431 can also map to a patient entry in a separate patient database stored by the database storage system, or stored elsewhere. The patient history data can include patient risk factor data 432 which can include previous medical history, family medical history, smoking and/or drug habits, pack years corresponding to tobacco use, environmental exposures, patient symptoms, etc. The patient history data 430 can also include longitudinal data 433, which can identify one or more additional medical scans corresponding to the patient, for example, retrieved based on patient identifier data 431 or otherwise mapped to the patient identifier data 431. Some or all additional medical scans can be included in the medical scan database, and can be identified based on their corresponding identifiers medical scan identifiers 353. Some or all additional medical scans can be received from a different source and can otherwise be identified. Alternatively or in addition, the longitudinal data can simply include some or all relevant scan entry data of a medical scan entry 352 corresponding to the one or more additional medical scans. The additional medical scans can be the same type of scan or different types of scans. Some or all of the additional scans may correspond to past medical scans, and/or some or all of the additional scans may correspond to future medical scans. The longitudinal data 433 can also include data received and/or determined at a date after the scan such as final biopsy data, or some or all of the diagnosis data 440. The patient history data can also include a longitudinal quality score 434, which can be calculated automatically by a subsystem, for example, based on the number of additional medical scans, based on how many of the additional scans in the file were taken before and/or after the scan based on the scan date data 426 of the medical scan and the additional medical scans, based on a date range corresponding to the earliest scan and corresponding to the latest scan, based on the scan types data 421 these scans, and/or based on whether or not a biopsy or other final data is included. As used herein, a "high" longitudinal quality score refers to a scan having more favorable longitudinal data than that with a "low" longitudinal quality score.

Diagnosis data 400 can include data that indicates an automated diagnosis, a tentative diagnosis, and/or data that can otherwise be used to support medical diagnosis, triage, medical evaluation and/or other review by a medical professional or other user. The diagnosis data 440 of a medical scan can include a binary abnormality identifier 441 indicating whether the scan is normal or includes at least one abnormality. In some embodiments, the binary abnormality identifier 441 can be determined by comparing some or all of confidence score data 460 to a threshold, can be determined by comparing a probability value to a threshold, and/or can be determined by comparing another continuous or discrete value indicating a calculated likelihood that the scan contains one or more abnormalities to a threshold. In some embodiments, non-binary values, such as one or more continuous or discrete values indicating a likelihood that the scan contains one or more abnormalities, can be included in diagnosis data 440 in addition to, or instead of, binary abnormality identifier 441. One or abnormalities can be identified by the diagnosis data 440, and each identified abnormality can include its own set of abnormality annotation data 442. Alternatively, some or all of the diagnosis data 440 can indicate and/or describe multiple abnormalities, and thus will not be presented for each abnormality in the abnormality annotation data 442. For example, the report data 449 of the diagnosis data 440 can describe all identified abnormalities, and thus a single report can be included in the diagnosis.

Figure 4B:
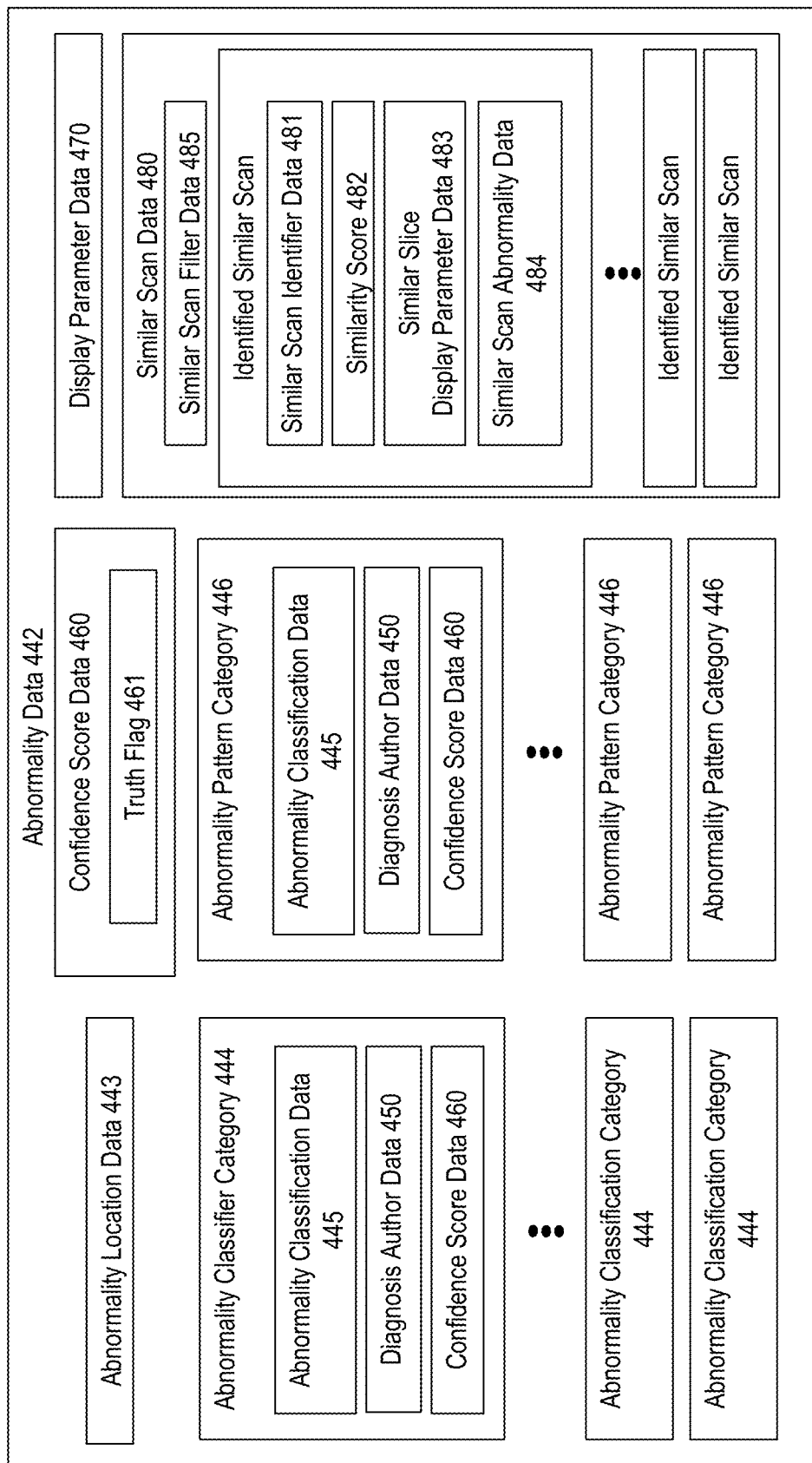
FIG. 4B is a schematic block diagram of abnormality data in accordance with various embodiments.

FIG. 4B presents an embodiment of the abnormality annotation data 442. The abnormality annotation data 442 for each abnormality can include abnormality location data 443, which can include an anatomical location and/or a location specific to pixels, image slices, coordinates or other location information identifying regions of the medical scan itself. The abnormality annotation data 442 can include abnormality classification data 445 which can include binary, quantitative, and/or descriptive data of the abnormality as a whole, or can correspond to one or more abnormality classifier categories 444, which can include size, volume, pre-post contrast, doubling time, calcification, components, smoothness, spiculation, lobulation, sphericity, internal structure, texture, or other categories that can classify and/or otherwise characterize an abnormality. Abnormality classifier categories 444 can be assigned a binary value, indicating whether or not such a category is present. For example, this binary value can be determined by comparing some or all of confidence score data 460 to a threshold, can be determined by comparing a probability value to a threshold, and/or can be determined by comparing another continuous or discrete value indicating a calculated likelihood that a corresponding abnormality classifier category 444 is present to a threshold, which can be the same or different threshold for each abnormality classifier category 444. In some embodiments, abnormality classifier categories 444 can be assigned one or more non-binary values, such as one or more continuous or discrete values indicating a likelihood that the corresponding classifier category 444 is present. For example, an abnormality that is a nodule can include abnormality classification data 445 assigned a spiculation value of "1" to indicate that spiculation is present, and a lobulation value of "0" to indicate that lobulation is not present. Some abnormality classifier categories 444 can be assigned one of a plurality of set options. For example, a nodule texture category can be assigned to one of "solid", "part solid/mixed", or "non-solid/ground glass opacity". As another example, a nodule calcification category can be assigned to one of "popcorn", "laminated", "solid", "non-central", "central", "absent", or "stippled". As another example, a nodule sphericity category can be assigned to one of "linear", "ovoid", or "round". As another example, a nodule internal structure category can be assigned to one of "soft", "fluid", "fat", or "air". As another example, abnormality classification data 445 can categorize an abnormality of a chest x-ray as one of "Airway Abnormality (bronchiectasis or bronchiolitis)", "Anatomic Variant", "Atalectasis and/or scarring", "Consolidation", "Diaphragmatic Abnormality", "Enlarged Cardiac Contour", "Foreign Body (non-medical)", "Hyperlucent Thorax", "Mediastinal Abnormality", "Musculoskeletal Abnormality", "Nodule and/or mass", "Pleural Effusion", "Pleural Lesion", "Post surgical change", "Reticular Opacities", "Skin abnormality (mole, nipple shadow)", "Support devices and medical devices", "Abdominal abnormality not otherwise covered", or "other". Some abnormality classifier categories can include a hierarchy of subcategories. For example, "Pulmonary Vasculature" can be "Plethora" or "Oligaemia", and "Pulmonary Vasculature" that identified as "Plethora" can be "Diffuse" or "Focal/Multifocal". Some categories can have an infinite number of possible values, for example, where "size" is an exact numerical measure of any value.

The abnormality classifier categories 444 can also include a malignancy category, and the abnormality classification data 445 can include a malignancy rating such as a Lung-RADS score, a Fleischner score, and/or one or more calculated values that indicate malignancy level, malignancy severity, and/or probability of malignancy. Alternatively or in addition, the malignancy category can be assigned a value of "yes", "no", or "maybe". The abnormality classifier categories 444 can also include abnormality pattern categories 446 such as cardiomegaly, consolidation, effusion, emphysema, and/or fracture, and the abnormality classification data 445 for each abnormality pattern category 446 can indicate whether or not each of the abnormality patterns is present.

The diagnosis data 440 as a whole and/or the abnormality annotation data 442 for each abnormality, can include custom codes or datatypes identifying the binary abnormality identifier 441, abnormality location data 443 and/or some or all of the abnormality classification data 445 of one or more abnormality classifier categories 444. Alternatively or in addition some or all of the abnormality annotation data 442 for each abnormality and/or other diagnosis data 440 can be presented in a Digital Imaging and Communications in Medicine (DICOM) format or other standardized image annotation format, and/or can be extracted into custom datatypes based on abnormality annotation data originally presented in DICOM format. Alternatively or in addition, the diagnosis data 440 and/or the abnormality annotation data 442 for each abnormality can be presented as one or more medical codes 447 such as SNOMED codes, Current Procedure Technology (CPT) codes, ICD-9 codes, ICD-10 codes, or other standardized medical codes used to label or otherwise describe medical scans.

Alternatively or in addition, the diagnosis data 440 can include natural language text data 448 annotating or otherwise describing the medical scan as a whole, and/or the abnormality annotation data 442 can include natural language text data 448 annotating or otherwise describing each corresponding abnormality. In some embodiments, some or all of the diagnosis data 440 is presented only as natural language text data 448. In some embodiments, some or all of the diagnosis data 440 is automatically generated by one or more subsystems based on the natural language text data 448, for example, without utilizing the medical scan image data 410, for example, by utilizing one or more medical scan natural language analysis functions trained by the medical scan natural language analysis system 114. Alternatively or in addition, some embodiments, some or all of the natural language text data 448 is generated automatically based on other diagnosis data 440 such as abnormality annotation data 442, for example, by utilizing a medical scan natural language generating function trained by the medical scan natural language analysis system 114.

The diagnosis data can include report data 449 that includes at least one medical report, which can be formatted to include some or all of the medical codes 447, some or all of the natural language text data 448, other diagnosis data 440, full or cropped images slices formatted based on the display parameter data 470 and/or links thereto, full or cropped images slices or other data based on similar scans of the similar scan data 480 and/or links thereto, full or cropped images or other data based on patient history data 430 such as longitudinal data 433 and/or links thereto, and/or other data or links to data describing the medical scan and associated abnormalities. The diagnosis data 440 can also include finalized diagnosis data corresponding to future scans and/or future diagnosis for the patient, for example, biopsy data or other longitudinal data 433 determined subsequently after the scan. The medical report of report data 449 can be formatted based on specified formatting parameters such as font, text size, header data, bulleting or numbering type, margins, file type, preferences for including one or more full or cropped image slices 412, preferences for including similar medical scans, preferences for including additional medical scans, or other formatting to list natural language text data and/or image data, for example, based on preferences of a user indicated in the originating entity data 423 or other responsible user in the corresponding report formatting data 570.

Annotation author data 450 can be mapped to the diagnosis data for each abnormality, and/or mapped to the scan as a whole. This can include one or more annotation author identifiers 451, which can include one or more user profile identifiers 355 of a user of the system, such as an individual medical professional, medical facility and/or medical entity that uses the system. Annotation author data 450 can be used to determine the usage data 520 of a user profile entry 354.

Annotation author data 450 can also include one or more medical scan analysis function identifiers 357 or other function identifier indicating one or more functions or other processes of a subsystem responsible for automatically generating and/or assisting a user in generating some or all of the diagnosis data, for example an identifier of a particular type and/or version of a medical scan image analysis functions that was used by the medical scan diagnosing system 108 used to generate part or all of the diagnosis data 440 and/or an interface feature identifier 359, indicating an one or more interface features presented to a user to facilitate entry of and/or reviewing of the diagnosis data 440. The annotation author data can also simply indicate, for one or more portions of the diagnosis data 440, if this portion was generated by a human or automatically generated by a subsystem of the medical scan processing system.

In some embodiments, if a medical scan was reviewed by multiple entities, multiple, separate diagnosis data entries 440 can be included in the medical scan entry 352, mapped to each diagnosis author in the annotation author data 450. This allows different versions of diagnosis data 440 received from multiple entities. For example, annotation author data of a particular medical scan could indicate that the annotation data was written by a doctor at medical entity A, and the medical code data was generated by user Y by utilizing the medical report labeling system 104, which was confirmed by expert user X. The annotation author data of another medical scan could indicate that the medical code was generated automatically by utilizing version 7 of the medical scan image analysis function relating to chest x-rays, and confirmed by expert user X. The annotation author data of another medical scan could indicate that the location and a first malignancy rating were generated automatically by utilizing version 7 of the medical scan image analysis function relating to chest x-rays, and that a second malignancy rating was entered by user Z. In some embodiments, one of the multiple diagnosis entries can include consensus annotation data, for example, generated automatically by a subsystem such as the medical scan annotation system 106 based on the multiple diagnosis data 440, based on confidence score data 460 of each of the multiple diagnosis data 440, and/or based on performance score data 530, 630, or 720 of corresponding user, medical scan analysis function, or interface feature, respectfully, identified in the annotation author data for each corresponding one of the multiple diagnosis data 440.

Confidence score data 460 can be mapped to some or all of the diagnosis data 440 for each abnormality, and/or for the scan as a whole. This can include an overall confidence score for the diagnosis, a confidence score for the binary indicator of whether or not the scan was normal, a confidence score for the location a detected abnormality, and/or confidence scores for some or all of the abnormality classifier data. This may be generated automatically by a subsystem, for example, based on the annotation author data and corresponding performance score of one or more identified users and/or subsystem attributes such as interactive interface types or medical scan image analysis functions indicated by the annotation author data. In the case where multiple diagnosis data entries 440 are included from different sources, confidence score data 460 can be computed for each entry and/or an overall confidence score, for example, corresponding to consensus diagnosis data, can be based on calculated distance or other error and/or discrepancies between the entries, and/or can be weighted on the confidence score data 460 of each entry. In various embodiments, the confidence score data 460 can includes a truth flag 461 indicating the diagnosis data is considered as "known" or "truth", for example, flagged based on user input, flagged automatically based on the author data, and/or flagged automatically based on the calculated confidence score of the confidence score data exceeding a truth threshold. As used herein, a "high" confidence score refers to a greater degree or more favorable level of confidence than a "low" confidence score.

Display parameter data 470 can indicate parameters indicating an optimal or preferred display of the medical scan by an interactive interface 275 and/or formatted report for each abnormality and/or for the scan as a whole. Some or all of the display parameter data can have separate entries for each abnormality, for example, generated automatically by a subsystem 101 based on the abnormality annotation data 442. Display parameter data 470 can include interactive interface feature data 471, which can indicate one or more selected interface features associated with the display of abnormalities and/or display of the medical scan as a whole, and/or selected interface features associated with user interaction with a medical scan, for example, based on categorized interface feature performance score data 720 and a category associated with the abnormality and/or with the medical scan itself. The display parameter data can include a slice subset 472, which can indicate a selected subset of the plurality of image slices that includes a single image slice 412 or multiple image slices 412 of the medical scan image data 410 for display by a user interface. The display parameter data 470 can include slice order data 473 that indicates a selected custom ordering and/or ranking for the slice subset 472, or for all of the slices 412 of the medical scan. The display parameter data 470 can include slice cropping data 474 corresponding to some or all of the slice subset 472, or all of the image slices 412 of the medical scan, and can indicating a selected custom cropped region of each image slice 412 for display, or the same selected custom cropped region for the slice subset 472 or for all slices 412. The display parameter data can include density window data 475, which can indicate a selected custom density window for display of the medical scan as a whole, a selected custom density window for the slices subset 472, and/or selected custom density windows for each of the image slices 412 of the slice subset 472, and/or for each image slice 412 of the medical scan. The density window data 475 can indicate a selected upper density value cut off and a selected lower density value cut off, and/or can include a selected deterministic function to map each density value of a pixel to a grayscale value based on the preferred density window. The interactive interface feature data 471, slice subset 472, slice order data 473, slice cropping data 474, and/or the density window data 475 can be selected via user input and/or generated automatically by one or more subsystems 101, for example, based on the abnormality annotation data 442 and/or based on performance score data 720 of different interactive interface versions.

Similar scan data 480 can be mapped to each abnormality, or the scan as a whole, and can include similar scan identifier data 481 corresponding to one or more identified similar medical scans, for example, automatically identified by a subsystem 101, for example, by applying the similar scan identification step 1376 of the medical scan image analysis system 112 and/or applying medical scan similarity analysis function to some or all of the data stored in the medical scan entry of the medical scan, and/or to some or all corresponding data of other medical scans in the medical scan database. The similar scan data 480 can also correspond to medical scans received from another source. The stored similarity data can be used to present similar cases to users of the system and/or can be used to train medical scan image analysis functions or medical scan similarity analysis functions.

Each identified similar medical scan can have its own medical scan entry 352 in the medical scan database 342 with its own data, and the similar scan identifier data 481 can include the medical scan identifier 353 each similar medical scan. Each identified similar medical scan can be a scan of the same scan type or different scan type than medical scan.

The similar scan data 480 can include a similarity score 482 for each identified similar scan, for example, generated based on some or all of the data of the medical scan entry 352 for medical scan and based on some or all of the corresponding data of the medical scan entry 352 for the identified similar medical scan. For example, the similarity score 482 can be generated based on applying a medical scan similarity analysis function to the medical image scan data of medical scans and 402, to some or all of the abnormality annotation data of medical scans and 402, and/or to some or all of the patient history data 430 of medical scans and 402 such as risk factor data 432. As used herein, a "high" similarity score refers a higher level of similarity that a "low" similarity score.

The similar scan data 480 can include its own similar scan display parameter data 483, which can be determined based on some or all of the display parameter data 470 of the identified similar medical scan. Some or all of the similar scan display parameter data 483 can be generated automatically by a subsystem, for example, based on the display parameter data 470 of the identified similar medical scan, based on the abnormality annotation data 442 of the medical scan itself and/or based on display parameter data 470 of the medical scan itself. Thus, the similar scan display parameter data 483 can be the same or different than the display parameter data 470 mapped to the identified similar medical scan and/or can be the same or different than the display parameter data 470 of the medical scan itself. This can be utilized when displaying similar scans to a user via interactive interface 275 and/or can be utilized when generating report data 449 that includes similar scans, for example, in conjunction with the medical scan assisted review system 102.

The similar scan data 480 can include similar scan abnormality data 484, which can indicate one of a plurality of abnormalities of the identified similar medical scan and its corresponding abnormality annotation data 442. For example, the similarity scan abnormality data 484 can include an abnormality pair that indicates one a plurality abnormalities of the medical scan, and indicates one of a plurality of abnormalities of the identified similar medical scan, for example, that was identified as the similar abnormality.

The similar scan data 480 can include similar scan filter data 485. The similar scan filter data can be generated automatically by a subsystem, and can include a selected ordered or un-ordered subset of all identified similar scans of the similar scan data 480, and/or a ranking of all identified similar scans. For example, the subset can be selected and/or some or all identified similar scans can be ranked based on each similarity score 482, and/or based on other factors such as based on a longitudinal quality score 434 of each identified similar medical scan.

The training set data 490 can indicate one or more training sets that the medical scan belongs to. For example, the training set data can indicate one or more training set identifiers 491 indicating one or more medical scan analysis functions that utilized the medical scan in their training set based on training set data 621, and/or indicating a particular version identifier 641 of the one or more medical scan analysis functions that utilized the medical scan in their training set. The training set data 490 can also indicate which portions of the medical scan entry were utilized by the training set, for example, based on model parameter data 623 of the corresponding medical scan analysis functions. For example, the training set data 490 can indicate that the medical scan image data 410 was included in the training set utilized to train version X of the chest x-ray medical scan image analysis function, or that the natural language text data 448 of this medical scan was used to train version Y of the natural language analysis function.

Figure 5:
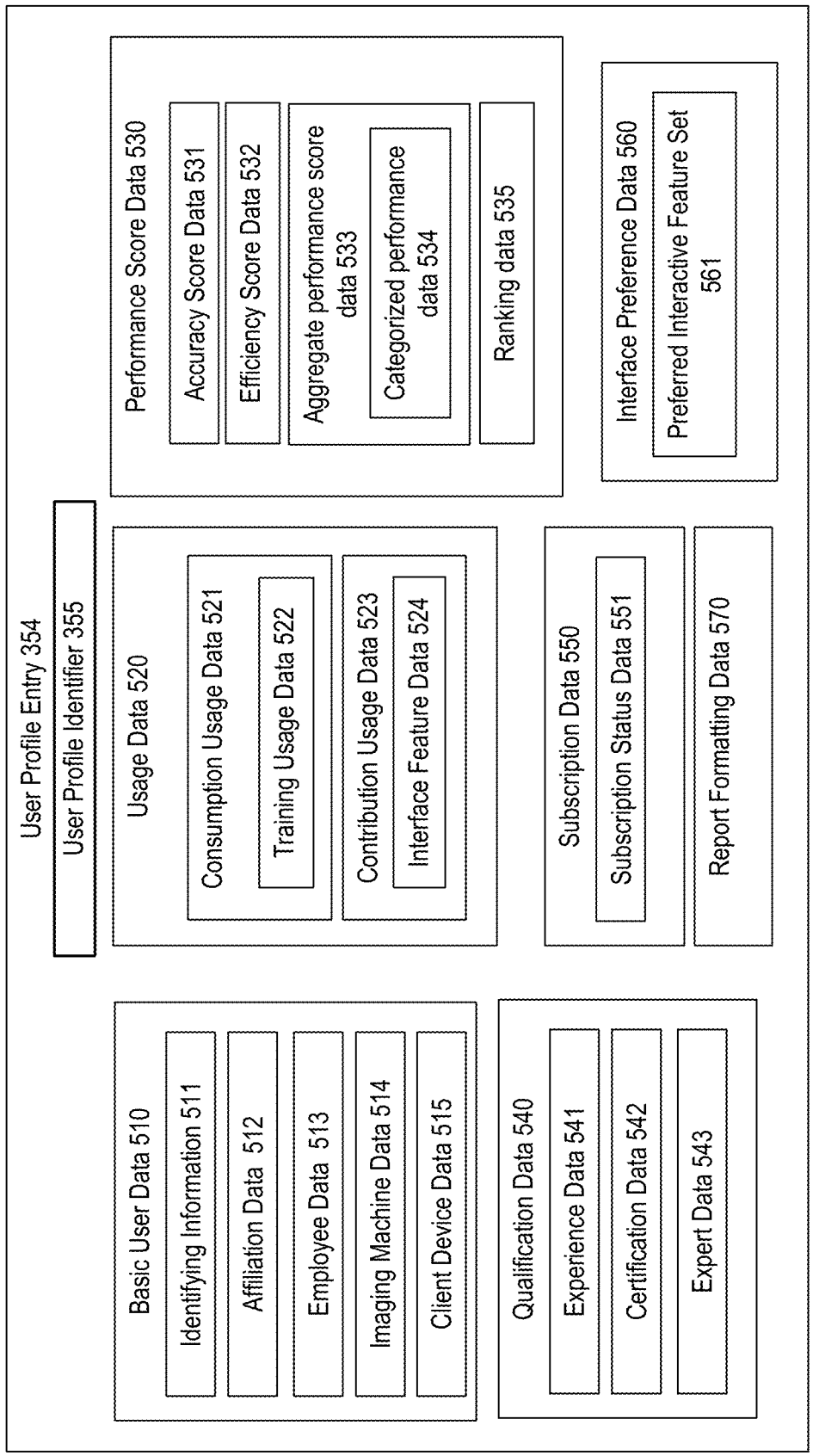
FIG. 5 is a schematic block diagram of a user profile entry in accordance with various embodiments.

FIG. 5 presents an embodiment of a user profile entry 354, stored in user database 344 or otherwise associated with a user. A user can correspond to a user of one or more of the subsystems such as a radiologist, doctor, medical professional, medical report labeler, administrator of one or more subsystems or databases, or other user that uses one or more subsystems 101. A user can also correspond to a medical entity such as a hospital, medical clinic, establishment that utilizes medical scans, establishment that employs one or more of the medical professionals described, an establishment associated with administering one or more subsystems, or other entity. A user can also correspond to a particular client device 120 or account that can be accessed one or more medical professionals or other employees at the same or different medical entities. Each user profile entry can have a corresponding user profile identifier 355.

A user profile entry 354 can include basic user data 510, which can include identifying information 511 corresponding to the user such as a name, contact information, account/login/password information, geographic location information such as geographic region data 424, and/or other basic information. Basic user data 510 can include affiliation data 512, which can list one or more medical entities or other establishments the user is affiliated with, for example, if the user corresponds to a single person such as a medical professional, or if the user corresponds to a hospital in a network of hospitals. The affiliation data 512 can include one or more corresponding user profile identifiers 355 and/or basic user data 510 if the corresponding affiliated medical entity or other establishment has its own entry in the user database. The user identifier data can include employee data 513 listing one or more employees, such as medical professionals with their own user profile entries 354, for example, if the user corresponds to a medical entity or supervising medical professional of other medical professional employees, and can list a user profile identifier 355 and/or basic user data 510 for each employee. The basic user data 510 can also include imaging machine data 514, which can include a list of machines affiliated with the user which can include machine identifiers, model information, calibration information, scan type information, or other data corresponding to each machine, for example, corresponding to the machine data 425. The user profile entry can include client device data 515, which can include identifiers for one or more client devices associated with the user, for example, allowing subsystems 101 to send data to a client device 120 corresponding to a selected user based on the client device data and/or to determine a user that data was received by determining the client device from which the data was received.

The user profile entry can include usage data 520 which can include identifying information for a plurality of usages by the user in conjunction with using one or more subsystems 101. This can include consumption usage data 521, which can include a listing of, or aggregate data associated with, usages of one or more subsystems by the user, for example, where the user is utilizing the subsystem as a service. For example, the consumption usage data 521 can correspond to each instance where diagnosis data was sent to the user for medical scans provided to the user in conjunction with the medical scan diagnosing system 108 and/or the medical scan assisted review system 102. Some or all of consumption usage data 521 can include training usage data 522, corresponding to usage in conjunction with a certification program or other user training provided by one or more subsystems. The training usage data 522 can correspond to each instance where diagnosis feedback data was provided by user for a medical scan with known diagnosis data, but diagnosis feedback data is not utilized by a subsystem to generate, edit, and/or confirm diagnosis data 440 of the medical scan, as it is instead utilized to train a user and/or determine performance data for a user.

Usage data 520 can include contribution usage data 523, which can include a listing of, or aggregate data associated with, usages of one or more subsystems 101 by the user, for example, where the user is generating and/or otherwise providing data and/or feedback that can is utilized by the subsystems, for example, to generate, edit, and/or confirm diagnosis data 440 and/or to otherwise populate, modify, or confirm portions of the medical scan database or other subsystem data. For example, the contribution usage data 523 can correspond to diagnosis feedback data received from user, used to generate, edit, and/or confirm diagnosis data. The contribution usage data 523 can include interactive interface feature data 524 corresponding to the interactive interface features utilized with respect to the contribution.

The consumption usage data 521 and/or the contribution usage data 523 can include medical scan entry 352 whose entries the user utilized and/or contributed to, can indicate one or more specific attributes of a medical scan entry 352 that a user utilized and/or contributed to, and/or a log of the user input generated by a client device of the user in conjunction with the data usage. The contribution usage data 523 can include the diagnosis data that the user may have generated and/or reviewed, for example, indicated by, mapped to, and/or used to generate the annotation author data 450 of corresponding medical scan entries 352. Some usages may correspond to both consumption usage of the consumption usage data 521 and contribution usage of the contribution usage data 523. The usage data 520 can also indicate one or more subsystems 101 that correspond to each consumption and/or contribution.

The user profile entry can include performance score data 530. This can include one or more performance scores generated based on the contribution usage data 523 and/or training usage data 522. The performance scores can include separate performance scores generated for every contribution in the contribution usage data 523 and/or training usage data 522 and/or generated for every training consumption usages corresponding to a training program. As used herein, a "high" performance score refers to a more favorable performance or rating than a "low" performance score.

The performance score data can include accuracy score data 531, which can be generated automatically by a subsystem for each contribution, for example, based on comparing diagnosis data received from a user to data to known truth data such as medical scans with a truth flag 461, for example, retrieved from the corresponding medical scan entry 352 and/or based on other data corresponding to the medical scan, for example, received from an expert user that later reviewed the contribution usage data of the user and/or generated automatically by a subsystem. The accuracy score data 531 can include an aggregate accuracy score generated automatically by a subsystem, for example, based on the accuracy data of multiple contributions by the user over time.

The performance data can also include efficiency score data 532 generated automatically by a subsystem for each contribution based on an amount of time taken to complete a contribution, for example, from a time the request for a contribution was sent to the client device to a time that the contribution was received from the client device, based on timing data received from the client device itself, and/or based on other factors. The efficiency score can include an aggregate efficiency score, which can be generated automatically by a subsystem based on the individual efficiency scores over time and/or based on determining a contribution completion rate, for example based on determining how many contributions were completed in a fixed time window.

Aggregate performance score data 533 can be generated automatically by a subsystem based on the aggregate efficiency and/or accuracy data. The aggregate performance data can include categorized performance data 534, for example, corresponding to different scan types, different anatomical regions, different subsystems, different interactive interface features and/or display parameters. The categorized performance data 534 can be determined automatically by a subsystem based on the scan type data 421 and/or anatomical region data 422 of the medical scan associated with each contribution, one or more subsystems 101 associated with each contribution, and/or interactive interface feature data 524 associated with each contribution. The aggregate performance data can also be based on performance score data 530 of individual employees if the user corresponds to a medical entity, for example, retrieved based on user profile identifiers 355 included in the employee data 513. The performance score data can also include ranking data 535, which can include an overall ranking or categorized rankings, for example, generated automatically by a subsystem or the database itself based on the aggregate performance data.

In some embodiments, aggregate data for each user can be further broken down based on scores for distinct scan categories, for example, based on the scan classifier data 420, for example, where a first aggregate data score is generated for a user "A" based on scores from all knee x-rays, and a second aggregate data score is generated for user A based on scores from all chest CT scans. Aggregate data for each user can be further based on scores for distinct diagnosis categories, where a first aggregate data score is generated for user A based on scores from all normal scans, and a second aggregate data score is generated for user A based on scores from all scans that contain an abnormality. This can be further broken down, where a first aggregate score is generated for user A based on all scores from scans that contain an abnormality of a first type and/or in a first anatomical location, and a second aggregate score is generated for A based on all scores from scans that contain an abnormality of a second type and/or in a second location. Aggregate data for each user can be further based on affiliation data, where a ranking is generated for a medical professional "B" based on scores from all medical professionals with the same affiliation data, and/or where a ranking is generated for a hospital "C" based on scores for all hospitals, all hospitals in the same geographical region, etc. Aggregate data for each user can be further based on scores for interface features, where a first aggregate data score is generated for user A based on scores using a first interface feature, and a second aggregate data score is generated for user A based on scores using a first interface feature.

The user profile entry can include qualification data 540. The qualification data can include experience data 541 such as education data, professional practice data, number of years practicing, awards received, etc. The qualification data 540 can also include certification data 542 corresponding to certifications earned based on contributions to one or more subsystems, for example, assigned to users automatically by a subsystem based on the performance score data 530 and/or based on a number of contributions in the contribution usage data 523 and/or training usage data 522. For example, the certifications can correspond to standard and/or recognized certifications to train medical professionals and/or incentivize medical professionals to use the system. The qualification data 540 can include expert data 543. The expert data 543 can include a binary expert identifier, which can be generated automatically by a subsystem based on experience data 541, certification data 542, and/or the performance score data 530, and can indicate whether the user is an expert user. The expert data 543 can include a plurality of categorized binary expert identifiers corresponding to a plurality of qualification categories corresponding to corresponding to scan types, anatomical regions, and/or the particular subsystems. The categorized binary expert identifiers can be generated automatically by a subsystem based on the categorized performance data 534 and/or the experience data 541. The categories be ranked by performance score in each category to indicate particular specialties. The expert data 543 can also include an expert ranking or categorized expert ranking with respect to all experts in the system.

The user profile entry can include subscription data 550, which can include a selected one of a plurality of subscription options that the user has subscribed to. For example, the subscription options can correspond to allowed usage of one or more subsystems, such as a number of times a user can utilize a subsystem in a month, and/or to a certification program, for example paid for by a user to receive training to earn a subsystem certification of certification data 542. The subscription data can include subscription expiration information, and/or billing information. The subscription data can also include subscription status data 551, which can for example indicate a number of remaining usages of a system and/or available credit information. For example, the remaining number of usages can decrease and/or available credit can decrease in response to usages that utilize one or more subsystems as a service, for example, indicated in the consumption usage data 521 and/or training usage data 522. In some embodiments, the remaining number of usages can increase and/or available credit can increase in response to usages that correspond to contributions, for example, based on the contribution usage data 523. An increase in credit can be variable, and can be based on a determined quality of each contribution, for example, based on the performance score data 530 corresponding to the contribution where a higher performance score corresponds to a higher increase in credit, based on scan priority data 427 of the medical scan where contributing to higher priority scans corresponds to a higher increase in credit, or based on other factors.

The user profile entry 354 can include interface preference data 560. The interface preference data can include a preferred interactive interface feature set 561, which can include one or more interactive interface feature identifiers 359 and/or one or more interactive interface version identifiers 712 of interface feature entries 358 and/or version identifiers of the interface features. Some or all of the interface features of the preferred interactive interface feature set 561 can correspond to display parameter data 470 of medical scans. The preferred interactive interface feature set 561 can include a single interactive feature identifier for one or more feature types and/or interface types, and/or can include a single interactive interface version identifier 712 for one or more interface categories. The preferred interactive interface feature set 561 can include a ranking of multiple features for the same feature type and/or interface type. The ranked and/or unranked preferred interactive interface feature set 561 can be generated based on user input to an interactive interface of the client device to select and/or rank some or all of the interface features and/or versions. Some or all of the features and/or versions of the preferred interactive feature set can be selected and/or ranked automatically by a subsystem such as the medical scan interface evaluator system, for example based on interface feature performance score data 720 and/or feature popularity data 721. Alternatively or in addition, the performance score data 530 can be utilized by a subsystem to automatically determine the preferred interactive feature set, for example, based on the scores in different feature-based categories of the categorized performance data 534.

The user profile entry 354 can include report formatting data 570, which can indicate report formatting preferences indicated by the user. This can include font, text size, header data, bulleting or numbering type, margins, file type, preferences for including one or more full or cropped image slices 412, preferences for including similar medical scans, preferences for including additional medical scans in reports, or other formatting preference to list natural language text data and/or image data corresponding to each abnormality. Some or all of the report formatting data 570 can be based on interface preference data 560. The report formatting data 570 can be used by one or more subsystems to automatically generate report data 449 of medical scans based on the preferences of the requesting user.

Figure 6:
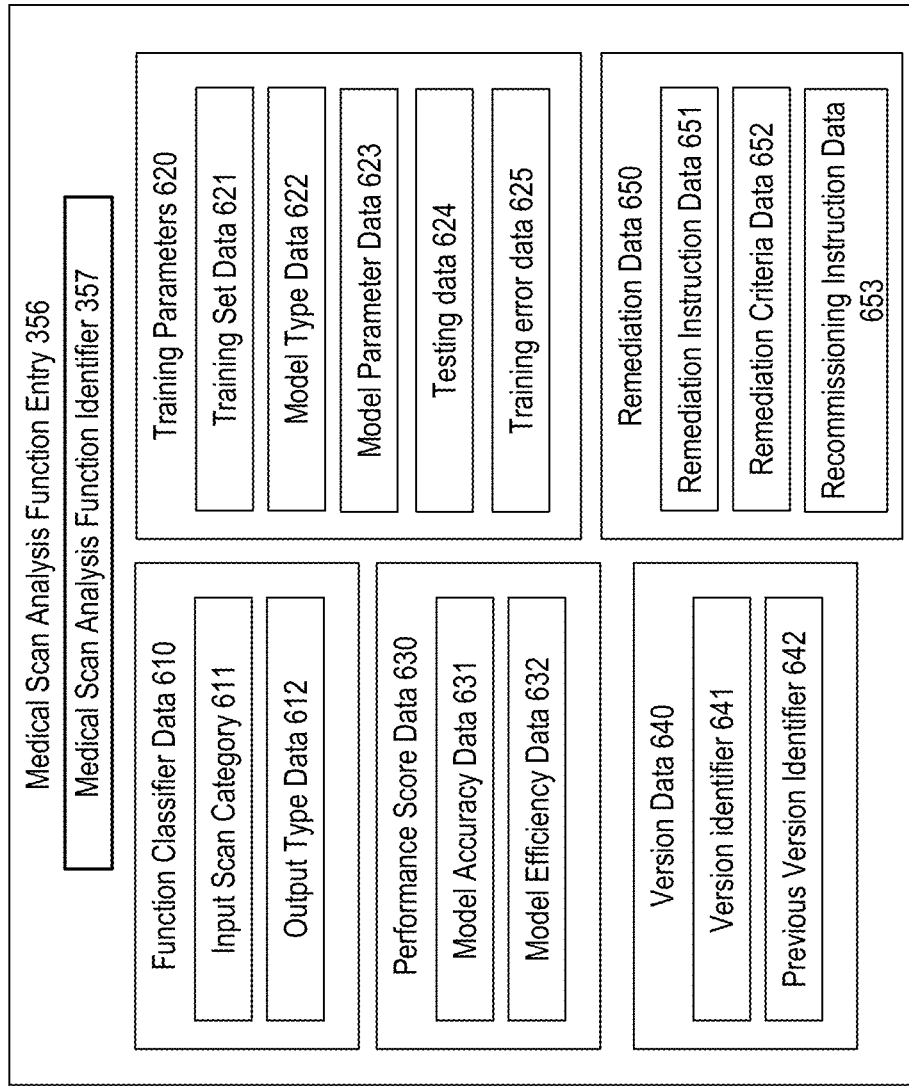
FIG. 6 is a schematic block diagram of a medical scan analysis function entry in accordance with various embodiments.

FIG. 6 presents an embodiment of a medical scan analysis function entry 356, stored in medical scan analysis function database 346 or otherwise associated with one of a plurality of medical scan analysis functions trained by and/or utilized by one or more subsystems 101. For example, a medical scan analysis function can include one or more medical scan image analysis functions trained by the medical scan image analysis system 112; one or more medical scan natural language analysis functions trained by the medical scan natural language analysis system 114; one or more medical scan similarity analysis function trained by the medical scan image analysis system 112, the medical scan natural language analysis system 114, and/or the medical scan comparison system 116; one or more medical report generator functions trained by the medical scan natural language analysis system 114 and/or the medical scan image analysis system 112, and/or the medical report analysis function trained by the medical scan natural language analysis system 114. Some or all of the medical scan analysis functions can correspond to medical scan inference functions of the medical scan diagnosing system 108 or other functions and/or processes described herein in conjunction with one or more subsystems 101. Each medical scan analysis function entry 356 can include a medical scan analysis function identifier 357.

A medical scan analysis function entry 356 can include function classifier data 610. Function classifier data 610 can include input and output types corresponding to the function. For example the function classifier data can include input scan category 611 that indicates which types of scans can be used as input to the medical scan analysis function.

For example, input scan category 611 can indicate that a medical scan analysis function is for chest CT scans from a particular hospital or other medical entity. The input scan category 611 can include one or more categories included in scan classifier data 420. In various embodiments, the input scan category 611 corresponds to the types of medical scans that were used to train medical scan analysis function. Function classifier data 610 can also include output type data 612 that characterizes the type of output that will be produced by the function, for example, indicating that a medical scan analysis function is used to generate medical codes 447. The input scan category 611 can also include information identifying which subsystems 101 are responsible for running the medical scan analysis function.

A medical scan analysis function entry 356 can include training parameters 620. This can include training set data 621, which can include identifiers for the data used to train the medical scan analysis function, such as a set of medical scan identifiers 353 corresponding to the medical scans used to train the medical scan analysis function, a list of medical scan reports and corresponding medical codes used to train the medical scan analysis function, etc. Alternatively or in addition to identifying particular scans of the training set, the training set data 621 can identify training set criteria, such as necessary scan classifier data 420, necessary abnormality locations, classifiers, or other criteria corresponding to abnormality annotation data 442, necessary confidence score data 460, for example, indicating that only medical scans with diagnosis data 440 assigned a truth flag 461 or with confidence score data 460 otherwise comparing favorably to a training set confidence score threshold are included, a number of medical scans to be included and proportion data corresponding to different criteria, or other criteria used to populate a training set with data of medical scans. Training parameters 620 can include model type data 622 indicating one or more types of model, methods, and/or training functions used to determine the medical scan analysis function by utilizing the training set 621. Training parameters 620 can include model parameter data 623 that can include a set of features of the training data selected to train the medical scan analysis function, determined values for weights corresponding to selected input and output features, determined values for model parameters corresponding to the model itself, etc. The training parameter data can also include testing data 624, which can identify a test set of medical scans or other data used to test the medical scan analysis function. The test set can be a subset of training set 621, include completely separate data than training set 621, and/or overlap with training set 621. Alternatively or in addition, testing data 624 can include validation parameters such as a percentage of data that will be randomly or pseudo-randomly selected from the training set for testing, parameters characterizing a cross validation process, or other information regarding testing. Training parameters 620 can also include training error data 625 that indicates a training error associated with the medical scan analysis function, for example, based on applying cross validation indicated in testing data 624.

A medical scan analysis function entry 356 can include performance score data 630. Performance data can include model accuracy data 631, for example, generated and/or updated based on the accuracy of the function when performed on new data. For example, the model accuracy data 631 can include or be calculated based on the model error for determined for individual uses, for example, generated by comparing the output of the medical scan analysis function to corresponding data generated by user input to interactive interface 275 in conjunction with a subsystem 101 and/or generated by comparing the output of the medical scan analysis function to medical scans with a truth flag 461. The model accuracy data 631 can include aggregate model accuracy data computed based on model error of individual uses of the function over time. The performance score data 630 can also include model efficiency data 632, which can be generated based on how quickly the medical scan analysis function performs, how much memory is utilized by medical scan analysis function, or other efficiency data relating to the medical scan analysis function. Some or all of the performance score data 630 can be based on training error data 625 or other accuracy and/or efficiency data determined during training and/or validation. As used herein, a "high" performance score refers to a more favorable performance or rating than a "low" performance score.

A medical scan analysis function entry 356 can include version data 640. The version data can include a version identifier 641. The version data can indicate one or more previous version identifiers 642, which can map to version identifiers 641 stored in other medical scan analysis function entry 356 that correspond to previous versions of the function. Alternatively or in addition, the version data can indicate multiple versions of the same type based on function classifier data 610, can indicate the corresponding order and/or rank of the versions, and/or can indicate training parameters 620 associated with each version.

A medical scan analysis function entry 356 can include remediation data 650. Remediation data 650 can include remediation instruction data 651 which can indicate the steps in a remediation process indicating how a medical scan analysis function is taken out of commission and/or reverted to a previous version in the case that remediation is necessary. The version data 640 can further include remediation criteria data 652, which can include threshold data or other criteria used to automatically determine when remediation is necessary. For example, the remediation criteria data 652 can indicate that remediation is necessary at any time where the model accuracy data and/or the model efficiency data compares unfavorably to an indicated model accuracy threshold and/or indicated model efficiency threshold. The remediation data 650 can also include recommissioning instruction data 653, identifying required criteria for recommissioning a medical scan analysis function and/or updating a medical scan analysis function. The remediation data 650 can also include remediation history, indicating one or more instances that the medical scan analysis function was taken out of commission and/or was recommissioned.

Figure 7:
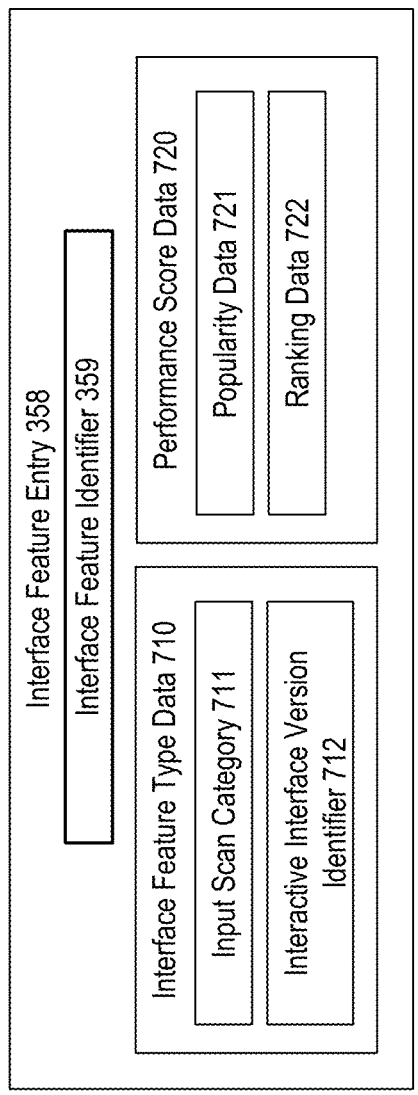
FIG. 7 is a schematic block diagram of an interface feature entry in accordance with various embodiments.

FIG. 7 presents an embodiment of an interface features entries 358, stored in interface feature database 348 or otherwise associated with one of a plurality of interface features utilized by interactive interface 275 in conjunction with one or more subsystems. Each interactive feature entry 358 can have a corresponding feature identifier 359. Some interactive feature entries can correspond to one or a plurality of features that can be used by one or more interactive interface versions, for example, each mapped to a corresponding interactive interface version identifier 712, where each interactive interface version can utilize multiple interface features. Some interactive feature entries can correspond to multiple features presented in conjunction, for example, corresponding to an interactive interface version that presents a plurality of interface features. Some or all of the interactive feature entries can correspond to scan display parameter data 470 of medical scan entries 352.

An interface features entry 358 can include interface feature type data 710. This can indicate if the interface feature corresponds to a particular type of textual and/or visual cue, a particular type of menu option, a particular type of response input method, a particular type of spatial interface layout, or other feature type. For example, the interface feature type can correspond to an abnormality location display cue. A first interface feature can correspond to a first abnormality location display cue that includes circling an abnormality in red, a second interface feature can correspond to a second abnormality location display cue that includes automatically displaying a cropped image slice that includes the abnormality, and a third interface feature can correspond to a third abnormality location display cue that includes overlaying an image slice with a confidence heat map based on the probability that each location of the image slice corresponds to an abnormality. Multiple interface features of the same type can be scored and or ranked to determine which particular feature is preferred for a particular interactive interface version, for example, in conjunction with the medical scan interface feature evaluator system 110. An input scan type corresponding to a scan type that can be utilized with the interface feature can be indicated in an input scan category 711.

The interface feature type data 710 can further include one or more interactive interface version identifiers 712 corresponding to one or more interface versions in which the feature is included. The version identifier can correspond to, for example, one or more subsystems 101 that utilize the version when presenting interactive interface 275. Multiple interface features of different types can be included in an interactive interface version, and each interactive interface version can be scored and or ranked to determine which particular version is preferred, for example, in conjunction with the medical scan interface feature evaluator system 110. In some embodiments, each version corresponds to its own interface features entry 358, and can indicate the set of interface features used by the interface version based on their corresponding interface feature identifiers 359. Thus, the one or more interactive interface version identifiers 712 of an interactive feature entry can correspond to interface feature identifiers 359 of interface versions stored in the database 348.

An interface features entry 358 can include performance score data 720 that corresponds to how well users perform when interface feature is utilized by interactive interface 275. Performance score data 720 can be based on aggregate accuracy score data 531 and/or efficiency score data 532 of the user database 344, categorized by the corresponding interactive interface feature data 524 indicated in the contribution usage data 523. The performance score data 720 can be generated by the medical scan interface feature evaluator system 110, and can be used to populate some or all of the accuracy score data 531 and/or efficiency score data 532 of the user database 344 and the corresponding interactive interface feature data 524 of the contribution usage data 523. The interface feature performance score data 720 can be categorized by data associated with each corresponding medical scan of user contributions. For example, the interface feature performance score data 720 can be categorized by scan classifier data 420, by abnormality location, classifiers, or other data indicated in diagnosis data 440, by annotation author data 450, or by other data relevant to categorizing the performance score data 720.

The interface feature performance score data can also include popularity data 721 that corresponds to how many users select to use the interface feature and/or how many medical scans include display parameter data automatically generated by a subsystem corresponding to interface feature. For example, in embodiments where users can indicate their own preferred interface features in interface preference data 560, the interface preference data 560 of the user database can be used to determine a popularity score and/or ranking corresponding to the interface feature.

The interface feature performance score data 720 can include ranking data 722 which can include an overall ranking of interface feature, and/or ranking with respect to other interface features of the same type based on accuracy, efficiency, and/or popularity. This can be used by a subsystem such as the medical scan interface feature evaluating system 110 to populate the display parameter data 470 of some or all medical scans in the medical scan database 342, for example, based on a categorized ranking of interface features corresponding to categories indicated by data of each the medical scan entry 352. As used herein, a "high" performance score refers to a more favorable performance or rating than a "low" performance score.

Figure 8A:
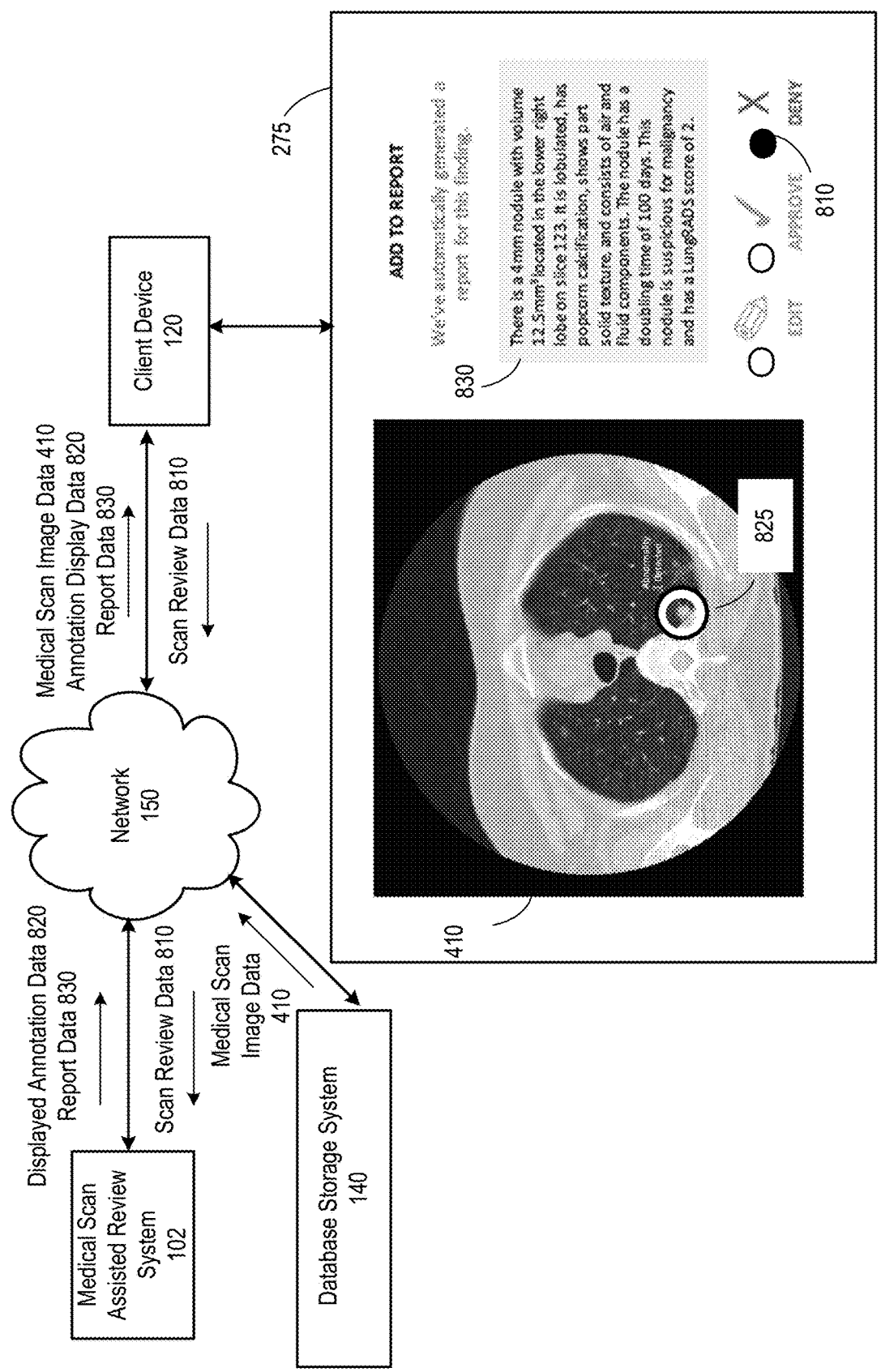
FIG. 8A is a schematic block diagram of a medical scan assisted review system in accordance with various embodiments.

FIG. 8A presents an embodiment of the medical scan assisted review system 102. The medical scan assisted review system 102 can be used to aid medical professionals or other users in diagnosing, triaging, classifying, ranking, and/or otherwise reviewing medical scans by presenting a medical scan for review by a user by transmitting medical scan data of a selected medical scan and/or interface feature data of selected interface features of to a client device 120 corresponding to a user of the medical scan assisted review system for display via a display device of the client device. The medical scan assisted review system 102 can generate scan review data 810 for a medical scan based on user input to the interactive interface 275 displayed by the display device in response to prompts to provide the scan review data 810, for example, where the prompts correspond to one or more interface features.

In various embodiments, the medical scan assisted review system 102 is operable to receive, via a network, a medical scan for review. Abnormality annotation data 442 is generated by identifying one or more of abnormalities in the medical scan by utilizing a computer vision model that is trained on a plurality of training medical scans. The abnormality annotation data 442 includes location data and classification data for each of the plurality of abnormalities and/or data that facilitates the visualization 825 of the abnormalities in the scan image data 410. Report data 830 including text describing each of the plurality of abnormalities is generated based on the abnormality data. The visualization 825 and the report data 830 (collectively displayed annotation data 820) is transmitted to a client device. A display device associated with the client device displays the visualization 825 in conjunction with the medical scan via an interactive interface, and the display device further displays the report data 830 via the interactive interface.

The scan review data 810 can correspond to feedback such as confirmation, additions, edits, or deletions of abnormality annotation data 442, which can correspond to some or all of the diagnosis data 440, presented to the user in conjunction with the medical scan. The scan review data 810 can also correspond to new annotation data or other diagnosis data entered by the user as part of a blind review and/or first review of the medical scan. The scan review data 810 can be used to generate diagnosis data 440 for the medical scan. Alternatively or in addition, the scan review data 810 can be compared to diagnosis data 440 already associated with the medical scan, for example, to automatically generate consensus data, to automatically generate performance score data 530 corresponding to the user, to automatically generate performance score data 630 corresponding to the medical scan analysis function used to generate the diagnosis data 440, and/or to automatically generate performance score data 720 corresponding to one or more interface features presented by the interactive interface 275 of the medical scan assisted review system 102.

In this fashion, the medical scan assisted review system 102 can be used in conjunction with other subsystems 101 of the medical scan processing system 100. For example, the medical scan assisted review system 102 can be utilized to generate medical codes 447 in conjunction with the use of the of the medical scan report labeling system 104, to generate abnormality annotation data 442 and/or final consensus annotation data in conjunction with the use of the medical scan annotator system 106, to confirm and/or edit diagnosis data 440 and to generate performance score data 630 based on expert review in conjunction with the use of the medical scan diagnosing system 108, and/or to generate performance score data 720 in conjunction with the user of the medical scan interface feature evaluator system 110.

Some or all of the displayed annotation data 820 presented in conjunction with the medical scan can be retrieved from the diagnosis data 440 of the medical scan database 342 and/or be generated automatically by the medical scan assisted review system 102 in response to selecting the medical scan for review, for example, by utilizing the medical scan image analysis system 112, the medical scan natural language analysis system 114, and/or medical scan diagnosing system 108, or by utilizing functions stored locally by the medical scan assisted review system 102. In some embodiments, the medical scan assisted review system automatically generates some or all of the displayed annotation data 820 in response to receiving a medical scan via the network 150 that was uploaded by the user or triaged from a different user or entity. In some embodiments, the medical scan assisted review system automatically generates some or all of the displayed annotation data 820 after the medical scan is initially displayed to the user in response to the user selecting a menu option or otherwise electing that the displayed annotation data 820 be generated automatically, and the displayed annotation data 820 can be displayed in conjunction with the medical scan once it is generated.

Features of the interactive interface presented to the user can include one or more interface features and can be automatically determined or selected by the medical scan assisted review system 102, for example, based on the performance score data 720 of interface features in the interface feature database 348 and/or generated by the medical scan interface feature evaluating system 110, based on the display parameter data 470 of the medical scan retrieved from the medical scan database and/or generated by the medical scan image analysis system 112, and/or based on user preferences corresponding to the user of the client device retrieved from the user database 344. The user can also elect to turn interface features on or off, show or hide one or more interface features from view, and/or switch between multiple interface feature modes at any time by selecting a menu option or based on other user input to the client device, for example, where the medical scan assisted review system can retrieve the features of the newly selected mode from the interface feature database 348 and/or where multiple interface version types are stored in the application data.

The interactive interface 275 can present a medical scan to a user by displaying medical scan image data 410. This can include displaying a single image slice 412 of the medical scan and/or displaying a selected number or automatically determined number of image slices 412 simultaneously in adjacent views. If the medical scan only includes a single image, the single image can be displayed. If multiple image slices are available, the interactive interface 275 can allow a user to scroll through ordered slice images of the medical scan, where the image slices are displayed one at a time sequentially in a forwards or backwards direction based on user input to move a scroll bar displayed by the interface, user input to arrows presented on a keyboard of the client device, user input to a scroll wheel on a mouse of the client device, or other user input indicating the user elects to navigate sequentially forwards or backwards through the slice images. The interactive interface can allow a user to jump to particular slices of the medical scan, for example, where a slice is selected via user input to the interactive interface based on a slice number, thumbnail image, a point selected on a scroll bar, or other indicator. The interactive user interface can also allow a user to zoom in on a selected region of a particular slice, display multiple slices at the same time, or otherwise navigate the medical scan data visually based on selecting menu options presented by the interactive user interface or based on other user input.

As described herein, "jumping" to an image slice 412 selected by the user or selected automatically by the medical scan assisted review system 102 can include immediately displaying the selected image slice 412 instead of the currently displayed image slice 412. In other embodiments, "jumping" to a selected image slice includes visually scrolling through previous image slices, for example, starting at the first image slice of the medical scan or currently displayed image slice of the medical scan, visually scrolling forward or backward to the selected image slice. This effect can emulate the use of a scroll bar to transition from the current scroll through slices and/or provide the user with context while jumping to the selected slice. Visually scrolling can include, for example, rapidly displaying, at a predetermined rate determined by the system or selected by the user, all of the intermediate image slices between the first or current slice and the selected slice, or a uniformly distributed proportion of intermediate slices between the first or current slice and the selected slice, in forward sequence or backwards sequence based on the slice number ordering. For example, intermediate slices can be rapidly displayed in forward sequence until the selected slice is reached, or, if a current slice corresponds to a slice higher number than the selected slice, intermediate slices can be rapidly displayed in backward order until the selected slice is reached. In some embodiments, the rate at which the intermediate slices are rapidly displayed is constant. In other embodiments, the rate at which intermediate slices are rapidly displayed is variable, for example, where the first intermediate slices, furthest away in the ordering from the selected slice, are displayed at a high rate, and where intermediate slices are automatically displayed at gradually lower rates as the currently displayed intermediate slice gets closer to the selected slice in the ordering. Displaying slices at a high rate can correspond to displaying each slice for a first time duration that is shorter than a second time duration corresponding to displaying slices at a low rate. In various embodiments, the user can instead manually scroll to a selected slice using a scroll bar or other similar interface feature, and intermediate slices will be rapidly displayed in sequence in a similar fashion.

The interactive interface 275 can automatically present the displayed annotation data 820 to indicate abnormalities identified in diagnosis data 440 of the medical scan by not only displaying text, but also by circling or surrounding the abnormality by a shape, facilitating automatically jumping to a selected slice that includes the abnormality, outlining the abnormality, highlighting the abnormality or otherwise indicating the abnormality in a contrasting and/or non-grayscale color, displaying an identified zoomed-in or cropped image slice that includes the abnormality, displaying the image based on an identified Hounsfield window selected to best display the abnormality, etc. Such means of indicating the abnormality can correspond to one or more interface features indicated in the display parameter data 470 and/or interface preference data 560. Each abnormality can be indicated based on abnormality annotation data 442 such as the abnormality location data 443, abnormality classification data 445, confidence score data 460, and/or other data included in the diagnosis data 440 or otherwise associated with the abnormality. If the diagnosis data 440 indicates that no abnormalities are present, the interactive interface can display text and/or a visual prompt indicating that no abnormalities were detected in the medical scan.

The identified abnormalities can be indicated automatically upon presenting the medical scan, for example, where a selected slice that includes the abnormality is initially presented with the abnormality circled in red. The user can indicate whether to display and/or hide the indicated abnormalities via a menu option or other user input to the interactive interface. For example, a user may elect to first view the medical scan normally without detected abnormalities indicated to allow blind, unbiased review and/or diagnosis of the medical scan, and can later elect to view one or more identified abnormalities after the blind, unbiased review. The identified abnormalities can be displayed via on each image slice of the medical scan that include the abnormalities, via one or more interface features, as a user elects to scroll through image slices, jump to a selected image slice, or view multiple slices simultaneously. Multiple identified abnormalities of the same medical scan can be indicated at the same time, for example, where multiple abnormalities are circled on a displayed image slice. Alternatively, multiple detected abnormalities can be displayed one at a time in sequence, and the user can indicate via a menu option or other user input to the interactive interface to progress to the next detected abnormality. Progressing to the next detected abnormality can include automatically jumping to a new slice that includes the next abnormality, circling or otherwise indicating a new abnormality in a new location on the same displayed image slice, changing the density window displayed based on a new density window indicated in the display parameter data of the next abnormality, and/or otherwise changing the view based on different display parameter data 470 associated with the next detected abnormality.

The displayed annotation data 820 can include classification data in the report data 830 of each abnormality, which can be displayed in conjunction with indicating each abnormality. For example, data describing size, volume, pre-post contract, doubling time, calcification, components, smoothness, texture, diagnosis data, one or more medical codes, a malignancy rating such as a Lung-RADS score, or other classifying data. The classification data can be based on abnormality classification data 445 for one or more abnormality classifier categories 444, and/or can be based on other abnormality annotation data 442. The classification data can be displayed according to one or more interface features indicated in the display parameter data 470 and/or interface preference data 560. For example, the classification data can be displayed as text or graphics which can be overlaid on a displayed image slice and included with visualization 825, displayed report data 830 such as text displayed in a text window adjacent to or on top of the displayed image slice, or otherwise displayed by the interactive interface.

Alternatively or in addition, some or all of the classification data is displayed via other visual means, for example, where quantitative data of one or more classification categories is displayed in accordance with a color heat map. For example, the detected abnormality can be indicated in accordance with a malignancy heat map, where different colors such as RGB values or other non-grayscale colors correspond to different malignancy scores, and where the abnormality is circled or surrounded by a shape, outlined, highlighted, or otherwise displayed in conjunction with the color corresponding to the malignancy score of the abnormality based on the malignancy heat map. In some embodiments, some or all of the abnormality classification data is displayed automatically in conjunction with indicating the abnormality. In other embodiments, some or all of the abnormality classification data is displayed in response to selecting a menu option, clicking on or hovering over a region of the interactive interface associated with the indicated abnormality, or otherwise electing to view the classification data via user input to the interactive interface.

The displayed annotation data 820 can include confidence data of each abnormality, which can be displayed in conjunction with indicating each abnormality. For example, a confidence score corresponding to a calculated probability that the detected abnormality exists and/or corresponding to a calculated probability that the detected abnormality is malignant can be displayed as numerical text, which can be overlaid on a displayed image slice, displayed in a text window adjacent to the displayed image slice, or otherwise displayed according to one or more interface features indicated in the display parameter data 470 and/or interface preference data 560.

The confidence data can correspond to confidence score data 460 and can be retrieved from the medical scan database, and/or can be indicated in the output of the medical scan analysis function used to automatically generate the displayed annotation data 820 and/or can be generated automatically based on a performance score data 530 or qualification data 540 associated with a user or medical entity from which the displayed annotation data 820 originated. The confidence data can also include one or more classifier confidence scores corresponding to at least one of the classifying categories, and the classifier confidence score data can be displayed in conjunction with the classifier data, for example, where a numerical score is displayed as text adjacent to the corresponding text for each classifier category. Alternatively or in addition, some or all of the confidence data is displayed via graphics or other visual means, for example, where confidence score data of one or more classification categories is displayed in accordance with a confidence heat map, where different colors such as RGB values or other non-grayscale colors correspond to different confidence scores, and where the abnormality is circled or surrounded by a shape, outlined, highlighted, or otherwise displayed in conjunction with the color corresponding to the confidence data of the abnormality based on the confidence heat map.

In some embodiments, a raw probability heat map corresponding to raw pixel probability data can be displayed. For example, the probability matrices generated by the medical scan image analysis system 112 that include a plurality of abnormality probabilities mapped to a plurality of pixel locations for each image slices of a medical scan can be received by the medical scan assisted review system 102. Every pixel, or uniformly distributed proportion of pixels, of one or more displayed image slices 412 can be indicated in accordance with the raw probability heat map, where different colors such as RGB values or other non-grayscale colors correspond to different raw abnormality probability scores. The density values corresponding to each pixel can be preserved in the display of each image slice 412 by determining a darkness or lightness of the pixel color based on each density value.

In embodiments where multiple heat maps are employed, for example, if a malignancy heat map is employed and a confidence score heat map is employed, the user can elect to switch to a different heat map view based on user input, and/or the same image slice can be displayed in multiple adjacent windows, where each window corresponds to a different heat map. The one or more heat maps can be displayed for each image slice in the medical scan as the user elects to scroll through images slices, jump to a selected image slice, or view multiple image slices simultaneously. If multiple windows are employed to display the same slice corresponding to different heat maps views, the user can use a single scroll bar or other single user input indicator to jump to a different image slice, and the multiple windows can simultaneously display the same new indicated image slice in accordance with their heat map view.

In some embodiments, the some or all of the confidence data is displayed automatically in conjunction with indicating the abnormality. In other embodiments, some or all of the confidence data is displayed in response to selecting a menu option, clicking on or hovering over a region of the interactive interface associated with the indicated abnormality, or otherwise electing to view the confidence data via user input to the interactive interface. In some embodiments, the user can select confidence score thresholds for the confidence data via a sliding bar or other user input, and only abnormality annotation data and/or categorized classification data with a corresponding confidence score that meets, exceeds, or otherwise compares favorably to the corresponding confidence score threshold set by the user will be displayed. For example, if the user sets a calcification confidence score threshold to 90%, and the confidence score corresponding to the calcification data of the classification data is 85%, the calcification data will be hidden and/or removed from display by the interactive interface. The user may later elect to change the calcification confidence score threshold to 80%, and the calcification data will be added to the display immediately and/or in response to later user input indicating the user elects to view classification data.

Upon presenting each abnormality to the user for review, the interactive interface 275 presented by the medical scan assisted review system can present a menu option or otherwise prompt the user to provide scan review data 810. The medical scan assisted review system 102 can automatically generate scan review data 810 in response to user input indicating the review of the displayed annotation data 820. The scan review data 810 can include a binary value indicating whether or not the annotation is correct based on user input indicating that the indicated abnormality is correct or incorrect, for example, where the user will indicate that the annotation is incorrect upon determining that the scan is normal, or determining the identified abnormality is not malignant. The scan review data 810 can also include a binary value indicating whether or not the abnormality location and/or each classification category is correct or incorrect. The scan review data 810 can also include edited classification data based on user input modifying data of one or more of the classification categories and/or edited location data based on user input modifying the location, for example, based on user input identifying the actual location of the abnormality by circling, drawing a shape around, outlining, clicking on, zooming in on, cropping, or highlighting a new point or region that includes the abnormality, and/or moving borders outlining the identified region to change the size and or shape of the region, by erasing or otherwise removing highlighted or otherwise indicated portions of the region, by highlighting additional portions adjacent to the region, by dragging a shape surrounding the abnormality to a new location, or otherwise indicating a new location by utilizing one or one or more interface features indicated in the display parameter data 470 and/or interface preference data 560.

Generating the scan review data 810 can further include modifying diagnosis data 440, removing an identified abnormality from the diagnosis data 440, and/or adding a new abnormality and its corresponding data to the diagnosis data 440. The scan review data 810 can further be used by the system to generate performance score data 530 corresponding to the user, to rank medical entities, to generate model accuracy data 631, to generate performance score data 720 corresponding to one or more interface features, to generate consensus data such as a final consensus annotation and/or generate other data as described in conjunction with the other subsystems 101 described herein. In other embodiments, another subsystem 101 can generate and/or modify some or all of this data immediately in response to determining the scan review data 810 was generated and/or at a later time based on the user feedback indicated in the scan review data 810.

In various embodiments, generating the scan review data 810 includes automatically generating and/or updating one or more confidence scores of the confidence data associated with the abnormality and/or one or more classification category confidence scores associated with the abnormality, and confidence score data 460 of one or more abnormalities of the medical scan can be updated in the medical scan database 342 accordingly. For example, when the user indicated that the abnormality is correctly identified, the confidence score can be changed to 100% based on the abnormality being confirmed by user. The confidence score can also be assigned to a different value based on performance score data 530 and/or qualification data 540 of user. The confidence score can increase slightly, for example, changing from 70% to 80% when the abnormality is confirmed by a novice user, and can increase more drastically, for example, changing from 70% to 99%, when the abnormality is confirmed by an expert user. In embodiments where the scan review data 810 corresponds to annotations entered for the first time, a confidence score can be automatically calculated based on the annotation and/or data in the user profile and mapped to the medical scan.

The confidence score for the edited abnormality data can also be assigned a confidence score of 100% based on determining the edited abnormality data of the scan review data 810, or assigned a new calculated confidence score based on a calculated discrepancy between the user edits and the identified confidence score, for example, where the confidence score is lowered from 70% to 66% if the discrepancy is small, or lowered from 70% to 30% if the discrepancy is high. For example, calculating the discrepancy can include calculating the Euclidian distance between a feature vector corresponding to the original abnormality data and the edited abnormality data, and the change in confidence score can be proportional or otherwise a function of the magnitude of the calculated discrepancy. The new confidence score for the edited diagnosis data can also be weighted based on the performance score data 530 or qualification data 540 of the user, for example, where the new confidence score is assigned a higher value when the user has a high performance score or qualification level and is assigned a lower value when the user has a low performance score or qualification level. Even if a discrepancy detected, the confidence score can still increase based on the user having a high score, where the magnitude of the increase in the confidence score is proportional to, or a function of, both the magnitude of the discrepancy and the performance score of the user. New confidence scores can be assigned to each classification category based on individual discrepancies in each category and/or based on categorized performance data 534 or categorized portions of qualification data 540. The discrepancies between the user edits of the scan review data 810 and the one or more identified abnormalities in the displayed annotation data 820, the feedback completion time, or other data can further be used to generate and/or update performance score data 530 of user.

In various embodiments, the medical scan assisted review system 102 can generate annotation data in the scan review data 810 based on user input for new abnormalities identified in the medical scan, and/or to provide other descriptive information regarding the medical scan indicated by the user in the scan review data. This annotation data can include DICOM formatted annotations of one or more identified abnormalities based on user input. The user can elect to enter a new annotation mode based on selecting a menu option, can automatically enter the new annotation mode once all identified abnormalities of the displayed annotation data 820 are presented, and/or can automatically enter new annotation mode by clicking on or otherwise selecting a point or region of the displayed image slice that does not include or is not within a threshold proximity to an already identified abnormality of the displayed annotation data 820. Alternatively, the user may be presented with a medical scan that needs annotations provided for the first time, and the interactive interface 275 will automatically enter the new annotation mode described in response to presenting the medical scan for annotation. The scan review data 810 can thus include annotation data of new annotations entered by the user in new annotation mode. Once generated, these new annotations created in the new annotation mode can be treated as a new entry to the identified abnormality data of the displayed annotation data 820, and can be formatted to match format of the rest of the identified abnormality data and can be displayed by the interactive interface 275 accordingly.

New annotation data of the scan review data 810 can be generated based on the location of the one or more additional abnormalities indicated by user input that can include circling, drawing a shape around, outlining, clicking on, highlighting, or otherwise identifying a point or region that includes the new abnormality, for example, based on the selected interface features. Classification data of the new annotation data can be automatically generated by the medical scan assisted review system 102 by applying an abnormality classifying function to the identified region of the image slice or an identified region of a plurality of image slices, where the abnormality classifying function is included in the medical scan analysis function database 346 and/or corresponds to a medical scan image analysis function generated by the medical scan image analysis system 112. This automatically generated classification data can be included in the displayed annotation data and/or can be otherwise presented to the user for review, and scan review data 810 corresponding to confirmation and/or edits of the automatically generated classification data can be generated based on user input in the same fashion as other review of displayed annotation data. Alternatively, all of the classification data for the new annotation data can be generated in the scan review data based on user input describing and/or classifying the newly identified abnormality. For example, the user can interact with drop down menus, check boxes, and/or enter text directly via voice and/or keyboard input to enter the classification data. The user can be prompted to answer questions about the abnormality or the scan in its entirety. This newly entered classification data can include abnormality classification data 445 for some or all of the abnormality classifier categories 444 and/or abnormality pattern categories 446 described herein. In various embodiments, new annotation data can be generated in accordance with some or all interface features presented in accordance with FIGS. 10C-10V.

In various embodiments, the new abnormality can be identified by the user on a single image slice, corresponding to the single image slice being viewed by the user. At least one adjacent image slice on either side can be identified automatically to include the abnormality, for example, based on processing the identified abnormality or the identified two-dimensional region to detect the abnormality in adjacent slices based a medical scan similarity analysis function such as medical scan similarity analysis function or other function based on the identified region in the image slice.

In various embodiments, the user can indicate when they are finished identifying new abnormalities by indicating that no further abnormalities are present via a menu option. The user can perform this step without identifying any new abnormalities, for example, in response to determining that the scan is normal and that no abnormalities are present, or determining that the abnormalities already identified by the medical scan assisted review system 102 in the displayed annotation data 820 are sufficient.

In some embodiments, the new abnormalities are entered by the user based on a blind review of the medical scan. For example, the medical scan assisted review system 102 can hide the identified abnormalities of the displayed annotation data 820 or otherwise allow the user to blindly identify abnormalities in the scan without displaying annotation data. Thus, annotation data for these abnormalities are generated in the scan review data 810 accordingly based on user input identifying the abnormalities blindly. Annotation data of the scan review data 810 can then be compared to abnormality annotation data of the displayed annotation data 820 or other annotation data generated by a different source, for example, abnormality annotation data 442 assigned a truth flag 461. This comparison can be used to generate the scan review data 810 and/or the confidence data, generate performance data for the user, to rank medical entities, to generate model accuracy data, to generate interface evaluation data, to generate consensus data, and/or generate other data as described in conjunction with the other subsystems described herein. After receiving the user's annotation data, the interactive interface can display the hidden abnormality data normally and/or can visually indicate differences between the abnormality indicated by the scan review data 810 and indicated in the displayed annotation data 820. For example, the interactive interface can display the user identified abnormality data indicated by scan review data 810 in one color, and can display identified abnormalities of the displayed annotation data 820 generated by the different source in another color, can indicate regions of the user identified abnormalities that are or aren't overlapping regions of the identified abnormalities of the displayed annotation data 820, can indicate abnormalities of the displayed annotation data 820 that the user did not identify, can indicate abnormalities annotated by the user that are not included in the displayed annotation data 820, or otherwise visually indicate automatically detected differences between the scan review data 810 and the displayed annotation data 820. Such means can be used to visually compare more than two sets of annotations received from more than two sets of sources, for example, in conjunction with annotations of a scan received from multiple users of the medical scan annotator system 106 presented to an expert for final review.

A set of similar medical scans and/or set of full or cropped image slices with similar abnormalities can be determined automatically, or in response to the user electing to view similar scans via user input, for some or all identified abnormalities in the scan review data 810 and/or the displayed annotation data 820, for example, by retrieving the similar scan data 480 of the medical scan from the medical scan data and/or utilizing the medical scan similarity analysis function or one or more portions of the similar scan identification step of the medical scan image analysis system 112. This set of similar medical scans and/or set of full or cropped image slices can be presented to the user via the interactive interface to aid the user in reviewing, confirming, populating, and/or editing the abnormality data, for example, based on similar scan display parameter data 483 or display parameter data 470 associated with the similar scans. The identified set of similar medical scans and/or set of full or cropped image slices for each abnormality can be further filtered to generate a smaller set of similar medical scans and/or set of full or cropped image slices and/or to automatically select a single medical scan and/or full or cropped image slice. The set can be automatically filtered based on the medical scan similarity analysis function, based on the similar scan filter data 485 associated with the similar scans, and/or can be automatically filtered based on other factors such by determining scans in the subset with a similar classification and/or location, scans with a high longitudinal quality score 434, determining scans corresponding to patients with a similar patient history and/or risk factors, ranking the identified set based on similarity score, or other criteria. This filtering criteria can be determined automatically, can be selected by the user via the interactive interface, and/or user preference data that includes the filter criteria can be retrieved from the user database such as similar scan filter data 485.

One or more adjacent windows can be presented that each display one or more image slices of the full or filtered set of similar medical scans. Abnormality data for some or all of set of similar medical scans and/or set of full or cropped image slices can be automatically generated and/or retrieved from a database, and can be presented in conjunction with the display of the similar medical scans, for where example, where the abnormality is circled, highlighted or otherwise indicated as discussed previously, and/or the classification data is presented by the interactive interface as discussed previously. In various embodiments, only abnormalities of the similar scans that are identified as similar abnormalities to one or more abnormalities of the medical scan, for example, based on the similar scan abnormality data 484, will be identified and/or displayed by the medical scan assisted review system 102. A single adjacent window can be designated for displaying similar scans, and the user can elect to switch between different similar scans based on user input. In various embodiments, the similar scans will be displayed to the user one at a time based on an ordering designated in the similar scan filtering data 485, and the user can elect to switch to the next similar scan in order when they have completed reviewing the current scan.

The user can elect to confirm and/or remove similar scans from the set based on determining whether or not each similar scan is an appropriate match, and this input can be indicated in similarity review data of the scan review data 810. The similar scan data 480 of the medical scan and/or a similarity score corresponding to the pair that includes the medical scan and similar scan can be modified based on the similarity review data, for example, where the similar scan is removed from the similar scan data 480 in response to user input and/or where a similarity score decreases based on user input indicating that the similar scan is an inappropriate match. This can also be used to generate performance score data 630 for the medical scan similarity analysis function, where the medical scan similarity analysis function receives a favorable score in response to the user confirming the match and receives an unfavorable score in response to the user indicating the match is not appropriate.

In various embodiments, a first window displaying an image slice 412 of the medical scan and an adjacent second window displaying an image slice of a similar scan will display image slices 412 corresponding to the same image slice number in the sequence, for example, where the image slice 10 out of 30 is displayed for the medical scan in the first window, and image slice 10 out of 30 is displayed for the second medical scan in the second window. In various embodiments, the displayed slice of the similar scan can be selected by automatically determining the appropriate anatomical region corresponding to the currently displayed slice of the current scan. For example, the medical scan assisted review system can automatically select the appropriate corresponding image slice in the previous scan based on the similar scan display parameter data 483, by determining which image slice of the previous scan compares most favorably to the currently displayed image slice of the current scan based on performing a medical scan similarity analysis function on the image slices as described herein, by determining the outline of an anatomical region of the slice and determining a slice in the previous scan that most closely matches the anatomical region borders, and/or by another visual comparison. In such embodiments, the user can use a single scroll bar or other single user input indication to jump to a different image slice, and the multiple windows can simultaneously display the same numbered image slice or can scroll or jump by the same number of slices if different slice numbers are initially displayed. In some embodiments, three or more adjacent windows corresponding to the medical scan and two or more similar scans are displayed, and can all be controlled with the single scroll bar in a similar fashion.

In other embodiments, the selected slice of the similar medical scan in the second window is a single or subset of slice images identified in the set, is automatically selected based on identifying a slice image of the similar scan that includes a most similar view of the abnormality as the currently displayed slice for the current scan. For example, slice 12 of the medical image includes a view of the abnormality that is most similar to slice 31 of the similar medical image, and slice 31 will automatically be selected for display in conjunction with the user selecting to view slice 12. The user can then switch to view slice 13 of the medical image that includes a different view of the abnormality that is most similar to slice 35 of the similar medical image, and slice 35 will automatically be selected for display in conjunction with the user scrolling or jumping from slice 12 to slice 13 of the medical image. In other embodiments, the user can scroll or otherwise navigate through slices for the medical scan and one or more similar medical scans separately.

In various embodiments, longitudinal data, such as one or more additional scans of longitudinal data 433 of the medical scan or of similar scans, can be displayed in conjunction with the medical scan automatically, or in response to the user electing to view longitudinal data via user input. For example, the medical scan assisted review system can retrieve a previous scan or a future scan for the patient from a patient database or from the medical scan database automatically or in response to the user electing to view past patient data. One or more previous scans can be displayed in one or more corresponding windows adjacent to the current medical scan. For example, the user can select a past scan from the longitudinal data for display. Alternatively or in addition, the user can elect longitudinal parameters such as amount of time elapsed, scan type, electing to select the most recent and/or least recent scan, electing to select a future scan, electing to select a scan at a date closest to the scan, or other criteria, and the medical scan assisted review system can automatically select a previous scan that compares most favorably to the longitudinal parameters. The selected additional scan can be displayed in an adjacent window alongside the current medical scan. In some embodiments, multiple additional scans will be selected and can be displayed in multiple adjacent windows.

In various embodiments, a first window displaying an image slice 412 of the medical scan and an adjacent second window displaying an image slice of a selected additional scan will display image slices 412 determined to corresponding with the currently displayed slice 412 of the medical scan. As described with respect to selecting a slice of a selected similar medical scan for display, this can be achieved based on selecting the image slice with a matching slice number, based on automatically determining the image slice that most closely matches the anatomical region corresponding to the currently displayed slice of the current scan, and/or based on determining the slice in the previous scan with the most similar view of the abnormality as the currently displayed slice. The user can use a single scroll bar or other single user input indication to jump to a different image slice, and the multiple windows can simultaneously display the same numbered image slice, or can scroll or jump by the same number of slices if different slice numbers are initially displayed. In some embodiments, three or more adjacent windows corresponding to the medical scan and two or more additional scans are displayed, and can all be controlled with the single scroll bar in a similar fashion.

The medical scan assisted review system 102 can automatically detect previous states of the identified abnormalities based on the abnormality data, such as the abnormality location data. The detected previous states of the identified abnormality can be circled, highlighted, or otherwise indicated in their corresponding window. The medical scan assisted review system 102 can retrieve classification data for the previous state of the abnormality by retrieving abnormality annotation data 442 of the similar abnormality mapped to the previous scan from the medical scan database 342. This data may not be assigned to the previous scan, and the medical scan assisted review system can automatically determine classification or other diagnosis data for the previous medical scan by utilizing the medical scan image analysis system as discussed. Alternatively or in addition, some or all of the abnormality classification data 445 or other diagnosis data 440 for the previous scan can be assigned values determined based on the abnormality classification data or other diagnosis data determined for the current scan. Such abnormality classification data 445 or other diagnosis data 440 determined for the previous scan can be mapped to the previous scan, and or mapped to the longitudinal data 433, in the database and/or transmitted to a responsible entity via the network.

The medical assisted review system can automatically generate state change data such as a change in size, volume, malignancy, or other changes to various classifiers of the abnormality. This can be achieved by automatically comparing image data of one or more previous scans and the current scan and/or by comparing abnormality data of the previous scan to abnormality data of the current scan. In some embodiments, such metrics can be calculated by utilizing the medical scan similarity analysis function, for example, where the output of the medical scan similarity analysis function such as the similarity score indicates distance, error, or other measured discrepancy in one or more abnormality classifier categories 444 and/or abnormality pattern categories 446. This calculated distance, error, or other measured discrepancy in each category can be used to quantify state change data, indicate a new classifier in one or more categories, to determine if a certain category has become more or less severe, or otherwise determine how the abnormality has changed over time. In various embodiments, this data can be displayed in one window, for example, where an increase in abnormality size is indicated by overlaying or highlighting an outline of the current abnormality over the corresponding image slice of the previous abnormality, or vice versa. In various embodiments where several past scans are available, such state change data can be determined over time, and statistical data showing growth rate changes over time or malignancy changes over time can be generated, for example, indicating if a growth rate is lessening or worsening over time. Image slices corresponding to multiple past scans can be displayed in sequence, for example, where a first scroll bar allows a user to scroll between image slice numbers, and a second scroll bar allows a user to scroll between the same image slice over time. In various embodiments the abnormality data, heat map data, or other interface features will be displayed in conjunction with the image slices of the past image data.

In various embodiments, longitudinal data 433 can also be retrieved for identified similar medical scans. This can include one or more previous medical scans taken before the identified similar medical scans and/or one or more future medical scans taken after the identified similar medical scan. The previous and/or future scans can be displayed in adjacent windows for display, for example with automatic matching slice selection and/or simultaneous scrolling as previously described. In various embodiments, some or all of the previous and/or future scans can be the same type or different type of scan, for example where the current scan and identified similar scan is an x-ray, and the future scan of the identified scan is an MM. This can allow a user to view richer data for a similar type of abnormality to aid in generating and/or editing the diagnosis data. In various embodiments, for example, where the longitudinal data includes biopsy results or other diagnosis data, the medical scan can automatically display these results in conjunction with the similar medical scans. In various embodiments, these results can be used by the user to generate, confirm, and/or review the diagnosis data for the current medical scan. In various embodiments, the medical scan assisted review system 102 or another subsystem 101 can automatically generate some or all of the scan review data 810 and/or diagnosis data 440 for the current medical scan based on the biopsy data and/or diagnosis data corresponding to automatically retrieved future medical scans that correspond to the automatically identified the similar medical scans. This can also be used to automatically generate or adjust confidence score data 460 with respect to the diagnosis data 440 of the medical scan, for example, where a confidence score previously generated increases in response to determining that diagnosis data 440 of a future medical scan of the identified similar scan matches or otherwise compares favorably to the previously generated diagnosis data 440, and where a confidence score previously generated decreases in response to determining that diagnosis data 440 of a future medical scan of the identified similar scan matches or otherwise compares unfavorably to the previously generated diagnosis data 440.

The displayed annotation data 820 can include report data 830 corresponding to each abnormality, or the entire scan, which can be automatically generated and/or retrieved for display to the user in conjunction with each abnormality, allowing the user to confirm and/or edit the report data 830. The report data 830 can include some or all of natural language text data 448 and/or report data 449 of the medical scan. Generating the report data 830 can include automatically generating text describing each abnormality based on location data and/or classifying data of the abnormality such as abnormality annotation data 442, for example, by utilizing a medical scan report generator function or other generator function trained on a training set of abnormality data or other diagnosis data and corresponding medical reports, annotations, or other natural language data or text describing the medical scan. Alternatively, some or all of the report data 830 can correspond to annotations and/or a report written by another user as natural language text, for example retrieved from the medical scan database 342. The report data 830 can be generated and/or retrieved for display by the medical scan assisted review system 102, in conjunction with initially displaying each abnormality and/or in response to generating the scan review data 810 for each abnormality based on user feedback. When report data 830 is presented to the user for review, the user can elect to accept the report data 830 as it stands based on user input to the interactive interface 275. The user can also elect to revise some or all of the report data 830, for example, where the natural language text of the report is presented in a text editor window and the user can type new text and/or delete existing text. The revisions entered by the user can be included in the scan review data 810, and can be used to modify diagnosis data 440 by extracting relevant terms from the revised natural language text, for example, by utilizing the medical scan natural language analysis function. Alternatively, when scan review data 810 is generated based on other user input indicating edits to the displayed annotation data, for example, if a user highlights a region with a new abnormality and/or modifies classifier data of an existing category based on a menu option, modified natural text data can be automatically generated in response to the scan review data 810 indicating that the displayed annotation data needs to be edited. Thus, original natural text data displayed in the report data 830, for example, in conjunction with initially indicating an abnormality, can be automatically changed to the modified natural language text in response to generating the scan review data 810, where the displayed report data 830 automatically reflects the modified natural language text.

The medical scan assisted review system 102 can generate a final report in response to the user finalizing edits of the report data 830 and/or confirming the report data 830. Report formatting data, for example, fixed criteria of the medical scan assisted review system 102 in generating reports, criteria stored in report formatting data 570 of user database 344 and/or criteria learned based on a training set of formatted reports can be used to determine font, text size, header data, bulleting or numbering type, margins, file type or other formatting to list natural language text data corresponding to each abnormality to generate the final report. Some or all of the report data 830 such as a final formatted report, the raw natural language text data, or one or more full or cropped images slices included in the report data 830 can be displayed to the user via the interactive interface 275, mapped to the medical scan in the medical scan database as report data 449, and/or transmitted to a responsible entity based on triaging data.

The report data 830 also include one or more full or cropped image slices of medical scans, such as full or cropped images for some or all of the identified abnormalities of the displayed annotation data 820, full or cropped images of the similar abnormalities selected from the identified full or filtered set of similar scans, and/or full or cropped images selected from one or more additional scans. For example, including the full medical scan or full similar scans in the report may not be feasible, so one or more full or cropped image slices of the medical scan or similar scans can be included as embedded images in the report. Full and/or cropped image slices of medical scan, identified additional scans, and/or identified similar scans can be automatically selected based on the corresponding abnormality location data 443, display parameter data 470, similar scan display parameter data 483, scan review data 810 report formatting data 570, and/or other criteria. The interactive interface can also prompt the user to select one or more image slices to be included from the medical scan, identified additional scans, and/or identified similar scans, and scan review data 810 can indicate the selected slices to be included in the report. The medical scan assisted review system 102 can automatically select at least one slice or region of the user selected slices of scan review data 810 based on abnormality location data 443, display parameter data 470, similar scan display parameter data 483, report formatting data 570, and/or other criteria. Alternatively, the user can also indicate preferred cropped regions for the report via user input, for example, by zooming in and/or selecting a cropped region of each image slice as discussed previously, and the scan review data 810 can indicate selected cropped regions of each selected slice. Some or all of the cropped or full user selected image slices in the scan review data 810 can be used by the medical scan assisted review system 102 or another subsystem 101 to automatically generate and/or modify display parameter data 470 and/or similar scan display parameter data 483 for some or all of the corresponding additional and/or similar medical scans and/or to automatically determine and/or modify report formatting data 570 of user.

In some embodiments, the density data is lost when a report including a full or cropped slice image is generated, for example, when only grayscale image data is preserved. In such cases, generating each full or cropped image for the report can include automatically determining an optimal density window for each selected image slice, for example, based on the current density window used to display the image slice, based on display parameter data 470 and/or 483, based on report formatting data 570, by automatically determining a density window that provides optimal contrast the abnormality in the image, by automatically determining a density window that provides optimal context for the abnormality in the image, or otherwise optimally presents the abnormality in the selected image. The selected density window can be used to convert each two-dimensional cropped or full image slice to a grayscale image in the report.

In various embodiments, one or more abnormalities can be visually indicated some or all of the images included in the report data, where an abnormality is circled, highlighted, or otherwise presented, for example, by utilizing one or more interface features or other visual features discussed in conjunction with the displayed annotation data 820. In some embodiments, a heat map overlay is included in one or more images included in the report data 830. The presentation of abnormality data can be based on interface features or other data indicated in the display parameter data 470, based on interface features or other data indicated in report formatting data 570, and/or based on interface features or other data corresponding to a current view displayed by the user interface. For example, in various embodiments, the user can select an option presented by the interactive interface 275 to take one or more full or cropped screenshot of the current view of one or more image slices of additional and/or similar medical scans, presented with one or more interface features that indicate one or more abnormalities, and the screenshot can be included in the report data 830.

In addition to including full or cropped image slices of similar abnormalities, identifying information can also be included in the report data 830 for each similar scan in the report. The identifying information in the report data 830 can include some or all corresponding similar scan data 480, a medical scan identifier for similar scans, corresponding patient identifier, and/or hyperlink to access each similar medical scan and/or patient data of each similar medical scan. Similar identifying information can also be included for some or all additional medical scans included in the report data 830. In various embodiments, a second user can access the report on their client device can click on or otherwise select a presented image of a similar abnormality, the medical scan identifier, patient identifier, and/or the hyperlink of an identified similar medical scan and/or identified additional medical scan. The corresponding full medical scan image data 410, corresponding diagnosis data 440, patient history data 430, or other data of the corresponding medical scan or 402 will automatically be retrieved from the medical scan database 342 or another storage system in response to this user input. This information can be displayed to the second user via an interactive interface displayed by a display device corresponding to their client device 120. In various embodiments, the second user can interact with a displayed medical scan and/or 402 based on interface features of interface preference data 560 of the second user and/or display parameter data 470 of the corresponding medical scan and/or 402, for example, by interacting with interactive interface 275 presented on their client device 120 in conjunction with one or more features of the medical scan assisted review system 102.

In an example embodiment, the medical scan assisted review system 102 can be used to review a medical scan selected by the user from the database 342, automatically selected by a subsystem for transmission to user, or uploaded to the medical scan processing system 100 by user. Diagnosis data 440 can be retrieved from the database 342 and/or can be automatically generated, for example, by utilizing a medical scan image analysis function selected by the medical scan diagnosing system 108. In response to retrieving and/or generating the diagnosis data 440, the medical scan can automatically be presented to the user by utilizing the medical scan assisted review system 102, allowing a user to review the diagnosis data 440 presented as displayed annotation data 820. The scan review data 810 can be generated automatically based on feedback entered by the user as described herein, and report data 830 can be generated automatically based on confirmations and/or edits indicated in the scan review data 810. The report data 830 and/or other modified information indicated by the scan review data 810 can be mapped to the diagnosis data 440 and/or report data 830. The usage data 520 and/or performance score data for the user, performance score data 630 for the medical scan image analysis function, and/or performance score data for one or more interface features utilized by the medical scan assisted review system 102 can be generated and/or updated accordingly.

In some embodiments, this process or a similar process is executed by the medical scan processing system in response to receiving a medical scan from a client device 120, for example, immediately after a medical scan is taken for a patient, the scan can automatically be uploaded to the medical scan processing system 100 for processing to generate the diagnosis data 440, and will be immediately presented to the user of client device 120, or to another user selected by a subsystem 101, for example, based on comparing scan classifier data 420 to performance score data 530 and/or qualification data 540.

FIGS. 8B-8S present an example embodiment of the interactive interface 275 presented in conjunction with the medical scan assisted review system 102, utilized as a lung screening assessment system. In various embodiments, the lung screening assessment system is operable to receive a chest computed tomography (CT) scan that includes a plurality of cross sectional images. Nodule classification data of the chest CT scan is generated by utilizing a computer vision model that is trained on a plurality of training chest CT scans to identify a nodule in the plurality of cross sectional images and determine an assessment score. A lung screening report that includes the assessment score of the nodule classification data is generated for display on a display device associated with a user of the lung screening assessment system. Such a lung screening assessment system can utilize some or all features of the medical scan assisted review system 102 and/or features of other subsystems as described herein.

In FIG. 8B, the interactive interface 275 presents a listed queue of scans for review. The insights column indicates how many nodules were automatically detected by the medical scan assisted review system. The user can select to view a particular lung screening scan by selecting the corresponding row.

Figure 8C:
FIGS. 8B-8S are graphical illustrations of an example interactive interface displayed on a client device in conjunction with various embodiments.
FIGS. 8T-8Y are graphical illustrations of an example interactive interface displayed on a client device in conjunction with various embodiments.

In FIG. 8C, the interactive interface 275 presents a particular scan in response to the user selecting the corresponding row in conjunction with the view presented in FIG. 8B. The user can navigate through slice images, select regions of interest (ROIs), view annotations, and/or view insights generated automatically by the medical scan assisted review system 102. Here, the interactive interface 275 prompts the user to review a finding, automatically identified by the medical scan assisted review system 102.

Figure 8D:
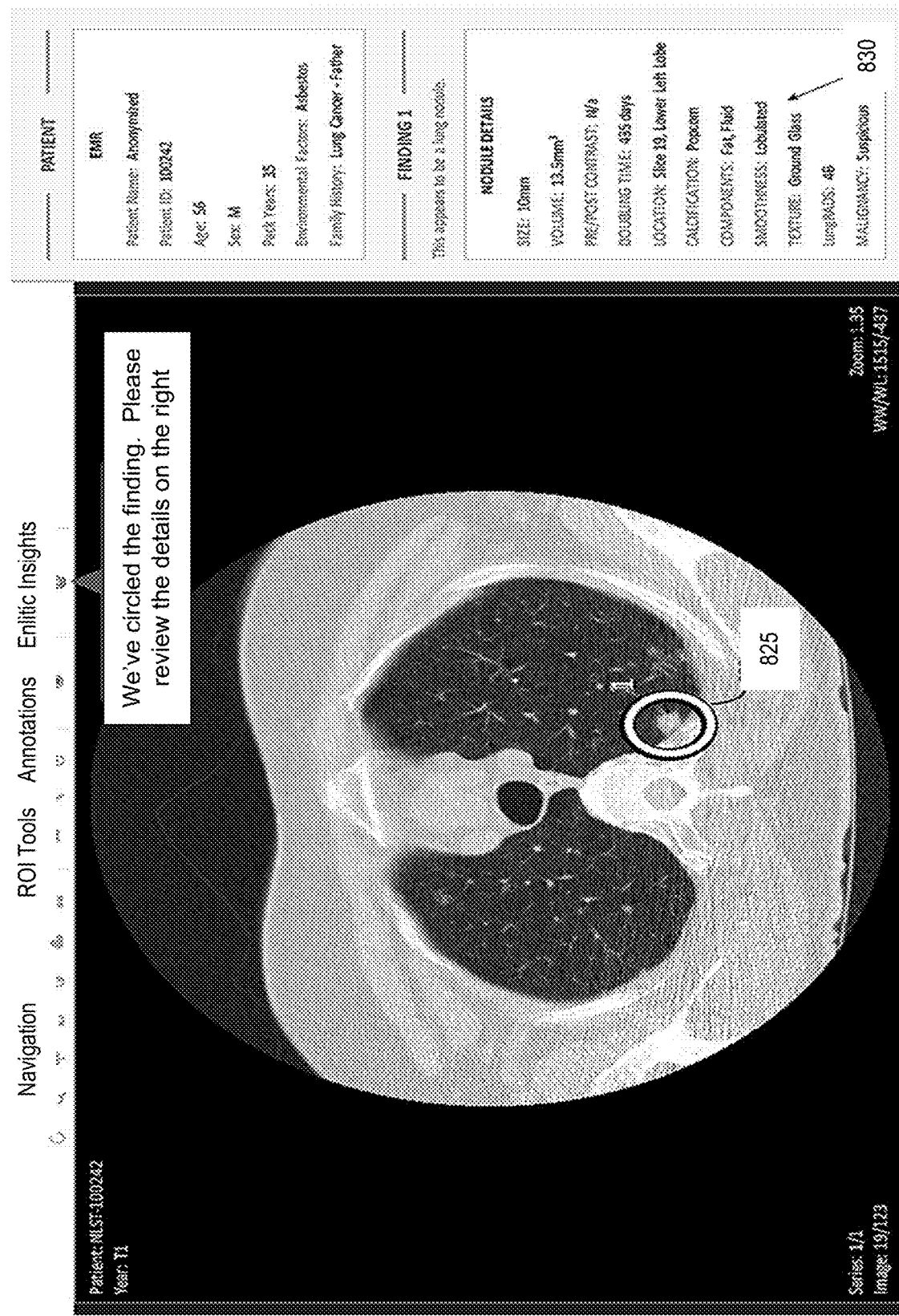

In FIG. 8D, the interactive interface 275 automatically jumps to slice 19 in response to user input electing to view the automatically detected finding, and interactive interface 275 automatically presents the visualization 825 by circling the detected nodule and by listing the nodule details.

Figure 8E:
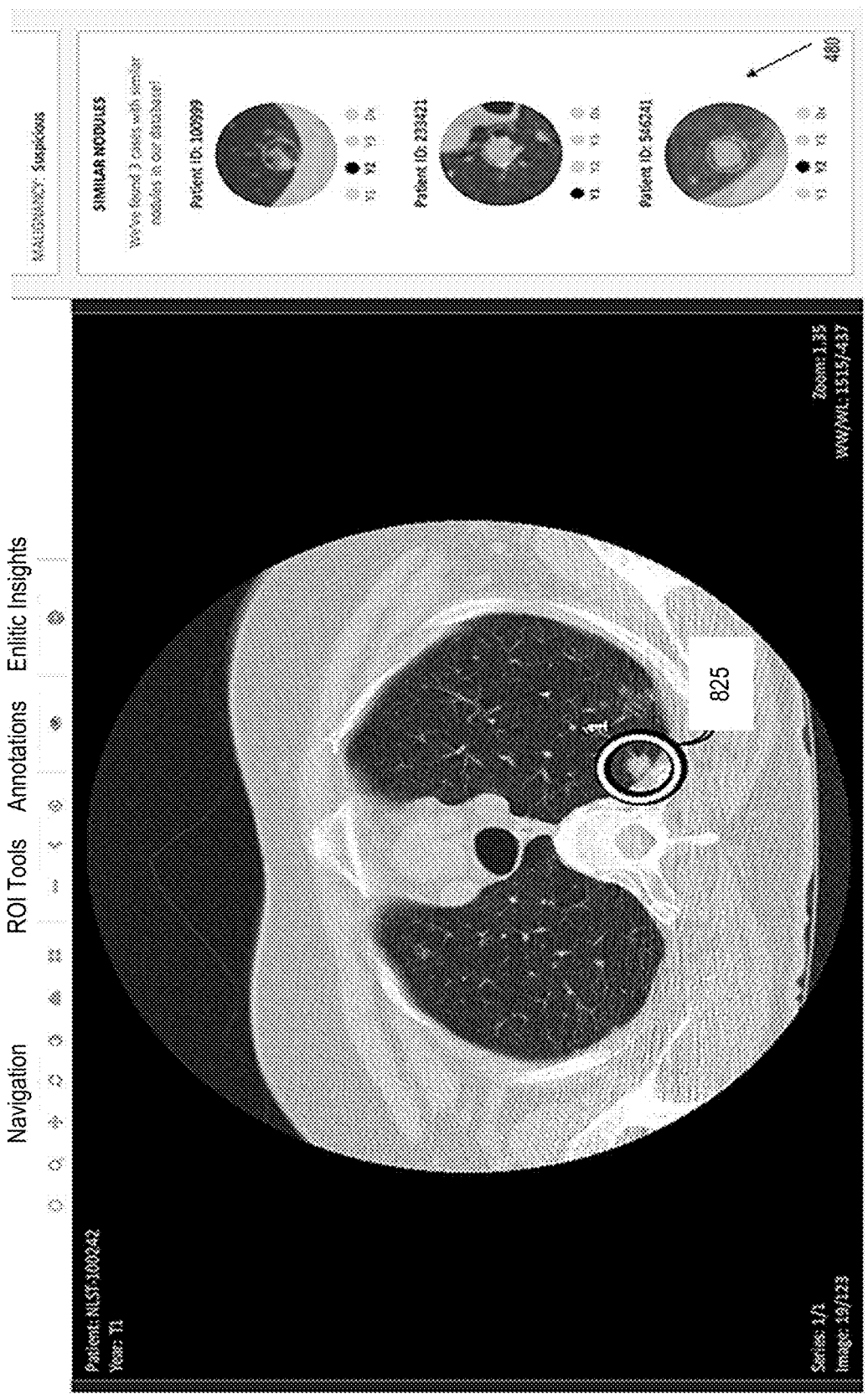
Figure 8F:
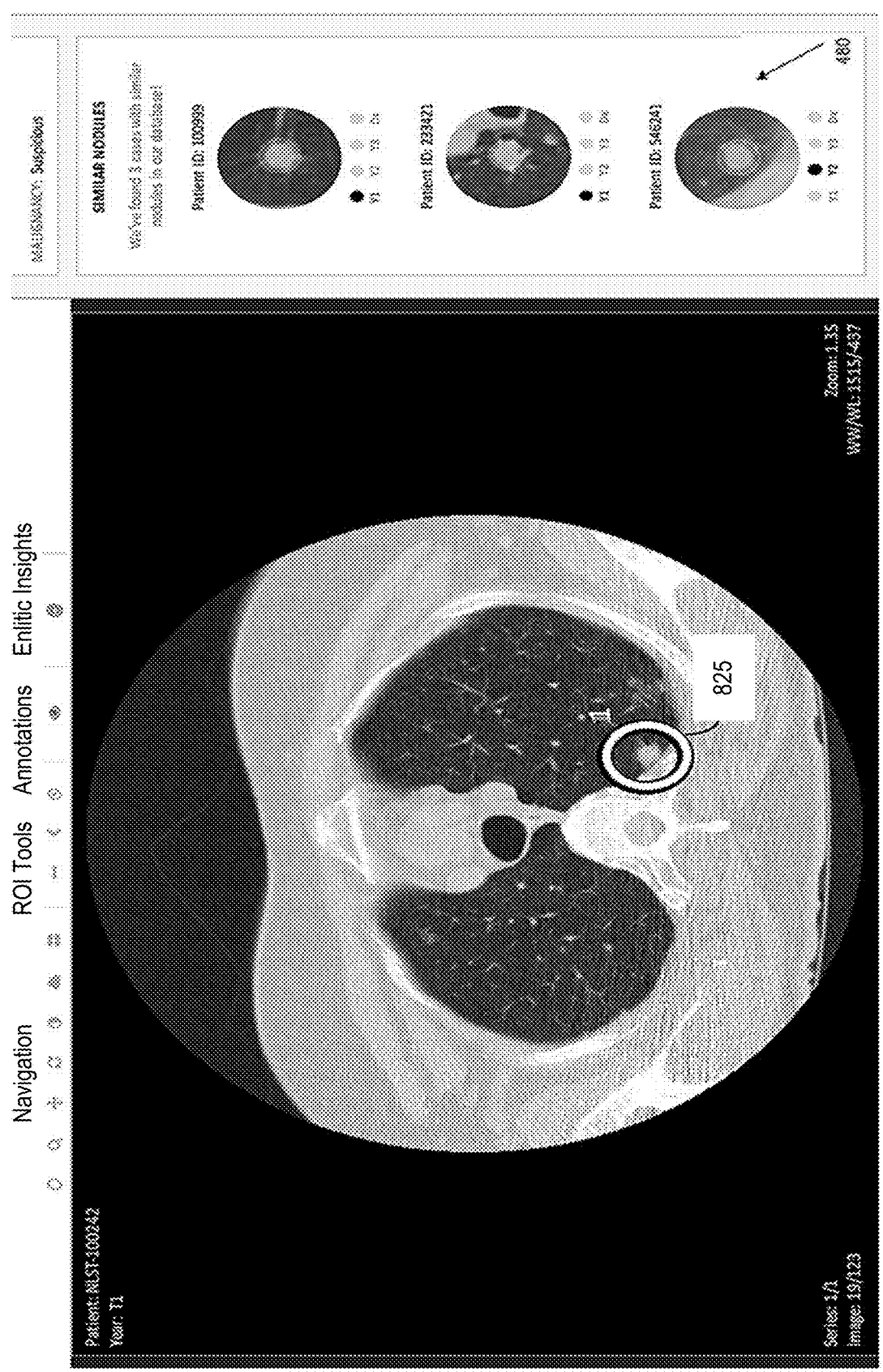
Figure 8G:
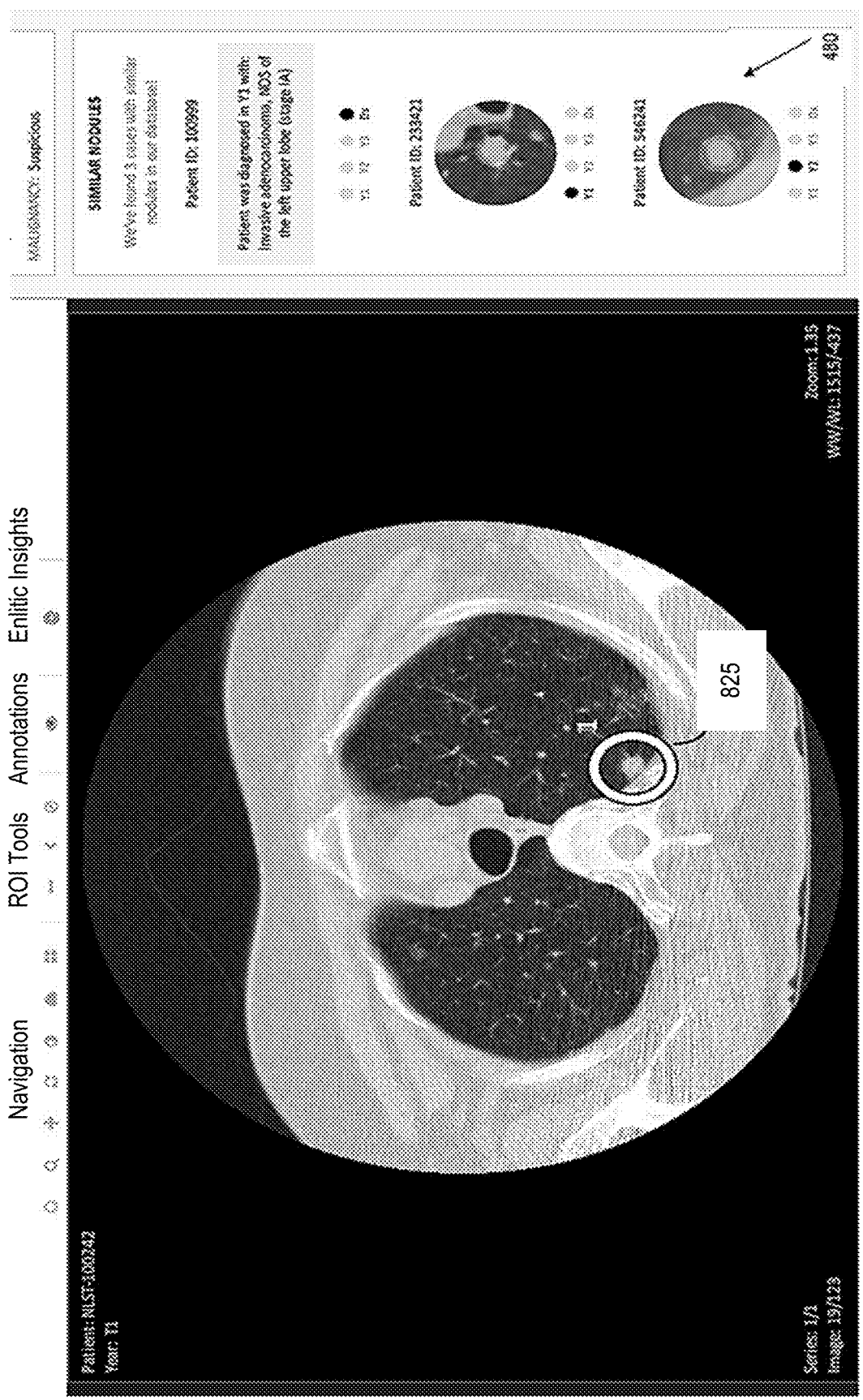

In FIG. 8E, the interactive interface 275 presents cropped slice images of medical scans corresponding to three similar nodules. Each of the three similar nodules have corresponding longitudinal data, and are automatically selected based on having at least three years of data available, along with final biopsy results. The user can change the displayed view of any of the similar nodules by selecting from Y1 (year 1 scan), Y2 (year 2 scan), Y3 (year 3 scan), or Dx (official biopsy results). In FIG. 8F, the user elects to change the view of the cropped image slice that includes the similar nodule corresponding to patient ID 100999 from Y2 to Y1, and the interactive interface 275 automatically presents the Y1 cropped image that includes the nodule in response. In FIG. 8G, the user elects to view the final biopsy results, and final biopsy results corresponding to the similar nodule are displayed by the interactive interface accordingly.

Figure 8H:
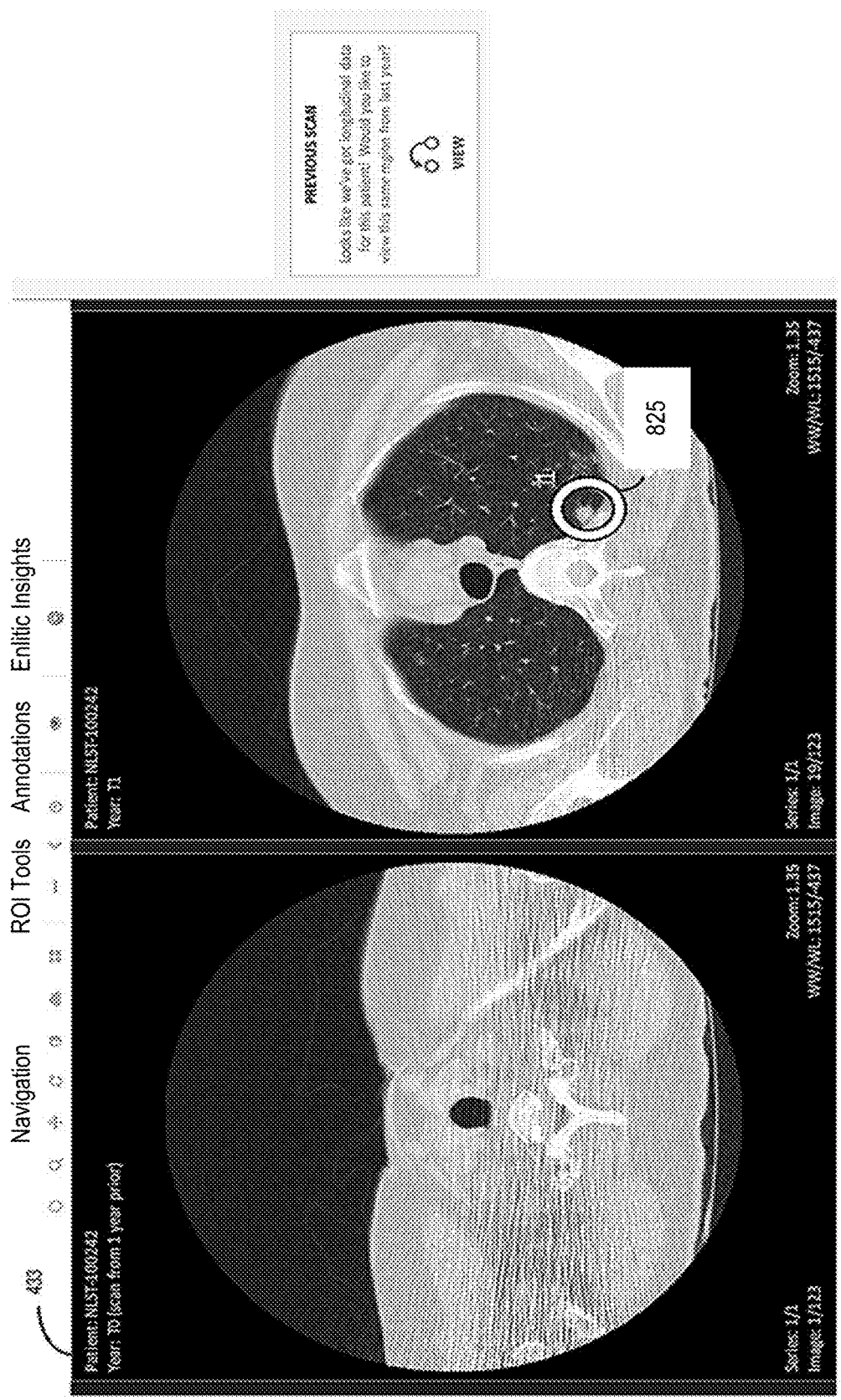
Figure 8I:
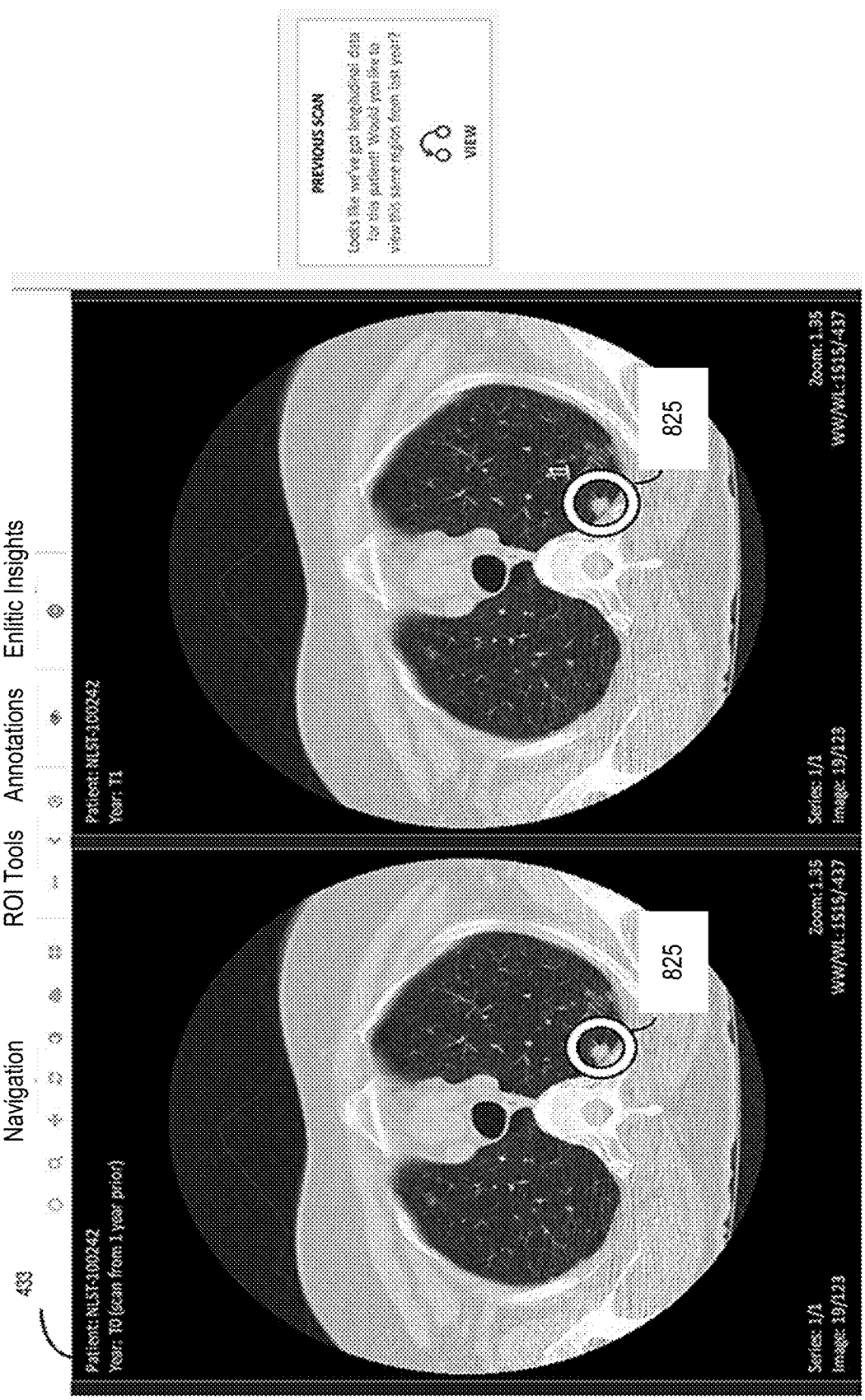

In FIG. 8H, the interactive interface 275 presents an option to view a previous scan for the patient, and the interactive interface 275 automatically displays the previous scan in an adjacent window. The user can elect to scroll through the previous scan independently. In FIG. 8I, the interactive interface 275 automatically displays a corresponding image slice by jumping to slice 19, and circles the previous state of the identified nodule in the previous scan. The user can scroll or otherwise navigate through both scans simultaneously as discussed herein.

Figure 8J:
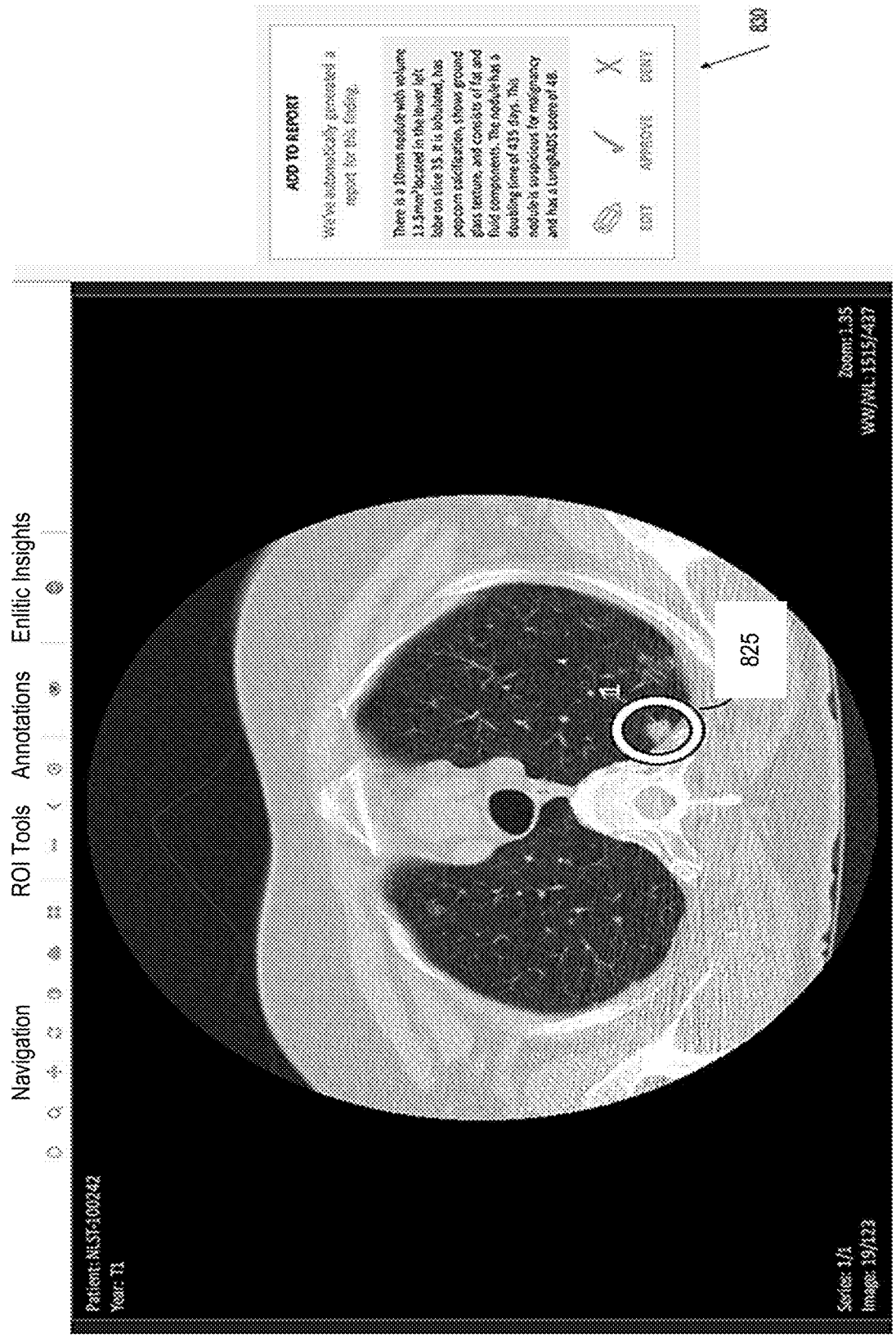
Figure 8K:
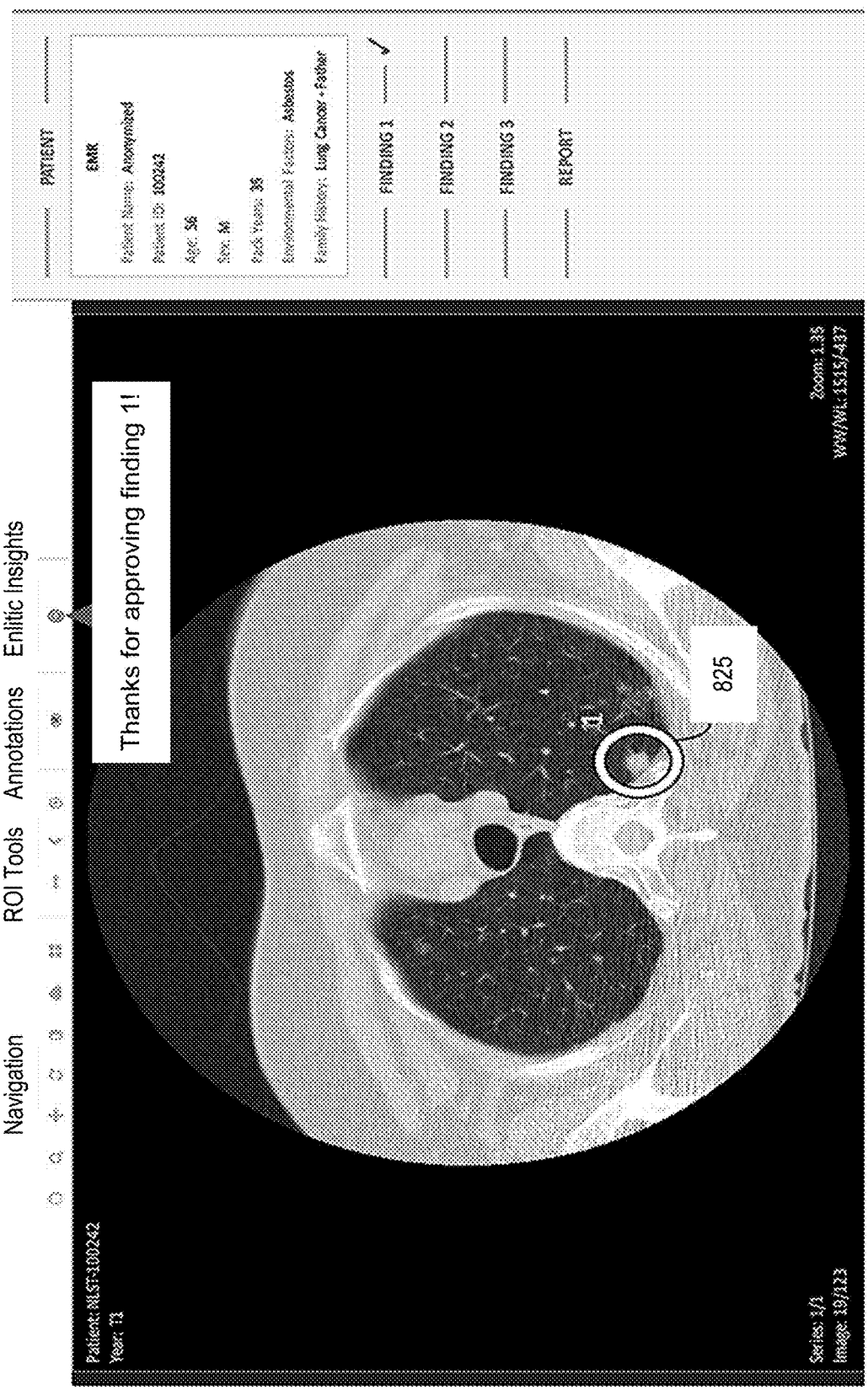
Figure 8L:
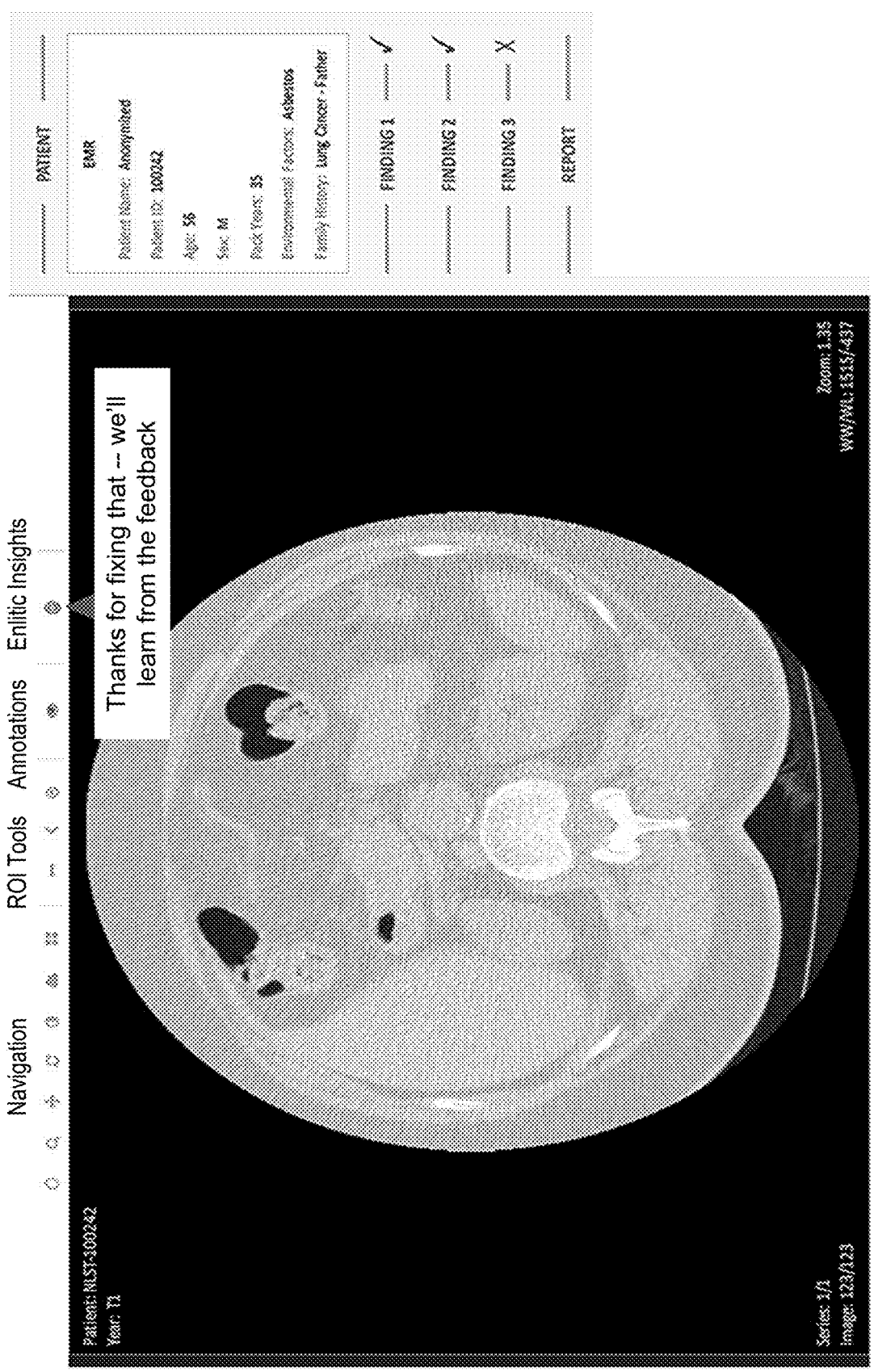

In FIG. 8J, the interactive interface 275 presents automatically generated report data 830 in a text window. Scan review data 810 can be automatically generated in response to the user electing to edit some or all of the text in the report, can elect to approve the report as it stands, or elect to deny the report to remove the automatically identified nodule entirely. In FIG. 8K, the interactive interface displays that the first finding was approved in response to the scan review data 810 indicating that the user elected to approve the first report, and prompts the user to select additional findings 2 or 3 for review, or to view the final report. In FIG. 8L, the interactive interface indicates that the third finding was denied by the user in response to the scan review data 810 indicating that the user elected to approve the third report, and this scan review data 810 is utilized by the medical scan assisted review system 102 to learn from this user feedback, for example, by generating performance score data 630 for a medical scan analysis function responsible for generating the diagnosis data 440 associated with abnormality for the third finding.

Figure 8M:

In FIG. 8M, a final report is displayed to the user for review, and includes the approved report data 830 for confirmed findings 1 and 2, but not denied finding 3. Scan review data 810 can be automatically generated in response to the user electing to edit the final report, finalize the final report or add a new finding.

Figure 8N:
Figure 8O:
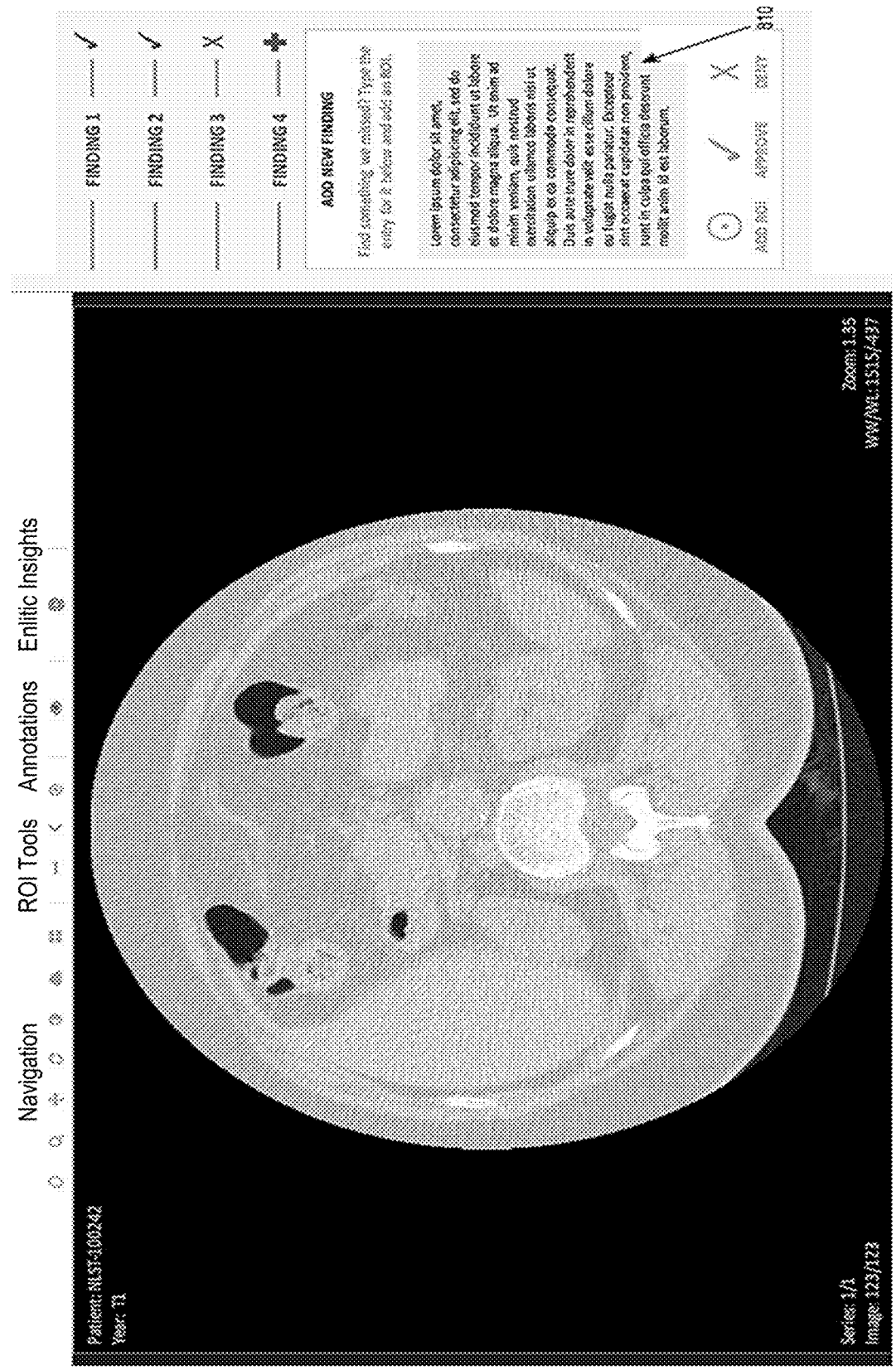
Figure 8P:
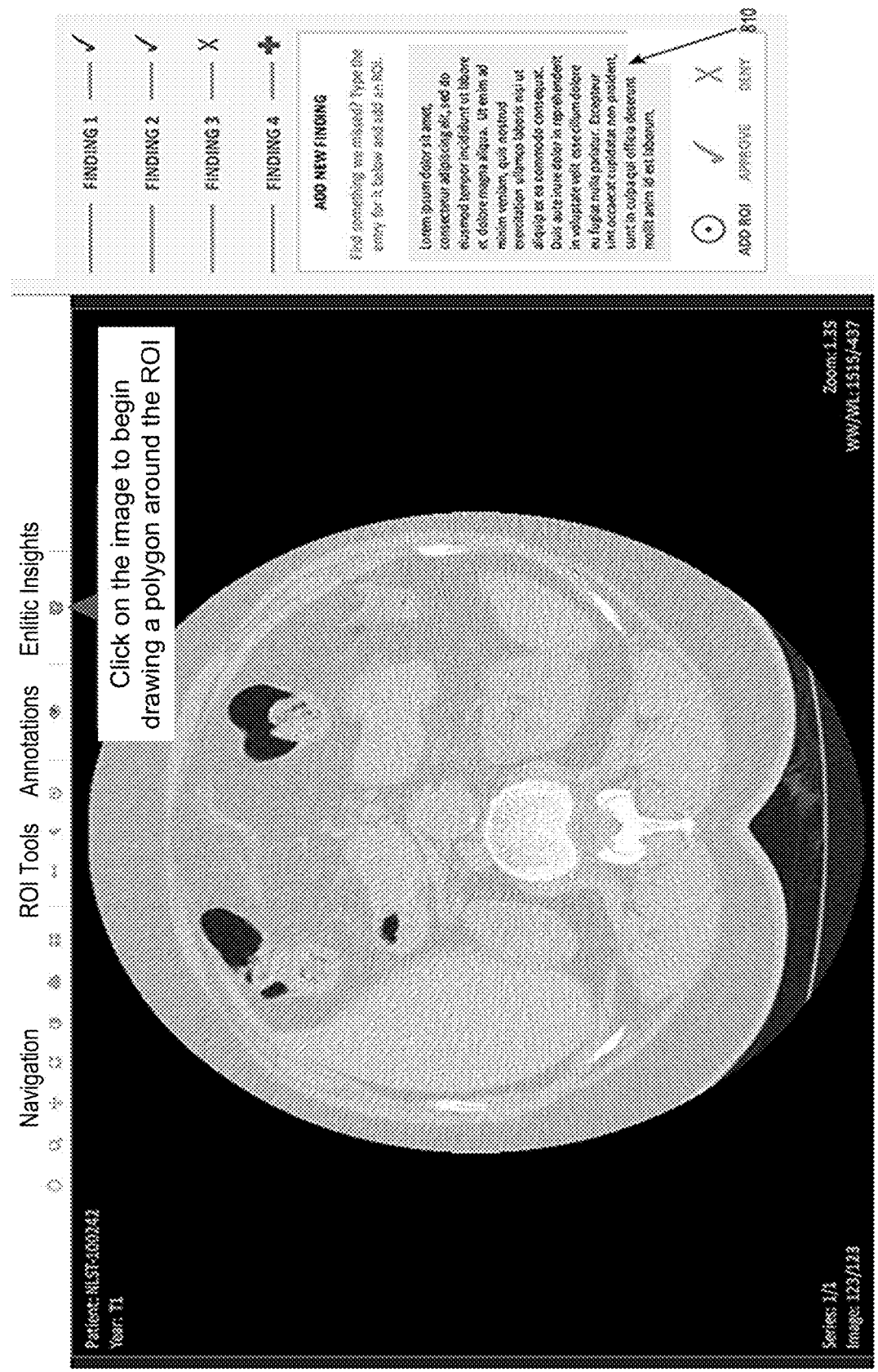
Figure 8Q:
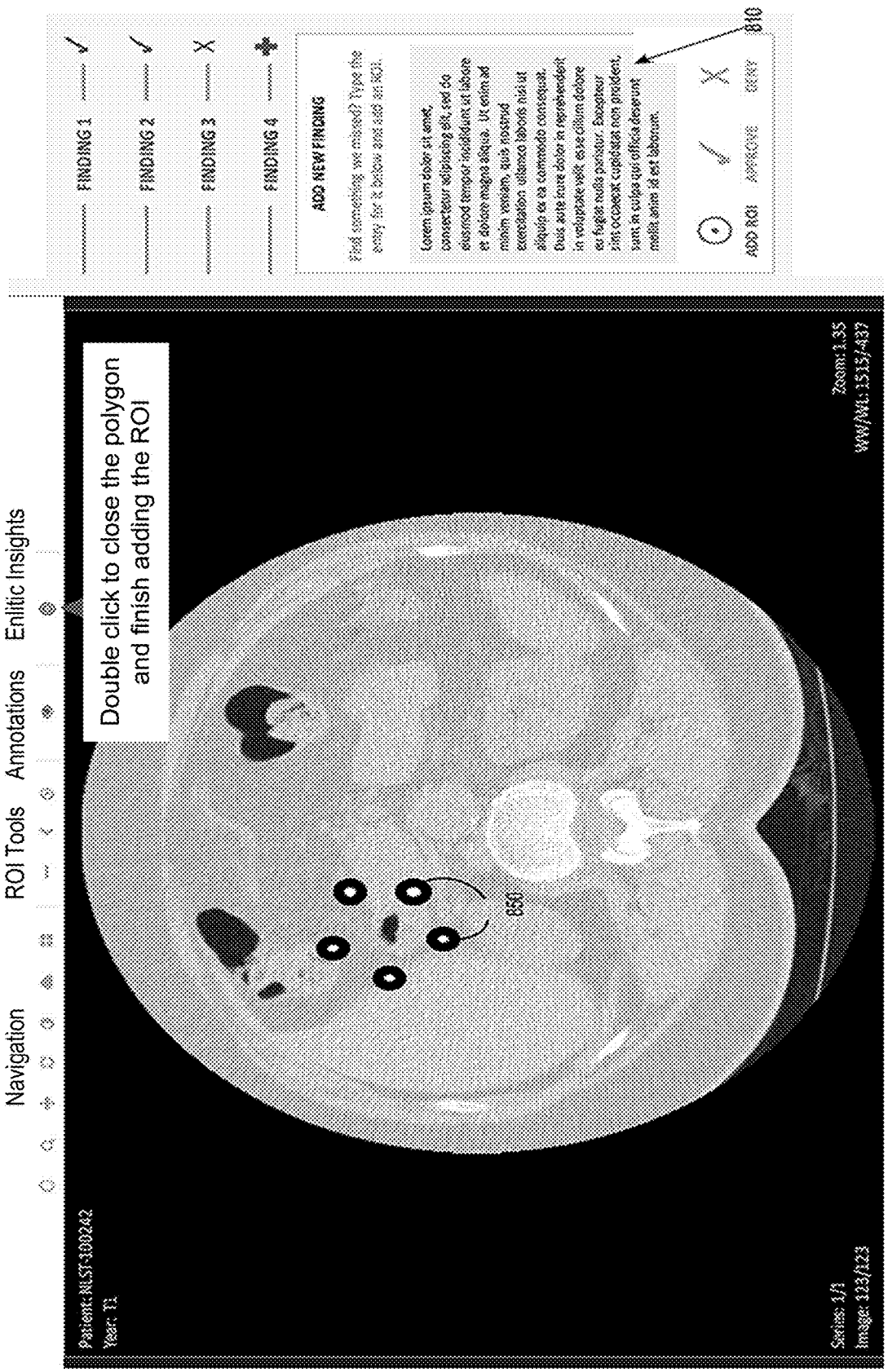
Figure 8R:
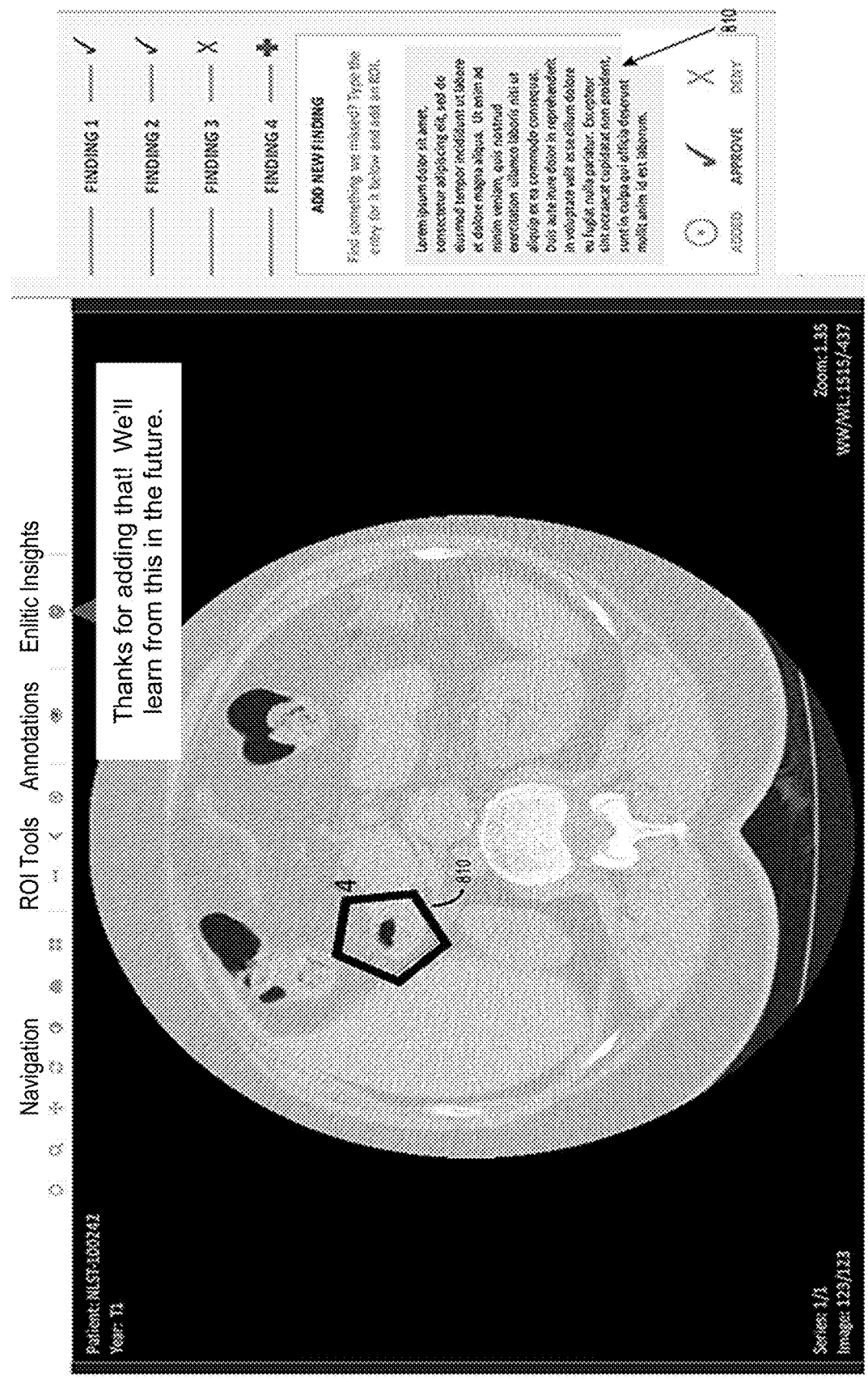

In FIG. 8N, the interactive interface enters the new abnormality mode in response to the scan review data 810 indicating that the user elects to enter a new finding. The user can type the report entry corresponding to the new finding in a text window as shown in FIG. 8O. In FIG. 8P, the user elects to select the region of interest corresponding to the new finding, such as a nodule that was overlooked by the medical scan assisted review system, and the interactive interface 275 prompts the user to indicate the region of interest by selecting points on the image slice corresponding to vertices of a polygon that surrounds the nodule. In FIG. 8Q, the interactive interface displays five vertices 850 selected by the user, and the interactive interface 275 prompts the user to indicate when they have finished by double clicking. The medical scan assisted review system 102 automatically generates scan review data 810 corresponding to the new finding based on the text entered by the user in the text window and the polygon indicating the region of interest, automatically determined based on the five vertices 850 indicated by the user, as presented in the interactive interface 275 of FIG. 8R in response to the user electing to approve the new finding, and this scan review data 810 corresponding to the new finding can be added to the medical scan database and/or utilized in training sets used to improve the performance of the medical scan assisted review system 102 or other subsystems in subsequent uses.

FIG. 8S presents an example final report, automatically generated by the medical scan assisted review system 102 based on report data 830 in response to the user electing to finalize the final report. Natural language text corresponding to the automatically identified findings 1 and 2, as well as the report data 830 corresponding to the added finding indicated by the user are included. Cropped images of each finding in medical scan are also included in the report automatically. A report completion time and patient history are also included in the report.

FIGS. 8T-8Y present an example of a medical scan assisted review system 102 utilized as a chest x-ray differential diagnosis system. In various embodiments, the chest x-ray differential diagnosis system is operable to generate abnormality pattern data is generated for each of a received plurality of chest x-rays by identifying at least one pattern in each chest x-ray corresponding to an abnormality by utilizing a computer vision model that is trained on a plurality of training chest x-rays. Differential diagnosis data is generated for each chest x-ray based on the abnormality pattern data. Filtering parameters are received from a client device, and a filtered chest x-ray queue that includes a subset of chest x-rays is selected based on the filtering parameters and the differential diagnosis data is generated for transmission to the client device for display. Differential diagnosis data corresponding a chest x-ray indicated in chest x-ray selection data received from the client device is transmitted to the client device for display via the display device in conjunction with the chest x-ray.

In various embodiments, the differential diagnosis data for each of the plurality of chest x-rays includes a plurality of binary values indicating whether each of a plurality of abnormality pattern types are present or not present based on the abnormality pattern data. For example, the plurality of abnormality pattern types can include cardiomegaly, consolidation, effusion, emphysema, and/or fracture. In various embodiments, the abnormality pattern data includes confidence score data corresponding to each of the plurality of abnormality pattern types. Generating the differential diagnosis data includes comparing the confidence score data for each of the plurality of abnormality pattern types to a confidence score threshold. The binary values can indicate the corresponding abnormality pattern type is present when the corresponding confidence score data compares favorably to the first confidence score threshold, and can indicate the corresponding abnormality pattern type is not present when the corresponding confidence score data compares unfavorably to the confidence score threshold. The confidence score threshold can be the same or different for each abnormality pattern type. The confidence score threshold can be determined automatically by the chest x-ray differential diagnosis system or another subsystem, or can be set by a user via input to the interactive interface.

A plurality of triaged and/or uploaded scans can be queued for review by a selected user, and the medical scan assisted review system 102 can present a listed queue of scans for review via another view of the interactive interface 275 presented by the display device. This can be based on a plurality of medical scans triaged to the user and/or in response to receiving a plurality of medical scans uploaded to the medical scan processing system 100 by user. The queue of scans can be displayed as line item data in a row, and corresponding data can be displayed such as include patient data, risk factor data, priority score data, a diagnosis summary, abnormality classifier data, confidence score data, or other data retrieved from the medical scan database 342 or generated by one or more subsystems 101.

The queue of scans can be displayed via the interactive interface 275 in an order based on an automatically generated priority score or a priority score retrieved from scan priority data 427 of the medical scan database 342. For example, the priority score can be based on a manually assigned score for an incoming scan, based on the date of the scan, based on a severity of patient symptoms, severity of previous diagnosis data of the scan, or severity of the diagnosis data 440 automatically generated for the medical scan, for example, based on a malignancy score indicated in diagnosis data 440. The user can re-sort and/or filter the queue based on one or more selected criteria, selected via user input to the interactive interface and/or determined based on queue criteria preferences associated with the user, for example, mapped to user profile entry 354. The selected criteria can include such as selecting to view the filtered list of scans based on criteria for one or more selected abnormality pattern types. For example, the user can select to view the filtered list of scans where an abnormality pattern corresponding to cardiomegaly was detected, and can further select to sort the list of scans in reverse order by a confidence score corresponding to detection of cardiomegaly of confidence score data 460. As another example, consider the case where diagnosis data 440 has multiple entries corresponding to multiple diagnosis authors, for example with a first entry was generated based on user input by another user of the system and a second entry generated automatically by utilizing a medical scan image analysis function. The user can select to view the filtered list of scans where an abnormality was detected by the first diagnosis author that was not reported by the second diagnosis author, or vice versa. This can be used to quickly find discrepancies between known diagnosis data and other diagnosis data generated by a subsystem, for example, by utilizing a medical scan analysis function. The user can continue to re-sort and/or further filter or un-filter the queue by adding or removing sorting and/or filter criteria.

The user can be automatically presented a medical scan for review from the top of a sorted and/or filtered queue, or the original queue, by the medical scan assisted review system 102 as described herein. Alternatively or in addition, the user can select a scan from the original queue of scans, or the re-sorted and/or filtered queue of scans, based on clicking the corresponding row of the selected scan or other input to the interactive interface, and the selected medical scan will be presented by the medical scan assisted review system 102 as described herein. The medical scan review system can return to the displayed queue of scans after a user has completed review of the current scan. The user can elect to re-order and/or re-filter the queue by providing new criteria, such as selecting a new confidence score threshold or selecting new abnormality pattern type. The user can also elect to select a new medical scan for review from the displayed queue. In other embodiments, medical scan review system can automatically display the next scan in the queue once the review of the current scan is complete, without returning the view of listed scans.

In some embodiments, the user can elect to confirm the diagnosis data 440 for a selected medical scan without viewing the medical scan. For example, where the user can elect to confirm the diagnosis data 440 by selecting a menu option presented for each scan in the list of scans via the interactive interface 275. This can be based on confidence score data 460 displayed as a line item in conjunction with the medical scan, for example, where the user elects to confirm diagnosis data 440 without viewing the scan because the displayed confidence score is 99%. The user can select auto-confirm criteria, such as "automatically confirm all normal scans" or "automatically confirm all diagnosis data that indicates cardiomegaly with a confidence score that is greater than 90%". In such embodiments, the queue can be automatically filtered based on the auto-confirm criteria, where automatically confirmed medical scans are not listed. The auto-confirm criteria can be selected via user input to the interactive interface 275 and/or determined based on queue criteria preferences associated with the user, for example, mapped to user profile entry 354. In some embodiments, the auto-confirm criteria will be learned and selected by a subsystem and/or the auto-confirm criteria will be entered by an administrator.

In various embodiments, the medical scan assisted review system 102 will only display medical scans with detected abnormalities, for example, where normal scans are included in the auto-confirm criteria. For example, medical scans automatically determined to be normal with at least a threshold confidence score will not be presented to the user for review, and will automatically be filtered from the queue. Diagnosis data, report data, and/or a flag indicating the scan is normal will automatically be mapped to the medical scan in the medical scan database and/or transmitted to the responsible medical entity without user intervention. For quality control, a threshold proportion of normal scans, or other auto-confirmed scans based on other criteria, can be randomly or pseudo-randomly selected and presented to the user for review.

Figure 8T:
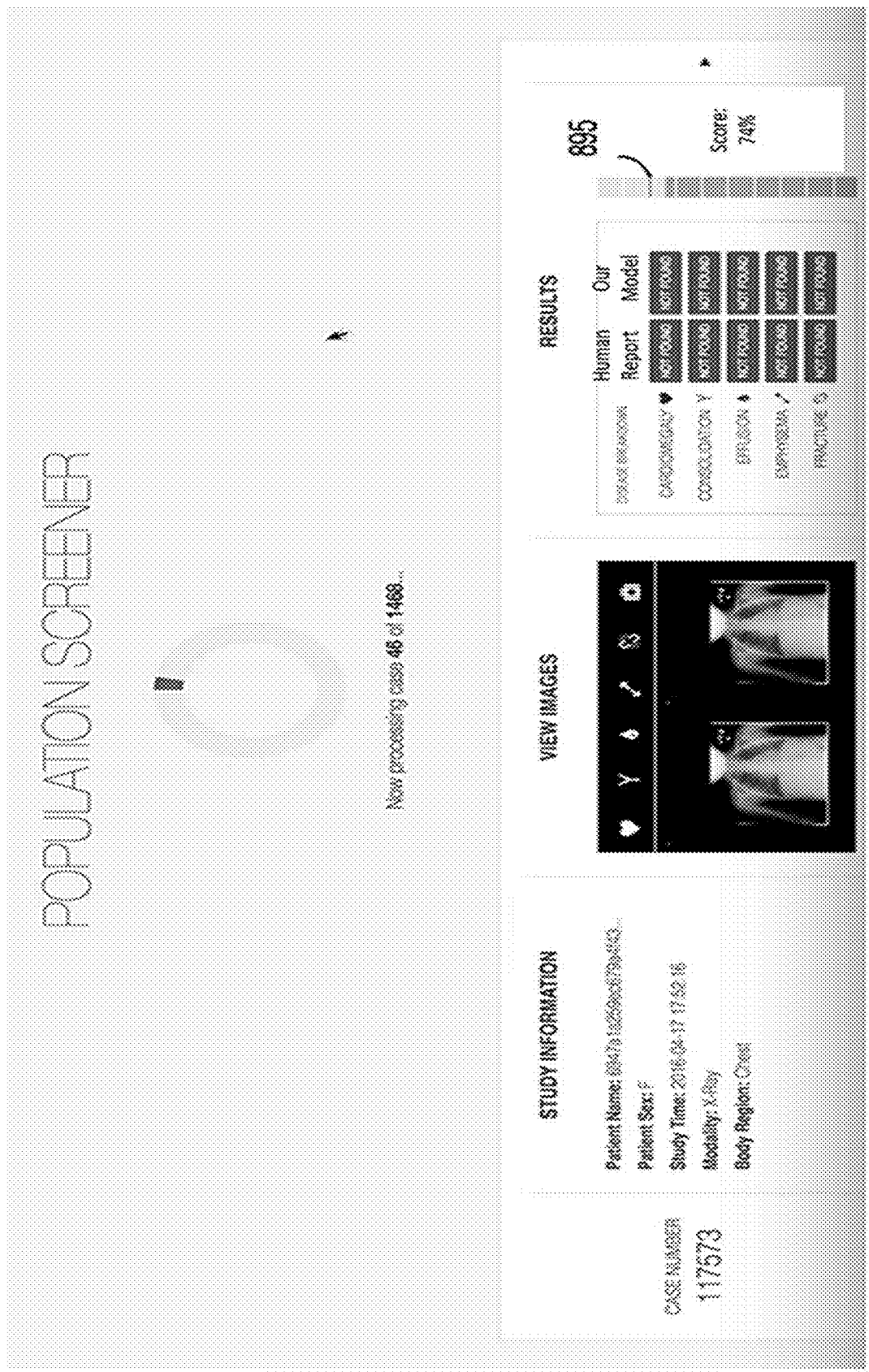
Figure 8U:
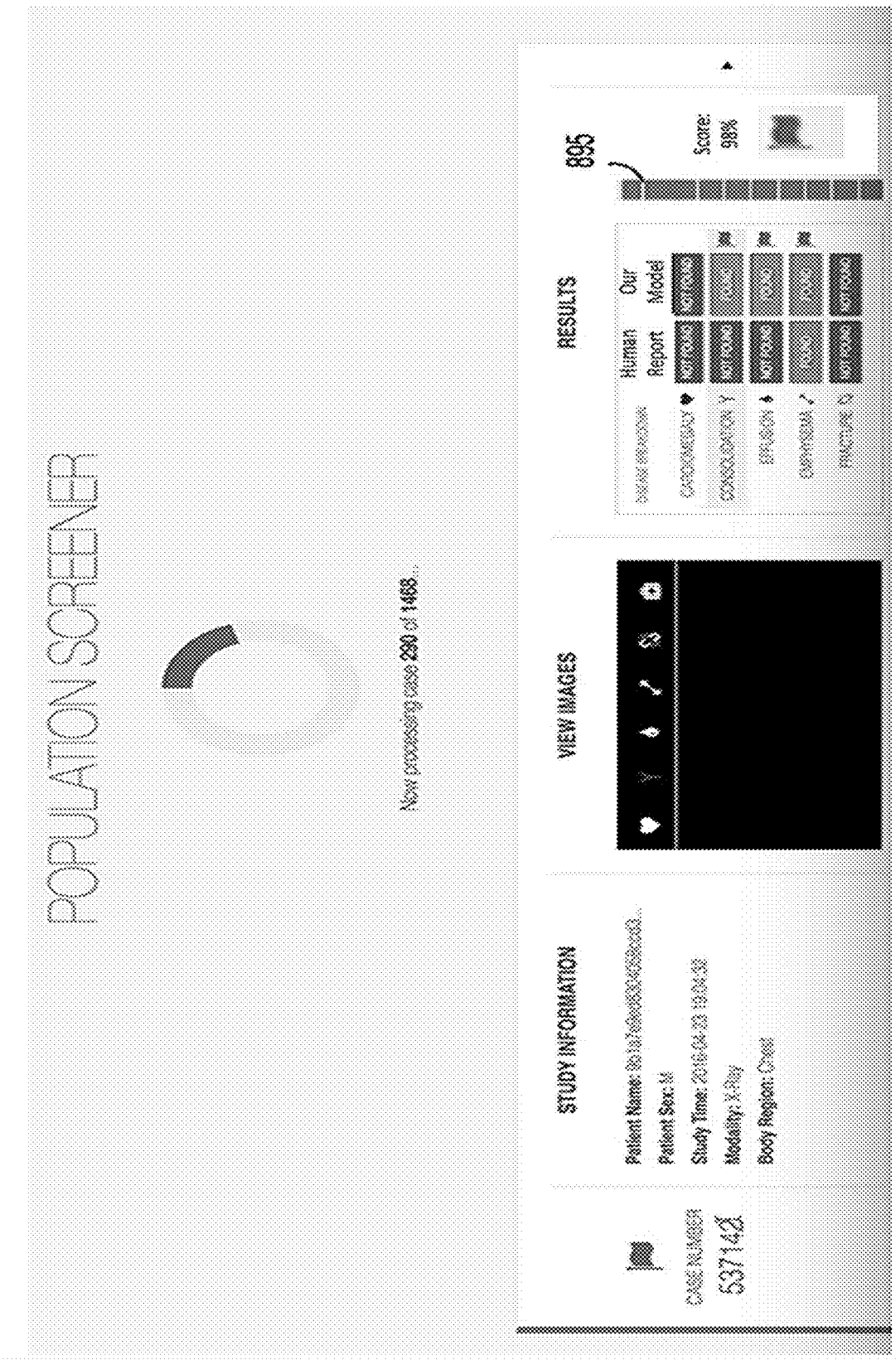

As illustrated in FIGS. 8T-8U, the interface can display progress of processing a collection of chest x-ray models, for example, displaying that 48 out of 1498 chest x-rays have been processed. Each processed chest x-ray can be shown in real-time, with patient information, the x-ray, and results. The results can be broken down into the different abnormality pattern categories and can display if each of the abnormalities was found in previous findings, for example, in a human report, and also display if the finding was found by the medical scan differential diagnosis system by utilizing a model such as a medical scan image analysis function. An abnormality confidence threshold 895 can be displayed, and an abnormality confidence score can be displayed for each x-ray. For example, in FIG. 8T, the score is 74%, which is below the threshold 895. Thus, the results for the model show that no abnormality patterns were found. In FIG. 8U, the score is 98%, which is above the threshold 895. The results show that the model found consolidation, effusion, and emphysema patterns, while the human report only found emphysema.

Figures 8V, 8W:
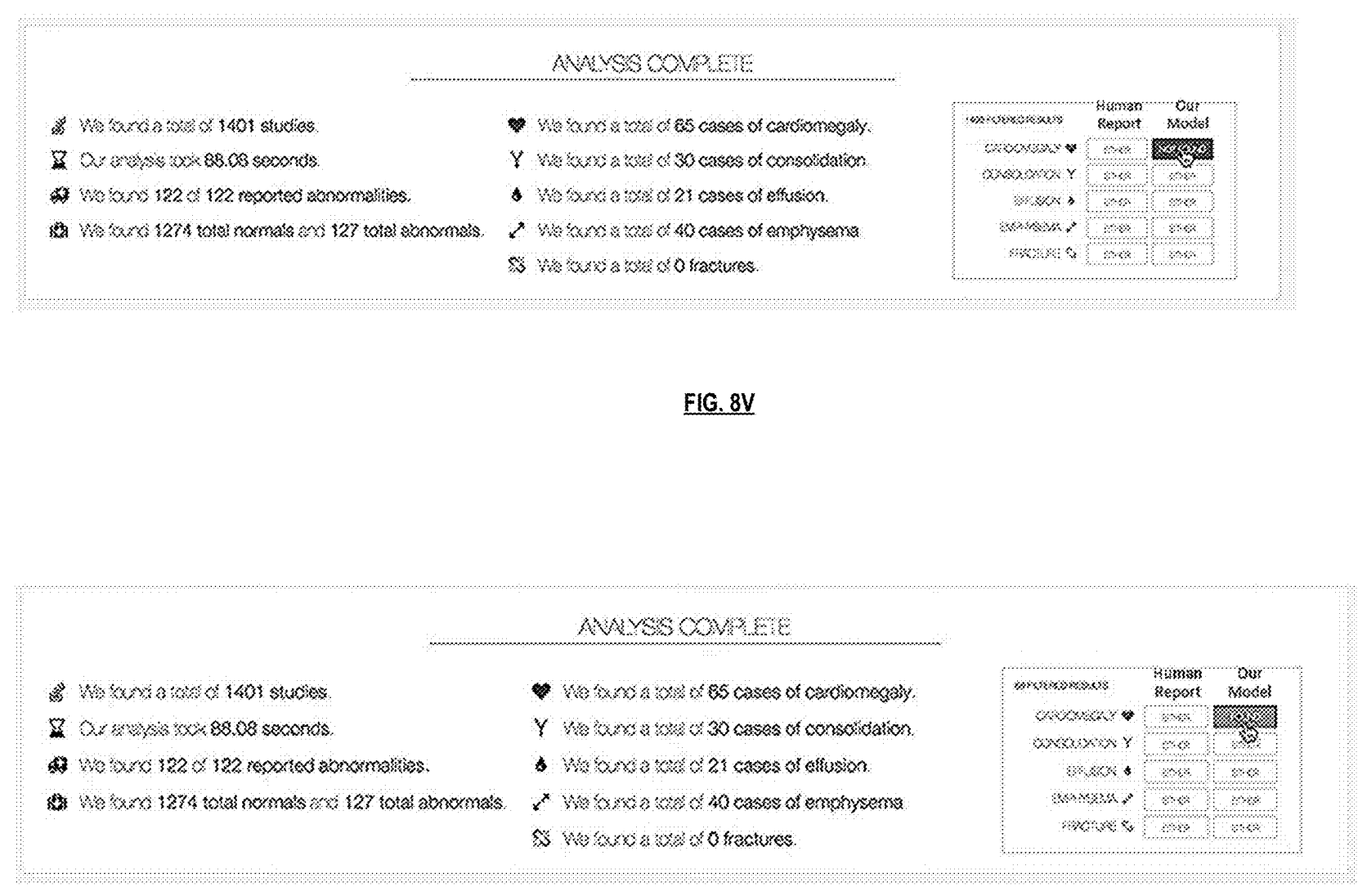
Figure 8X:
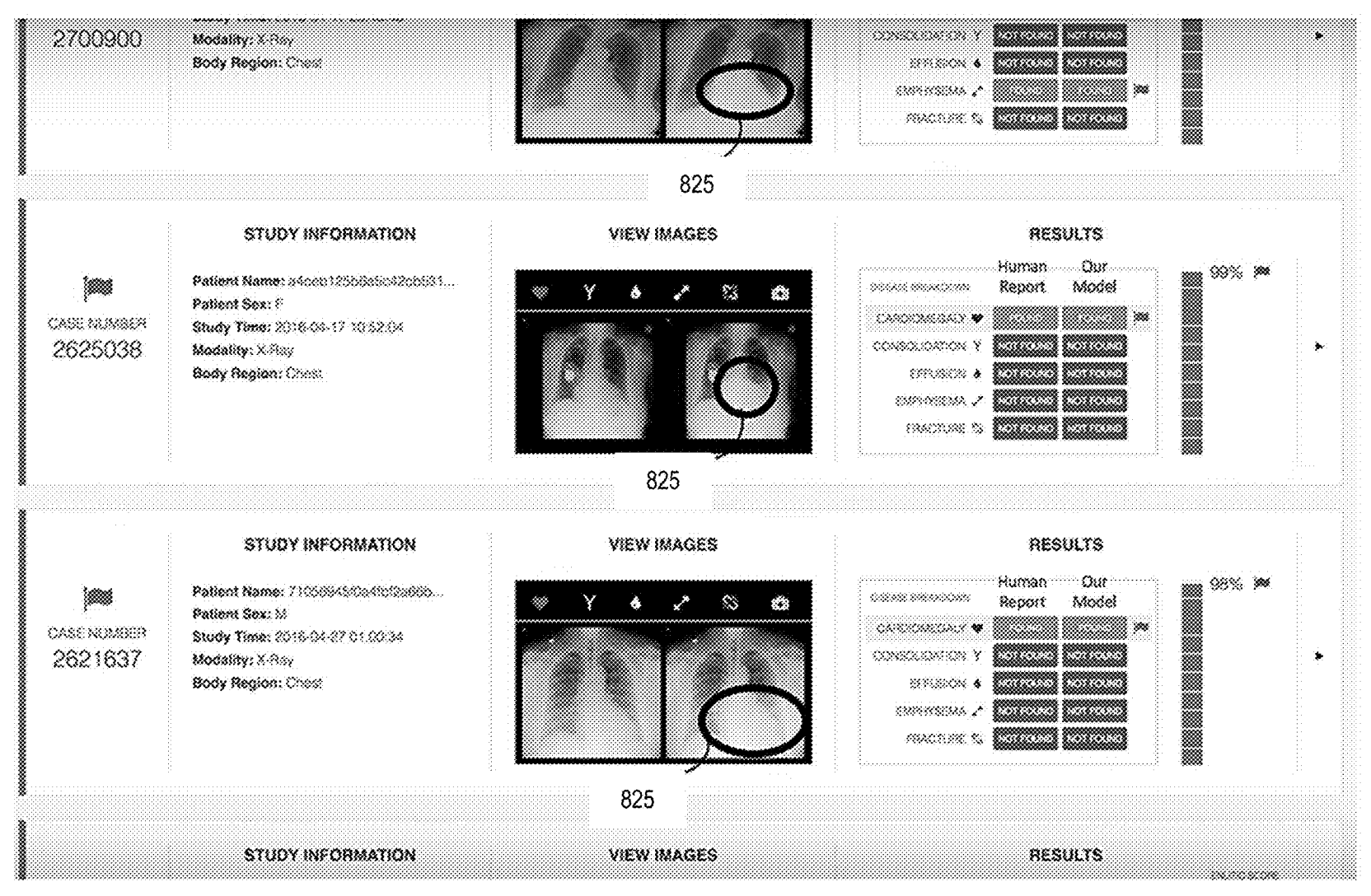
Figure 8Y:

After all of the chest x-rays are processed, the interface can display batch statistics as shown in FIGS. 8V-8W. The user can choose filter criteria by selecting to view one or more abnormality patterns that were found or not found by a previous report or by the model. For example, in FIG. 8V, filtering criteria has been applied to display a queue of scans where cardiomegaly was not found by the medical scan differential diagnosis system. Conversely, in FIG. 8W, filtering criteria has been applied to display a queue of scans where cardiomegaly was found by the medical scan differential diagnosis system. FIG. 8X shows a view of the queue of scans after the filtering criteria in FIG. 8W was applied, and the interface can enable the user to scroll through the queue. Each entry in the queue can display the identified abnormality pattern by highlighting the pattern in red or otherwise indicating the pattern via a visualization 825. The user can select one of the scans for further review, as shown in FIG. 8Y, and can view the text of the original report.

Figure 9A:
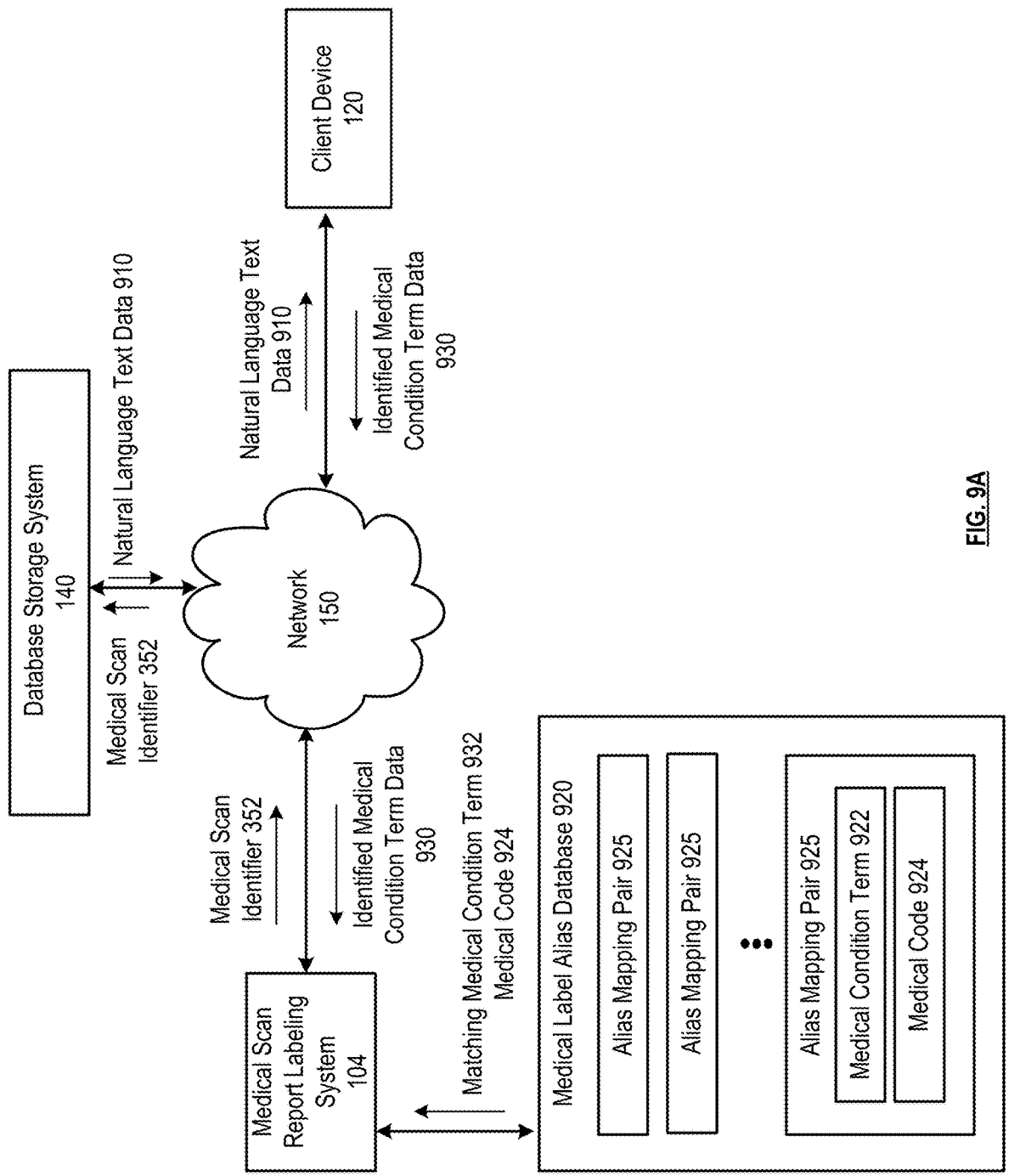
FIGS. 9A-9B are schematic block diagrams of a medical scan report labeling system in accordance with various embodiments.
Figure 9B:
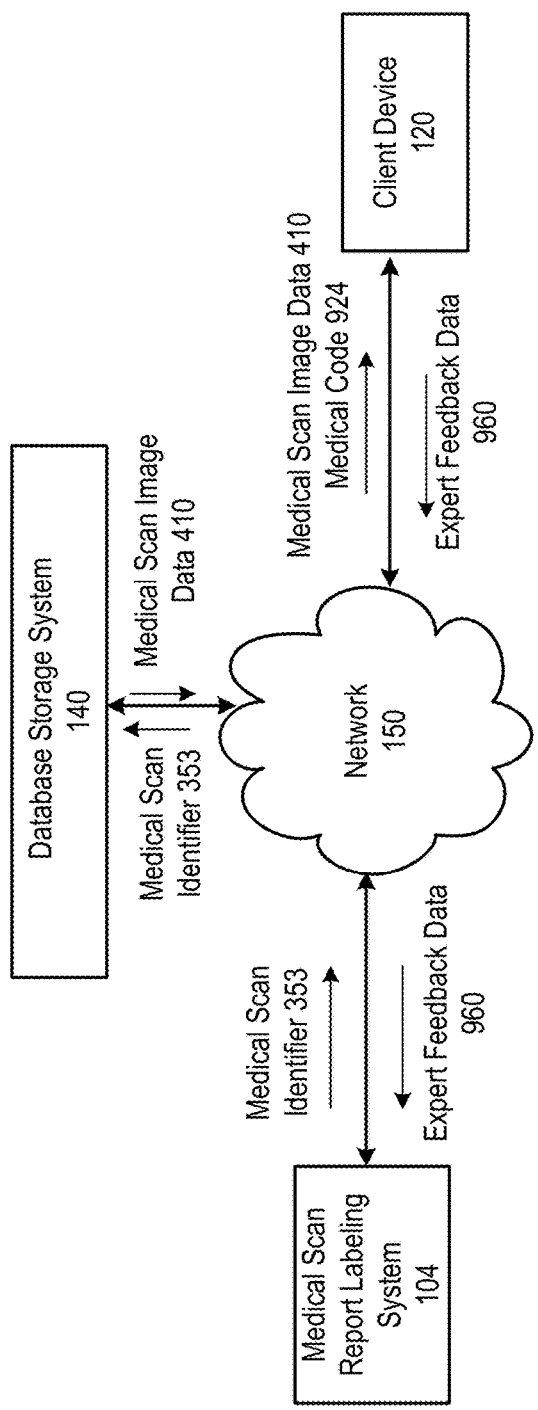

FIGS. 9A and 9B present an embodiment of a medical scan report labeling system 104. The medical scan report labeling system 104 can be used to automatically assign medical codes 447 to medical scans based on user identified keywords, phrases, or other relevant medical condition terms of natural text data 910 in a medical scan report of the medical scan, identified by users of the medical scan report labeling system 104 via interactive interface 275.

In various embodiments, the medical scan report labeling system 104 is operable to transmit a medical report that includes natural language text to a first client device for display. Identified medical condition term data is received from the first client device in response. An alias mapping pair in a medical label alias database is identified by determining that a medical condition term of the alias mapping pair compares favorably to the identified medical condition term data. A medical code that corresponds to the alias mapping pair and a medical scan that corresponds to the medical report are transmitted to a second client device of an expert user for display, and accuracy data is received from the second client device in response. The medical code is mapped to the first medical scan in the medical scan database when the accuracy data indicates that the medical code compares favorably to the medical scan.

As illustrated in FIG. 9A, the medical scan report labeling system 104 can retrieve the natural language text data 910 corresponding to a medical scan. For example, the medical scan report labeling system 104 can utilize the medical scan database 342 of the database storage system 140 to determine the natural language text data 910 of the medical scan, for example, by retrieving natural language text data 448, extracting natural language text data from report data 449, and/or utilizing a medical report generating function to generate the natural language text data 910 deterministically and automatically based on other data of the medical scan entry 352 such as medical scan image data 410, diagnosis data 440, or other data. When the natural text data 910 is deterministically and automatically generated, the natural language text data 910 is a computer-generated representation in a form similar to natural language text. The medical scan report labeling system 104 can utilize the user database 344 of the database storage system 140 to select a user. Alternatively, a different medical scan database and/or user database can be utilized by the medical scan report labeling system 104. In some embodiments, the natural language text data 910 can correspond to a medical report written by a user of the system or other medical professional and/or radiologist, for example, based on reviewing the medical scan.

The subsystem memory device 245 can include a medical label alias database 920 that can include a plurality of alias mapping pairs 925 that can be retrieved, edited, added, and/or removed by the medical scan report labeling system 104. Each alias mapping pair 925 can include one of a plurality of medical condition terms 922 and a corresponding one of a plurality of medical codes 924, which can include SNOMED codes, CPT codes, ICD-9 codes, ICD-10 codes, or other standardized medical codes used to label, annotate, or otherwise describe medical scans. Each medical condition term 922 in the medical label alias database 920 is unique, and each of the plurality of medical condition terms can include at least one word. Thus, a corresponding medical code 924 is a deterministic function of a given medical condition term 922. Multiple medical condition terms can map to the same medical code. The medical label alias database 920 can also be stored in the database storage system 140 and can be accessed by the medical scan report labeling system 104 and/or other subsystems 101 via network 150.

The medical scan report labeling system 104 can automatically select a medical report data 449 of a medical report from the database for transmission to an automatically selected client device 120 corresponding to a selected user of the system, such as user identified as a medical scan labeler in the qualification data 540 or other data of a user profile entry 354. The selected client device 120 can display the natural text data 910 of the medical report via the interactive interface 275 displayed by the display device 270 corresponding to the client device 120. In some embodiments, only the natural text data 910 is displayed, and medical scan image data 410 is not displayed to the user. The interactive interface 275 can prompt the user to identify one or more medical condition terms based on natural language text data 910. The client device 120 can generate identified medical condition term data 930 based on the user input, for transmission to the medical scan report labeling system 104. The identified medical condition term data 930 can be generated based on a segment of consecutive words in the natural language text data 910 of the medical report identified by the user, based on a plurality of words in the natural language text data 910 of the medical report identified by the user, where at least two of the plurality of words are not consecutive words in the natural language text data 910, and/or based on a plurality of words identified by the user where at least one word in the plurality of words is not included in the natural language text data of the medical report. For example, the interactive interface 275 can prompt the user to click on or highlight words in the text. The interactive interface can prompt the user to indicate which of a plurality of identified medical condition terms each identified word or phrase is designated for by allowing the user to highlight in multiple colors or to otherwise indicate a switch between medical condition terms. When the user identifies a relevant word or phrase of a medical condition term that is not explicitly stated in the natural language text data 910, the user can indicate this word or phrase based on other user input such as text and/or voice input to a keyboard and/or microphone of the client device. The generated identified medical condition term data 930 can include the raw user input, and/or can be pre-processed by the client device, for example, identifying separate groups of medical condition terms, parsing text and/or keyboard input, etc. The prompts and/or user input methods utilized by the interactive interface to generate identified medical condition term data 930 can include one or more interface features, for example, indicated in the interface preference data 560 or display parameter data 470 corresponding to the medical scan, and/or the user can interact with the user interface to identify medical terms based on techniques described in conjunction with the medical scan assisted review system 102.

Upon receiving the identified medical condition term data 930, the medical scan report labeling system 104 can automatically determine if the identified medical condition terms data 930 compares favorably to any medical condition terms 922 included in the medical label alias database 920. This can include searching for the exact same medical condition term 922 indicated by the identified medical condition term data 930 in the database, determining a most similar medical condition term 922 term in the database that compares most favorably to the identified medical condition term data 930, and/or identifying the matching medical condition term 932 in the database by determining one or more keywords of the identified medical condition term data 930 that match the one or more words of a medical condition term 922. For example, a medical condition term of a first alias mapping pair 925 and a string of words in the identified medical condition term data 930 received from the client device 120 term data may differ by at least one word, and determining that medical condition term 922 compares favorably to the identified medical condition term data includes calculating a similarity score between the medical condition term 922 and the identified medical condition term data 930 and further includes determining that the similarity score compares favorably to a similarity threshold, and/or further determining that the similarity score is more favorable than similarity scores calculated for other medical condition terms 922 and the identified medical condition term data 930. In some embodiments, determining the matching medical condition term 932 includes performing a medical scan natural language analysis function and/or a natural language similarity function trained by the medical scan natural language analysis system 114 or the medical scan comparison system 116. In various embodiments, the identified medical condition term data 930 can include multiple identified medical condition terms, and medical condition terms 922 in the database that compare favorably to each of these multiple identified medical condition terms can be identified separately.

If the medical scan report labeling system 104 determines that a medical condition term 922 in the database compares favorably to the identified medical condition term data 930, the corresponding medical code 924 indicated in the alias mapping pair of the medical condition term in the database can be retrieved. This medical code 924 can be automatically assigned as the label for the medical scan, and can be mapped to the medical scan in the medical scan database accordingly as medical code 447 and/or can be utilized to generate some or all of the diagnosis data 440.

FIG. 9B illustrates an embodiment of the medical scan report labeling system 104 upon determining that no medical condition term 922 in the database compare favorably to the identified medical condition term data 930, the medical scan report can be transmitted to a client device associated with an expert user or other medical professional. The expert medical professional can be selected, for example, based on an overall or category-based and/or ranked performance score data 530 in the user database 344, as described herein in accordance with other subsystems such as the medical scan annotator system 106. The expert user can also be identified based on a local database of identified experts of the medical scan report labeling system and/or based on the expert data 543 of user profile entries 354 of the user database 344.

The natural language text data 910 of the medical report and/or the corresponding medical scan image data 410 can be displayed to the expert user via an interactive interface 275 displayed by a display device corresponding to the client device of the expert user, for example, in conjunction with the medical scan assisted review system 102 and/or by utilizing one or more interface features indicated by the display parameter data 470 of the corresponding medical scan and/or interface preference data 560 of the expert user. The medical code can be entered manually by the expert user and/or can be generated automatically based on scan review data 810 and/or other diagnosis feedback data provided by the expert user to the interactive interface 275. The selected expert user can enter one or more new alias mapping pair 925 based on the medical scan image data 410 and/or corresponding medical report natural language text data 910, for example, by identifying one or more appropriate medical codes 924 for the medical scan, and by determining one or more words in the natural language text data that should map to each of the one or more appropriate medical codes 924 in the future to create one or more corresponding medical condition terms 922. These one or more new alias mapping pairs 925 can be added to the medical label alias database 920. The one or more medical codes 924 identified by the expert user can also be mapped to the medical scan in the medical scan database 342 as medical code 447 and/or can be utilized to generate some or all of the diagnosis data 440.

The expert may determine that the medical report otherwise does not include a new medical condition term that should map to the appropriate medical code. The expert can still enter or indicate the appropriate medical code via the interactive interface without indicating corresponding medical terms. The expert user can indicate via a menu option or other user input to the interactive interface that the medical report is an inaccurate description of the medical image in response to determining that the medical report does not include any medical condition term that appropriately maps to the medical code. This information can be used by the medical scan report labeling system 104 or other subsystem to alert a medical professional and/or hospital associated with the medical report, for example, indicated in the originating entity data 423 or annotation author data 450 of the error, for example, by transmitting a notification to a client device 120 of a corresponding user. The medical scan report labeling system 104 can generate new performance score data for the medical professional and/or medical entity, and the performance score data 530 of the user profile entry 354 corresponding to the medical professional and/or medical entity can be automatically updated accordingly. A new medical report can be automatically generated by the medical scan report labeling system 104 or another subsystem and can be mapped to the medical scan, for example, by modifying the report data 449 and/or natural language text data 448 of the corresponding medical scan entry 352 in the medical scan database. The new medical report can automatically be generated based on the medical code or other diagnosis feedback data provided by the expert via the user interface, for example, utilizing scan review data 810 to generate report data 830 as described in conjunction with the medical scan assisted review system 102.

In some embodiments, even when the medical scan report labeling system 104 retrieves a medical code of an alias mapping pair 925 based on a medical condition term in the database compares favorably to the identified medical condition term data received from the client device, the medical code and corresponding medical scan are sent to a client device of a selected expert user for display to the expert user via the interactive interface displayed by a display device corresponding to the client device of the expert user, allowing the expert user to verify that the medical code is appropriate for the medical scan before it is mapped to the medical scan in the medical scan database. For example, a random or psuedo-random sampling of proposed medical codes and their corresponding medical scans can be sent to expert users automatically based on a fixed verification percentage. Different users can be assigned different verification percentages, for example, based on performance score data 530 and/or qualification data 540 information in user profile entries 354 of the user database 344. For example, a higher proportion of medical codes for a first user can be sampled than that of a second user in response to the first user having less training, having a lower performance score, being a newer user of the medical scan report labeling system, or another indication in the user profile entry 354 requiring that the first user have more medical codes verified by an expert. In various embodiments, different medical codes can be assigned different verification percentages, for example, based on a severity of the medical code and/or a rarity of the medical code. In various embodiments, different alias mapping pairs to the same medical code can be assigned different verifications percentages, for example, based on an ambiguity or rarity of the medical condition term of the alias mapping pair 925. Verification percentages can be assigned to some or all alias mapping pairs 925 in the medical alias mapping database, for example, based on a corresponding ambiguity and/or rarity score, and can be automatically generated and/or updated by the medical scan report labeling system based on aggregate accuracy data corresponding to usage of the alias mapping pair. Similarly, confidence score data 460 can be mapped to the medical codes 924 assigned by a normal user, or an expert user, based on user experience such as performance score data 530 and/or qualification data 540 information and/or based on an ambiguity or rarity score of the corresponding medical code 924. Whether or not the assigned medical codes 924 are reviewed by an expert user can be based on the confidence score data 460.

Upon presenting the proposed medical code 924 and medical scan to the user via the interactive interface 275, the client device 120 can generate expert feedback data 960 based on user input by expert user in response to a prompt displayed by the display device via the interactive interface to provide feedback based on the medical scan and the medical code. For example, the expert user can indicate whether or not the medical code corresponds to the medical scan, and can provide a corrected medical code in response to determining the medical code is incorrect. The expert feedback data 960 can be included in the scan review data 810 generated in conjunction with the medical scan assisted review system 102, and/or can be otherwise generated based on the expert input identifying abnormalities or otherwise annotating the medical scan, where the expert feedback data 960 is generated based on a blind review or can be based on response to displayed annotation data 820 corresponding to the medical codes 924 determined based on the alias mapping pair 925 identified by the user. The expert feedback data 960 generated in response to expert user input can be transmitted to the medical scan report labeling system 104 or another subsystem 101, and the medical scan database and/or the medical label alias database can be updated accordingly.

In this fashion, the expert user can also indicate that the identified alias mapping pair is an inappropriate mapping based on the medical scan, can indicate a modified alias mapping pair or indicate that the alias mapping pair be removed from the database, and/or can provide a new alias mapping pair that includes the corrected medical code and an appropriate medical condition term based on the medical report, for example, if medical report is also sent to the client device of the expert user and the natural text data of the medical report is also displayed to the expert user via the interactive interface. Such information can also be included in the expert feedback data 960 generated by the client device.

The ambiguity score and/or rarity score of the identified alias mapping pair 925 can be automatically updated based on this expert feedback. For example, an ambiguity score can increase to indicate the identified alias mapping pair 925 is more ambiguous if the accuracy score data indicates that the medical code was inappropriate and where the ambiguity score decreases if the accuracy score data indicates that the medical code was appropriate. The rarity score can simply be updated to reflect that an identified alias mapping pair 925 is less rare each time the identified alias mapping pair 925 is used and/or can be based on a number of times the identified alias mapping pair 925 is used in a recent, fixed duration of time. The corresponding verification percentage can automatically be updated based on the updated ambiguity score and/or rarity score.

In various embodiments, once a medical code 924 is mapped to a medical scan in the medical scan database, a mapping that includes the corresponding medical scan report and the medical code can be added to a report labeling training set that includes a subset of the plurality of medical reports and a corresponding set of medical codes. In various embodiments, all medical reports are added to the report labeling training set once labeling is complete. In various embodiments, only medical reports corresponding to medical codes verified by an expert are added to the training set. The medical scan report labeling system and/or another subsystem such as the medical scan natural language analysis system 114 can generate a medical report analysis function based on the training set, for example, based on the natural language processing techniques described in conjunction with medical scan natural language analysis system 114. The medical report analysis function can take a full medical report or natural language text data extracted from a medical report as input, and can generate one or more medical codes as output. The medical report analysis function be utilized to automatically assign medical codes to other medical scans that have yet to be labeled and/or to verify previously assigned medical codes based on a corresponding medical report. This can be utilized by one or more subsystems to automatically assign a medical code 924 to a medical scan itself rather than sending the medical report to a user of the medical scan report labeling system. This can also be used to automatically verify and/or correct medical codes generated based on user input to the medical scan report labeling system, for example, in addition to or instead of expert review.

In some embodiments, the medical report analysis function can include automatically determining one or more keywords and/or a medical condition term in the natural language text 910 of the medical scan report and can automatically search the medical label alias database for a match to determine the medical code. In various embodiments, generating and/or executing the medical report analysis function can include automatically generating new alias mapping pairs 925 to be added to the database based on new identified medical condition terms 922, and/or can include automatically modifying or removing existing alias mapping pairs from the database. Alternatively, the medical report analysis function can directly determine the medical code from the natural language text data without utilizing the medical label alias database. A medical code 924 outputted by the medical report analysis function can be mapped to the medical scan directly in the medical scan database and/or can be sent to an expert user for verification based on the conditions described previously, along with the medical scan and/or the medical report.

Feedback from the expert via the interactive interface can be used to generate model accuracy data, such as model accuracy data 631, generated automatically by the client device 120 of the expert user in response to a prompt displayed by the display device via the interactive interface to provide model accuracy data or other scan review data 810 based on the medical code and the medical report and/or medical scan image data 410, and the model accuracy data can be sent to the medical scan report labeling system or another subsystem 101. The model accuracy data can be mapped to the medical report analysis function, and/or existing model accuracy data can be automatically updated. This can include generating and/or modifying model accuracy data 631 of the medical report analysis function in the medical scan analysis function database 346.

The medical code 924 generated by the medical report analysis function can be mapped to the medical scan in the medical scan database when the model accuracy data indicates that the medical code is appropriate. The medical report analysis function can be automatically modified based on the model accuracy data indicating that the medical code is incorrect and/or based on a corrected medical code provided by the expert, for example, in conjunction with the remediation process of the medical scan diagnosis system and/or based on the remediation data 650 of the medical report analysis function. The expert can also manually identify parameters or rules of the medical report analysis function that need modification based on such detected discrepancies, and these can be sent to the medical scan report labeling system with the model accuracy data for integration into the model by the medical scan report labeling system 104 and/or the medical scan natural language analysis system 114.

In various embodiments, the medical report generating function can be generated by the medical scan natural language analysis system 114 or other subsystem 101 based on a training set of determined medical codes generated by the medical scan report labeling system 104, and the corresponding medical report, for example, where the medical report generator function takes one or more medical codes assigned to a medical scan as input, and automatically generates natural language text data 448 and/or report data 449, based on natural language patterns and/or report formatting patterns detected in conjunction with the medical scans that are labeled by particular medical codes 924. The medical scan natural language analysis system 114 can also utilize the medical report generating function, for example, determining medical condition terms that are mapped to input medical code 924 to generate the natural language text data 448 and/or report data 449.

In various embodiments, the medical scan image analysis function can be generated by the medical scan image analysis system 112 or other subsystem 101 based on a training set of determined medical codes generated by the medical scan report labeling system 104, and the corresponding medical scan image data 410, for example, where the medical scan image analysis function takes medical scan image data assigned to a medical scan as input, and automatically generates one or more corresponding medical codes 924 as output, for example, without utilizing natural language text data 448 and/or report data 449.

Figure 10A:
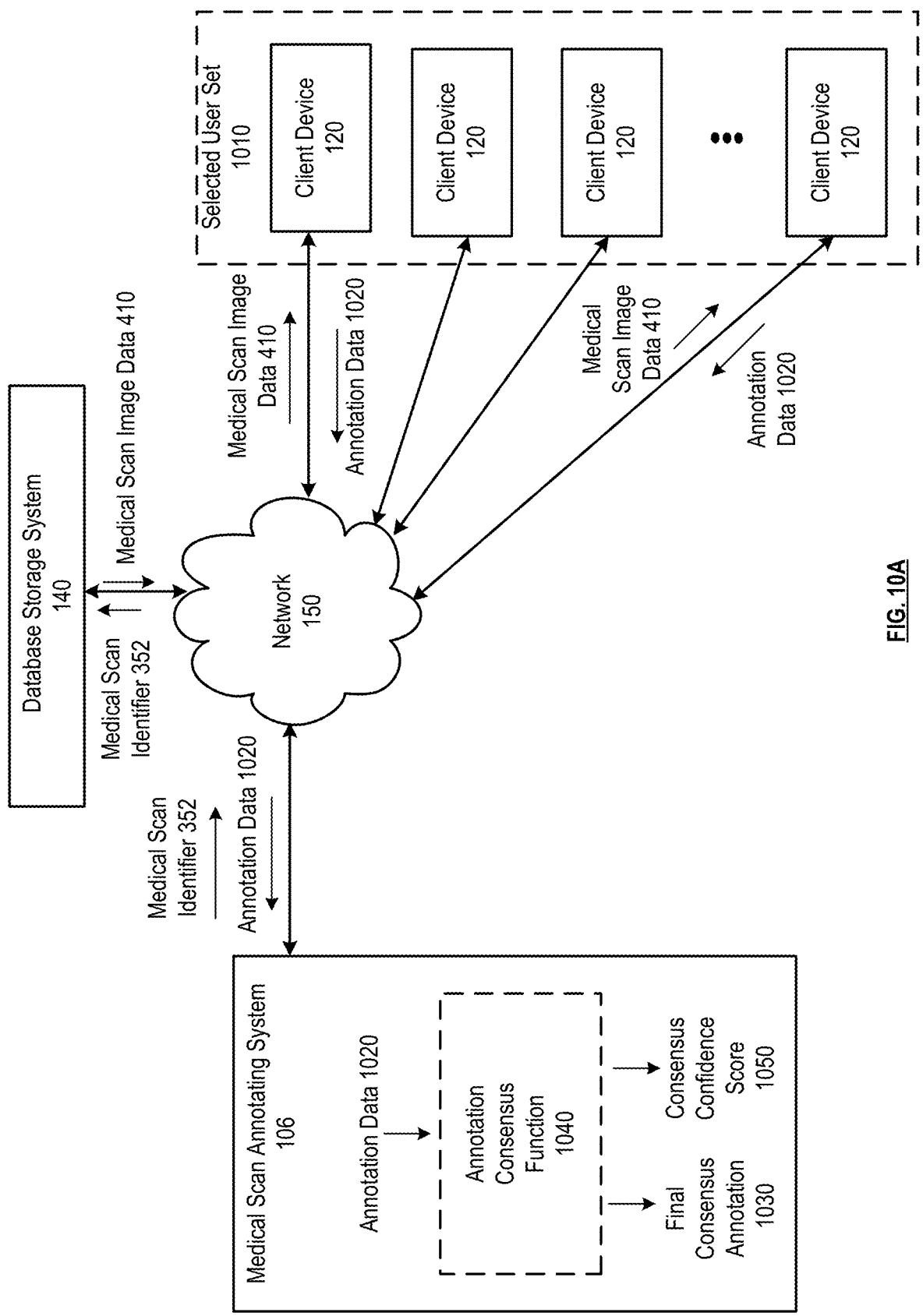
FIGS. 10A-10B are schematic block diagrams of a medical scan annotating system in accordance with various embodiments.
Figure 10B:
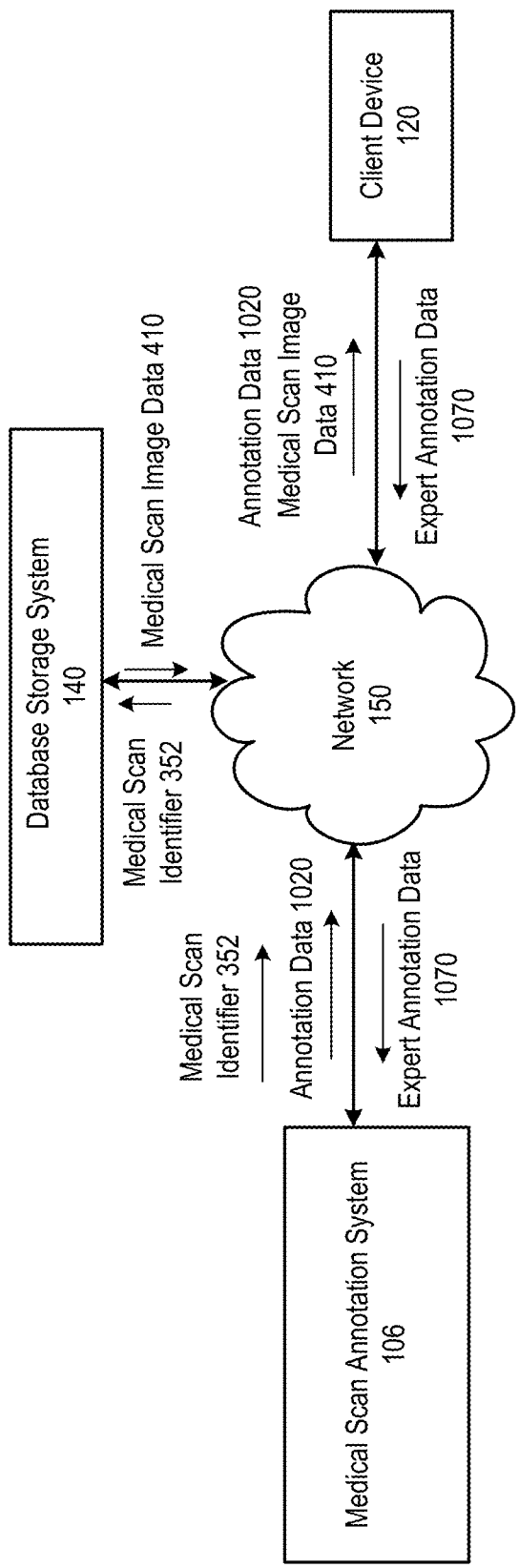

FIGS. 10A and 10B present an embodiment of a medical scan annotator system 106, the medical scan annotator system 106 can be used to gather annotations of medical scans based on review of the medical scan image data 410 by users of the system such as radiologists or other medical professionals. Medical scans that require annotation, for example, that have been triaged from a hospital or other triaging entity, can be sent to multiple users selected by the medical scan annotator system 106, and the annotations received from the multiple medical professionals can be processed automatically by a processing system of the medical scan annotator system, allowing the medical scan annotator system to automatically determine a consensus annotation of each medical scan. Furthermore, the users can be automatically scored by the medical scan annotator system based on how closely their annotation matches to the consensus annotation or some other truth annotation, for example, corresponding to annotations of the medical scan assigned a truth flag 461. Users can be assigned automatically to annotate subsequent incoming medical scans based on their overall scores and/or based on categorized scores that correspond to an identified category of the incoming medical scan. In various embodiments, the medical scan annotator system can utilize the medical scan database 342 and/or user database 344, or another other medical scan database and/or user database, for example, stored in local memory.

In various embodiments, the medical scan annotator system 106 is operable to select a medical scan for transmission via a network to a first client device and a second client device for display via an interactive interface, and annotation data is received from the first client device and the second client device in response. Annotation similarity data is generated by comparing the first annotation data to the second annotation data, and consensus annotation data is generated based on the first annotation data and the second annotation data in response to the annotation similarity data indicating that the difference between the first annotation data and the second annotation data compares favorably to an annotation discrepancy threshold. The consensus annotation data is mapped to the medical scan in a medical scan database.

As illustrated in FIG. 10A, the medical scan annotator system 106 can select a medical scan from the medical scan database 342 for transmission via network 150 to one or more client devices 120 associated with a selected user set 1010 corresponding to one or more users in the user database 344. A medical scan can be selected for annotation based on an assigned priority and/or based on a turn-based queue, for example, based on the scan priority data 427 of the corresponding medical scan entry 352. The client device 120 of each user of the selected user set 1010 can display one or more received medical scans to the via the interactive interface 275 displayed by a display device corresponding to the client device 120, for example, by displaying medical scan image data 410 in conjunction with the medical scan assisted review system 102.

The interactive interface 275 displayed by client devices 120 of each user in the selected user set 1010 can include a prompt to provide annotation data 1020 corresponding to the medical scan. This can include a prompt to provide a text and/or voice description via a keyboard and/or microphone associated with the client device. This can also include a prompt to indicate one or more abnormalities in the medical scan, for example, by clicking on or outlining a region corresponding to each abnormality via a mouse and/or touchscreen. For example, the interactive interface can prompt the user whether or not an abnormality is present. If the user indicates an abnormality is present, the interactive interface can prompt the user to identify the region that includes the abnormality. This can include allowing the user to scroll through one or more slices, to identify one or more slices that contain the abnormality, and to select a region of the one or more slices that contains the abnormality. Once the region is identified, the interactive interface can prompt the user to provide descriptive information classifying an abnormality based on its size, type, etc. To aid the user in providing this information, the user interface can automatically crop one or more slices based on the identified region and/or zoom in on the identified region. In various embodiments, the medical scan can be presented for annotation by utilizing the medical scan assisted review system 102, for example, presented in the new annotation mode. The interactive interface 275 can present the medical scan by utilizing interface features indicated in the display parameter data 470 and/or the interface preference data 560 of the user, and/or the user can indicate the annotation data via the interactive interface 275 by utilizing interface features indicated in the display parameter data 470 and/or the interface preference data 560 of the user. For example, some or all of the annotation data 1020 can correspond to, or be automatically generated based on, the scan review data 810 generated based on the user input.

Annotation data 1020 can be transmitted from each client device of users in the selected user set 1010 to the medical scan annotator system 106, for example, in response to receiving input data via the interactive interface indicating that the annotations are complete. The annotation data 1020 can be raw annotation data corresponding directly to the user input, or can be further processed by the client device before transmission. For example, a more precise region corresponding to each abnormality can be determined automatically based on the user input and by determining actual boundary points of the abnormality by utilizing image processing techniques and/or text and/or voice input can be processed and/or parsed, for example, by utilizing a medical scan natural language analysis function and/or medical report analysis function to generate medical codes 447 or other diagnosis data 440 corresponding to the medical scan. Such processing can also be performed by the medical scan annotation system 106 and/or another subsystem when the raw annotation data is received.

The medical scan annotator system 106 can evaluate the set annotation data 1020 received from the selected user set 1010 to determine if a consensus is reached, and/or generate a final consensus annotation 1030, for example, by performing an annotation consensus function 1040. For example, consider a selected user set 1010 that includes three users. If two users annotate a medical scan as "normal" and the third user annotates the medical scan as "contains abnormality", the annotation consensus function 1040 performed by medical scan annotator system 106 may determine that the final consensus annotation 1030 is "normal" by following a majority rules strategy. Alternatively, the medical scan annotator system 106 can determine that a consensus is not reached because one of the users indicated that an abnormality is present, and that the medical scan should not be passed off as normal because a level of confidence that the scan is normal, determined by a calculated consensus confidence score 1050, does not exceed a consensus confidence threshold. The confidence thresholds required for consensus can differ for different types of scans and/or severity of diagnosis.

If the medical scan annotator system 106 determines that a consensus is achieved, it can automatically generate the final consensus annotation 1030, and can map this final consensus annotation to the medical image in the medical scan database in diagnosis data 440, and/or transmit the consensus annotation to an originating entity of the medical scan. The medical scan annotator system 106 can also map the calculated consensus confidence score to the medical image in the confidence score data 460. In some embodiments, a truth flag 461 will automatically be assigned to all final consensus annotation 1030 in the confidence score data 460 and/or will automatically be assigned to final consensus annotation 1030 that exceeds a truth threshold. In some embodiments, annotation data 1020 received from each user and/or a corresponding annotation confidence score can also be stored in the medical database, mapped to the corresponding user and/or the corresponding performance score in the annotation author data 450.

In some embodiments, for example where annotation data 1020 includes several attributes, the annotation consensus function 1040 performed by the medical scan annotation system 106 can determine whether a consensus is reached by calculating a difference between two or more received annotation data 1020, for example, by generating a feature vector for annotation data 1020 received from each user. Each feature vector can be generated based on keywords, medical codes, abnormality location in the medical scan, abnormality size and/or shape in the medical scan, a classification of the abnormality, or other attributes listed in annotation data 1020 received from each user. Performing the annotation consensus function 1040 can further include calculating the Euclidian distance or other vector distance between the two or more feature vectors. Performing the annotation consensus function 1040 can further include determining if consensus is reached by determining if the average of these Euclidian distances is below a certain discrepancy threshold, for example, after determining and removing outlier annotations from the set. Similarly, the annotation consensus function 1040 can further include determining if consensus is reached by first generating the final consensus annotation 1030, and then calculating the Euclidian distance between each annotation feature vector and the final consensus annotation 1030, where consensus is determined to reached and the final consensus annotation is confirmed only if the average of these calculated Euclidian distances is below a certain discrepancy threshold. The annotation consensus function 1040 can calculate the final consensus annotation 1030 itself by creating a consensus feature vector, where each attribute of the consensus feature vector is determined by calculating a mean, median or mode of each corresponding annotation feature extracted from all of the received annotation data 1020. In this fashion, calculating the consensus confidence score 1050 can include calculating such an average Euclidian distance, where distances with larger magnitudes correspond to lower or otherwise less favorable consensus confidence scores 1050, and where distances with smaller magnitudes correspond to higher or otherwise more favorable consensus confidence scores 1050. Alternatively or in addition, the final consensus annotation 1030 can be generated based on the most closely matching annotations and/or based on another average, for example, calculating an average identified region that includes an abnormality.

The annotation consensus function 1040 further determine whether or not consensus is reached based on overall or categorized performance score data 530 and/or qualification data 540 of each user in the selected user set 1010. For example, each annotation data 1020 can be weighted based the performance scores and/or qualifications of the corresponding user. In the example where two users annotate a medical scan as "normal" and a third user annotates a medical scan as "contains abnormality", the medical scan annotator system 106 may determine that the consensus is "contains abnormality" based on the third user having a much higher performance score and/or being more highly qualified than the first two users. The final consensus annotation 1030 can be generated based on the annotation received from a user with the highest ranking in the category corresponding to the medical scan. The final consensus annotation 1030 can be generated based on calculating a weighted average annotation by computing a weighted consensus feature vector, where feature vectors of higher ranked users receive a higher weight. In some embodiments, each feature of the feature vector can be computed using a different set of user weights, for example, where the different feature weights for each user is determined based on corresponding category-based performance score data and/or qualification data.

Alternatively or in addition, the performance score data 720 associated with the interface features of the interactive interface 275 used by each user to annotate the image can also be utilized to weight the different annotations in reaching consensus. Such weights can be applied when generating a consensus feature vector, where each annotation feature vector is weighted according to the performance score data 720 of one or more corresponding interface features used by the corresponding user.

In some embodiments, confidence scores for each individual annotation can also be calculated for each user's annotation, and the consensus confidence score 1050 can be generated based on these confidence scores, for example, based on an average confidence score, based on confidence scores of annotation data that matches the final consensus annotation 1030, etc. In some embodiments, the final consensus annotation 1030 can be generated based on these confidence scores, for example, where annotation feature vectors are weighted based on a corresponding confidence score. The confidence scores for each annotation data 1020 can be generated automatically, for example, based on performance score data 530 and/or performance score data 720 as discussed herein. Individual confidence scores and/or a consensus confidence score 1050 can also be updated retroactively as new annotation data is received, for example, if new annotation data is received from another user, for example corresponding to an expert review when consensus is not reached, and/or if new annotation data is automatically generated by a subsystem after the consensus data is generated.

The medical scan annotator system 106 can also utilize auto-generated annotation data of the medical scan to determine if consensus is reached and/or to generate the final consensus annotation 1030. The auto-generated annotation data can be automatically generated by medical scan annotator system 106 by utilizing one or more medical scan analysis functions. The auto-generated annotation data can also be retrieved from the medical scan database 342 if it was generated by a subsystem 101 previously. One or more auto-generated annotations can be assigned their own weights and/or confidence scores, for example, based on the model accuracy data 631 and/or another determined performance of the function and/or subsystem responsible for creating each auto-generated annotation. Each auto-generated annotation data can be thus treated as an annotation from another user, and can be used to determine if consensus is reached and/or to generate the consensus annotation in the same fashion.

Alternatively, the auto-generated annotation can be merely verified based on the annotation data 1020 received from the selected user set 1010 by determining that the user annotations are close enough to the auto-generated annotation based on the discrepancy threshold. For example, this process may be utilized by the medical scan diagnosing system 108 to perform the output quality assurance step 1107. The auto-generated annotation can be sent to the selected user set 1010 as part of this verification process, for example, displayed by each interactive interface 275 in conjunction with the medical scan assisted review system 102 as displayed annotation data 820, and the annotation data 1020 received from the selected user set 1010 can be include verification of and/or corrections of the auto-generated annotation. Alternatively, the medical scan can be sent without the auto-generated annotation and/or the auto-generated annotation can be hidden from view as part of a blind review, to ensure that the users are not biased in creating annotation data by the auto-generated annotation.

FIG. 10B illustrates an embodiment of the medical scan annotator system 106 upon determining that a consensus is not achieved, for example, because the calculated consensus confidence score 1050 does not exceed the consensus confidence threshold. The medical scan annotator system can select an expert user, for example, a user whose qualification data 540 indicates they are an expert in the category corresponding to the medical scan or who otherwise is identified as an expert based on their performance score data. The expert can receive the medical scan on a corresponding client device and annotate the image, for example, where the interactive interface 275 displays the medical scan image data 410 in conjunction with the medical scan assisted review system 102 and where the expert's annotations correspond to the scan review data 810, and where the interactive interface utilizes interface features indicated in the display parameter data 470 of the medical scan and/or indicated in the interface preference data 560 of the user profile entry 354 of the expert user. The expert can view the annotation data 1020 generated by the selected user set 1010, for example, presented as the displayed annotation data 820 of the medical scan assisted review system 102. Annotation data 1020 of each user can be displayed one at a time and the expert user can elect to advance to the next user's annotation data 1020. Alternatively, all of the annotation data 1020 can be displayed simultaneously for example, in different colors corresponding to each user's annotations and/or overlaid as translucent, highlighted regions, for example, where a portion of the highlighted region is more opaque when multiple users agree that the portion is included in the abnormality. In other embodiments, the annotation data 1020 can be hidden from the expert user, and the expert user can enter their own annotations in conjunction with a blind review to reduce bias.

Expert annotation data 1070 can be generated automatically, for example included in the scan review data 810, and can be transmitted automatically to the medical scan annotation system 106. The medical scan annotator system can automatically assign the received expert annotation data 1070 as the final consensus annotation 1030, and/or can assign a truth flag 461 to the expert annotation data 1070 in the confidence score data 460 of the medical scan. Alternatively, the expert annotation data 1070 can be compared to the previous annotation data 1020 and determine if consensus has been reached. For example, the expert annotation data 1070 and the annotation data 1020 can be collectively utilized by the annotation consensus function 1040, where the expert annotation data 1070 is assigned its own, higher weight than the other annotations. If consensus has still not been reached, the medical scan annotation system can continue to transmit the image other users and processing received annotations until consensus is reached, for example, selecting a new selected user set 1010 and/or selecting a new expert user.

The user profile entries 354 of each user in the selected user set 1010 and/or each expert user can be automatically updated by the medical scan annotator system 106 or another subsystem 101 by generating and/or updating performance score data 530 for each user based comparing their annotation to the final consensus annotation 1030. For example, the accuracy score data 531 of the performance score data 530 can be generated by calculating the Euclidian distance between a feature vector of a user's annotation and the feature vector of the consensus annotation as described previously, where a higher performance score is assigned to a user whose annotation is a smaller Euclidian distance from the consensus, and a lower performance score is assigned to a user whose annotation is a larger Euclidian distance from the consensus. The efficiency score data 532 of the performance score data can be automatically generated, for example, based on an annotation duration determined based on a difference between a first time that each user received the medical scan and a second time each user completed the annotation. The efficiency score data 532 can be further based on a difference between the annotation duration of each user and an average annotation duration computed for annotation durations of the selected user set. Aggregate performance data for each user can be generate and/or updated based on past accuracy and/or efficiency scores, based on how many scans have been annotated in total, based on measured improvement of the user over time, etc. Similarly, the performance score data 630 corresponding to medical scan analysis functions utilized to generate the auto-generated annotation data can be generated and/or updated by comparing the auto-generated annotation data to the final consensus annotation 1030 in a similar fashion and/or by comparing the computed annotation duration of a corresponding medical scan analysis functions to other computed annotation durations of other medical scan analysis functions that generated auto-generated annotation data for the medical scan.

The selected user set 1010 can be selected based on the performance score data 530 and/or qualification data 540 of each user corresponding to previous uses only the medical scan annotation system 106, or corresponding to usage of several subsystems 101. For example, a medical professional with a user profile indicating that he/she ranks above a certain threshold in annotating CT scans and/or indicating that he/she is highly qualified in the study of the lungs can be automatically selected by the medical scan annotator system to annotate a triaged medical scan identified as a lug CT scan. The size of the selected user set 1010 that receive a medical scan can be optimized based on the quality of the users selected, for example, based on calculating the probability of reaching consensus and/or calculating the probability that a consensus confidence score will be above a confidence threshold, and ensuring the probability falls above a probability threshold. For example, a first medical scan can be sent to a two medical professionals with high scores, qualifications, rankings, or correct annotation percentages. A second medical scan may be sent to ten medical professionals with lower scores or qualifications based on calculating that the probability of a correct consensus probability falls above a probability threshold.

In some embodiments, the medical scan annotator system 106 can first select a medical scan for annotation automatically, and in response, the selected user set 1010 can be determined automatically to annotate the selected medical scan based on determining users with highly ranked overall scores and/or based on categorized performance data 534 and/or qualification data 540 that corresponds to an identified scan classifier data 420 of the selected medical scan. Alternatively or in addition, the selected user set 1010 can be determined based on the size of a queue of medical scans already assigned to each user. For example, the selected user set 1010 can correspond to users with matching qualifications that correspond to the scan classifier data 420 and/or correspond to users with the lowest queues of other medical scans to annotate.

In other embodiments, the medical scan annotator system 106 can first determine one or more available users automatically, for example, based on medical scan queue lengths for each user in the system and/or in response to one or more users requesting to annotate a medical scan. In such cases, some or all of these identified users can be added to the selected user set 1010, and the medical scan can be selected based on corresponding categorized performance data 534, qualification data 540 or other relevant user profile data of users in the selected user set 1010.

Figure 10C:
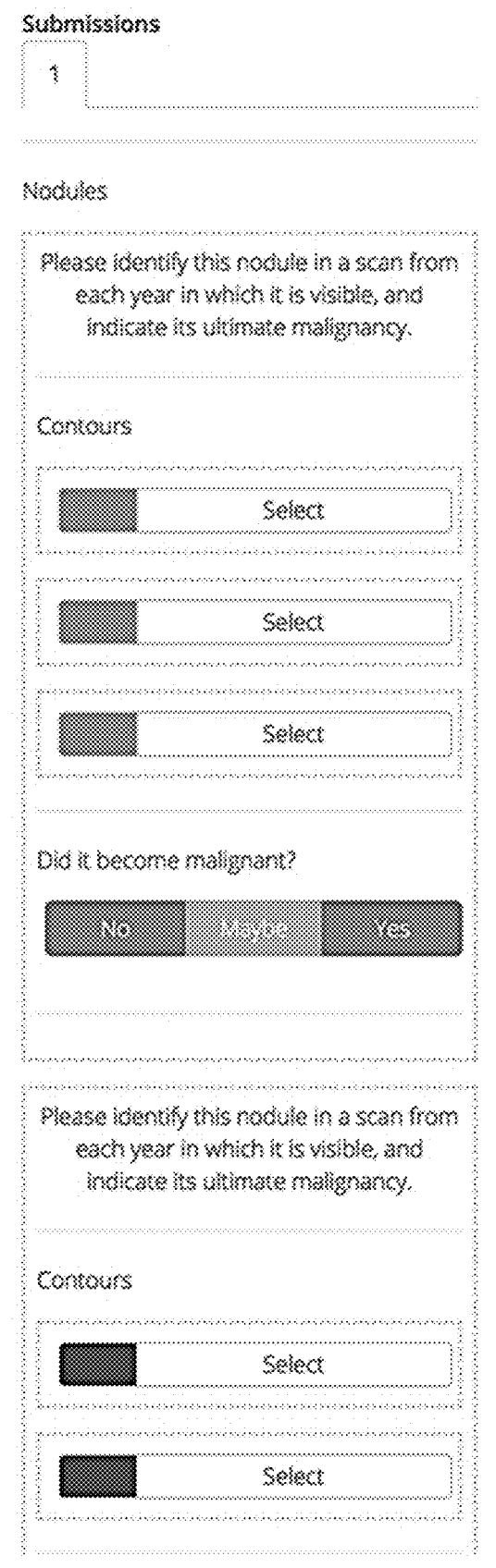
Figure 10K:
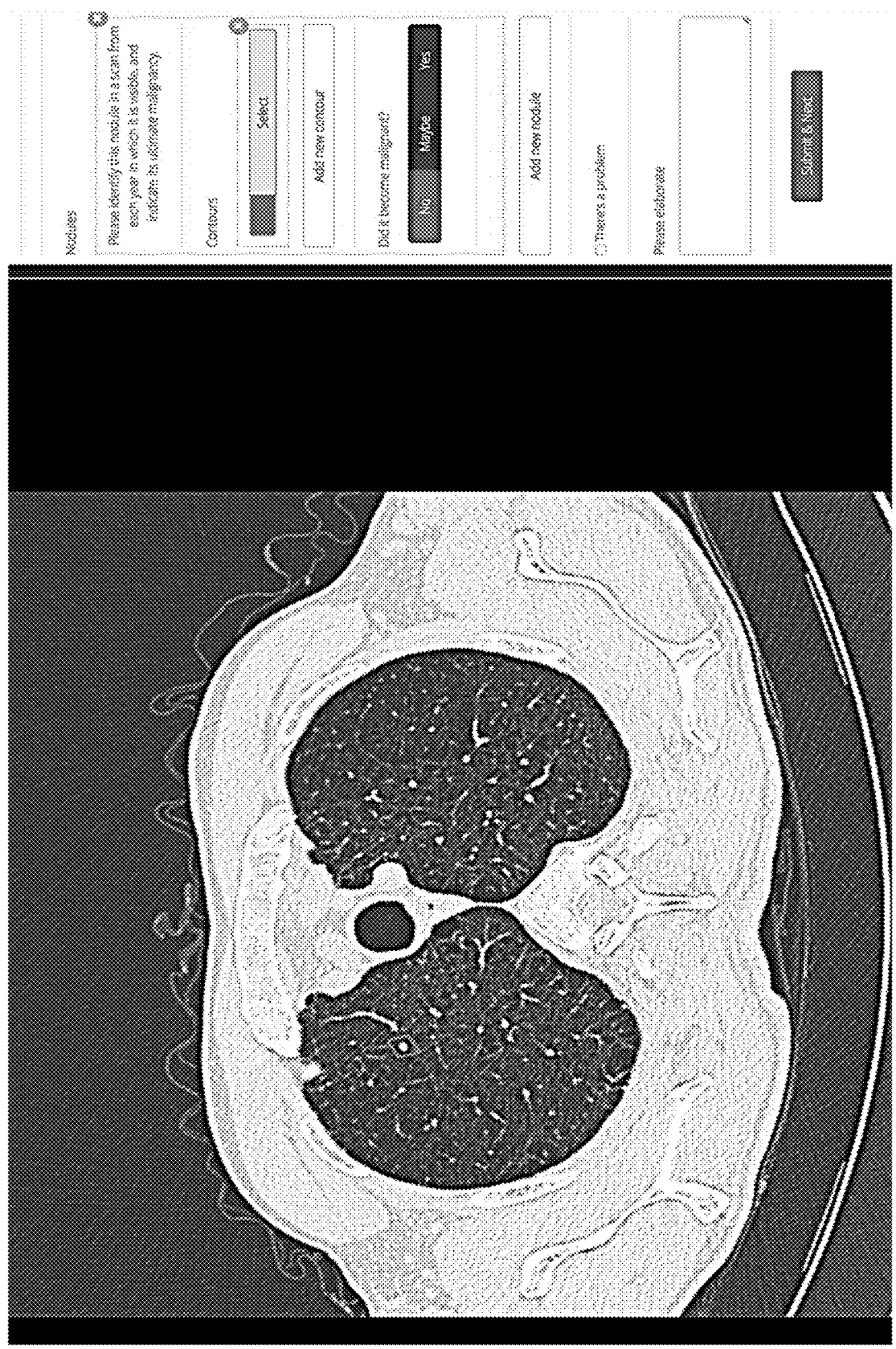
FIGS. 10C-10V are graphical illustrations of an example interactive interface displayed on a client device in conjunction with various embodiments.
Figure 10L:
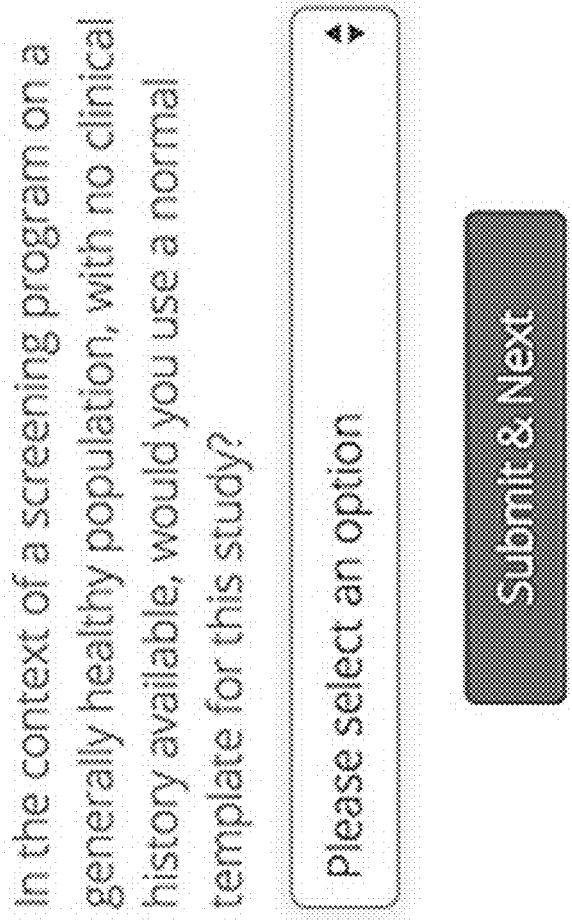
Figure 10M:
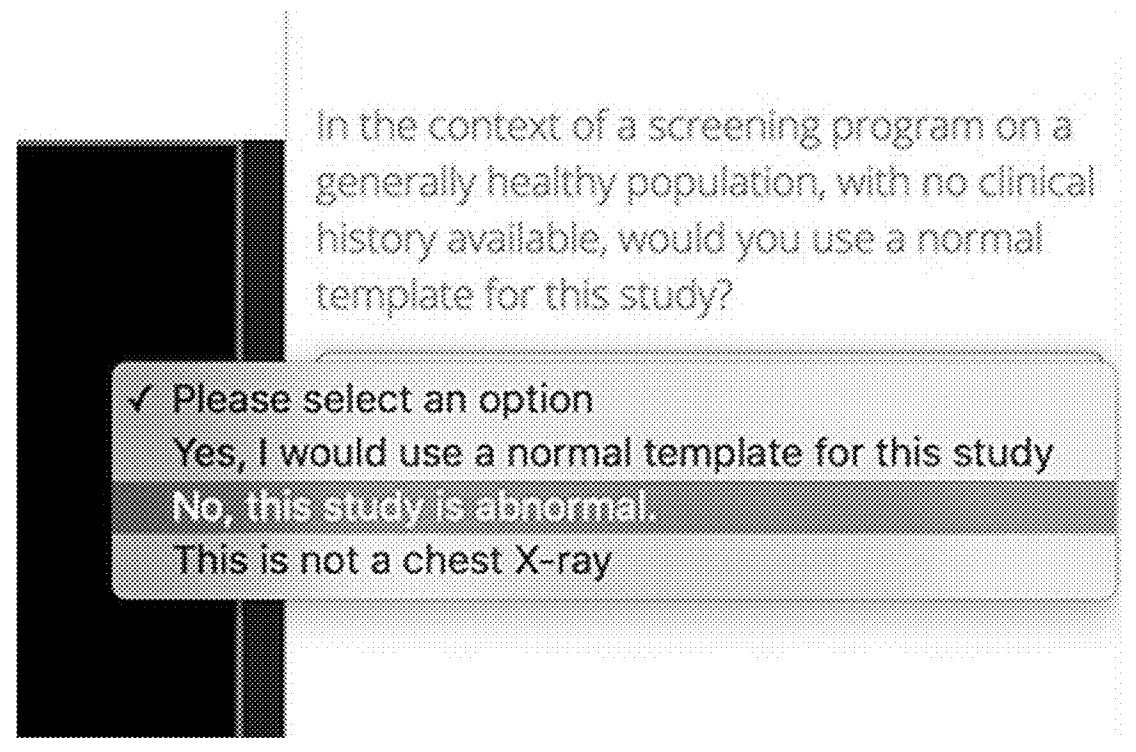
Figure 10O:
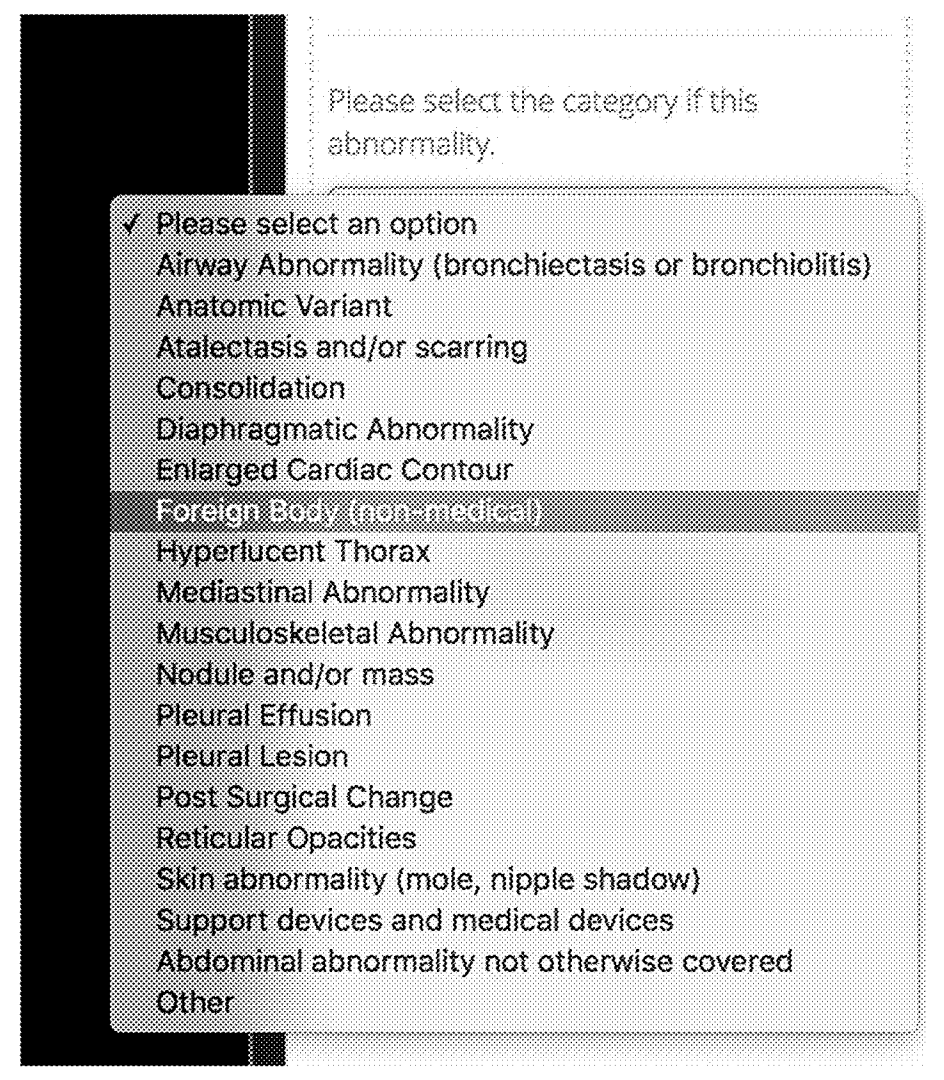

FIGS. 10C-10V present example embodiments of a user interface of a medical scan annotator system 106, for example, presented in conjunction with the medical scan assisted review system 102. Some or all features presented in FIGS. 10C-10V can also be utilized in conjunction with other subsystems and can be included in the interface features. FIGS. 10C-10G present interface features for chest CT nodule characterization, and can be displayed in conjunction with a chest CT scan, for example, as presented in FIGS. 8B-8S. Annotation data 1020 can be generated based on user selections in the user interface, and can be used to populate abnormality classification data 445 for abnormality classifier categories 444 such as "nodule spiculation", "nodule lobulation", "nodule texture", "nodule calcification", "nodule sphericity" and/or "nodule internal structure" for the associated medical scan. FIGS. 10H-10J present interface features for presentation to a user in conjunction with an identifying chest CT nodule, allowing a user to add new contours for one or more scans for a patient, for example, over multiple years, and indicate malignancy. As shown in FIG. 10K, the scan can be presented in conjunction with these interface features. FIGS. 10L-10O present interface features for presentation to a user in conjunction with identifying abnormalities in a chest x-ray. Users can classify each abnormality and draw a shape around each abnormality in the scan.

Figure 10P:
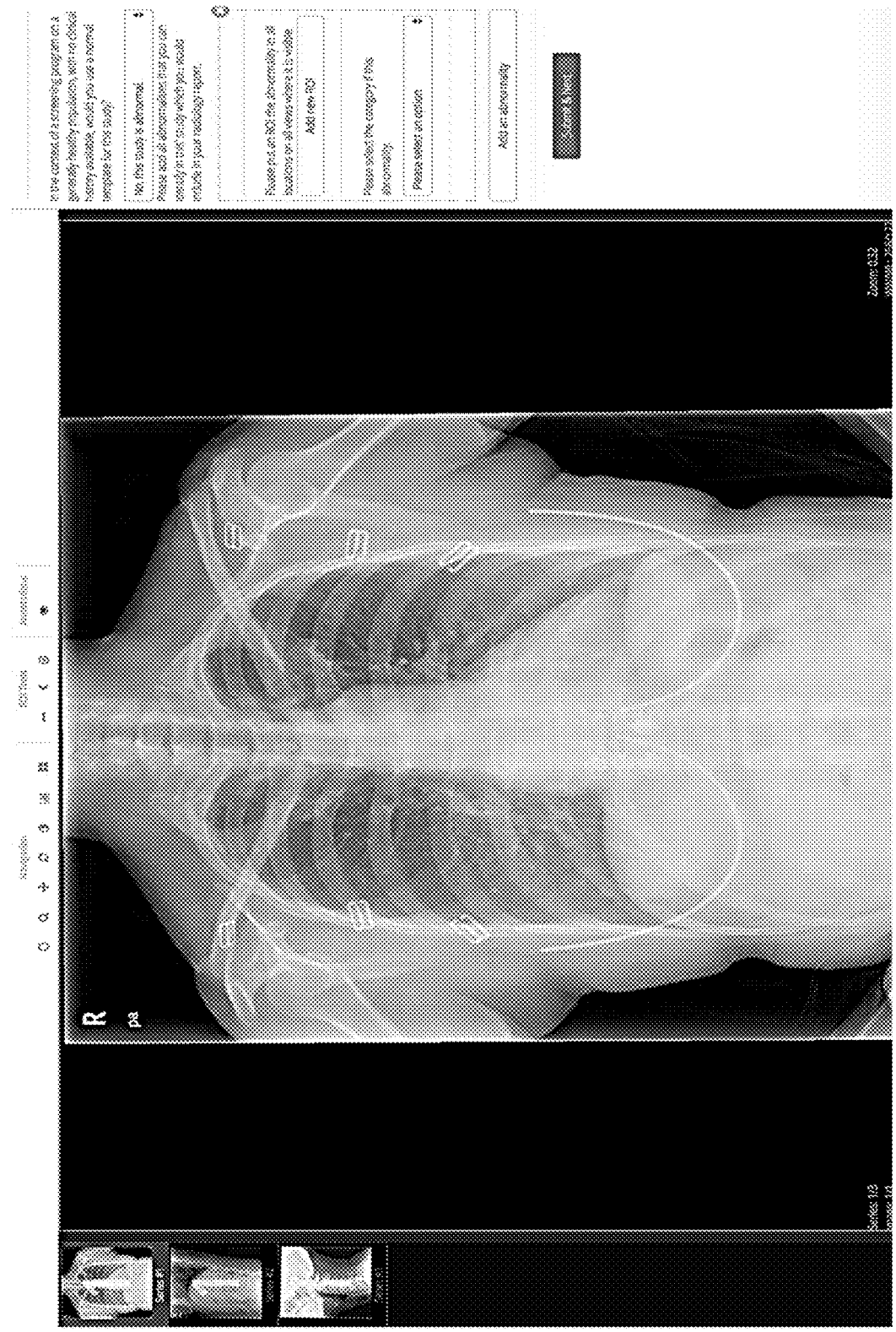
Figure 10Q:
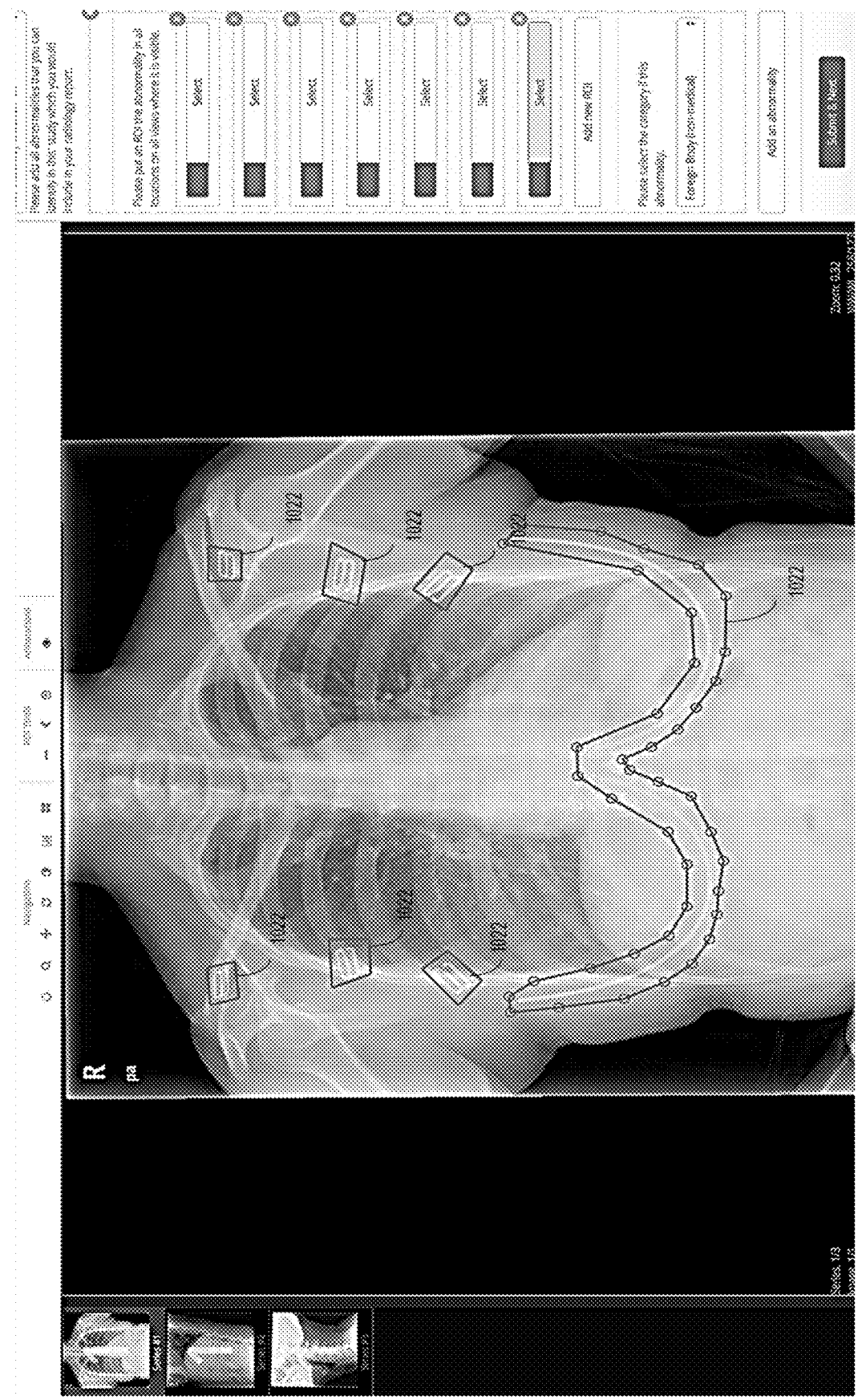

FIG. 10P presents a view of a chest x-ray presented via the interface before a user identifies regions of interest, and FIG. 10Q presents a view of the chest x-ray via the interface after the user identifies regions of interest of multiple abnormalities, indicated by seven polygons 1022. The user can generate polygons as described in conjunction with FIGS. 8P-8R. FIG. 10R presents interface features for comparing chest x-ray severity for multiple patients, displayed in conjunction with multiple x-rays that can be displayed in adjacent views or can be displayed one at a time where the user can toggle between them. A user can compare multiple scans corresponding to multiple patients, and provide feedback indicating differences between the patients, comparing if one patient's case is more severe than another, or determine which of two scans appears to be more normal.

FIGS. 10S-10V present interface features for chest x-ray triage classification, displayed in conjunction with a chest x-ray. A user can select abnormality classification data that can be used to generate annotation data 1020 and/or to populate abnormality classification data 445. As shown, some or all abnormality classification categories displayed, which can be determined based on abnormality classifier categories 444, can be presented, and hierarchal subcategories can be presented in response to a user selecting one of a plurality of abnormality classification categories that are present.

Figure 11A:
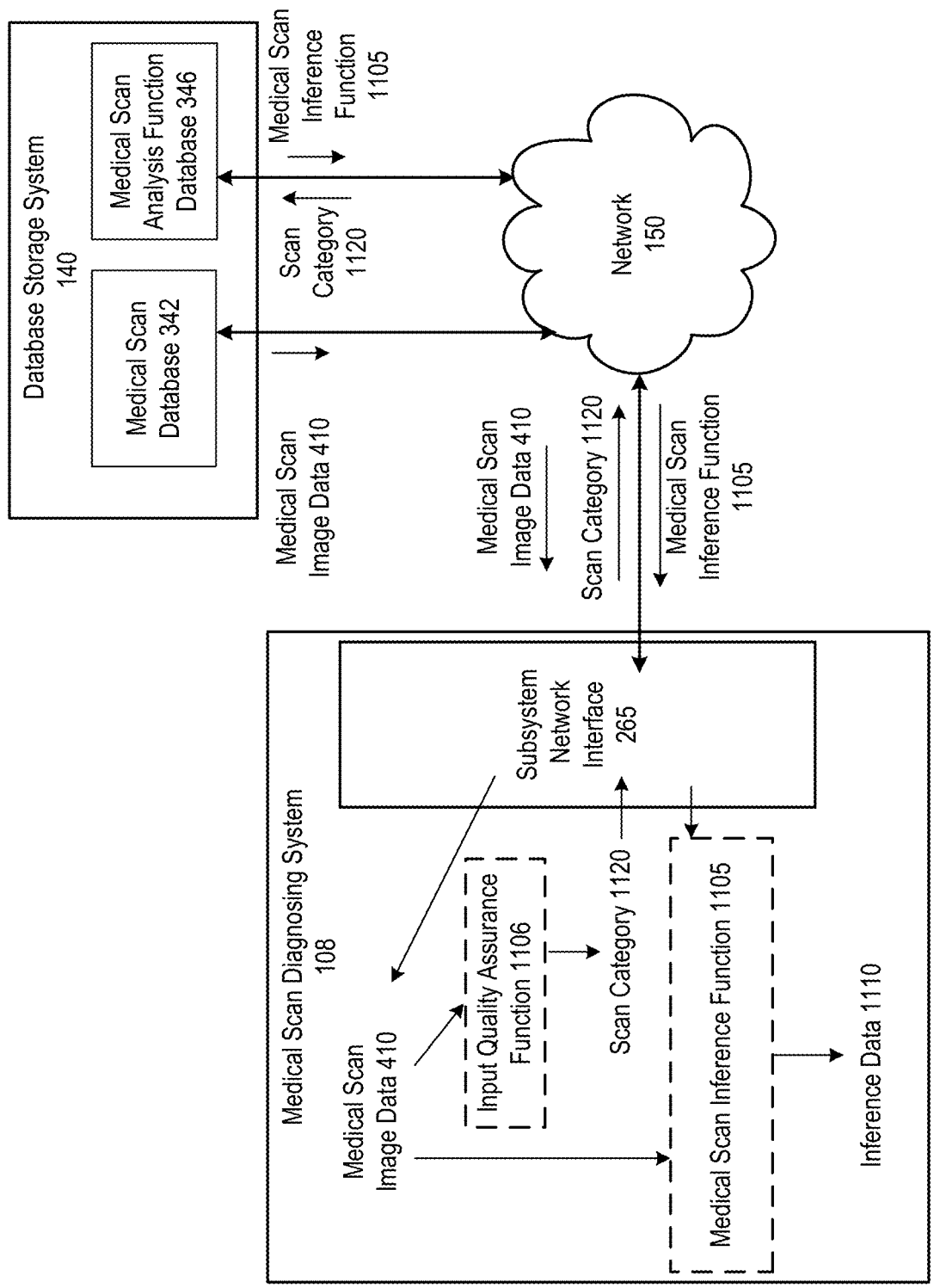
FIGS. 11A-11C are schematic block diagram of a medical scan diagnosing system in accordance with various embodiments.
Figure 11B:
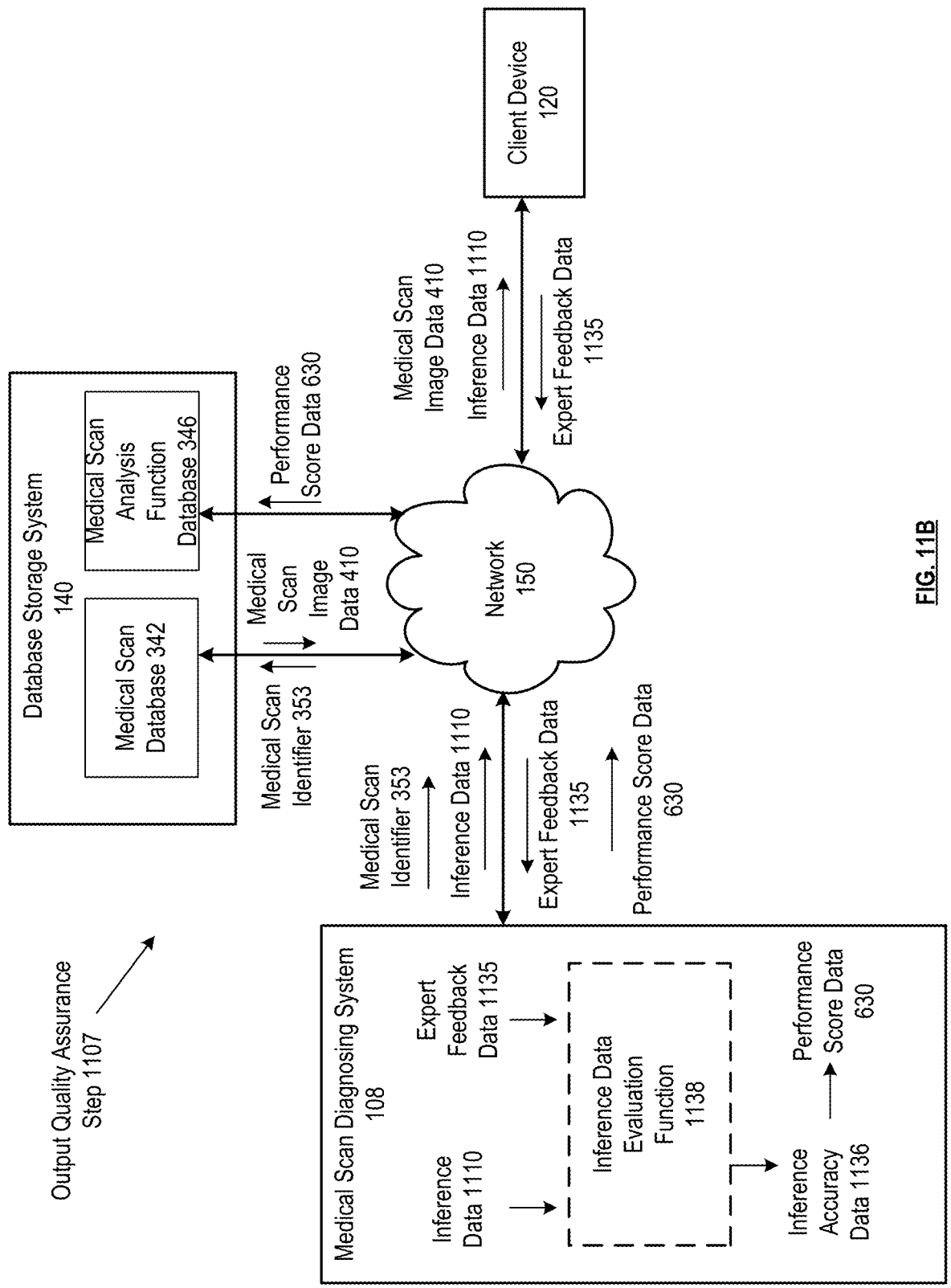

FIGS. 11A and 11B present an embodiment of a medical scan diagnosing system 108.

A medical scan diagnosing system 108 can be used by hospitals, medical professionals, or other medical entities to automatically produce inference data 1110 for given medical scans by utilizing computer vision techniques and/or natural language processing techniques. This automatically generated inference data 1110 can be used to generate and/or update diagnosis data 440 or other corresponding data of the corresponding medical scan entry 352. The medical scan diagnosing system can utilize the medical scan database 342, user database 344, and/or medical scan analysis function database 346 by communicating with the database storage system 140 via the network 150, and/or can utilize another medical scan database, user database, and/or function database stored in local memory.

In various embodiments, the medical scan diagnosing system 108 is operable to receive a medical scan. Diagnosis data of the medical scan is generated by performing a medical scan inference function on the medical scan. The first medical scan is transmitted to a first client device associated with a user of the medical scan diagnosing system in response to the diagnosis data indicating that the medical scan corresponds to a non-normal diagnosis. The medical scan is displayed to the user via an interactive interface displayed by a display device corresponding to the first client device. Review data is received from the first client device, where the review data is generated by the first client device in response to a prompt via the interactive interface. Updated diagnosis data is generated based on the review data. The updated diagnosis data is transmitted to a second client device associated with a requesting entity.

The medical scan diagnosing system 108 can generate inference data 1110 for medical scans by utilizing a set of medical scan inference functions 1105, stored and run locally, stored and run by another subsystem 101, and/or stored in the medical scan analysis function database 346, where the function and/or parameters of the function can be retrieved from the database by the medical scan diagnosing system. For example, the set of medical scan inference function 1105 can include some or all medical scan analysis functions described herein or other functions that generate inference data 1110 based on some or all data corresponding to a medical scan such as some or all data of a medical scan entry 352. Each medical scan inference function 1105 in the set can correspond to a scan category 1120, and can be trained on a set of medical scans that compare favorably to the scan category 1120. For example, each inference function can be trained on a set of medical scans of the one or more same scan classifier data 420, such as the same and/or similar scan types, same and/or similar anatomical regions locations, same and/or similar machine models, same and/or similar machine calibration, same and/or similar contrasting agent used, same and/or similar originating entity, same and/or similar geographical region, and/or other classifiers. Thus, the scan categories 1120 can correspond to one or more of a scan type, scan anatomical region data, hospital or other originating entity data, machine model data, machine calibration data, contrast agent data, geographic region data, and/or other scan classifying data 420. For example, a first medical scan inference function can be directed to characterizing knee x-rays, and a second medical scan inference function can be directed to chest CT scans. As another example, a first medical scan inference function can be directed to characterizing CT scans from a first hospital, and a second medical scan image analysis function can be directed to characterizing CT scans from a second hospital.

Training on these categorized sets separately can ensure each medical scan inference function 1105 is calibrated according to its scan category 1120, for example, allowing different inference functions to be calibrated on type specific, anatomical region specific, hospital specific, machine model specific, and/or region specific tendencies and/or discrepancies. Some or all of the medical scan inference functions 1105 can be trained by the medical scan image analysis system and/or the medical scan natural language processing system, and/or some medical scan inference functions 1105 can utilize both image analysis and natural language analysis techniques to generate inference data 1110. For example, some or all of the inference functions can utilize image analysis of the medical scan image data 410 and/or natural language data extracted from abnormality annotation data 442 and/or report data 449 as input, and generate diagnosis data 440 such as medical codes 447 as output. Each medical scan inference function can utilize the same or different learning models to train on the same or different features of the medical scan data, with the same or different model parameters, for example indicated in the model type data 622 and model parameter data 623. Model type and/or parameters can be selected for a particular medical scan inference function based on particular characteristics of the one or more corresponding scan categories 1120, and some or all of the indicated in the model type data 622 and model parameter data 623 can be selected automatically by a subsystem during the training process based on the particular learned and/or otherwise determined characteristics of the one or more corresponding scan categories 1120.

As shown in FIG. 11A, the medical scan diagnosing system 108 can automatically select a medical scan for processing in response to receiving it from a medical entity via the network. Alternatively, the medical scan diagnosing system 108 can automatically retrieve a medical scan from the medical scan database that is selected based on a request received from a user for a particular scan and/or based on a queue of scans automatically ordered by the medical scan diagnosing system 108 or another subsystem based on scan priority data 427.

Once a medical scan to be processed is determined, the medical scan diagnosing system 108 can automatically select an inference function 1105 based on a determined scan category 1120 of the selected medical scan and based on corresponding inference function scan categories. The scan category 1120 of a scan can be determined based one some or all of the scan classifier data 420 and/or based on other metadata associated with the scan. This can include determining which one of the plurality of medical scan inference functions 1105 matches or otherwise compares favorably to the scan category 1120, for example, by comparing the scan category 1120 to the input scan category of the function classifier data 610.

Alternatively or in addition, the medical scan diagnosing system 108 can automatically determine which medical scan inference function 1105 is utilized based on an output preference that corresponding to a desired type of inference data 1110 that is outputted by an inference function 1105. The output preference designated by a user of the medical scan diagnosing system 108 and/or based on the function of a subsystem 101 utilizing the medical scan diagnosing system 108. For example, the set of inference functions 1105 can include inference functions that are utilized to indicate whether or not a medical scan is normal, to automatically identify at least one abnormality in the scan, to automatically characterize the at least one abnormality in the scan, to assign one or more medical codes to the scan, to generate natural language text data and/or a formatted report for the scan, and/or to automatically generate other diagnosis data such as some or all of diagnosis data 440 based on the medical scan. Alternatively or in addition, some inference functions can also be utilized to automatically generate confidence score data 460, display parameter data 470, and/or similar scan data 480. The medical scan diagnosing system 108 can compare the output preference to the output type data 612 of the medical scan inference function 1105 to determine the selected inference function 1105. For example, this can be used to decide between a first medical scan inference function that automatically generates medical codes and a second medical scan inference function that automatically generates natural language text for medical reports based on the desired type of inference data 1110.

Prior to performing the selected medical scan inference function 1105, the medical scan diagnosing system 108 can automatically perform an input quality assurance function 1106 to ensure the scan classifier data 420 or other metadata of the medical scan accurately classifies the medical scan such that the appropriate medical scan inference function 1105 of the appropriate scan category 1120 is selected. The input quality assurance function can be trained on, for example, medical scan image data 410 of plurality of previous medical scans with verified scan categories. Thus, the input quality assurance function 1106 can take medical scan image data 410 as input and can generate an inferred scan category as output. The inferred scan category can be compared to the scan category 1120 of the scan, and the input quality assurance function 1106 can determine whether or not the scan category 1120 is appropriate by determining whether the scan category 1120 compares favorably to the automatically generated inferred scan category. The input quality assurance function 1106 can also be utilized to reassign the generated inferred scan category to the scan category 1120 when the scan category 1120 compares favorably to the automatically generated inferred scan category. The input quality assurance function 1106 can also be utilized to assign the generated inferred scan category to the scan category 1120 for incoming medical scans that do not include any classifying data, and/or to add classifiers in scan classifier data 420 to medical scans missing one or more classifiers.

Alternatively or in addition, performing the input quality assurance function 1106 can include performing a selected one of a plurality of classifier verification functions corresponding to the scan category 1120 to determine a binary verification value indicating whether the assigned scan category 1120 is accurate. Each verification function can be trained on a set of medical scans known to be correctly classified with the corresponding scan category 1120, for example, where a knee x-ray verification function is trained on a plurality of scans classified as "knee x-rays", and in some embodiments, is also trained on a plurality of medical scans that are classified as "not knee x-rays." In some embodiments, each verification function can be trained on the medical scan image data 410 and the binary indicator of whether or not the scan is assigned to the corresponding scan category 1120.

In various embodiments, upon utilizing the input quality assurance function 1106 to determining that the scan category 1120 determined by a scan's scan classifier data 420 or other metadata is inaccurate, the medical scan diagnosing system 108 can transmit an alert and/or an automatically generated inferred scan category to the medical entity indicating that the scan is incorrectly classified in the scan classifier data 420 or other metadata. In some embodiments, the medical scan diagnosing system 108 can automatically update performance score data 530 corresponding to the originating entity of the scan indicated in originating entity data 423, or another user or entity responsible for classifying the scan, for example, where a lower performance score is generated in response to determining that the scan was incorrectly classified and/or where a higher performance score is generated in response to determining that the scan was correctly classified.

In some embodiments, the medical scan diagnosing system 108 can transmit the medical scan and/or the automatically generated inferred scan category to a selected user. The user can be presented the medical scan image data 410 and/or other data of the medical scan via the interactive interface 275, for example, displayed in conjunction with the medical scan assisted review system 102. The interface can prompt the user to indicate the appropriate scan category 1120 and/or prompt the user to confirm and/or edit the inferred scan category, also presented to the user. For example, scan review data 810 can be automatically generated to reflect the user generated and/or verified scan category 1120, This user indicated scan category 1120 can be utilized to select to the medical scan inference function 1105 and/or to update the scan classifier data 420 or other metadata accordingly. In some embodiments, for example, where the scan review data 810 indicates that the selected user disagrees with the automatically generated inferred scan category created by the input quality assurance function 1106, the medical scan diagnosing system 108 can automatically update performance score data 630 of the input quality assurance function 1106 by generating a low performance score and/or determine to enter the remediation step 1140 for the input quality assurance function 1106.

The medical scan diagnosing system 108 can also automatically perform an output quality assurance step 1107 after a medical scan inference function 1105 has been performed on a medical scan to produce the inference data 1110, as illustrated in the embodiment presented in FIG. 11B. The output quality assurance step 1107 can be utilized to ensure that the selected medical scan inference function 1105 generated appropriate inference data 1110 based on expert feedback. The inference data 1110 generated by performing the selected medical scan inference function 1105 can be sent to a client device 120 of a selected expert user, such as an expert user in the user database selected based on categorized performance data 534 and/or qualification data 540 that corresponds to the scan category 1120 and/or the inference itself, for example, by selecting an expert user best suited to review an identified abnormality classifier category 444 and/or abnormality pattern category 446 in the inference data 1110 based on the categorized performance data 534 and/or qualification data 540. The selected user can also correspond to a medical professional or other user employed at the originating entity and/or corresponding to the originating medical professional, indicated in the originating entity data 423.

The medical scan and/or the inference data 1110 can be displayed to the selected expert user via the interactive interface 275 displayed by a display device corresponding to the client device 120 of the expert user, for example, in conjunction with the medical scan assisted review system 102. Inference data 1110 can displayed in conjunction with medical scan image data 410 as displayed annotation data

820 by utilizing one or more interface features indicated by interface preference data 560 of the expert user, the display parameter data 470 of the medical scan, or other display parameters automatically generated by the medical scan inference function 1105. In other embodiments, a blind review is utilized, and the inference data 1110 can be hidden from the expert user.

The client device can generate expert feedback data 1135, such as scan review data 810, for transmission back to the medical scan diagnosing system 108, where the expert feedback data 1135 is generated based on user input to the interactive interface entered in response to a prompt displayed by the display device via the interactive interface 275 to provide the expert feedback data by utilizing one or more interface features indicated by interface preference data 560 of the expert user, the display parameter data 470 of the medical scan, or other display parameters automatically generated by the medical scan inference function 1105. The expert feedback data 1135 can include indications of whether or not the inference data is correct and/or edits of the inference data 1110. In the case where a blind review is utilized, expert user can enter their own annotations without being biased by the inference data 1110 generated by the medical scan inference function 1105, and the expert feedback data 1135 can include these expert annotations.

The medical scan diagnosing system 108 can evaluate the expert feedback data 1135 to generate inference accuracy data 1136, indicating whether or not the inference data 1110 is accurate, by performing an inference data evaluation function 1138. If the inference data 1110 is determined to be accurate, the diagnosis data 440 or other data corresponding to the medical scan can be updated accordingly based on the inference data 1110, and/or the inference data can be transmitted to the originating entity or other requesting entity. If the inference data 1110 is determined to be inaccurate, the inference data can be automatically modified based on the expert feedback data received from the client device, and the modified inference data 1110 and/or diagnosis data indicated in the expert feedback data 1135 can be mapped to the medical scan in the diagnosis data 440.

Inference accuracy data 1136 can also be based on a determined discrepancy determined by performing the inference data evaluation function 1138. For example, the inference accuracy data 1136 can be based on a magnitude of the difference between the inference data 1110 and the expert feedback data, and can be mapped to the medical scan. The inference accuracy data 1136 can be further based on confidence data, determined based on an inference confidence score corresponding to the inference data 1110, for example, automatically generated by the medical scan inference function 1105 in conjunction with generating the inference data 1110 and/or based on the performance score data 630 of the medical scan inference function 1105 that was utilized. The inference accuracy data 1136 can be further based on a confidence score generated for the expert review data and/or can be based on performance score data 530 corresponding to the expert user.

In some embodiments, performing the inference data evaluation function 1138 can include performing the annotation consensus function 1040 or utilizing other features of the medical scan annotator system 106 to determine whether or not consensus is reached between the inference data 1110 and the expert feedback data 1135, for example, by determining whether or not a calculated consensus confidence score 1050 exceeds a consensus confidence threshold as described herein. The inference accuracy data 1136 can be based on the consensus confidence score 1050. In some embodiments, inference data 1110 can be replaced with the final consensus annotation 1030 generated by performing the annotation consensus function 1040. The final consensus annotation can utilize weights, where the expert feedback data is weighted based on a confidence score of the expert feedback data 1135 and/or the performance score data 530 of the expert user, and/or where the inference data 1110 is weighted based on the inference confidence score and/or the performance score data 630 of the medical scan inference function 1105.

Alternatively or in addition, performing the inference data evaluation function 1138 can include comparing one or more binary values of expert annotations in the expert feedback data to corresponding binary values of the inference data 1110, such as "normal" and "abnormality detected", and conclude that the medical scan diagnosis is accurate if the expert's binary values match the corresponding binary values of the inference data 1110. The inference data evaluation function 1138 can include comparing indicated locations of detected abnormalities of the expert feedback data and an abnormality location indicated in the automatically generated inference data 1110, and determine the inference data is accurate when the distance between these locations is within a threshold distance. This calculated distance can be used to determine the discrepancy level used to generate the inference accuracy data 1136. The inference data evaluation function 1138 can include comparing an expert classification of the detected abnormality with an automatically generated classification of the detected abnormality in the inference data 1110 and determine that the inference data 1110 is accurate when the classification data matches. The inference data evaluation function 1138 can include generating a first feature vector that includes features of the scan review data 810 corresponding to the expert feedback data, generating a second feature vector that includes features of the inference data 1110, and computing a Euclidian distance between the two feature vectors, where the inference data 1110 is determined to be accurate if a magnitude of the calculated Euclidian di stance falls within a threshold Euclidian distance. This calculated Euclidian distance can be used to determine the discrepancy level used to generate the inference accuracy data 1136. In embodiments where the expert feedback data 1135 is based on review of displayed inference data, the inference data evaluation function 1138 can include determining the inference data is accurate when the expert feedback data indicates that the diagnosis is correct.

In some embodiments, the inference data 1110 generated for all medical scans processed by the medical scan diagnosing system 108 will undergo this output quality assurance step 1107 and be sent to a selected expert. Alternatively, a random or psuedo-random sampling of diagnosed medical scans undergo the expert review, for example, based on a fixed output assurance percentage. Different originating entities can be assigned different output assurance percentages, for example, based on a user profile information such as subscription data 550 for the user or other usage limits assigned to the entity. Different inference data 1110 can be assigned different output assurance percentages, for example, where every medical scan flagged as "not normal" is reviewed by an expert. In such cases, a fixed percentage of medical scans flagged as "normal" can also be reviewed by a selected expert for additional quality assurance. Different diagnosis can also be randomly or psuedo-randomly sampled based on different output assurance percentages, for example, where a higher proportion of medical scans with rarer and/or more severe diagnoses are reviewed than medical scans with less rare and/or less severe diagnoses, for example, based on verification percentage of a medical code 447 of the inference data 1110, based on severity and/or rarity of some or all of the inference data 1110, and/or based on an ambiguity score and/or rarity score associated with an alias mapping pair 925 utilized to generate the inference data 1110. In some embodiments, the inference confidence score can be utilized to determine whether or not the inference data 1110 undergoes the output quality assurance step 1107. For example, only inference data 1110 with an inference confidence score that fails to exceed a confidence score threshold is sent to the expert for review. The confidence score threshold can be the same or different for different originating entities, the same or different for different scan categories, and/or the same or different for different diagnosis types.

Performance score data 630 can be generated and/or updated for the medical scan inference function 1105 based on the inference accuracy data 1136 or other indication of whether or not the inference data 1110 was accurate, where a high score is awarded for accurate inference data and a low score is awarded for inaccurate inference data. The performance score data 630 can be further based on the determined discrepancy level between the inference data and the expert feedback data. The performance score data 630 can further be weighted based on the severity of the diagnosis, where the performance score data is higher for detected abnormalities that are more severe and/or rare than less severe and/or rare. For example, performance score data is scored lower for failing to detect abnormalities that are more severe than less severe. The performance score data 630 can further be based on whether the inaccuracy was a false positive diagnosis or a false negative diagnosis. For example, performance score data is scored lower for a false negative diagnosis than a false positive diagnosis. Performance score data 630 can also include determining efficiency of the medical scan inference function 1105, for example, by computing a duration of time to compute the inference data, amount of memory utilized, or other efficiency data. Performance score data 530 can be generated and/or updated for the expert user, for example, where a higher performance score is award for higher discrepancy levels than lower discrepancy levels and/or where a higher performance score is awarded for detecting abnormalities that are more severe than less severe.

Figure 11C:
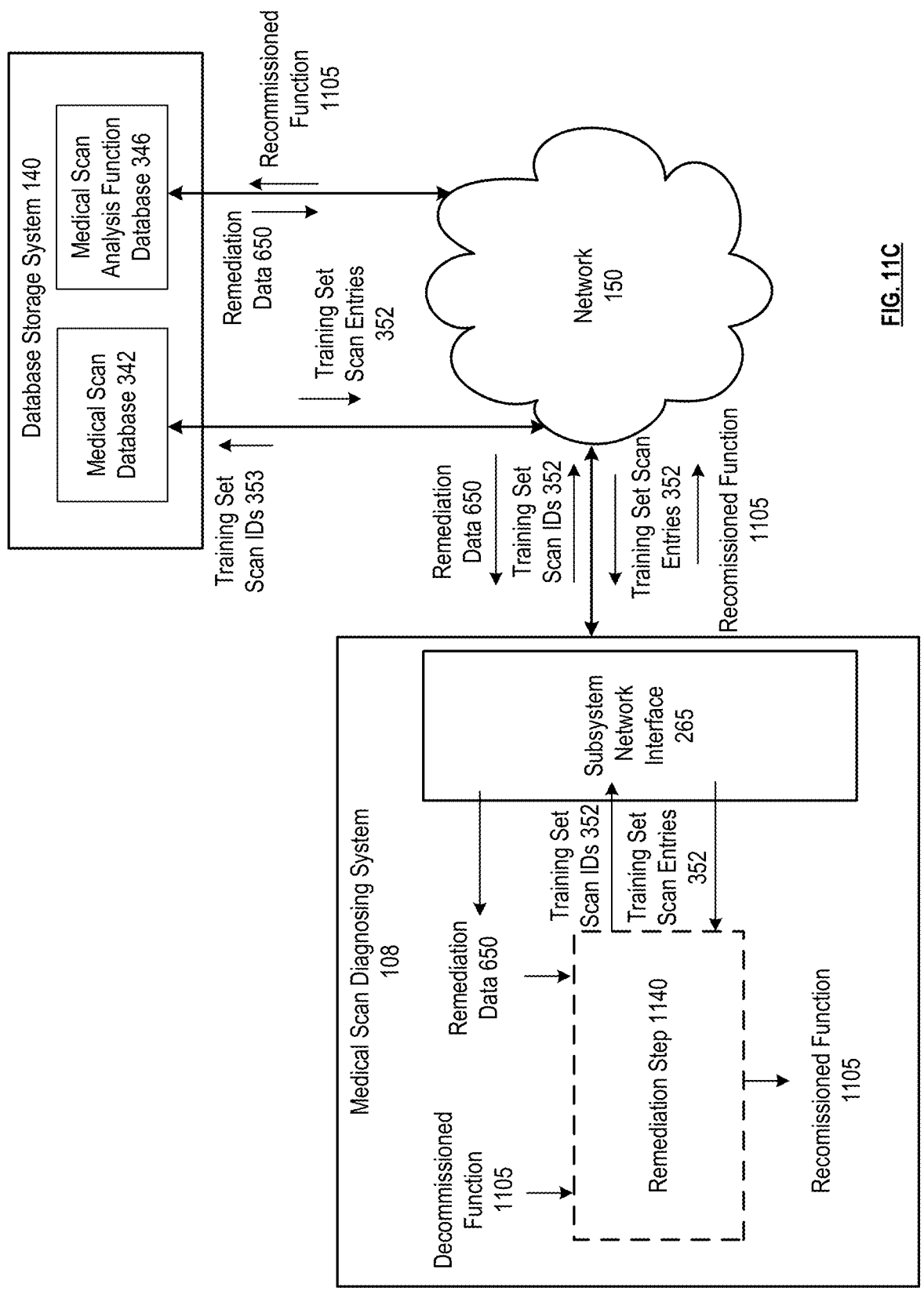

FIG. 11C illustrates an embodiment of the medical scan diagnosing system 108 in conjunction with performing a remediation step 1140. The medical scan diagnosing system 108 can monitor the performance of the set of medical scan inference functions 1105, for example, based on evaluating the inference accuracy data 1136 outputted by the inference data evaluation function 1138 and/or based monitoring on the performance score data 630 in the medical scan analysis function database, and can determine whether or not if the corresponding medical scan inference function 1105 is performing properly. This can include, for example, determining if a remediation step 1140 is necessary for a medical scan inference function 1105, for example, by comparing the performance score data 630 and/or inference accuracy data 1136 to remediation criteria data 652. Determining if a remediation step 1140 is necessary can also be based on receiving an indication from the expert user or another user that remediation is necessary for one or more identified medical scan inference functions 1105 and/or for all of the medical scan inference functions 1105.

In various embodiments, a remediation evaluation function is utilized to determine if a remediation step 1140 is necessary for medical scan inference function 1105. The remediation evaluation function can include determining that remediation is necessary when recent accuracy data and/or efficiency data of a particular medical scan inference function 1105 is below the normal performance level of the particular inference function. The remediation evaluation function can include determining that remediation is necessary when recent or overall accuracy data and/or efficiency data of a particular medical scan inference function 1105 is below a recent or overall average for all or similar medical scan inference functions 1105. The remediation evaluation function can include determining that remediation is necessary only after a threshold number of incorrect diagnoses are made. In various embodiments, multiple threshold number of incorrect diagnoses correspond to different diagnoses categories. For example, the threshold number of incorrect diagnoses for remediation can be higher for false negative diagnoses than false positive diagnoses. Similarly, categories corresponding to different diagnosis severities and/or rarities can have different thresholds, for example where a threshold number of more severe and/or more rare diagnoses that were inaccurate to necessitate remediation is lower than a threshold number of less severe and/or less rare diagnoses that were inaccurate.

The remediation step 1140 can include automatically updating an identified medical inference function 1105. This can include automatically retraining identified medical inference function 1105 on the same training set or on a new training set that includes new data, data with higher corresponding confidence scores, or data selected based on new training set criteria. The identified medical inference function 1105 can also be updated and/or changed based on the review data received from the client device. For example, the medical scan and expert feedback data 1135 can be added to the training set of the medical inference function 1105, and the medical scan inference function 1105 can be retrained on the updated training set. Alternatively or in addition, the expert user can identify additional parameters and/or rules in the expert feedback data based on the errors made by the inference function in generating the inference data 1110 for the medical scan, and these parameters and/or rules can be applied to update the medical scan inference function, for example, by updating the model type data 622 and/or model parameter data 623.

The remediation step 1140 can also include determining to split a scan category 1120 into two or more subcategories. Thus, two or more new medical scan inference functions 1105 can be created, where each new medical scan inference functions 1105 is trained on a corresponding training set that is a subset of the original training set and/or includes new medical scan data corresponding to the subcategory. This can allow medical scan inference functions 1105 to become more specialized and/or allow functions to utilize characteristics and/or discrepancies specific to the subcategory when generating inference data 1110. Similarly, a new scan category 1120 that was not previously represented by any of the medical scan inference functions 1105 can be added in the remediation step, and a new medical scan inference functions 1105 can be trained on a new set of medical scan data that corresponds to the new scan category 1120. Splitting a scan category and/or adding a scan category can be determined automatically by the medical scan diagnosing system 108 when performing the remediation step 1140, for example, based on performance score data 630. This can also be determined based on receiving instructions to split a category and/or add a new scan category from the expert user or other user of the system.

After a medical scan inference function 1105 is updated or created for the first time, the remediation step 1140 can further undergo a commissioning test, which can include rigorous testing of the medical scan inference function 1105 on a testing set, for example, based on the training parameters 620. For example, the commissioning test can be passed when the medical scan inference function 1105 generates a threshold number of correct inference data 1110 and/or the test can be passed if an overall or average discrepancy level between the inference data and the test data is below a set error threshold. The commissioning test can also evaluate efficiency, where the medical scan inference function 1105 only passes the commissioning test if it performs at or exceeds a threshold efficiency level. If the medical scan inference function 1105 fails the commissioning test, the model type and/or model parameters can be modified automatically or based on user input, and the medical scan inference function can be retested, continuing this process until the medical scan inference function 1105 passes the commissioning test.

The remediation step 1140 can include decommissioning the medical scan inference function 1105, for example, while the medical scan inference function is being retrained and/or is undergoing the commissioning test. Incoming scans to the medical scan diagnosing system 108 with a scan category 1120 corresponding to a decommissioned medical scan interface function 1105 can be sent directly to review by one or more users, for example, in conjunction with the medical scan annotator system 106. These user-reviewed medical scans and corresponding annotations can be included in an updated training set used to train the decommissioned medical scan inference function 1105 as part of the remediation step 1140. In some embodiments, previous versions of the plurality of medical scan image analysis functions can be stored in memory of the medical scan diagnosing system and/or can be determined based on the version data 640 of a medical scan inference function 1105. A previous version of a medical scan inference function 1105, such as most recent version or version with the highest performance score, can be utilized during the remediation step 1140 as an alternative to sending all medical scans to user review.

In various embodiments, the output assurance threshold or other aspects of the output quality assurance step 1107 are stricter for a rebuilding period of time after a medical scan inference function passes the commissioning test. For example, all of, or a higher percentage of, inference data 1110 generated by the new and/or updated medical scan inference function 1105 can be reviewed by an expert user, and/or can be reviewed by a higher ranked expert user. The output quality assurance step 1107 can be returned to normal after a fixed amount of time where the remediation step is not needed for the recommissioned medical scan inference function 1105, when the performance score data 630 exceeds a certain threshold, when a threshold number or proportion of accurate inference data 1110 is generated, or when other criteria is met indicating that the medical scan inference function is performing favorably. In some embodiments, the medical scan inference function automatically is commissioned normally after passing the commissioning test.

A medical scan image analysis function can also undergo the remediation step 1140 automatically in response to a hardware and/or software update on processing, memory, and/or other computing devices where the medical scan inference function 1105 is stored and/or performed. Different medical scan inference functions 1105 can be containerized on their own devices by utilizing a micro-service architecture, so hardware and/or software updates may only necessitate that one of the medical scan inference functions 1105 undergo the remediation step 1140 while the others remain unaffected. A medical scan inference function 1105 can also undergo the remediation step 1140 automatically in response to normal system boot-up, and/or periodically in fixed intervals. For example, in response to a scheduled or automatically detected hardware and/or software update, change, or issue, one or more medical scan image inference functions 1105 affected by this hardware or software can be taken out of commission until they each pass the commissioning test. Such criteria can be indicated in the remediation criteria data 652.

The medical scan diagnosing system 108 can automatically manage usage data, subscription data, and/or billing data for the plurality of users corresponding to user usage of the system, for example, by utilizing, generating, and/or updating some or all of the subscription data 550 of the user database. Users can pay for subscriptions to the system, which can include different subscription levels that can correspond to different costs. For example, a hospital can pay a monthly cost to automatically diagnose up to 100 medical scans per month. The hospital can choose to upgrade their subscription or pay per-scan costs for automatic diagnosing of additional scans received after the quota is reached and/or the medical scan diagnosing system 108 can automatically send medical scans received after the quota is reached to an expert user associated with the hospital. In various embodiments incentive programs can be used by the medical scan diagnosing system to encourage experts to review medical scans from different medical entities. For example, an expert can receive credit to their account and/or subscription upgrades for every medical scan reviewed, or after a threshold number of medical scans are reviewed. The incentive programs can include interactions by a user with other subsystems, for example, based on contributions made to medical scan entries via interaction with other subsystems.

Figure 12A:
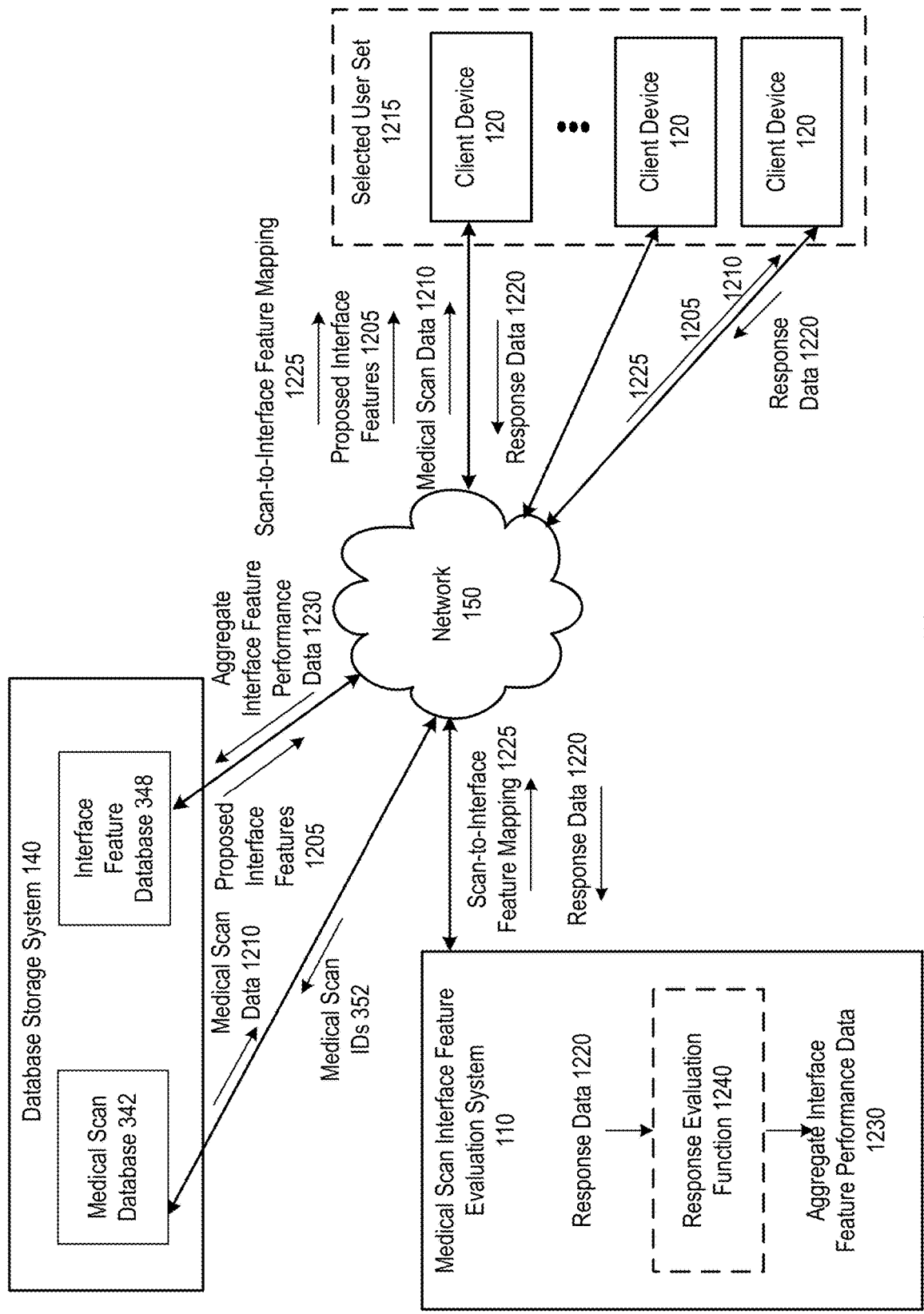
FIG. 12A is a schematic block diagram of a medical scan interface feature evaluator system in accordance with various embodiments.

FIG. 12A presents an embodiment of a medical scan interface feature evaluator system 110. A medical scan interface feature evaluator can be used evaluate proposed interface features or currently used interface features of an interactive interface 275 to present medical scans for review by medical professionals or other users of one or more subsystems 101.

In various embodiments, the medical scan interface feature evaluator system 110 is operable to generate an ordered image-to-prompt mapping by selecting a set of user interface features to be displayed with each of an ordered set of medical scans. The set of medical scans and the ordered image-to-prompt mapping are transmitted to a set of client devices. A set of responses are generated by each client device in response to sequentially displaying each of the set of medical scans in conjunction with a mapped user interface feature indicated in the ordered image-to-prompt mapping via a user interface. Response score data is generated by comparing each response to truth annotation data of the corresponding medical scan. Interface feature score data corresponding to each user interface feature is generated based on aggregating the response score data, and is used to generate a ranking of the set of user interface features.

Users can receive medical scan data 1210 such as medical scan image slices 410 and/or natural language text data 448 for one or more selected medical scans with previously generated annotation or diagnosis data, for example with high confidence score data 460 and/or a truth flag 461, or to be compared to expert review subsequently provided, for example, received from an expert user in conjunction with the medical scan annotation system 106 or another user identified as an expert in the qualification data 540, for example, in conjunction with the medical scan annotator system 106. Medical scan data 1210 for each scan can be presented to selected users based on a selected subset of proposed interface features 1205 which can include some or all interface features, for example, in conjunction with the medical scan assisted review system 102, where known annotation data is hidden and/or presented as displayed annotation data 820 via the selected subset of proposed interface features 1205. The client device can generate response data 1220 based on user input via the interactive interface 275. The response data 1220 can include scan review data 810, for example, where each medical scan data 1210 is presented to the user in conjunction with the medical scan assisted review system 102. The medical scan interface feature evaluator system 110 can perform a response evaluation function 1240 to generate aggregate interface feature performance data 1230 based on the response data 1220, for example, where received annotations are compared to corresponding known or later provided diagnosis data or other corresponding data of each medical scan. The aggregate interface feature performance data 1230 can be used to score and/or rank the plurality of interface features, to generating and/or evaluating performance score data 720, to generate display parameter data 470 for medical scans, to automatically generate interface preference data 560, and/or to determine default interface features for some or all of the subsystems 101. The medical scan interface feature evaluating system 110 can utilize the medical scan database 342, user database 344, and/or interface feature database 348 by communicating with the database storage system 140 via the network 150, and/or can utilize another medical scan database, user database, and/or interface feature database stored in local memory.

Interactive interface features evaluated by the medical scan interface feature evaluator system can include textual and/or visual cues, menu options, response input methods, spatial interface layouts, some or all of the interface features, or other features of interactive interface 275 as discussed herein in conjunction with one or more subsystems 101 and/or store in interface feature database 348. Some or all of the interactive interface features can include medical scan display parameters as discussed herein, for example, indicated in display parameter data 470 of each medical scan entry.

Textual and/or visual cues can include, for example, text-based interface features that instruct a user such as "click on a detected abnormality" and/or ask questions of a user such as "what kind of abnormality was detected?" Textual and visual cues can be used to present annotations and/or diagnosis data that already correspond to the system for verification by the user, or to otherwise aid the user in generating their own annotation and/or diagnosis data. For example, annotations and/or diagnosis data previously provided by another medical professional and/or generated automatically by the medical scan interface feature evaluator system 110 or another system of the medical scan processing system can be presented, where detected abnormalities are circled, highlighted, or otherwise visually indicated.

Menu options can include, for example, options to zoom in on selected or automatically identified areas of interest, scroll through scan slices, automatically jump to the next slice that includes a detected abnormality, view similar medical scans and their associated data, where the similar medical scans are automatically identified from a plurality of medical scans and/or identified by a previous user, view past medical scans associated with the same patient, automatically reveal and/or hide previously generated annotation and/or diagnosis data, or other options for viewing the medical scan and associated data such as diagnosis data 440 or other data of a medical scan entry 352.

Response input methods can include allowing users to provide annotation or diagnosis data by selecting one of a plurality of annotation options, click on an abnormality, outline a region that includes an abnormality, to select or upload similar medical scans or medical reports for similar cases, to shade in an abnormality, provide descriptive text and/or voice data for the scan or one or more detected abnormalities, or other response types.

Spatial interface layouts can include presenting one slide at a time with a scroll bar, presenting a selected number of slices at once, for example, as thumbnails, presenting a scan slice next to, or overlaid with, annotation text or other diagnosis data, presenting the medical scan side by side with a similar medical scan that is automatically selected and/or selected or uploaded by the user, presenting the medical scan side by side with a past medical scan of the same patient, visually overlaying or otherwise identifying changes in medical scans of the same patient over time, etc. Herein, such textual and/or visual cues, menu options, response input methods, and/or spatial interface layouts will be referred to interchangeably as "interface features". Interface features can also include other interactive interface characteristics presented and/or described herein in conjunction with other subsystems of the medical scan processing system.

In various embodiments, a plurality of proposed interface features 1205 are stored in the interface feature database 348 and/or a database in memory of the medical scan interface feature evaluator system 110. Some or all of the plurality of proposed interface features can be received from one or more administrators of the medical scan interface feature evaluator system, and/or generated automatically by the medical scan interface feature evaluator system based on previous aggregate statistics of previously proposed interface features of the system. All of the proposed interface features can undergo evaluation, or a subset of proposed interface features can be selected, for example, manually by an administrator via the administrator interactive interface or automatically by the medical scan interface feature evaluator system based on received or automatically determined interface feature criteria. A plurality of users of the system can also be selected. For example, users can be selected based on overall and/or categorized performance score data 530 of the user database 344 and/or otherwise generated and/or received by one or more subsystems of the medical scan processing system. Different users can be assigned a different set of medical scans from the subset randomly or psuedo-randomly and/or based on the performance and/or specification data.

Each medical scan assigned to a user is further assigned one of the plurality of proposed interface features. This plurality of scan-to-interface feature mappings 1225, designating a plurality of (scan, interface feature) pairs, can further be ordered by the medical scan interface evaluating system based on an automatically generated order determined to be optimal for evaluating the interface features, or based on ordering criteria designated by an administrator. The set of proposed interface features 1205, medical scan data 1210, and scan-to-interface feature mappings 1225 are sent to client devices corresponding to each user in a selected user set 1215. Data of each medical scan is presented to the client device of the corresponding use in accordance with the assigned proposed interface feature, for example, sequentially based on the determined order, via an interactive interface on a display device associated with the client device. The medical scan interface feature evaluating system 110 receives responses corresponding to each displayed (scan, interface feature) pair in the response data 1220 transmitted from each of the client devices entered by the user via the interactive interface. In some embodiments, the medical scan assisted review system 102 is utilized in displaying the selected interface features on a user client device in conjunction with the corresponding medical scans based on the scan-to-interface feature mapping 1225.

In various embodiments, a first user may receive the same or different medical scans than a second user. Some or all of the same medical scans sent to a first user and a second user can be paired to the same or different proposed interface features. For example, a first user may receive scan X paired to interface feature A and scan Y paired to interface feature B, and a second user may receive scan X paired to interface feature B and scan Y paired to interface feature C. Some users may receive one or more of the same scans paired to multiple proposed interface features. For example, a third user may receive scan Z paired to interface feature I, then interface feature II, then interface feature III. The distribution of scans and interface features can be determined automatically to optimize the integrity of the response data received from the set of users to best aggregate scoring data for the interface features and/or the users themselves.

The medical scan interface feature evaluating system 110 can performing the response evaluation function 1240, for example, to score each response by comparing the response to truth data, such as known diagnosis data or data entered by an expert, or other known data for example, diagnosis data 440 with confidence score data 460 that includes a truth flag 461 or otherwise compares favorably to a truth threshold. Scoring each response can include determining if the diagnosis is correct or incorrect, for example, determining that a normal scan is correctly labeled as normal, or a scan that includes an abnormality is incorrectly labeled as normal, generating a first feature vector based on the response data and a second feature vector based on the truth data and calculating a Euclidian distance, and/or utilizing other performance and/or accuracy measures described herein. Each response can also be scored for efficiency, for example, based on the amount of time taken for a user to enter their annotations, diagnosis, or other relevant input. In various embodiments, performing the response evaluation function can include performing part of all of the inference data evaluation function 1138 and/or the annotation consensus function 1040.

In some embodiments, the response data can include interface feature feedback data in response to data generated by the client device in response to an interface feature for the user to provide feedback, for example, "On a scale from 1-5, how effective did you find this proposed interface feature?" The score data can also be generated based on the particular user, for example, based on user performance score data 530. For example, a response for an interface feature used with a chest x-ray received from a particular user that usually performs poorly on diagnosing chest x-rays may be scored more highly if the response includes a correct diagnosis. Performing the response evaluation function 1240 can include scoring each response based on such user feedback.

The medical scan interface evaluating system can generate aggregate interface feature performance data 1230 based on individual scores for each response. The aggregate interface feature performance data 1230 can include scoring and/or ranking data for each of the proposed interface features, which can be used to generate and/or update performance score data 720. The aggregate interface feature performance data 1230 can further be used to generate and/or update performance score data 530 for each selected user from whom responses data was received and evaluated. For example, all of the performance scores across multiple users that viewed interface feature I can be averaged or otherwise aggregated, and can be compared to an aggregate score generated based on all of the scores across multiple users that viewed interface feature II.

The aggregate interface feature performance data 1230 can include categorized aggregate data, where aggregate data for each interface feature can be further broken down based on scores for distinct scan categories, for example, based on the scan classifier data 420, for example, where a first aggregate data score is generated for interface feature I based on scores from all knee x-rays, and a second aggregate data score is generated for interface feature I based on scores from all chest x-rays. Aggregate data for each interface feature can be further based on scores for distinct diagnosis categories, where a first aggregate data score is generated for interface feature I based on scores from all normal scans, and a second aggregate data score is generated for interface feature I based on scores from all scans that contain an abnormality. This can be further broken down, where a first aggregate score is generated for interface feature I based on all scores from scans that contain an abnormality of a first type and/or in a first anatomical location, and a second aggregate score is generated for interface feature I based on all scores from scans that contain an abnormality of a second type and/or in a second location. Aggregate data for each interface feature can be further based on scores for distinct user types, where a first aggregate data score is generated for interface feature I based on scores from all novice users and/or users with low performance scores, and a second aggregate data score is generated for interface feature I based on scores from all expert users and/or users with high performance scores. Aggregate data for each interface feature can be further based on scores for distinct medical entities, where a first aggregate data score is generated for interface feature I based on scores from a first hospital, and a second aggregate data score is generated for interface feature I based on scores from a second hospital.

The aggregate interface feature performance data 1230 can be sent to an administrator client device for display by a corresponding administrator and/or can be stored in the database of interface features database 348, where interface feature scores are mapped to their corresponding interface feature in the database in the performance score data 720. The aggregate interface feature performance data 1230 can be used to rank the interface features holistically, and/or rank the interface features among different scan type and/or user/entity type categories. The medical scan interface feature evaluator system 110 can provide recommendations to an administrator for which proposed interface features should be used in practice to aid users in annotating, diagnosing, and/or otherwise reviewing new and/or triaged medical scans. The same and/or different interface features can be recommended for use by different users, different hospitals, and/or different scan types based on the aggregate interface feature performance data 1230. In some embodiments, these recommendations are automatically processed by the medical scan processing system 100 to determine which proposed interface features are used by other subsystems 101, and/or the other subsystems can automatically select a highly ranked interface feature in a particular scan-based and/or user-based category for display by its interactive interface along with medical scan data. In some embodiments, interface preference data 560 can be generated automatically for some or all of the users based on the aggregate interface feature performance data 1230 for storage in the user database. This can be used to customize interface features utilized by in some or all of the subsystems 101 for particular users and/or medical entities, such as particular medical professionals and/or particular hospitals.

The aggregate interface feature performance data 1230 can be also be used by the medical scan interface feature evaluator system 110 to automatically remove and/or modify some or all of the proposed interface features 1205, and/or to automatically generate new proposed interface features 1205. The medical scan interface feature evaluator data can make such removal, modification, and/or new proposed interface feature recommendations to an administrator. The aggregate interface feature performance data 1230 can be also be used by the medical scan interface feature evaluator system 110 to automatically select a new set of proposed interface features and/or scan-to-interface feature mappings to be sent to the same or different users, where the new medical scans and/or user set can also be selected based on aggregate interface feature performance data 1230. This process can be repeated multiple times to narrow the proposed interface features 1205, tweak, adjust or otherwise modify the proposed interface features 1205, finalize the proposed interface features 1205, gain further insights in specific categories, evaluate interface features for a new type of users or new type of scan, periodically check that interface features being used by other subsystems remain current and optimal, or to otherwise determine new interface feature rankings.

The aggregate interface feature performance data 1230 can be used to generate some or all of the user performance score data 530 and/or to otherwise rank users and/or hospitals. While many of the proposed interface features may be in testing mode, some interface features may be ranked highly enough to score user and/or hospital performance. For example, if 95% of users score highly on medical scans presented with interface feature A, and a first user consistently receives low scores on medical scans presented with interface feature A, the medical scan interface evaluating system can use this data to determine that the first user has a low performance score and/or low rank. This can be used by the medical scan interface evaluating system to automatically remove low ranked users from future sets of users selected when evaluating new proposed interface features. This information can also be stored in a user database used by other subsystems or otherwise can be used by other subsystems in conjunction with other user performance tracking as described herein.

Figure 12B:
FIGS. 12B-12C are graphical illustrations of an example interactive interface displayed on a client device in conjunction with various embodiments.
Figure 12C:

FIGS. 12B-12C present example embodiments of an interactive interface presented in conjunction with the medical scan interface feature evaluator system 110. In an example embodiment, three types of interface features are tested using wrist x-rays. A first interface feature presents a wrist x-ray and includes no annotation data. A second interface feature, as shown in FIG. 12B, presents hand-generated regions of interest 1290 encircling suspected sites of fracture in conjunction with presenting the wrist x-ray. The third interface feature, as shown in FIG. 12C, includes a marquee listing bones suspicious for fracture and a measure of confidence in that judgement in conjunction with presenting the wrist x-ray. In the example displayed in FIG. 12C, metacarpal and scaphoid are listed as suspicious for fracture, with the confidence presented as one out of four blocks shaded.

Figure 13B:
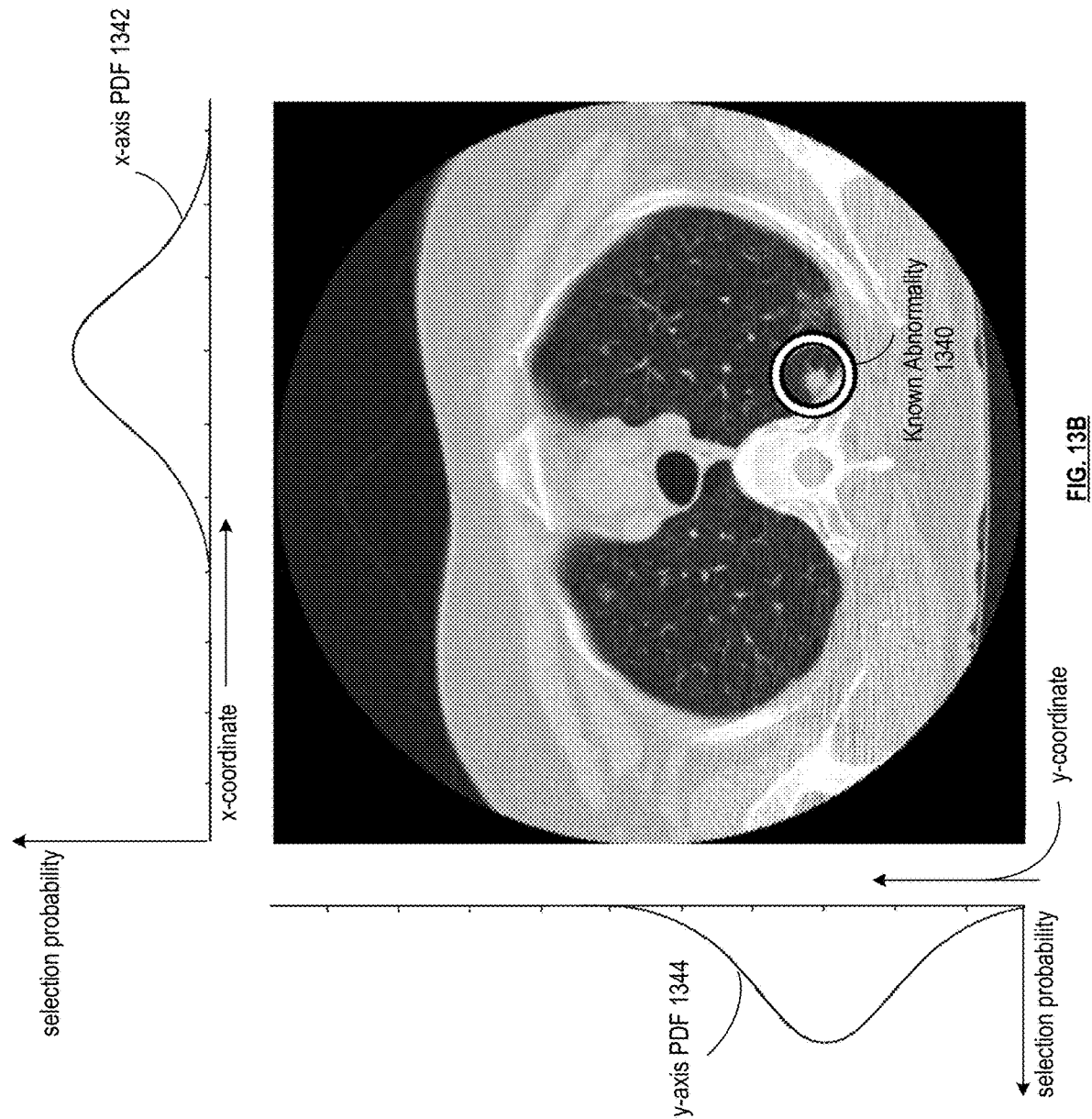
FIG. 13B is a graphical illustration of probability density functions in accordance with various embodiments.
Figure 13D:
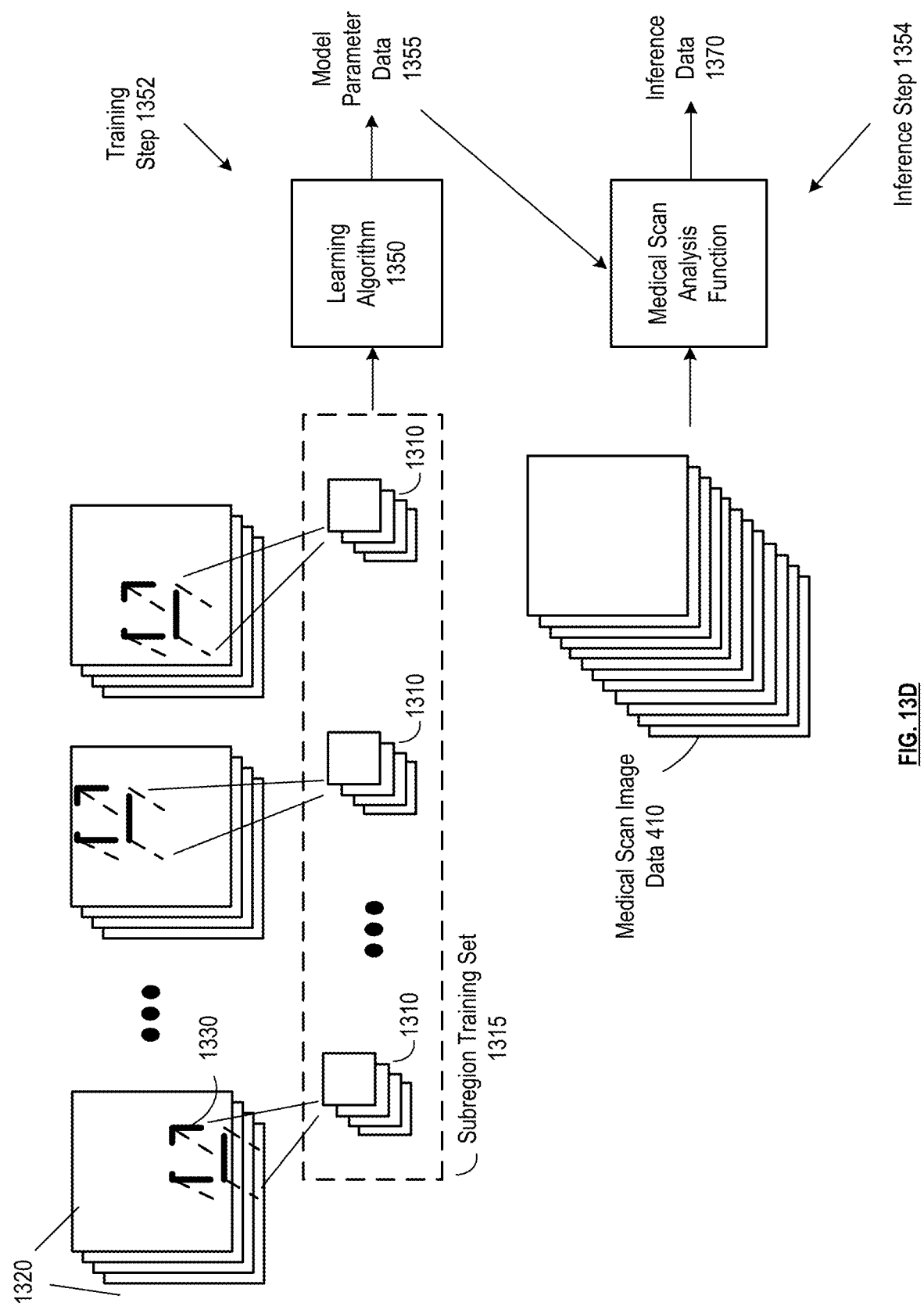
FIG. 13D is a flowchart representation of an inference step in accordance with various embodiments.
Figure 13E:
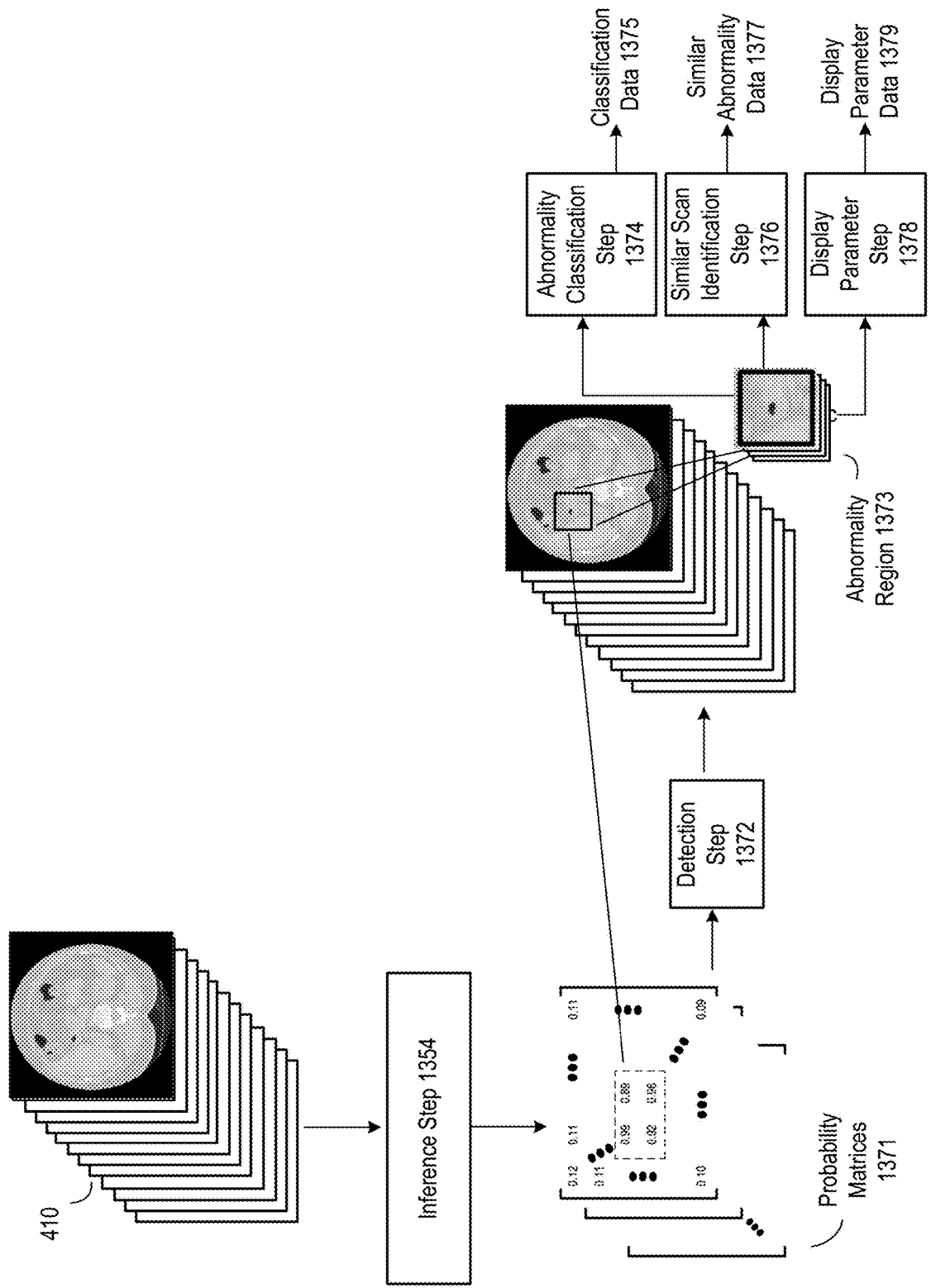
FIG. 13E is a flowchart representation of a detection step in accordance with various embodiments.

FIG. 13 presents an embodiment of a medical scan image analysis system 112. A medical scan image analysis system 112 can be used to generate and/or perform one or more medical scan image analysis functions by utilizing a computer vision-based learning algorithm on a training set of medical scans with known annotation data, diagnosis data, labeling and/or medical code data, report data, patient history data, patient risk factor data, and/or other metadata associated with medical scans. These medical scan image analysis functions can be used to generate inference data for new medical scans that are triaged or otherwise require inferred annotation data, diagnosis data, labeling and/or medical code data, and/or report data. For example, some medical scan image analysis functions can correspond to medical scan inference functions of the medical scan diagnosing system or other medical scan analysis functions of the medical scan analysis function database 348. The medical scan image analysis functions can be used to determine whether or not a medical scan is normal, to detect the location of an abnormality in one or more slices of a medical scan, and/or to characterize a detected abnormality. The medical scan image analysis system can be used to generate and/or perform computer vision based medical scan image analysis functions utilized by other subsystems of the medical scan processing system as described herein, aiding medical professionals to diagnose patients and/or to generate further data and models to characterize medical scans. The medical scan image analysis system can include a processing system that includes a processor and a memory that stores executable instructions that, when executed by the processing system, facilitate performance of operations.

In various embodiments, the medical scan image analysis system 112 is operable to receive a plurality of medical scans that represent a three-dimensional anatomical region and include a plurality of cross-sectional image slices. A plurality of three-dimensional subregions corresponding to each of the plurality of medical scans are generated by selecting a proper subset of the plurality of cross-sectional image slices from each medical scan, and by further selecting a two-dimensional subregion from each proper subset of cross-sectional image slices. A learning algorithm is performed on the plurality of three-dimensional subregions to generate a fully convolutional neural network. Inference data corresponding to a new medical scan received via the network is generated by performing an inference algorithm on the new medical scan by utilizing the fully convolutional neural network. An inferred abnormality is identified in the new medical scan based on the inference data.

A training set of medical scans used to train one more medical scan image analysis functions can be received from one or more client devices via the network and/or can be retrieved from the medical scan database 342, for example, based on training set data 621 corresponding to medical scan image analysis functions. Training set criteria, for example, identified in training parameters 620 of the medical scan image analysis function, can be utilized to automatically identify and select medical scans to be included in the training set from a plurality of available medical scans. The training set criteria can be automatically generated based on, for example, previously learned criteria, and/or training set criteria can be received via the network, for example, from an administrator of the medical scan image analysis system. The training set criteria can include a minimum training set size. The training set criteria can include data integrity requirements for medical scans in the training set such as requiring that the medical scan is assigned a truth flag 461, requiring that performance score data 530 for a hospital and/or medical professional associated with the medical scan compares favorably to a performance score threshold, requiring that the medical scan has been reviewed by at least a threshold number of medical professionals, requiring that the medical scan and/or a diagnosis corresponding to a patient file of the medical scan is older than a threshold elapsed time period, or based on other criteria intended to insure that the medical scans and associated data in the training set is reliable enough to be considered "truth" data. The training set criteria can include longitudinal requirements such the number of required subsequent medical scans for the patient, multiple required types of additional scans for the patient, and/or other patient file requirements.

The training set criteria can include quota and/or proportion requirements for one or more medical scan classification data. For example, the training set criteria can include meeting quota and/or proportion requirements for one or more scan types and/or human body location of scans, meeting quota or proportion requirements for a number of normal medical scans and a number of medicals scans with identified abnormalities, meeting quota and/or proportion requirements for a number of medical scans with abnormalities in certain locations and/or a number of medical scans with abnormalities that meet certain size, type, or other characteristics, meeting quota and/or proportion data for a number of medical scans with certain diagnosis or certain corresponding medical codes, and/or meeting other identified quota and/or proportion data relating to metadata, patient data, or other data associated with the medical scans.

In some embodiments, multiple training sets are created to generate corresponding medical scan image analysis functions, for example, corresponding to some or all of the set of medical scan inference functions 1105. Some or all training sets can be categorized based on some or all of the scan classifier data 420 as described in conjunction with the medical scan diagnosing system 108, where medical scans are included in a training set based on their scan classifier data 420 matching the scan category of the training set. In some embodiments, the input quality assurance function 1106 or another input check step can be performed on medical scans selected for each training set to confirm that their corresponding scan classifier data 420 is correct. In some embodiments, the input quality assurance function can correspond to its own medical scan image analysis function, trained by the medical scan image analysis system, where the input quality assurance function utilizes high level computer vision technology to determine a scan category 1120 and/or to confirm the scan classifier data 420 already assigned to the medical scan.

In some embodiments, the training set will be used to create a single neural network model, or other model corresponding to model type data 622 and/or model parameter data 623 of the medical scan image analysis function that can be trained on some or all of the medical scan classification data described above and/or other metadata, patient data, or other data associated with the medical scans. In other embodiments, a plurality of training sets will be created to generate a plurality of corresponding neural network models, where the multiple training sets are divided based on some or all of the medical scan classification data described above and/or other metadata, patient data, or other data associated with the medical scans. Each of the plurality of neural network models can be generated based on the same or different learning algorithm that utilizes the same or different features of the medical scans in the corresponding one of the plurality of training sets. The medical scan classifications selected to segregate the medical scans into multiple training sets can be received via the network, for example based on input to an administrator client device from an administrator. The medical scan classifications selected to segregate the medical scans can be automatically determined by the medical scan image analysis system, for example, where an unsupervised clustering algorithm is applied to the original training set to determine appropriate medical scan classifications based on the output of the unsupervised clustering algorithm.

In embodiments where the medical scan image analysis system is used in conjunction with the medical scan diagnosing system, each of the medical scan image analysis functions associated with each neural network model can correspond to one of the plurality of neural network models generated by the medical scan image analysis system. For example, each of the plurality of neural network models can be trained on a training set classified on scan type, scan human body location, hospital or other originating entity data, machine model data, machine calibration data, contrast agent data, geographic region data, and/or other scan classifying data as discussed in conjunction with the medical scan diagnosing system. In embodiments where the training set classifiers are learned, the medical scan diagnosing system can determine which of the medical scan image analysis functions should be applied based on the learned classifying criteria used to segregate the original training set.

A computer vision-based learning algorithm used to create each neural network model can include selecting a three-dimensional subregion 1310 for each medical scan in the training set. This three-dimensional subregion 1310 can correspond to a region that is "sampled" from the entire scan that may represent a small fraction of the entire scan. Recall that a medical scan can include a plurality of ordered cross-sectional image slices. Selecting a three-dimensional subregion 1310 can be accomplished by selecting a proper image slice subset 1320 of the plurality of cross-sectional image slices from each of the plurality of medical scans, and by further selecting a two-dimensional subregion 1330 from each of the selected subset of cross-sectional image slices of the each of the medical scans. In some embodiments, the selected image slices can include one or more non-consecutive image slices and thus a plurality of disconnected three-dimensional subregions will be created. In other embodiments, the selected proper subset of the plurality of image slices correspond to a set of consecutive image slices, as to ensure that a single, connected three-dimensional subregion is selected.

Consider the case where the selected image slices correspond to a set of consecutive image slices. Selecting the two-dimensional subregions 1330 from each image slice in the of a scan can include selecting the same region of pixels or a region determined from same vertical and horizontal borders to generate a three-dimensional subregion that corresponds to a prism shape. For example, selecting the same-sized square region centered at the same (x,y) coordinate pair of each of the image slices of a scan would result in a three-dimensional subregion that corresponds to a rectangular prism, and selecting the same-sized circular region centered at the same (x,y) coordinate pair of each of the image slices would result in a three-dimensional subregion that corresponds to a cylindrical shape. In other embodiments, different sized and/or shaped two-dimensional subregions can be selected from each image slice of the scan. For example, different sized circular regions can be selected that are centered at the same (x,y) coordinate pair of each of the image slices, where the largest circle is selected from the center image slice in the set of ordered consecutive slices, where the smallest circles are selected from the first and last image slices in the set of ordered consecutive slices, where the circles selected from the first slice to the center slice monotonically increase in size, and where the circles selected from the center slice to the last slice monotonically decrease in size. Such as strategy would result in a three-dimensional subregion that resembles a sphere.

Each three-dimensional region selected from each of the plurality of medical scans in the training set can correspond to the same size or different sizes, and can correspond to the same shape or different shapes. If different shapes and/or sizes are selected for different medical scans, the shape and/or size can be determined randomly or psuedo-randomly and/or deterministically based on characteristics of the scan itself, such as based on the size and/or shape of a known abnormality 1340 in the scan. For example, in some embodiments, the three-dimensional region can be selected to include a known abnormality. The known abnormality 1340 can be closely "surrounded" by a subregion, for example, where the diameter of a spherical subregion is selected based on a maximum distance between any two boundary points of the known abnormality. The known abnormality 1340 can also be completely "outlined" by the subregion, where the shape of each two-dimensional region is determined based on tracing a perimeter of the known abnormality in each image slice.

In some embodiments, an ideal shape and/or size for the three-dimensional subregions can be identified. The identified ideal shape and/or size can include a single shape and/or size, or a set of ideal shapes and/or a range of ideal sizes. The identified ideal shape and/or size can include a range for the total number of pixels, a range for the total number of bytes, a range for the total number of image slices, a range for the number of pixels in each two-dimensional subregion, a range for a diameter of circular subregions, a horizontal and/or vertical range for two-dimensional subregions, a set of two-dimensional shapes, or other shape and/or size criteria. The ideal shape and/or size requirements can be based on system requirements such as processing restrictions, memory restrictions, efficiency requirements, and/or computation time requirements, as processing subregions that are too large may not be reasonable the software and/or hardware available to the medical scan image analysis system. Alternatively or in addition, the ideal shape and/or size requirements can be based on model accuracy requirements, as building a neural network model based on regions that are too small may result in a poor model that results in inaccurate inferences by the model on new medical scans. The identified ideal shape and/or size can be based on requirements received via the network, for example, from an administrator client device based on user input by an administrator. The identified ideal shape and/or size can also be generated automatically by the medical scan image analysis system, for example, by calculating a maximum region size based on known or determined system requirements and/or by generating multiple models that utilized different shapes and/or sizes and determining the ideal shape and/or size based on testing the multiple models and determining which of the multiple models achieve a desired model accuracy.

Selecting the three-dimensional subregion also includes determining a location for selection. In some embodiments, the location of the three-dimensional subregion is based on a uniform distribution. In other embodiments, the location of the three-dimensional subregion is selected based on a non-uniform distribution. For example, selecting the three-dimensional subregion can be based on the location of a known abnormality 1340. As discussed previously, the three-dimensional subregion can be selected to include the entire known abnormality 1340. The three-dimensional subregion can also be selected to include at least a part of the known abnormality. The location of the three-dimensional subregion can be deterministic, for example, where a center of the abnormality is centered in the three-dimensional subregion.

In various embodiments, a probability distribution function (PDF) can be used to determine the center location of the subregion, where selecting a subregion that is closer to the center to the subregion is more probable than selecting a subregion that is further from the center of the subregion. FIG. 13B presents an example embodiment of utilizing an x-axis PDF 1342, centered at a central x coordinate of the abnormality 1340, to select an x coordinate, and utilizing a y-axis PDF 1344, centered at a central y coordinate of the abnormality 1340, to select a y coordinate, where the selected x and y coordinates are used to determine the location of the subregion. In this fashion, consider a first possible subregion centered at a first location that is a first distance away from a center or nearest border of the known abnormality, and a second possible subregion centered at a second location that is a second distance away from the center or nearest border of the known abnormality. The PDF could dictate that selecting the first possible subregion is more probable than selecting the second possible subregion as a result of the first distance being shorter than the second distance. The two-dimensional subregions can be selected based on the ideal two-dimensional subregion size and/or shape requirements and the selected center (x,y) coordinate pair. In embodiments where the ideal two-dimensional subregion size requirements includes a size range, the subregion will further be determined based on probabilities assigned to each of the sizes in the range. In embodiments where the ideal two-dimensional subregion shape requirements includes a set of shapes and/or a set of shape parameters, the subregion will further be determined based on based on probabilities assigned to each of the shapes in the set of shapes and/or probabilities assigned to values of each parameter in the set of shape parameters.

Similarly, as illustrated in FIG. 13C, a center image slice of the selected proper image slice subset 1320 can be based on a slice PDF 1346, for example, centered about a central slice that includes the known abnormality in the plurality of ordered image slices. The remainder of the image slices will be determined based on the ideal slice number requirements and the center image slice. In embodiments where the ideal slice number requirement includes a range, the remainder of the image slices can be further determined based on probabilities assigned to each number of slices in the ideal slice number range or based on other deterministic factors.

Each PDF, such as PDFs 1342, 1344, and 1346, can be based on a Gaussian distribution or other distribution centered at the location of the abnormality with three random or psuedo-random variables: the center of the consecutive subset of image slices and the center (x,y) coordinate pair for the two-dimensional subregions of each image slice. In various embodiments, the PDF model and/or model parameters are determined based on received PDF data. For example, the received PDF parameter data can include the PDF itself, can indicate that a Gaussian distribution with a center slice variance parameter of 3 slices, with an x variance parameter of 10 pixels, and a y variance parameter of 10 pixels. The PDF model and/or parameters of a selected PDF model can also be automatically generated by the medical scan image analysis system, for example, after testing models generated utilizing different PDFs to determine the model that produces the most accurate inferences.

In some embodiments, all possible subregion locations are assigned a non-zero probability. In other embodiments, some locations are assigned a probability of zero, and thus subregions corresponding to such locations will not be selected. For example, all subregions at locations that do not include the abnormality are assigned a probability of zero and are never sampled. In some embodiments, subregions at locations that do not correspond to a region of interest, for example, locations that do not correspond to a location of the human body corresponding to the neural network model to be created can be assigned a probability of zero. For example, if the training set is created to generate a neural network model for detecting abnormalities in the lung, regions of each cross-sectional image slice that do not include the lung, or entire slices for example at the beginning or end of the scan that do not include the lung, can be assigned a probability of zero. This masking step can include determining regions of the scan that do not correspond to the region of interest, for example, by applying another computer vision-based masking function. The computer vision-based masking function can be generated automatically by the medical scan image analysis system or other system of the medical scan processing system, for example, where the computer vision-based masking function is trained on the training data, for example, where regions to be masked are identified manually in the training data.

In some embodiments, a density windowing step can be applied to the full scan or the selected three-dimensional subregion. The density windowing step can include utilizing a selected upper density value cut off and/or a selected lower density value cut off, and masking pixels with higher values than the upper density value cut off and/or masking pixels with lower values than the lower density value cut off. The upper density value cut off and/or a selected lower density value cut off can be determined based on based on the range of density values included in the region that includes the abnormality, and/or based on the range of density values associated with the abnormality itself, based on user input to a subsystem, based on display parameter data associated with the medical scan or associated with medical scans of the same type, and/or can be learned in the training step.

Having determined the subregion training set 1315 of three-dimensional subregions 1310 corresponding to the set of full medical scans in the training set, the medical scan image analysis system can complete a training step 1352 by performing a learning algorithm on the plurality of three-dimensional subregions to generate model parameter data 1355 of a corresponding learning model. While a convolutional neural network is a preferred embodiment, the learning model can additionally or alternatively include one or more of a Bayesian model, a support vector machine model, a cluster analysis model, or other supervised or unsupervised learning model. The model parameter data 1355 generated by performing the learning algorithm 1350, and the model parameter data 1355 can be utilized to determine the corresponding medical scan image analysis functions. For example, some or all of the model parameter data 1355 can be mapped to the medical scan analysis function in the model parameter data 623 or can otherwise define the medical scan analysis function.

The training step 1352 can include creating feature vectors for each three-dimensional subregion of the training set for use by the learning algorithm 1350 to generate the model parameter data 1355. The feature vectors can include the pixel data of the three-dimensional subregions such as density values and/or grayscale values of each pixel based on a determined density window. The feature vectors can also include other features as additional input features or desired output features, such as known abnormality data such as location and/or classification data, patient history data such as risk factor data or previous medical scans, diagnosis data, responsible medical entity data, scan machinery model or calibration data, contrast agent data, medical code data, annotation data that can include raw or processed natural language text data, scan type and/or anatomical region data, or other data associated with the image, such as some or all data of a medical scan entry 352. Features can be selected based on administrator instructions received via the network and/or can be determined based on determining a feature set that reduces error in classifying error, for example, by performing a cross-validation step on multiple models created using different feature sets. The feature vector can be split into an input feature vector and output feature vector. The input feature vector can include data that will be available in subsequent medical scan input, which can include for example, the three-dimensional subregion pixel data and/or patient history data. The output feature vector can include data that will be inferred in in subsequent medical scan input and can include single output value, such as a binary value indicating whether or not the medical scan includes an abnormality or a value corresponding to one of a plurality of medical codes corresponding to the image. The output feature vector can also include multiple values which can include abnormality location and/or classification data, diagnosis data, or other output. The output feature vector can also include a determined upper density value cut off and/or lower density value cut off, for example, characterizing which pixel values were relevant to detecting and/or classifying an abnormality. Features included in the output feature vector can be selected to include features that are known in the training set, but may not be known in subsequent medical scans such as triaged scans to be diagnosed by the medical scan diagnosing system, and/or scans to be labeled by the medical scan report labeling system. The set of features in the input feature vector and output feature vector, as well as the importance of different features where each feature is assigned a corresponding weight, can also be designated in the model parameter data 1355.

Consider a medical scan image analysis function that utilizes a neural network. The neural network can include a plurality of layers, where each layer includes a plurality of neural nodes. Each node in one layer can have a connection to some or all nodes in the next layer, where each connection is defined by a weight value. Thus, the model parameter data 1355 can include a weight vector that includes weight values for every connection in the network. Alternatively or in addition, the model parameter data 1355 can include any vector or set of parameters associated with the neural network model, which can include an upper density value cut off and/or lower density value cut off used to mask some of the pixel data of an incoming image, kernel values, filter parameters, bias parameters, and/or parameters characterizing one or more of a plurality of convolution functions of the neural network model. The medical scan image analysis function can be utilized to produce the output vector as a function of the input feature vector and the model parameter data 1355 that characterizes the neural network model. In particular, the medical scan image analysis function can include performing a forward propagation step plurality of neural network layers to produce an inferred output vector based on the weight vector or other model parameter data 1355. Thus, the learning step 1405 utilized in conjunction with a neural network model can include determining the model parameter data 1355 corresponding to the neural network model, for example, by populating the weight vector with optimal weights that best reduce output error.

In particular, determining the model parameter data 1355 can include utilizing a backpropagation strategy. The forward propagation algorithm can be performed on at least one input feature vector corresponding to at least one medical scan in the training set to propagate the at least one input feature vector through the plurality of neural network layers based on initial and/or default model parameter data 1355, such as an initial weight vector of initial weight values set by an administrator or chosen at random. The at least one output vector generated by performing the forward propagation algorithm on the at least one input feature vector can be compared to the corresponding at least one known output feature vector to determine an output error. Determining the output error can include, for example, computing a vector distance such as the Euclidian distance, or squared Euclidian distance, between the produced output vector and the known output vector, and/or determining an average output error such as an average Euclidian distance or squared Euclidian distance if multiple input feature vectors were employed. Next, gradient descent can be performed to determine an updated weight vector based on the output error or average output error. This gradient descent step can include computing partial derivatives for the error with respect to each weight, or other parameter in the model parameter data 1355, at each layer starting with the output layer. Chain rule can be utilized to iteratively compute the gradient with respect to each weight or parameter at each previous layer until all weight's gradients are computed. Next updated weights, or other parameters in the model parameter data 1355, are generated by updating each weight based on its corresponding calculated gradient. This process can be repeated on at least one input feature vector, which can include the same or different at least one feature vector used in the previous iteration, based on the updated weight vector and/or other updated parameters in the model parameter data 1355 to create a new updated weight vector and/or other new updated parameters in the model parameter data 1355. This process can continue to repeat until the output error converges, the output error is within a certain error threshold, or another criterion is reached to determine the most recently updated weight vector and/or other model parameter data 1355 is optimal or otherwise determined for selection.

Having determined the medical scan neural network and its final other model parameter data 1355, an inference step 1354 can be performed on new medical scans to produce inference data 1370, such as inferred output vectors. The inference step can include performing the forward propagation algorithm to propagate an input feature vector through a plurality of neural network layers based on the final model parameter data 1355, such as the weight values of the final weight vector, to produce the inference data. This inference step 1354 can correspond to performing the medical scan image analysis function, as defined by the final model parameter data 1355, on new medical scans to generate the inference data 1370, for example, in conjunction with the medical scan diagnosing system 108 to generate inferred diagnosis data or other selected output data for triaged medical scans based on its corresponding the input feature vector.

The inference step 1354 can include applying the density windowing step to new medical scans. If the training step 1352 was used to determine optimal upper density value cut off and/or lower density value cut off values to designate an optimal density window, the inference step 1354 can include masking pixels of incoming scans that fall outside of this determined density window before applying the forward propagation algorithm. Similarly, if learned parameters of one or more convolutional functions correspond to the optimal upper density value cut off and/or lower density value cut off values, the density windowing step is inherently applied when the forward propagation algorithm is performed on the new medical scans.

In some embodiments where a medical scan analysis function is defined by model parameter data 1355 corresponding to a neutral network model, the neural network model can be a fully convolutional neural network. In such embodiments, only convolution functions are performed to propagate the input feature vector through the layers of the neural network in the forward propagation algorithm. This enables the medical scan image analysis functions to process input feature vectors of any size. For example, as discussed herein, the pixel data corresponding to the three-dimensional subregions is utilized input to the forward propagation algorithm when the training step 1352 is employed to populate the weight vector and/or other model parameter data 1355. However, when performing the forward propagation algorithm in the inference step 1354, the pixel data of full medical scans can be utilized as input, allowing the entire scan to be processed to detect and/or classify abnormalities, or otherwise generate the inference data 1370. This may be a preferred embodiment over other embodiments where new scans must also be sampled by selecting a three-dimensional subregions and/or other embodiments where the inference step requires "piecing together" inference data 1370 corresponding to multiple three-dimensional subregions processed separately.

In embodiments that utilize a fully convolutional neural network, padded data can be generated for each of the plurality of three-dimensional subregions in the training step 1352 and/or for each full medical scan in the inference step 1354 to allow the convolution functions to be applied on all portions of the subregion or full medical scan during the forward propagation algorithm. For example, padded data for each two-dimensional region, for example, at each of for boundaries of a rectangular region of the three-dimensional subregion, can be generated, and/or padded slices can be generated to be included before and/or after the set of consecutive slices. The amount of padded data to be generated at each two-dimensional boundary, or the number of padded slices to be generated before and/or after the consecutive slices can be based on parameters of the convolutional function utilized in the forward propagation step. The padded data can include zero-padded data. In some embodiments, the padded data can be generated based on a data reflection at a plurality of boundaries of the three-dimensional subregion or the full medical scan. Generating padded data based on data reflection rather than zero-padding can create more natural, seamless boundaries that are more contextually appropriate, and can better emulate actual image data at these boundaries.

The inferred output vector of the inference data 1370 can include a plurality of abnormality probabilities mapped to a pixel location of each of a plurality of cross-sectional image slices of the new medical scan. For example, the inferred output vector can indicate a set of probability matrices 1371, where each matrix in the set corresponds to one of the plurality of image slices of the medical scan, where each matrix is a size corresponding to the number of pixels in each image slice, where each cell of each matrix corresponds to a pixel of the corresponding image slice, whose value is the abnormality probability of the corresponding pixel.

A detection step 1372 can include determining if an abnormality is present in the medical scan based on the plurality of abnormality probabilities. Determining if an abnormality is present can include, for example, determining that a cluster of pixels in the same region of the medical scan correspond to high abnormality probabilities, for example, where a threshold proportion of abnormality probabilities must meet or exceed a threshold abnormality probability, where an average abnormality probability of pixels in the region must meet or exceed a threshold abnormality probability, where the region that includes the cluster of pixels must be at least a certain size, etc. Determining if an abnormality is present can also include calculating a confidence score based on the abnormality probabilities and/or other data corresponding to the medical scan such as patient history data. The location of the detected abnormality can be determined in the detection step 1372 based on the location of the pixels with the high abnormality probabilities. The detection step can further include determining an abnormality region 1373, such as a two-dimensional subregion on one or more image slices that includes some or all of the abnormality. The abnormality region 1373 determined in the detection step 1372 can be mapped to the medical scan to populate some or all of the abnormality location data 443 for use by one or more other subsystems 101 and/or client devices 120. Furthermore, determining whether or not an abnormality exists in the detection step 1372 can be used to populate some or all of the diagnosis data 440 of the medical scan, for example, to indicate that the scan is normal or contains an abnormality in the diagnosis data 440.

An abnormality classification step 1374 can be performed on a medical scan in response to determining an abnormality is present. Classification data 1375 corresponding to one or more classification categories such as abnormality size, volume, pre-post contract, doubling time, calcification, components, smoothness, texture, diagnosis data, one or more medical codes, a malignancy rating such as a Lung-RADS score, or other classifying data as described herein can be determined based on the detected abnormality. The classification data 1375 generated by the abnormality classification step 1374 can be mapped to the medical scan to populate some or all of the abnormality classification data 445 of the corresponding abnormality classifier categories 444 and/or abnormality pattern categories 446 and/or to determine one or more medical codes 447 of the medical scan. The abnormality classification step 1374 can include performing an abnormality classification function on the full medical scan, or the abnormality region 1373 determined in the detection step 1372. The abnormality classification function can be based on another model trained on abnormality data such as a support vector machine model, another neural network model, or any supervised classification model trained on medical scans, or portions of medical scans, that include known abnormality classifying data to generate inference data for some or all of the classification categories. For example, the abnormality classification function can include another medical scan analysis function. Classification data 1375 in each of a plurality of classification categories can also be assigned their own calculated confidence score, which can also be generated by utilizing the abnormality classification function. Output to the abnormality classification function can also include at least one identified similar medical scan and/or at least one identified similar cropped image, for example, based on the training data. The abnormality classification step can also be included in the inference step 1354, where the inferred output vector or other inference data 1370 of the medical scan image analysis function includes the classification data 1375.

The abnormality classification function can be trained on full medical scans and/or one or more cropped or full selected image slices from medical scans that contain an abnormality. For example, the abnormality classification function can be trained on a set of two-dimensional cropped slices that include abnormalities. The selected image slices and/or the cropped region in each selected image slice for each scan in the training set can be automatically selected based upon the known location of the abnormality. Input to the abnormality classification function can include the full medical scan, one or more selected full image slices, and/or one or more selected image slices cropped based on a selected region. Thus, the abnormality classification step can include automatically selecting one or more image slices that include the detected abnormality. The slice selection can include selecting the center slice in a set of consecutive slices that are determined to include the abnormality or selecting a slice that has the largest cross-section of the abnormality, or selecting one or more slices based on other criteria. The abnormality classification step can also include automatically generating one or more cropped two-dimensional images corresponding to the one or more of the selected image slices based on an automatically selected region that includes the abnormality.

Input to the abnormality classification function can also include other data associated with the medical scan, including patient history, risk factors, or other metadata. The abnormality classification step can also include determining some or all of the characteristics based on data of the medical scan itself. For example, the abnormality size and volume can be determined based on a number of pixels determined to be part of the detected abnormality. Other classifiers such as abnormality texture and/or smoothness can be determined by performing one or more other preprocessing functions on the image specifically designed to characterize such features. Such preprocessed characteristics can be included in the input to the abnormality classification function to the more difficult task of assigning a medical code or generating other diagnosis data. The training data can also be preprocessed to include such preprocessed features.

A similar scan identification step 1376 can also be performed on a medical scan with a detected abnormality and/or can be performed on the abnormality region 1373 determined in the detection step 1372. The similar scan identification step 1376 can include generating similar abnormality data 1377, for example, by identifying one or more similar medical scans or one or more similar cropped two-dimensional images from a database of medical scans and/or database of cropped two-dimensional images. Similar medical scans and/or cropped images can include medical scans or cropped images that are visually similar, medical scans or cropped images that have known abnormalities in a similar location to an inferred abnormality location of the given medical scan, medical scans that have known abnormalities with similar characteristics to inferred characteristics of an abnormality in the given scan, medical scans with similar patient history and/or similar risk factors, or some combination of these factors and/or other known and/or inferred factors. The similar abnormality data 1377 can be mapped to the medical scan to populate some or all of its corresponding similar scan data 480 for use by one or more other subsystems 101 and/or client devices 120.

The similar scans identification step 1376 can include performing a scan similarity algorithm, which can include generating a feature vector for the given medical scan and for medical scans in the set of medical scans, where the feature vector can be generated based on quantitative and/or category based visual features, inferred features, abnormality location and/or characteristics such as the predetermined size and/or volume, patient history and/or risk factor features, or other known or inferred features. A medical scan similarity analysis function can be applied to the feature vector of the given medical scan and one or more feature vectors of medical scans in the set. The medical scan similarity analysis function can include computing a similarity distance such as the Euclidian distance between the feature vectors, and assigning the similarity distance to the corresponding medical scan in the set. Similar medical scans can be identified based on determining one or more medical scans in the set with a smallest computed similarity distance, based on ranking medical scans in the set based on the computed similarity distances and identifying a designated number of top ranked medical scans, and/or based on determining if a similarity distance between the given medical scan and a medical scan in the set is smaller than a similarity threshold. Similar medical scans can also be identified based on determining medical scans in a database that mapped to a medical code that matches the medical code of the medical scan, or mapped to other matching classifying data. A set of identified similar medical scans can also be filtered based on other inputted or automatically generated criteria, where for example only medical scans with reliable diagnosis data or rich patient reports, medical scans with corresponding with longitudinal data in the patient file such as multiple subsequent scans taken at later dates, medical scans with patient data that corresponds to risk factors of the given patient, or other identified criteria, where only a subset of scans that compare favorably to the criteria are selected from the set and/or only a highest ranked single scan or subset of scans are selected from the set, where the ranking is automatically computed based on the criteria. Filtering the similar scans in this fashion can include calculating, or can be based on previously calculated, one or more scores as discussed herein. For example, the ranking can be based on a longitudinal quality score, such as the longitudinal quality score 434, which can be calculated for an identified medical scan based on a number of subsequent and/or previous scans for the patient. Alternatively or in addition, the ranking can be based on a confidence score associated with diagnosis data of the scan, such as confidence score data 460, based on performance score data 530 associated with a user or medical entity associated with the scan, based on an amount of patient history data or data in the medical scan entry 352, or other quality factors. The identified similar medical scans can be filtered based on ranking the scans based on their quality score and/or based on comparing their quality score to a quality score threshold. In some embodiments, a longitudinal threshold must be reached, and only scans that compare favorably to the longitudinal threshold will be selected. For example, only scans with at least three scans on file for the patient and final biopsy data will be included.

In some embodiments, the similarity algorithm can be utilized in addition to or instead of the trained abnormality classification function to determine some or all of the inferred classification data 1375 of the medical scan, based on the classification data such as abnormality classification data 445 or other diagnosis data 440 mapped to one or more of the identified similar scans. In other embodiments, the similarity algorithm is merely used to identify similar scans for review by medical professionals to aid in review, diagnosis, and/or generating medical reports for the medical image.

A display parameter step 1378 can be performed based on the detection and/or classification of the abnormality. The display parameter step can include generating display parameter data 1379, which can include parameters that can be used by an interactive interface to best display each abnormality. The same or different display parameters can be generated for each abnormality. The display parameter data generated in the display parameter step 1378 can be mapped to the medical scan to populate some or all of its corresponding display parameter data 470 for use by one or more other subsystems 101 and/or client devices 120.

Performing the display parameter step 1378 can include selecting one or more image slices that include the abnormality by determining the one or more image slices that include the abnormality and/or determining one or more image slices that has a most optimal two-dimensional view of the abnormality, for example by selecting the center slice in a set of consecutive slices that are determined to include the abnormality, selecting a slice that has the largest cross-section of the abnormality, selecting a slice that includes a two-dimensional image of the abnormality that is most similar to a selected most similar two-dimensional-image, selecting the slice that was used as input to the abnormality classification step and/or similar scan identification step, or based on other criteria. This can also include automatically cropping one or more selected image slices based on an identified region that includes the abnormality. This can also select an ideal Hounsfield window that best displays the abnormality. This can also include selecting other display parameters based on data generated by the medical scan interface evaluating system and based on the medical scan.

Figure 14A:
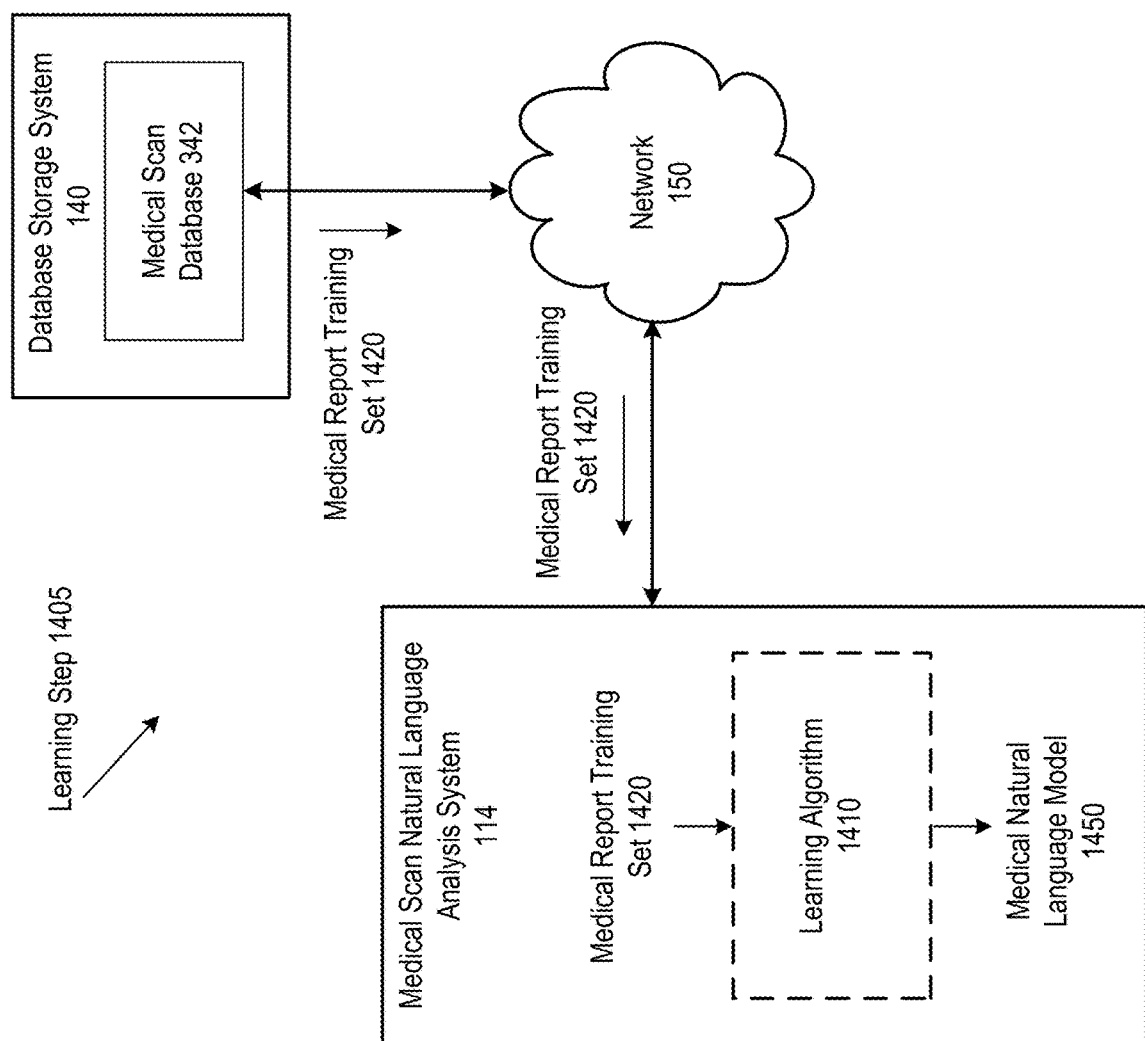
FIG. 14A-14B are schematic block diagrams of a medical scan natural language analysis system in accordance with various embodiments.
Figure 14B:
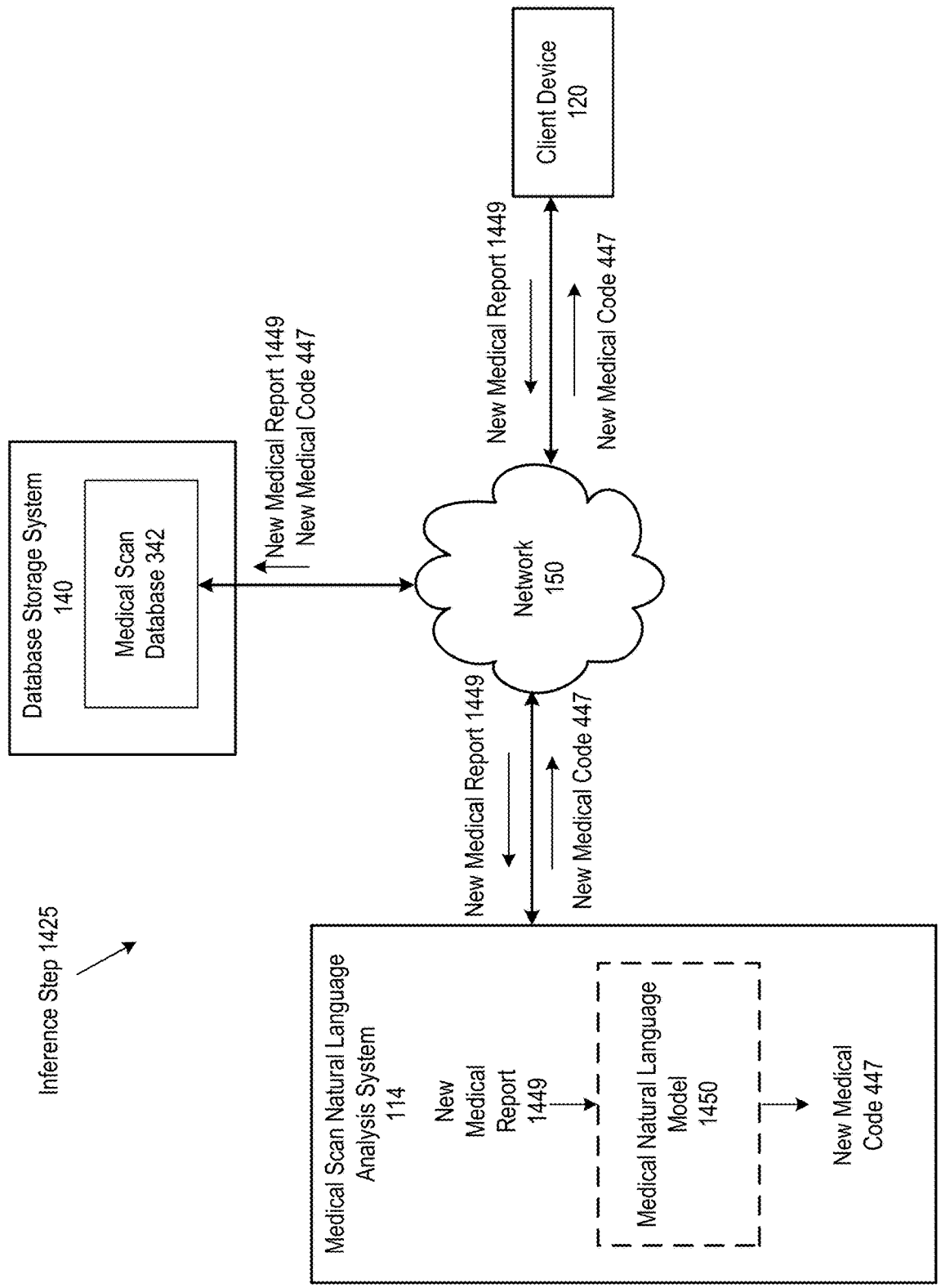

FIGS. 14A-14B present an embodiment of a medical scan natural language analysis system 114. The medical scan natural language analysis system 114 can determine a training set of medical scans with medical codes, such as medical codes 447, determined to be truth data. Corresponding medical reports, included in report data 449, and/or other natural language text data associated with a medical scan, such as natural language text data 448, can be utilized to train a medical scan natural language analysis function by generating a medical report natural language model. The medical scan natural language analysis function can be utilized to generate inference data for incoming medical reports for other medical scans to automatically determine corresponding medical codes, which can be mapped to corresponding medical scans as medical codes 447. Medical codes 447 assigned to medical scans by utilizing the medical report natural language model can be utilized by other subsystems, for example, to train other medical scan analysis functions, to be used as truth data to verify annotations provided via other subsystems, to aid in diagnosis, or otherwise be used by other subsystems as described herein.

In various embodiments, the medical scan natural language analysis system 114 is operable to generate a medical report natural language model based on a selected set of medical reports of a plurality of medical reports and the at least one medical code mapped to each of the selected set of medical reports. A medical report that is not included in the selected set is received via a network. A medical code is determined by utilizing the medical report natural language model on the first medical report. The medical code is mapped to a medical scan corresponding to the medical report, for example, where the medical scan is assigned to medical code 447. In various embodiments, additional diagnosis data 440 is also generated by the medical report natural language model and is mapped to the corresponding medical scan. In various embodiments, the medical scan natural language analysis system can generate and/or utilize the medical scan natural language analysis function as described herein in conjunction with generating and utilizing the medical report natural language model.

FIG. 14A presents a learning step 1405. A medical report training set 1420 that includes the selected set of medical reports of report data 449 and corresponding medical codes 447 can be retrieved from the medical scan database 342 by the medical scan natural language analysis system via the network 150. A learning algorithm 1410 can utilize natural language processing techniques to generate a medical report natural language model 1450 based on the medical report training set 1420. The medical report natural language model 1450 can include or be used to generate the medical scan natural language analysis function. FIG. 14B presents a training set 1425. A new medical report 1449 can be received from the medical scan database 342 or from a client device 120 via the network 150. The medical report natural language model 1450 can be utilized to determine at least one new medical code 447 from a plurality of possible medical codes 447. This new medical code 447 can be sent to a client device 120 and/or mapped to the report data 449 and/or corresponding medical scan in the medical scan database 342.

The medical scan natural language analysis system 114 can be utilized in conjunction with the medical scan report labeling system 104, and the systems can share access to the medical label alias database 920. The medical scan natural language analysis function can be utilized by the medical scan report labeling system 104 when performing the medical report analysis function to generate medical codes for medical reports automatically, where the medical scan natural language analysis function is trained on a set medical reports previously labeled and/or trained by the medical label alias database 920 of alias mapping pairs 925. Some or all of the automatically generated medical codes can still be sent to expert users for review, and performance score data 630 of medical scan natural language analysis function can be updated accordingly based on expert review. Model remediation, such as remediation step 1140, can be performed by the medical scan natural language analysis system 114 or another subsystem such as the medical scan diagnosing system 108 when the performance score data 630 indicates that the medical scan natural language analysis function needs to be retrained. The medical scan natural language analysis system 114 can also be used to generate new alias mapping pairs 925 for inclusion in the medical label alias database 920. The medical report natural language model can also be trained on medical reports corresponding to medical scans with medical codes 447 that have already been assigned in the medical scan database by other subsystems.

The medical report natural language model can be a fully convolutional neural network or another neural network. Generating the medical report natural language model can be based on techniques described in conjunction with the medical scan image analysis system 112 and based on learning algorithms that utilize natural language processing techniques. Generating the medical report natural language can include utilizing a forward propagation algorithm on the plurality of medical reports to generate a preliminary set of neural network parameters, and can include utilizing a back propagation algorithm to generate an updated set of neural network parameters based on a calculated set of parameter errors and the preliminary set of neural network parameters. Determining medical codes for new medical reports can include utilizing the forward propagation algorithm on the new medical reports based on the updated set of neural network parameters.

Utilizing the medical report natural language model to determine the first medical code can include identifying a relevant medical term in the first medical report. After processing the relevant medical term and the medical code can be transmitted to a client device via the network for display by a display device in conjunction with the medical report. The relevant medical term is identified in the natural language text data of the first medical report in conjunction with displaying the first medical code, for example, where the relevant medical term is highlighted or otherwise indicated. Display of the relevant medical term can be based on a corresponding interface feature, and can be presented in conjunction with the medical scan assisted review system 102 and/or can be presented to an expert user of the medical scan report labeling system 104. In various embodiments, the relevant medical term is associated with an alias mapping pair 925 utilized to determine the medical code. In other embodiments, a user of the client device can elect to add the relevant medical term and the medical code as a new alias mapping pair 925 for the medical label alias database 920.

The medical scan natural language analysis system 114 can also be utilized to generate the medical report generating function. The trained medical report natural language model 1450 can be utilized to take image data 410 of medical scans, diagnosis data 440, or other data of a medical scan entry 352 as input and produce a written report as output. The medical report generating function can be trained on the same or different training set as the medical scan natural language analysis function.

FIGS. 14C-14D provide examples of medical codes 447 determined by utilizing an embodiment of a medical scan natural language analysis system 114 on a report data 449. Some or all of the text of report data 449 and/or some or all medical codes 447 can be presented by an interactive interface displayed on a client device, can be mapped to medical scans in the medical scan database, and/or can be utilized by one or more additional subsystems. While the medical codes shown include ICD-9 codes and CPT codes determined based on the medical report, any medical codes 447 described herein can be determined.

Figure 15:
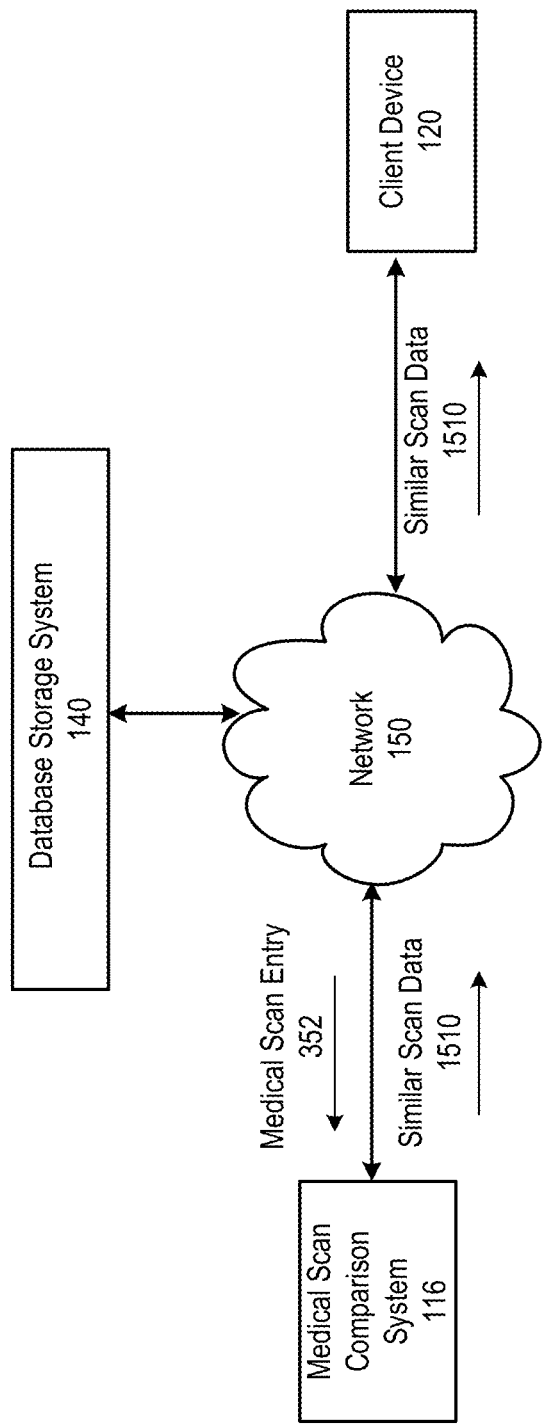
FIG. 15 is a schematic block diagram of a medical scan comparison system in accordance with various embodiments.

FIG. 15 presents an embodiment of a medical scan comparison system 116. Features of the medical scan comparison system 116 can be utilized by one or more subsystems to identify and/or display similar medical scans, for example, to perform or determine function parameters for the medical scan similarity analysis function, to generate or retrieve similar scan data 1510, which can include some or all of similar scan data 480, or otherwise compare medical scan data. The medical scan comparison system 116 can also utilize some or all features of other subsystems as described herein.

As illustrated in FIG. 15, the medical scan comparison system 116 can receive a medical scan via network 150. The medical scan comparison system can determine at least one similar medical scan and generate similar scan data 1510 for transmission to a client device 120 for display, for example, in conjunction with the medical scan assisted review system 102.

In various embodiments, the medical scan comparison system 116 is operable to receive a medical scan via a network and to generate similar scan data. The similar scan data includes a subset of medical scans from a medical scan database and is generated by performing an abnormality similarity function, such as medical scan similarity analysis function, to determine that a set of abnormalities included in the subset of medical scans compare favorably to an abnormality identified in the medical scan. At least one cross-sectional image is selected from each medical scan of the subset of medical scans for display on a display device associated with a user of the medical scan comparison system in conjunction with the medical scan.

Figure 16:
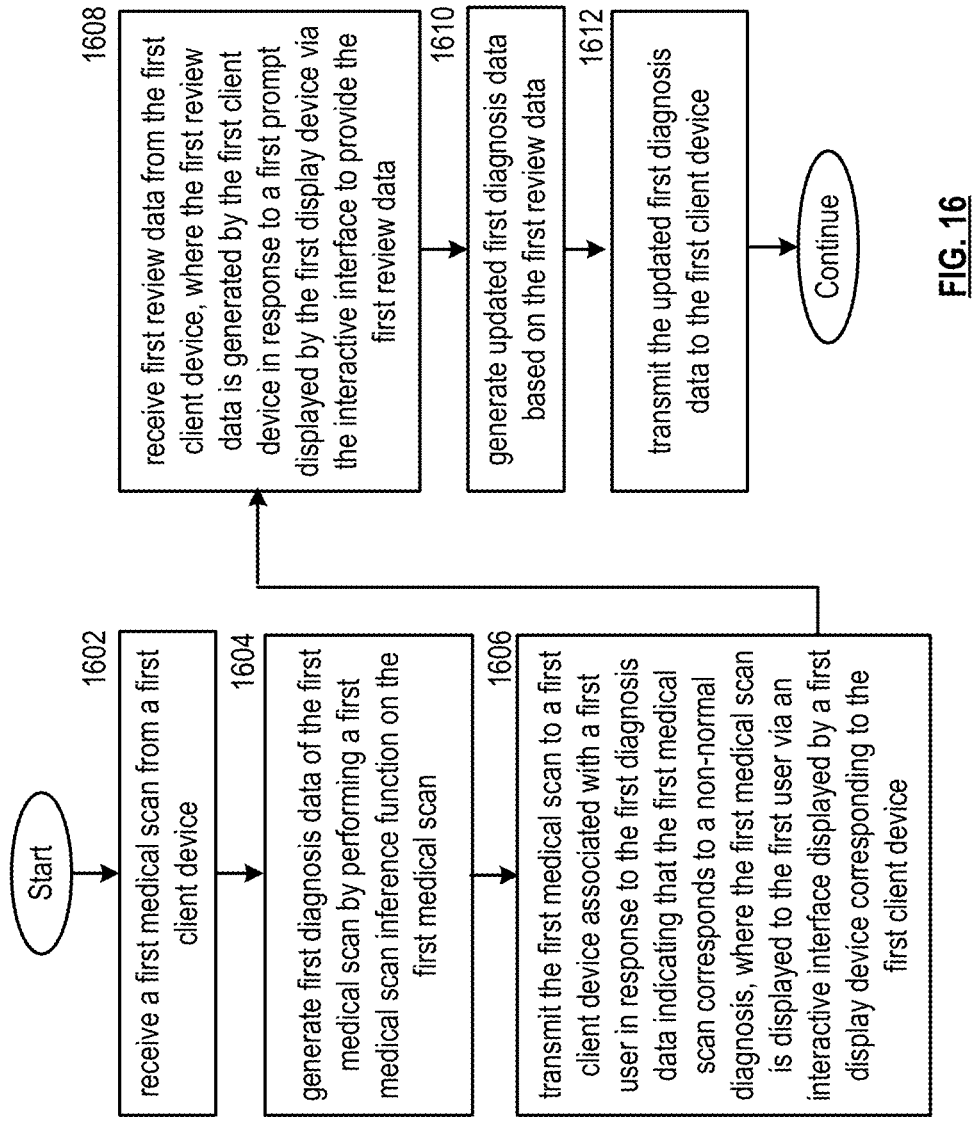
FIG. 16 is a flowchart representation of a method in accordance with an embodiment.

FIG. 16 presents an embodiment of a method for execution by a medical scan diagnosing system 108 or other subsystem as described herein that includes a processor. Step 1602 includes receiving, via a network, a first medical scan. Step 1604 includes generating first diagnosis data of the first medical scan by performing a first medical scan inference function on the first medical scan. Step 1606 includes transmitting, via the network, the first medical scan to a first client device associated with a first user of the medical scan diagnosing system in response to the first diagnosis data indicating that the first medical scan corresponds to a non-normal diagnosis, where the first medical scan is displayed to the first user via an interactive interface displayed by a first display device corresponding to the first client device. Step 1608 includes receiving, via a network, first review data from the first client device, where the first review data is generated by the first client device in response to a first prompt displayed by the first display device via the interactive interface to provide the first review data. Step 1610 includes generating updated first diagnosis data based on the first review data. Step 1612 includes transmitting, via the network, the updated first diagnosis data to a second client device associated with a requesting entity.

In various embodiments, an updated first medical scan inference function is generated in response to determining the first review data indicates that the first diagnosis data is incorrect. In various embodiments, the first diagnosis data is transmitted to the first client device, and the first diagnosis data is displayed to the first user via the interactive interface in conjunction with the first medical scan. In various embodiments, the first review data includes second diagnosis data in response to the first prompt displayed by the first display device via the interactive interface to provide the second diagnosis data. Determining the first review data indicates that the first diagnosis data is incorrect is based on comparing the first diagnosis data to the second diagnosis data.

In various embodiments, a second medical scan is received. Second diagnosis data of the second medical scan is generated by performing the first medical scan inference function on the second medical scan. Model quality check condition data is generated in response to the second diagnosis data indicating that the second medical scan corresponds to a normal diagnosis. The second medical scan is transmitted to the first client device in response to the model quality check condition data indicating that a quality check condition is met. The second medical scan is displayed to the first user via the interactive interface displayed by a first display device corresponding to the first client device. Second review data from the first client device, where the second review data is generated by the first client device in response to a second prompt displayed by the first display device via the interactive interface to provide the second review data. An updated first medical scan inference function is generated in response to determining the second review data indicates that the second diagnosis data is incorrect. In various embodiments, generating the model quality check condition data is based on determining if a quality check quota is met.

In various embodiments, the first medical scan inference function is selected from a plurality of medical scan inference functions based on a first medical scan classifier corresponding to the first medical scan. In various embodiments, a new medical scan classifier is generated by performing a medical scan classifier function on the first medical scan. The first medical scan inference function is selected based on the new medical scan classifier in response to determining that the first medical scan classifier compares unfavorably to the new medical scan classifier. In various embodiments, the first medical scan classifier is indicated in metadata of the first medical scan, retrieved from a medical scan database. Updated metadata corresponding to the first medical scan is generated based on the new medical scan classifier. The updated metadata is mapped to the first medical scan in the medical scan database. In various embodiments, the first medical scan classifier indicates one of a plurality of anatomical regions, and the plurality of medical scan inference functions correspond to the plurality of anatomical regions.

In various embodiments, a user database includes a plurality of registered entities that includes the requesting entity. The first medical scan is received from the second client device, and usage data corresponding to the requesting entity is retrieved from the user database in response to receiving the first medical scan. The first diagnosis data is generated in response to determining the usage data compares favorably to a usage quota.

In various embodiments, test diagnosis data is generated for each medical scan in a medical scan test set by performing the first medical scan inference function on each medical scan in the medical scan test set. Model quality check data is generated by comparing the test diagnosis data to truth diagnosis data corresponding to the medical scan test set. The first medical scan inference function is updated in response to determining that the model quality check data compares unfavorably to the truth diagnosis data. In various embodiments, the test diagnosis data is generated in response to determining an update to a hardware component and/or a software component of the processing system and/or the memory.

Figure 17:
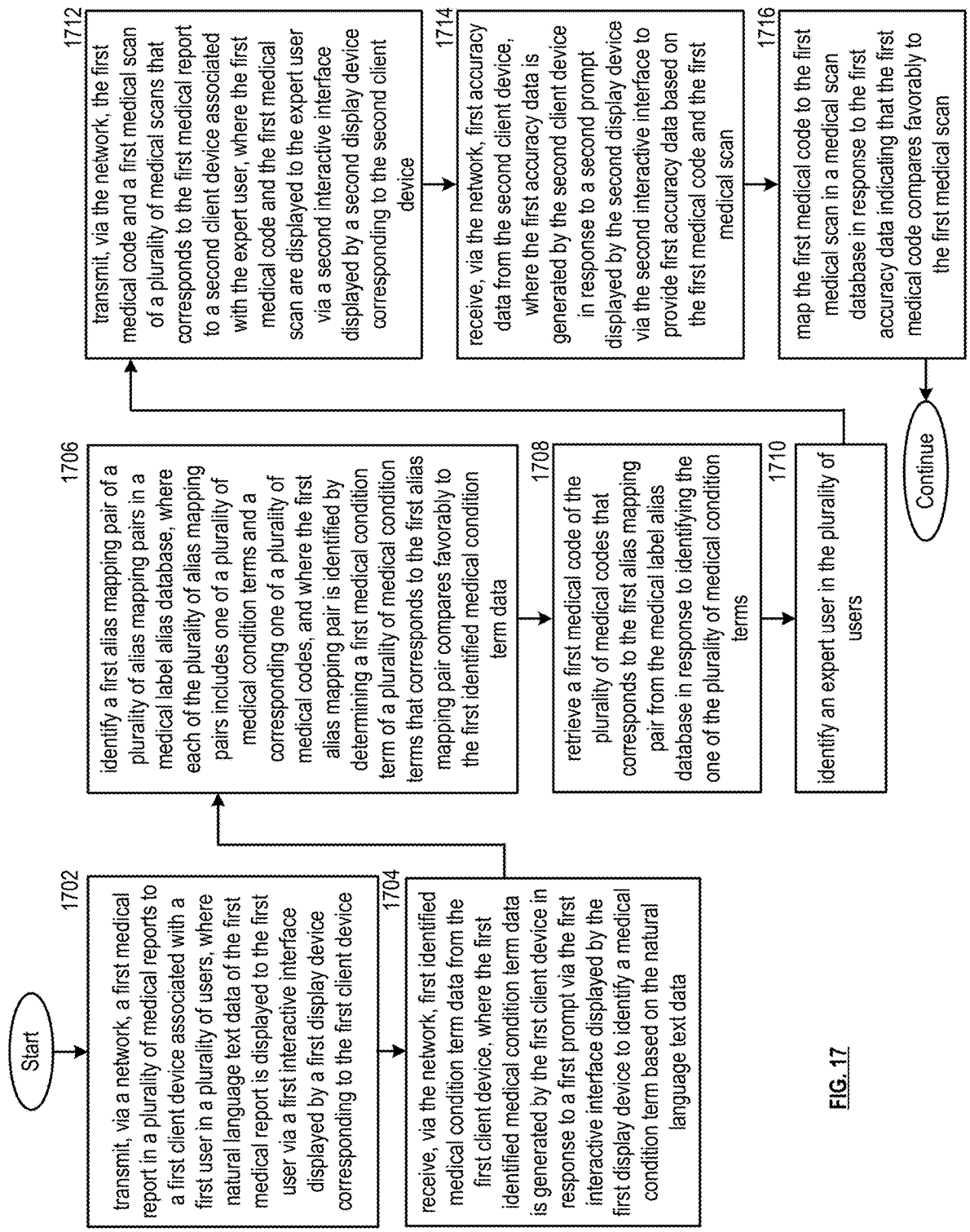
FIG. 17 is a flowchart representation of a method in accordance with an embodiment.

FIG. 17 presents an embodiment of a method for execution by a medical scan report labeling system 104 or other subsystem as described herein that includes a processor. Step 1702 include transmitting, via a network, a first medical report in a plurality of medical reports to a first client device associated with a first user in a plurality of users of the medical scan report labeling system, where natural language text data of the first medical report is displayed to the first user via a first interactive interface displayed by a first display device corresponding to the first client device. Step 1704 includes receiving, via the network, first identified medical condition term data from the first client device, where the first identified medical condition term data is generated by the first client device in response to a first prompt via the first interactive interface displayed by the first display device to identify a medical condition term based on the natural language text data. Step 1706 includes identifying a first alias mapping pair of a plurality of alias mapping pairs in a medical label alias database, where each of the plurality of alias mapping pairs includes one of a plurality of medical condition terms and a corresponding one of a plurality of medical codes, and where the first alias mapping pair is identified by determining a first medical condition term of a plurality of medical condition terms that corresponds to the first alias mapping pair compares favorably to the first identified medical condition term data. Step 1708 includes retrieving a first medical code of the plurality of medical codes that corresponds to the first alias mapping pair from the medical label alias database in response to identifying the one of the plurality of medical condition terms. Step 1710 includes identifying an expert user in the plurality of users. Step 1712 includes transmitting, via the network, the first medical code and a first medical scan of a plurality of medical scans that corresponds to the first medical report to a second client device associated with the expert user, where the first medical code and the first medical scan are displayed to the expert user via a second interactive interface displayed by a second display device corresponding to the second client device. Step 1714 includes receiving, via the network, first accuracy data from the second client device, where the first accuracy data is generated by the second client device in response to a second prompt displayed by the second display device via the second interactive interface to provide first accuracy data based on the first medical code and the first medical scan. Step 1716 includes mapping the first medical code to the first medical scan in a medical scan database in response to the first accuracy data indicating that the first medical code compares favorably to the first medical scan.

In various embodiments, the plurality of medical codes correspond to SNOMED codes, CPT codes, ICD-9 codes, and/or ICD-10 codes. In various embodiments, a corrected medical code is received from the second client device, where the corrected medical code is generated by the second client device in response to a third prompt displayed by the second display device via the second interactive interface to identify a corrected medical code, and where the third prompt is displayed in response to the first accuracy data indicating that the first medical code compares unfavorably to the first medical scan. The corrected medical code to the first medical scan in the medical scan database. In various embodiments, the first medical report is transmitted to the second client device for display to the expert user via a second interactive interface. A new alias mapping pair is received from the second client device that includes the corrected medical code, where the new alias mapping pair is generated by the second client device in response to a fourth prompt displayed by the second display device via the second interactive interface to identify a new alias mapping pair based on the first medical report and the first medical scan, and where a new medical condition term of the new alias mapping pair is not included in the medical label alias database. The new alias mapping pair is added to the medical label alias database.

In various embodiments, the first identified medical condition term data is generated by the first client device based on an identified segment of consecutive words in the natural language text data of the first medical report. In various embodiments, the first identified medical condition term data is generated by the first client device based on an identified plurality of words in the natural language text data of the first medical report, where at least two of the identified plurality of words are not consecutive words in the natural language text data of the first medical report. In various embodiments, the first identified medical condition term data is generated by the first client device based on a plurality of words, where at least one word in the plurality of words is not included in the natural language text data of the first medical report, and where the at least one word is based on keyboard and/or voice input via the first interactive interface. In various embodiments, the first medical condition term of the first alias mapping pair and the first identified medical condition term data received from the first client device differ by at least one word. Determining that first medical condition term compares favorably to the first identified medical condition term data includes calculating a similarity score between the first medical condition term and the first identified medical condition term data and further includes determining that the similarity score compares favorably to a similarity threshold.

In various embodiments, a second medical report in the plurality of medical reports is transmitted to a third client device associated with a third user in a plurality of users of the medical scan report labeling system. The natural language text data of the second medical report is displayed to the third user via a third interactive interface displayed by a third display device corresponding to the third client device. Second identified medical condition term data is received from the third client device, where the second identified medical condition term data is generated by the third client device in response to a third prompt via the third interactive interface displayed by the third display device to identify a medical condition term based on the natural language text data. The second medical report and a second medical scan of the plurality of medical scans that corresponds to the second medical report are transmitted to the second client device associated with the expert user in response to determining that the medical label alias database does not include a one of the plurality of medical condition terms that compares favorably to the second identified medical condition term data. The natural language text data of the second medical report and the one of the plurality of medical scans are displayed to the expert user via a second interactive interface displayed by a second display device corresponding to the second client device. A new alias mapping pair is received from the second client device. The new alias mapping pair is generated by the second client device in response to a fourth prompt displayed by the second display device via the second interactive interface to identify a new alias mapping pair based on the second medical report and the second medical scan, where a new medical condition term of the new alias mapping pair is not included in the medical label alias database. The new alias mapping pair is added to the medical label alias database, and a second medical code in the new alias mapping pair is mapped to the second medical scan.

In various embodiments, at least one of the plurality of medical codes is included in more than one of the plurality of alias mapping pairs. In various embodiments, the first medical report and the first medical code are added to a training set that includes a subset of the plurality of medical reports and a corresponding plurality of medical codes. A medical report natural language model is generated based on the training set. A second medical report in the plurality of medical reports that is not included in the training set is identified. A second medical code of the plurality of medical codes is determined by utilizing the medical report natural language model on the second medical report, and the second medical code is mapped to a second medical scan corresponding to the second medical report. In various embodiments, the second medical code, as well as the second medical report and/or second medical scan in the plurality of medical scans that corresponds to the second medical report, are transmitted to the second client device. The second medical code, as well as the second medical report and/or the second medical scan, are displayed to the expert user via a third interactive interface displayed by the second display device corresponding to the second client device. Model accuracy data is received from the second client device, where the model accuracy data is generated by the second client device in response to a third prompt displayed by the second display device via the third interactive interface to provide model accuracy data based on the first medical code and the second medical report and/or the second medical scan. The second medical code is mapped to the second medical scan in the medical scan database in response to the model accuracy data indicating that the second medical code compares favorably to the second medical report and/or the second medical scan.

Figure 18:
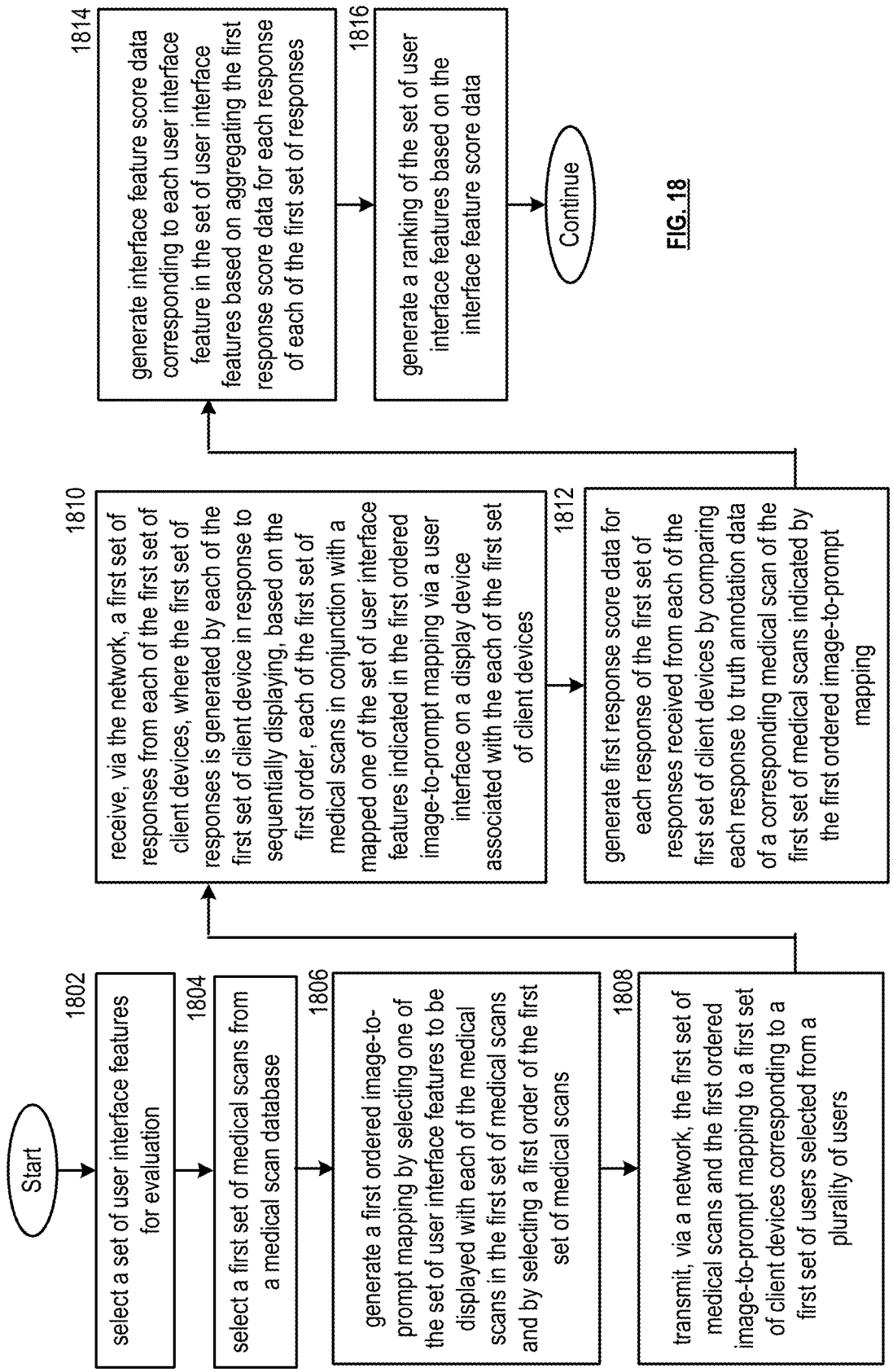
FIG. 18 is a flowchart representation of a method in accordance with an embodiment.

FIG. 18 presents an embodiment of a method for execution by a medical scan interface feature evaluator system 110 or other subsystem as described herein that includes a processor. Step 1802 includes selecting a set of user interface features for evaluation. Step 1804 includes selecting a first set of medical scans from a medical scan database. Step 1806 includes generating a first ordered image-to-prompt mapping by selecting one of the set of user interface features to be displayed with each of the medical scans in the first set of medical scans and by selecting a first order of the first set of medical scans. Step 1808 includes transmitting, via a network, the first set of medical scans and the first ordered image-to-prompt mapping to a first set of client devices corresponding to a first set of users selected from a plurality of users. Step 1810 includes receiving, via the network, a first set of responses from each of the first set of client devices, where the first set of responses is generated by each of the first set of client device in response to sequentially displaying, based on the first order, each of the first set of medical scans in conjunction with a mapped one of the set of user interface features indicated in the first ordered image-to-prompt mapping via a user interface on a display device associated with the each of the first set of client devices. Step 1812 includes generating first response score data for each response of the first set of responses received from each of the first set of client devices by comparing each response to truth annotation data of a corresponding medical scan of the first set of medical scans indicated by the first ordered image-to-prompt mapping. Step 1814 includes generating interface feature score data corresponding to each user interface feature in the set of user interface features based on aggregating the first response score data for each response of each of the first set of responses. Step 1816 includes generating a ranking of the set of user interface features based on the interface feature score data.

In various embodiments, a lowest ranked user interface feature in the ranking is automatically removed from the set of user interface features. In various embodiments, at least one response in the first set of responses indicates that a corresponding medical scan is normal in response to one of the first set of client devices displaying one of the set of user interface features that includes a prompt to select either that a displayed medical scan is normal or that the displayed medical scan includes an abnormality. Generating the first response score data for the at least one response includes assigning a low score to the one response based on determining that the truth annotation data of an at least one corresponding medical scan indicates at least one abnormality. In various embodiments, at least one response in the first set of responses includes abnormality classification data generated by one of the first set of client devices in response to displaying one of the set of user interface features that includes a prompt to classify an abnormality. Generating the first response score data of the at least one response includes comparing the abnormality classification data of the at least one response to the truth annotation data of an at least one corresponding medical scan. In various embodiments, at least one response in the first set of responses includes an identified region generated by one of the first set of client devices in response to displaying one of the set of user interface features that includes a prompt to identify a region of the displayed medical scan that includes an abnormality. Generating the first response score data includes comparing the identified region of the at least one response to the truth annotation data of an at least one corresponding medical scan.

In various embodiments, a second set of medical scans is selected from the medical scan database. A second ordered image-to-prompt mapping is generated by selecting one of the set of user interface features to be displayed with each of the medical scans in the second set of medical scans and by selecting a second order of the second set of medical scans, where the second ordered image-to-prompt mapping is different than the first ordered image-to-prompt mapping. The second set of medical scans and the set of user interface features are transmitted to a second client device corresponding to a second user selected from the plurality of users, where the second client device is not included in the first set of client devices. A second set of responses are received from the second client device, where the second set of responses is generated by the second client device in response to utilizing the second ordered image-to-prompt mapping to sequentially display each of the second set of medical scans in conjunction with a user interface based on the mapped one of the set of user interface features on a second user interface on a second display device associated with second client device. Second response score data is generated for each response of each of the second set of responses by comparing each of the second set of responses to the truth annotation data of a corresponding medical scan indicated by the second ordered image-to-prompt mapping. Generating the interface feature score data corresponding to each user interface feature in the set of user interface features is further based on the second response score data. In various embodiments, the first ordered image-to-prompt mapping is generated based on first performance score data of the first set of users, and the second ordered image-to-prompt mapping is generated based on second performance score data of the second user.

In various embodiments, a new medical scan is received via the network. A new interface mapping is generated for the new medical scan by selecting at least one user interface feature from the set of user interface features based on the ranking of the set of user interface features. The new medical scan and the new interface mapping are transmitted to a third client device associated with a third user selected from the plurality of users. Third response data is received from the third client device, where the third response data is generated by the third client device in response to utilizing the new interface mapping to display the new medical scan in conjunction with the selected at least one user interface feature a third user interface on a third display device associated with the one of the third client device. New annotation data is generated based on the third response data, and the new annotation data is mapped to the new medical scan in the medical scan database. In various embodiments, the at least one user interface feature is selected based by determining at least one highest ranked user interface feature in the ranking. In various embodiments, the first set of medical scans each correspond to one of a set of scan categories. The ranking includes a set of categorized rankings corresponding to the set of scan categories, and the at least one user interface feature is selected for the new interface mapping based on a one of the set of categorized rankings that corresponds to a scan category of the new medical scan.

Figure 19:
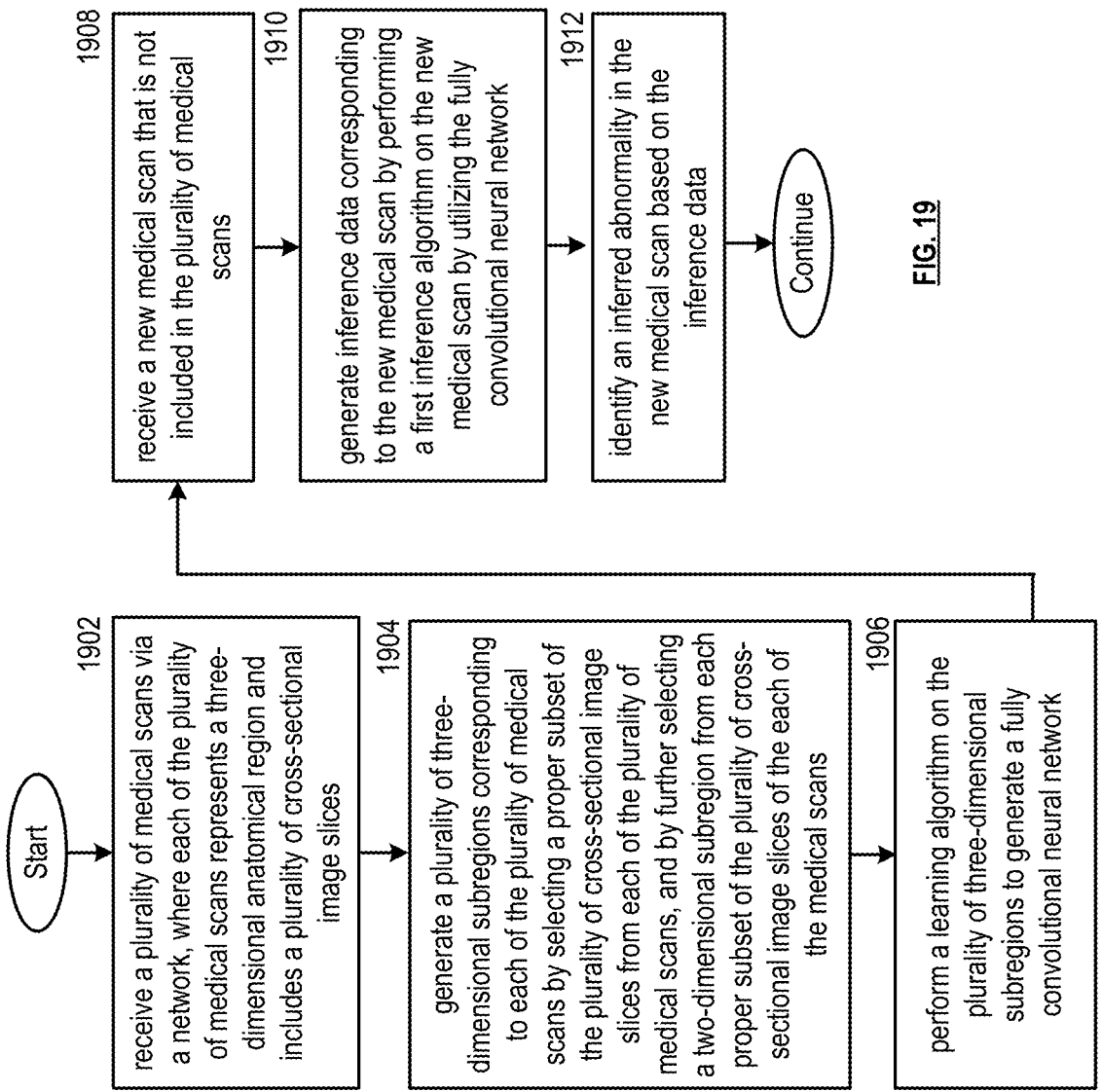
FIG. 19 is a flowchart representation of a method in accordance with an embodiment.

FIG. 19 presents an embodiment of a method for execution by a medical scan image analysis system 112 or other subsystem as described herein that includes a processor. Step 1902 includes receiving a plurality of medical scans via a network, where each of the plurality of medical scans represents a three-dimensional anatomical region and includes a plurality of cross-sectional image slices. Step 1904 includes generating a plurality of three-dimensional subregions corresponding to each of the plurality of medical scans by selecting a proper subset of the plurality of cross-sectional image slices from each of the plurality of medical scans, and by further selecting a two-dimensional subregion from each proper subset of the plurality of cross-sectional image slices of the each of the medical scans. Step 1906 includes performing a learning algorithm on the plurality of three-dimensional subregions to generate a fully convolutional neural network. Step 1908 includes receiving a new medical scan that is not included in the plurality of medical scans. Step 1910 includes generating inference data corresponding to the new medical scan by performing a first inference algorithm on the new medical scan by utilizing the fully convolutional neural network. Step 1912 includes identifying an inferred abnormality in the new medical scan based on the inference data.

In various embodiments, performing the learning algorithm includes utilizing a forward propagation algorithm on the plurality of three-dimensional subregions to generate a preliminary set of neural network parameters, and by utilizing a back propagation algorithm to generate an updated set of neural network parameters based on a calculated set of parameter errors and the preliminary set of neural network parameters. Performing the first inference algorithm includes utilizing the forward propagation algorithm on the new medical scan based on the updated set of neural network parameters.

In various embodiments, at least one of the plurality of medical scans includes a known abnormality. Selecting the proper subset of the plurality of cross-sectional image slices of the at least one of the plurality of medical scans is based on a known location of the known abnormality, and selecting the two-dimensional subregion from each proper subset of the plurality of cross-sectional image slices is based on the known location of the known abnormality. In various embodiments, each of the plurality of three-dimensional subregions of the at least one of the plurality of medical scans include the known abnormality. In various embodiments, the each of the plurality of three-dimensional subregions are selected randomly or psuedo-randomly. A first subregion option corresponding to a one of the plurality of medical scans has a first selection probability based on a first proximity of the first subregion option to the known location of the known abnormality, and a second subregion option corresponding to the one of the plurality of medical scans has a second selection probability based on a second proximity of the first subregion option to the known location of the known abnormality. The first selection probability is higher than the second selection probability based on the first proximity being nearer than the second proximity.

In various embodiments, a first number of pixels in a one three-dimensional subregions of the plurality of three-dimensional subregions is smaller than a second number of pixels in a corresponding one of the plurality of medical scans. In various embodiments, generating the inference data includes generating a plurality of abnormality probabilities. Each of the plurality of abnormality probabilities is mapped to a pixel location of each of a plurality of cross-sectional image slices of the new medical scan, and identifying the inferred abnormality is based on the plurality of abnormality probabilities. In various embodiments, classification data corresponding to the inferred abnormality is generated based on the inference data. In various embodiments, generating the classification data includes generating a new three-dimensional subregion of the new medical scan that includes the inferred abnormality and by performing a second inference algorithm on the new three-dimensional subregion.

In various embodiments, a density window for the plurality of medical scans is determined by determining a low end density cut-off value and high end density cut-off value based on Hounsfield units of the each of the plurality of medical scans. A plurality of preprocessed medical scans are generated by utilizing the density window to mask a first subset of pixels of the plurality of medical scans. The plurality of three-dimensional subregions are generated by utilizing the plurality of preprocessed medical scans. In various embodiments, an updated low end density cut-off value and an updated high end density cut-off value are generated in a first iteration of the learning algorithm. A plurality of processed medical scans are generated by utilizing the updated low end density cut-off value and the updated high end density cut-off value to mask a second subset of pixels of the plurality of medical scans. A subsequent iteration of the learning algorithm is performed on the plurality of processed medical scans to generate the fully convolutional neural network.

In various embodiments, padded data is generated for each of the plurality of three-dimensional subregions based on a data reflection at a plurality of boundaries of each of the plurality of three-dimensional subregions. Performing the learning algorithm includes convolving each of the plurality of three-dimensional subregions, where the padded data is utilized to convolve each of the plurality of three-dimensional subregions at the plurality of boundaries.

Figure 20:
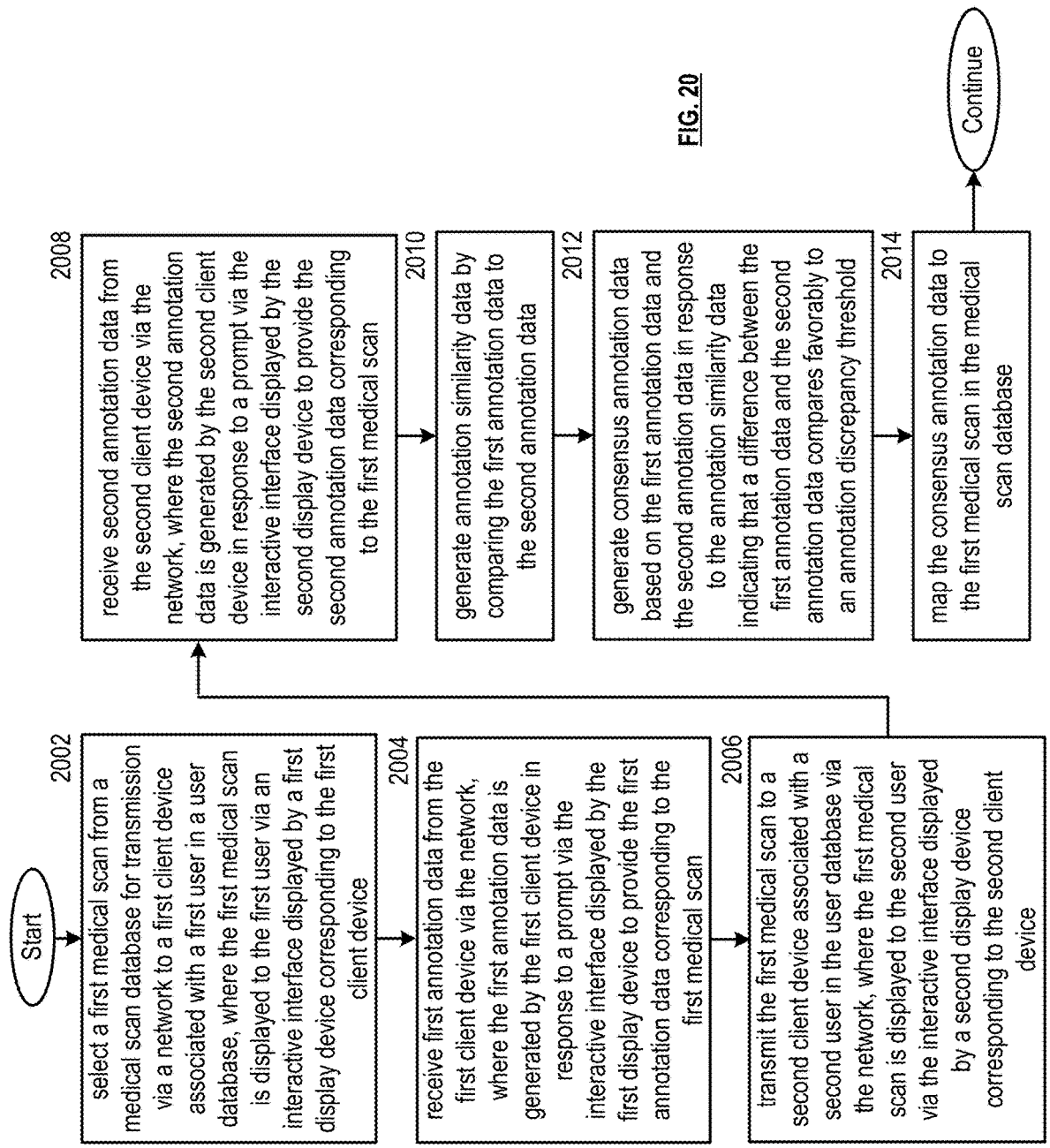
FIG. 20 is a flowchart representation of a method in accordance with an embodiment.

FIG. 20 presents an embodiment of a method for execution by a medical scan annotator system 106 or other subsystem as described herein that includes a processor. Step 2002 includes selecting a first medical scan from a medical scan database for transmission via a network to a first client device associated with a first user in a user database, where the first medical scan is displayed to the first user via an interactive interface displayed by a first display device corresponding to the first client device. Step 2004 includes receiving first annotation data from the first client device via the network, where the first annotation data is generated by the first client device in response to a prompt via the interactive interface displayed by the first display device to provide the first annotation data corresponding to the first medical scan. Step 2006 includes transmitting the first medical scan to a second client device associated with a second user in the user database via the network, where the first medical scan is displayed to the second user via the interactive interface displayed by a second display device corresponding to the second client device. Step 2008 includes receiving second annotation data from the second client device via the network, where the second annotation data is generated by the second client device in response to a prompt via the interactive interface displayed by the second display device to provide the second annotation data corresponding to the first medical scan. Step 2010 includes generating annotation similarity data by comparing the first annotation data to the second annotation data. Step 2012 includes generating consensus annotation data based on the first annotation data and the second annotation data in response to the annotation similarity data indicating that a difference between the first annotation data and the second annotation data compares favorably to an annotation discrepancy threshold. Step 2014 includes mapping the consensus annotation data to the first medical scan in the medical scan database.

In various embodiments, a first expert user is selected from a set of expert users in the user database in response to the annotation similarity data indicating that the difference between the first annotation data and the second annotation data compares unfavorably to the annotation discrepancy threshold. The medical scan is transmitted to a third client device associated with the first expert user. The first medical scan is displayed to the first expert user via the interactive interface displayed by a third display device corresponding to the third client device. Third annotation data is received from the third client device. The third annotation data is generated by the third client device in response to a first prompt via the interactive interface displayed by the third display device to provide third annotation data. The third annotation data is mapped to the first medical scan in the medical scan database. In various embodiments, the first annotation data and the second annotation data is transmitted to the third client device, and the first annotation data and the second annotation data are displayed via the interactive interface. In various embodiments, the interactive interface includes a prompt to select the first annotation data or the second annotation data. The third annotation data corresponds to the first annotation data in response to a selection of the first annotation data via the interactive interface. In various embodiments, the user database stores user performance data corresponding to the plurality of users. An annotation accuracy score is generated by comparing the first annotation data to the third annotation data. The user performance data corresponding to the first user is updated in the user database based on the annotation accuracy score.

In various embodiments, the medical scan database includes a set of triaged medical scans and a set of corresponding priority values received from a triaging entity via the network. The first medical scan is selected from the set of triaged medical scans based on a ranking of the set of corresponding priority values, and the third annotation data is transmitted to the triaging entity via the network. The user database stores user efficiency data corresponding to the plurality of users, where the set of triaged medical scans are assigned to a subset of the plurality of users based on the set of corresponding priority values and further based on the user efficiency data. In various embodiments, the user database stores user specialization data corresponding to the plurality of users. A medical scan category corresponding to the first medical scan is determined, and the first user is selected based on determining that the user specialization data compares favorably to the medical scan category.

In various embodiments, the user database stores user performance data corresponding to the plurality of users. A second medical scan is selected from the medical scan database for transmission via a network to a fourth client device associated with a fourth user of the medical scan annotator system, where the second medical scan is displayed to the fourth user via an interactive interface displayed by a fourth display device corresponding to the fourth client device. Fourth annotation data is received from the fourth client device, where the fourth annotation data is generated by the fourth client device based on user input to the interactive interface in response to a prompt via the interactive interface displayed by the fourth display device to provide the fourth annotation data corresponding to the second medical scan. Truth annotation data mapped to the second medical scan is retrieved from a medical scan database. An annotation accuracy score is generated by comparing the fourth annotation data to the truth annotation data. User performance data corresponding to the fourth user in the user database is updated based on the annotation accuracy score. In various embodiments, truth annotation data is received from a fifth client device corresponding to a second expert user. The truth annotation data to the second medical scan. In various embodiments, the truth annotation data is generated by performing an automated annotating function on the second medical scan that utilizes a computer vision model, where the computer vision model is trained on a subset of the plurality of medical scans. The truth annotation data is mapped to the second medical scan.

In various embodiments, the user performance data includes specialization data that includes a plurality of category specialty scores. At least one image category corresponding to the second medical scan is determined. At least one category specialty score of the specialization data of the fourth user is updated based on the annotation accuracy score, where the at least one category specialty score corresponds to the at least one image category. The fourth user is added to a set of expert users in the user database in response to determining that the updated user performance data compares favorably to an expert status threshold.

In various embodiments, the first annotation data indicates either that the first medical scan includes no abnormalities or that the first medical scan includes an abnormality. In various embodiments, the interactive interface prompts the first user to provide abnormality classification data in response to the first annotation data indicating that the first medical scan includes an abnormality, and the first annotation data further indicates the abnormality classification data. In various embodiments, the interactive interface prompts the first user to provide abnormality location data in response to the first annotation data indicating that the first medical scan includes an abnormality, and the first annotation data indicates the abnormality location data. In various embodiments, the first medical scan is a chest x-ray or a chest CT scan.

Figure 21:
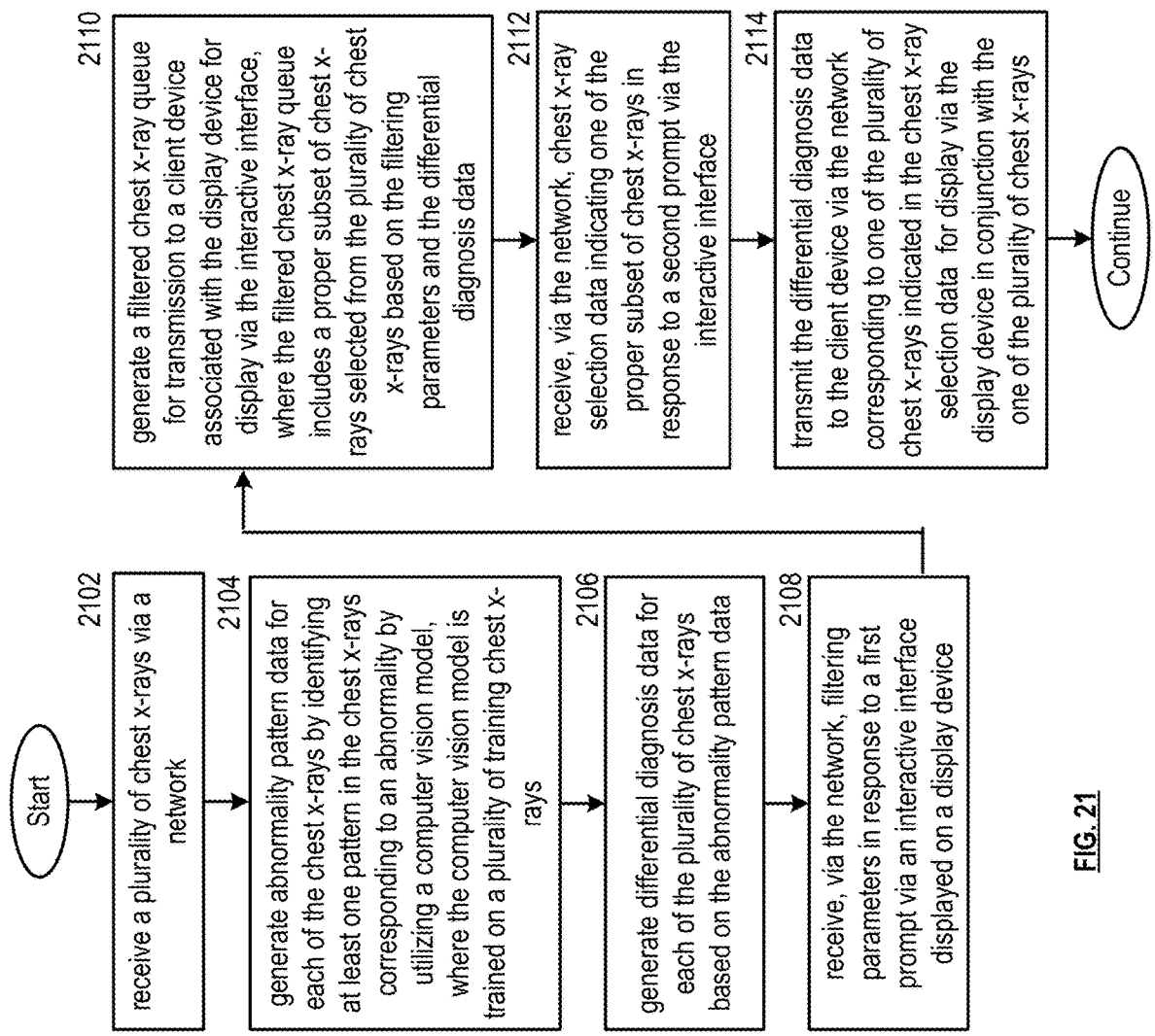
FIG. 21 is a flowchart representation of a method in accordance with an embodiment.

FIG. 21 presents an embodiment of a method for execution by a chest x-ray differential diagnosis system or other subsystem as described herein that includes a processor. Step 2102 includes receiving a plurality of chest x-rays via a network. Step 2104 includes generating abnormality pattern data for each of the chest x-rays by identifying at least one pattern in the chest x-rays corresponding to an abnormality by utilizing a computer vision model, where the computer vision model is trained on a plurality of training chest x-rays. Step 2106 includes generating differential diagnosis data for each of the plurality of chest x-rays based on the abnormality pattern data, Step 2108 includes receiving, via the network, filtering parameters in response to a first prompt via an interactive interface displayed on a display device associated with a user with a user of the chest x-ray differential diagnosis system. Step 2110 includes generating a filtered chest x-ray queue for transmission to a client device associated with the user for display via the interactive interface, where the filtered chest x-ray queue includes a proper subset of chest x-rays selected from the plurality of chest x-rays based on the filtering parameters and the differential diagnosis data. Step 2112 includes receiving, via the network, chest x-ray selection data indicating one of the proper subset of chest x-rays in response to a second prompt via the interactive interface. Step 2114 includes transmitting the differential diagnosis data to the client device via the network corresponding to one of the plurality of chest x-rays indicated in the chest x-ray selection data for display via the display device in conjunction with the one of the plurality of chest x-rays.

In various embodiments, the plurality of chest x-rays includes a normal subset of chest x-rays with corresponding differential diagnosis data indicating a normal diagnosis, and where the proper subset of chest x-rays is selected to automatically omit chest x-rays in the normal subset of chest x-rays. In various embodiments, the differential diagnosis data for each of the plurality of chest x-rays includes a plurality of binary values indicating whether each of a plurality of abnormality pattern types are present or not present based on the abnormality pattern data. In various embodiments, the abnormality pattern data includes confidence score data corresponding to each of the plurality of abnormality pattern types. Generating the differential diagnosis data includes comparing the confidence score data for each of the plurality of abnormality pattern types to a first confidence score threshold. A first one of the plurality of binary values indicates a corresponding first one of the plurality of abnormality pattern types is present when the corresponding confidence score data compares favorably to the first confidence score threshold, and a second one of the plurality of binary values indicates a corresponding second one of the plurality of abnormality pattern types is present when the corresponding confidence score data compares unfavorably to the first confidence score threshold.

In various embodiments, a new confidence score threshold is received in response to a third prompt displayed via the interactive interface. Updated differential diagnosis data is generated by applying the new confidence score threshold. An updated filtered chest x-ray queue is generated for transmission to the client device for display via the interactive interface by generating a new proper subset of chest x-rays based on the updated differential diagnosis data. In various embodiments, the filtering parameters indicate a subset of the plurality of abnormality pattern types, and generating the filtered chest x-ray queue includes selecting ones of the plurality of chest x-rays with differential diagnosis data that indicates that at least one of the subset of the plurality of abnormality pattern types in the filtering parameters is present to be included in the proper subset of chest x-rays. In various embodiments, the plurality of abnormality pattern types includes at least one of: cardiomegaly, consolidation, effusion, emphysema, or fracture. In various embodiments, the plurality of chest x-rays are ordered based on priority data.

In various embodiments, corrected diagnosis data is received in response to a third prompt via the interactive interface in conjunction with the display of the one of the plurality of chest x-rays and the differential diagnosis data. The corrected diagnosis data is mapped to the one of the plurality of chest x-rays in a chest x-ray database. In various embodiments, the plurality of chest x-rays are mapped to known diagnosis data in a chest x-ray database. A similarity score is generated by comparing the known diagnosis data to the differential diagnosis data. Accuracy data is generated by comparing the similarity score to an accuracy threshold, where the accuracy data indicates that a discrepancy is present when the similarity score compares unfavorably to the accuracy threshold, and where the accuracy data indicates that no discrepancy is present when the similarity score compares favorably to the accuracy threshold. Generating the filtered chest x-ray queue includes selecting only chest x-rays for the proper subset that have corresponding accuracy data indicating that a discrepancy is present.

Figure 22:
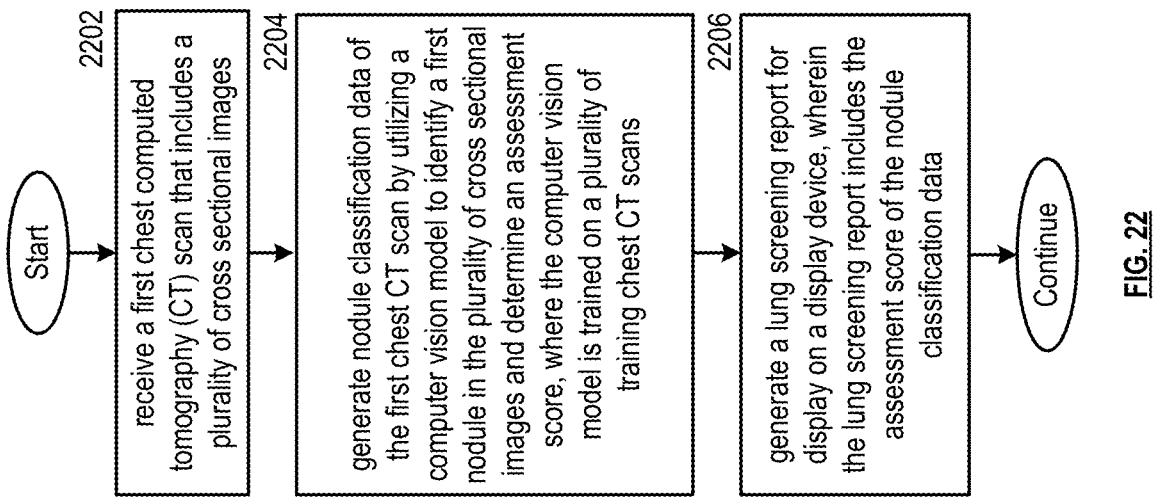
FIG. 22 is a flowchart representation of a method in accordance with an embodiment.

FIG. 22 presents an embodiment of a method for execution by a lung screening assessment system or other subsystem as described herein that includes a processor. Step 2202 includes receiving a first chest computed tomography (CT) scan that includes a plurality of cross sectional images. Step 2204 includes generating nodule classification data of the first chest CT scan by utilizing a computer vision model to identify a first nodule in the plurality of cross sectional images and determine an assessment score, where the computer vision model is trained on a plurality of training chest CT scans. Step 2206 includes generating a lung screening report for display on a display device associated with a user of the lung screening assessment system, where the lung screening report includes the assessment score of the nodule classification data.

In various embodiments, generating the nodule classification data includes calculating at least one of: a Fleischner score or a Lung-RADS score, where the assessment score indicates the at least one of: the Fleischner score or the Lung-RADS score. In various embodiments, generating the nodule classification data includes generating a first subset of chest CT scans from the plurality of training chest CT scans by applying a similarity function to determine that a set of nodules included in the first subset of chest CT scans compare favorably to the first nodule. At least one cross sectional image is selected from each chest CT scan of the first subset of chest CT scans for display on the display device in conjunction with the lung screening report.

In various embodiments, a set of patient records corresponding to the first subset of chest CT scans are retrieved, and the lung screening report includes data from at least one patient record in the set of patient records. In various embodiments, first patient risk factor data corresponding to the chest CT scan is retrieved, and patient risk factor data corresponding to each of the set of patient records is retrieved. A subset of patient records is selected by identifying corresponding patient risk factor data that compares favorably to the first patient risk factor data, and the lung screening report includes only data from patient records in the subset of patient records.

In various embodiments, each of the set of patient records includes a plurality of record entries and a corresponding plurality of dates. A subset of the plurality of dates are identified in the each of the set of patient records that are more recent than a date associated with the one of the plurality of chest CT scans corresponding to the each of the set of patient records. A subset of the plurality of record entries of the each of the set of patient records that correspond to the subset of the plurality of dates are identified. Longitudinal data corresponding to each of the set of patient records is generated based on each corresponding subset of the plurality of record entries, and the lung screening report includes the longitudinal data. In various embodiments, diagnosis prediction data corresponding to the first chest CT scan is generated based on the longitudinal data, and the lung screening report includes the diagnosis prediction data.

In various embodiments, generating the longitudinal data includes calculating a set of longitudinal quality scores corresponding to each patient record in the set of patient records. A ranking of the set of patient records is generated based on the set of longitudinal quality scores. At least one patient record is removed from the set of patient records that corresponds to at least one lowest ranking, and the lung screening report includes only data from remaining patient records in the set of patient records. In various embodiments, calculating the set of longitudinal quality scores is based on a number of subsequent chest CT scans included in the each of the set of patient records. In various embodiments, calculating the set of longitudinal quality scores is based on determining a duration of time between a first scan date of each chest CT scan in the first subset of chest CT scans and a second scan date of a most recent subsequent chest CT scan included in the corresponding patient record in the set of patient records. In various embodiments, a first longitudinal quality score in the set of longitudinal quality scores corresponds to a first patient record, and a second longitudinal quality score in the set of longitudinal quality scores corresponds to a second patient record. The first longitudinal quality score is more favorable than a second longitudinal quality score in response to determining that the first patient record includes biopsy data and the second patient record does not include biopsy data.

Figure 23:
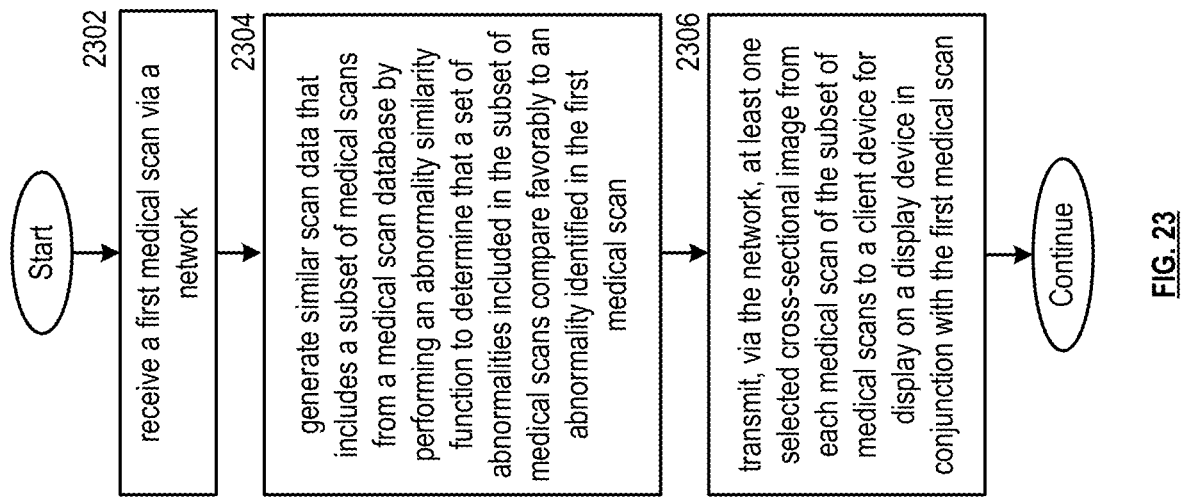
FIG. 23 is a flowchart representation of a method in accordance with an embodiment.

FIG. 23 presents an embodiment of a method for execution by a lung screening assessment system or other subsystem as described herein that includes a processor. Step 2302 includes receiving a first medical scan via a network. Step 2304 include generating similar scan data that includes a subset of medical scans from a medical scan database that includes a plurality of medical scans, where generating the similar scan data includes performing an abnormality similarity function to determine that a set of abnormalities included in the subset of medical scans compare favorably to an abnormality identified in the first medical scan. Step 2306 includes transmitting at least one selected cross-sectional image from each medical scan of the subset of medical scans to a client device for display on a display device associated with a user of the medical scan comparison system in conjunction with the first medical scan.

In various embodiments, first patient risk factor data corresponding to the first medical scan is retrieved from the medical scan database. A set of patient risk factor data corresponding to the subset of medical scans are retrieved from the medical scan database. A subset of patient risk factor data in the set of patient risk factor data that compares unfavorably to the first patient risk factor data is identified. An updated subset of medical scans is generated by removing medical scans that correspond to the subset of patient risk factor data, and the at least one selected cross-sectional image displayed by the display device are selected from each medical scan of the updated subset of medical scans.

In various embodiments, a set of patient records corresponding to the subset of medical scans is retrieved from the medical scan database. Medical scan report data is generated for display on the display device that includes data from at least one patient record in the set of patient records. In various embodiments, each of the set of patient records includes a plurality of record entries and a corresponding plurality of dates. A subset of the plurality of dates is identified in the each of the set of patient records that are more recent than a date associated with the one of the plurality of medical scans corresponding to the each of the set of patient records. A subset of the plurality of record entries of the each of the set of patient records that correspond to the subset of the plurality of dates is identified. Longitudinal data corresponding to each of the set of patient records based on each corresponding subset of the plurality of record entries is generated, and the medical scan report data includes the longitudinal data. In various embodiments, diagnosis prediction data corresponding to the first medical scan is generated based on the longitudinal data, and the medical scan report data includes the diagnosis prediction data.

In various embodiments, a set of longitudinal quality scores corresponding to the longitudinal data of each patient record in the set of patient records is calculated. A ranking of the set of patient records is generated based on the set of longitudinal quality scores. At least one patient record is removed from the set of patient records that corresponds to at least one lowest ranking. An updated subset of medical scans is generated by removing at least one medical scan corresponding to the at least one patient record. The medical scan report data includes only data from remaining patient records in the set of patient records, and the at least one selected cross-sectional image displayed by the display device are selected from each medical scan of the updated subset of medical scans.

In various embodiments, calculating the set of longitudinal quality scores is based on the number of subsequent medical scans included in the each of the set of patient records. In various embodiments, calculating the set of longitudinal quality scores is based on determining a duration of time between a first scan date of each medical scan in the subset of medical scans and a second scan date of a most recent subsequent medical scan included in the corresponding patient record in the set of patient records. In various embodiments, a first longitudinal quality score in the set of longitudinal quality scores corresponds to a first patient record, and a second longitudinal quality score in the set of longitudinal quality scores corresponds to a second patient record. The first longitudinal quality score is more favorable than a second longitudinal quality score in response to determining that the first patient record includes biopsy data and the second patient record does not include biopsy data.

In various embodiments, performing the abnormality similarity function includes comparing at least one cropped image slice of the first medical scan to a plurality of cropped images slices of the plurality of medical scans by applying computer vision techniques. At least one of the plurality of cropped image slices that compares favorably to a similarity threshold is identified, and the subset of medical scans correspond to the at least one of the plurality of cropped image slices that compare favorably to the similarity threshold. In various embodiments, the medical scan database includes a plurality of known abnormality classification data mapped to the plurality of medical scans. First abnormality classification data is determined for the abnormality of the first medical scan. A subset of known abnormality classification data of the plurality of known abnormality classification data that compares favorably to the first abnormality classification data is identified. Medical scans mapped to the subset of known abnormality classification data are included in the subset of medical scans.

Figure 24:
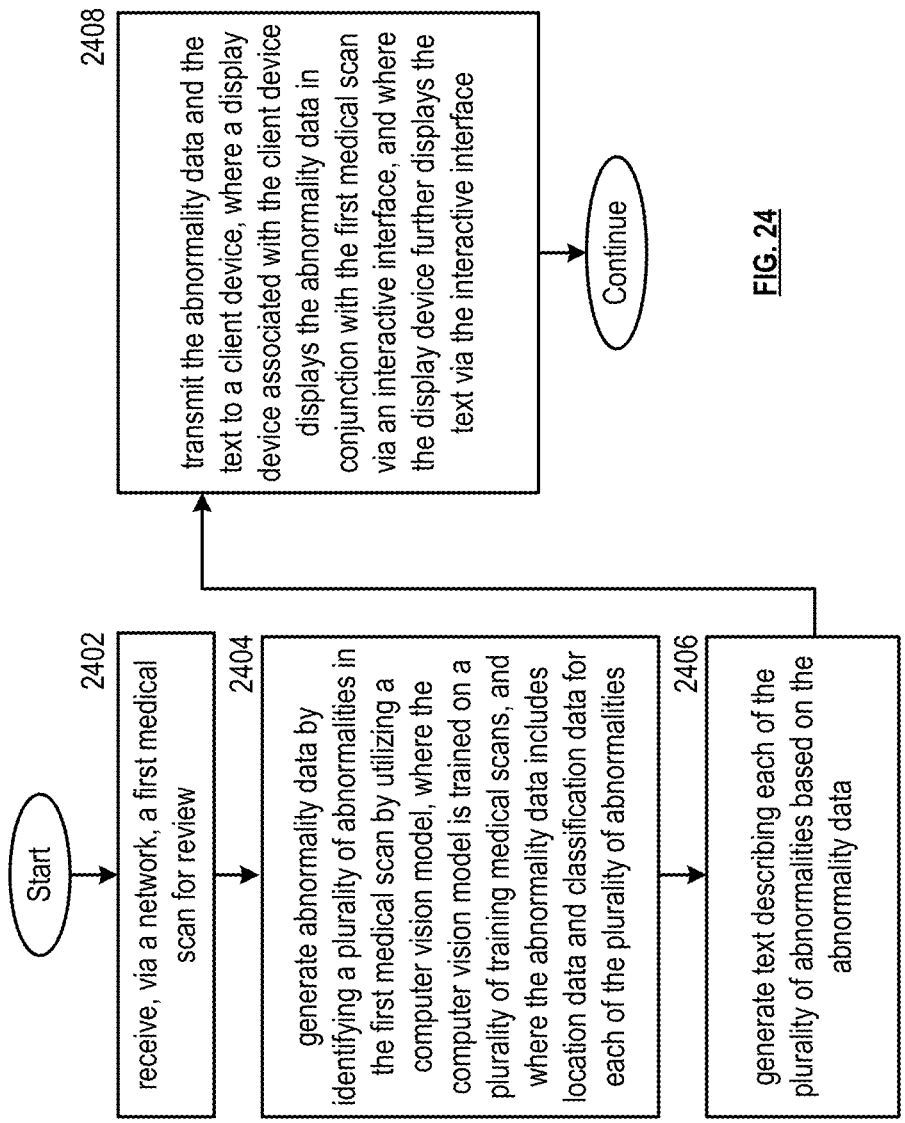
FIG. 24 is a flowchart representation of a method in accordance with an embodiment.

FIG. 24 presents an embodiment of a method for execution by a medical scan assisted review system 102 or other subsystem as described herein that includes a processor. Step 2402 includes receiving, via a network, a first medical scan for review. Step 2404 includes generating abnormality data by identifying a plurality of abnormalities in the first medical scan by utilizing a computer vision model, where the computer vision model is trained on a plurality of training medical scans, and where the abnormality data includes location data and classification data for each of the plurality of abnormalities. Step 2406 includes generating text describing each of the plurality of abnormalities based on the abnormality data. Step 2408 includes transmitting the abnormality data and the text to a client device associated with a user of the medical scan assisted review system, where a display device associated with the client device displays the abnormality data in conjunction with the first medical scan via an interactive interface, and where the display device further displays the text via the interactive interface.

In various embodiments, display device displays only abnormality data corresponding to one of the plurality of abnormalities in conjunction with the first medical scan in response to a first prompt via the interactive interface to select the one of the plurality of abnormalities for review. In various embodiments, a shape that surrounds the one of the plurality of abnormalities in the first medical scan is displayed via the interactive interface in response to the first prompt. In various embodiments, the first medical scan includes a plurality of image slices, and the interactive interface automatically jumps to a selected one of the plurality of image slices that includes the one of the plurality of abnormalities in response to the first prompt.

In various embodiments, the display device displays the first medical scan in a first view of the interactive interface. A set of similar medical scans are selected from the plurality of training medical scans by applying a similarity function to determine that a known abnormality included in each of the set of similar medical scan compares favorably to a corresponding one of the plurality of abnormalities. The set of similar medical scans are transmitted to the client device. One of the set of similar medical scans corresponding to the one of the plurality of abnormalities is automatically displayed in a second view of the interactive interface that is adjacent to the first view in response to a second prompt via the interactive interface.

In various embodiments, the first medical scan includes a first plurality of image slices. The one of the set of similar medical scans includes a second plurality of image slices. The second view of the interactive interface automatically jumps to a one of the second plurality of image slices in response to the second prompt that corresponds to a currently displayed one of the first plurality of image slices of the first view. In various embodiments, the one of the second plurality of image slices is selected based on determining that the one of the second plurality of image slices compares favorably to a cross sectional anatomical region of the currently displayed one of the first plurality of image slices of the first view. In various embodiments, the one of the second plurality of image slices is selected based on determining that the one of the second plurality of image slices includes a view of the known abnormality that compares favorably to the one of the plurality of abnormalities. In various embodiments, the first view scrolls to a new one of the first plurality of image slices in response to a third prompt to scroll to the new one of the first plurality of image slices via the interactive interface, and the second view simultaneously scrolls to a corresponding new one of the second plurality of image slices in response to the third prompt.

In various embodiments, each of the set of similar medical scans is associated with a patient record, and each of the set of similar medical scans are selected based on the associated patient record comparing favorably to a longitudinal quality threshold. In various embodiments, a more recent medical scan indicated in the patient record associated with the one of the set of similar medical scans corresponding to the one of the plurality of abnormalities is transmitted, where the more recent medical scan is displayed by display device in response to a third prompt via the interactive interface. New abnormality data is received via the network in response a second prompt via the interactive interface. A location of the new abnormality data is based on a region identified in the medical scan via the interactive interface. Updated abnormality data is generated based on the new abnormality data. In various embodiments, edited text data is received via the network in response to a second prompt via the interactive interface. Updated abnormality data and updated natural language text are generated based on the edited text data.

FIG. 25 presents an embodiment of a method for execution by a medical scan natural language analysis system or other subsystem as described herein that includes a processor. Step 2502 includes generating a medical report natural language model based on a selected set of medical reports of the plurality of medical reports and the at least one medical code mapped to each of the selected set of medical reports. Step 2504 includes receiving a first medical report that is not included in the selected set via a network. Step 2506 includes determining a first medical code by utilizing the medical report natural language model on the first medical report. Step 2508 includes mapping the first medical code of the plurality of medical codes to a first medical scan corresponding to the first medical report.

In various embodiments, generating the medical report natural language model is further based on a plurality of alias mapping pairs. Each of the plurality of alias mapping pairs includes a one of a plurality of medical condition terms and a corresponding one of a plurality of medical codes. Each of the plurality of medical condition terms in the plurality of alias mapping pairs are unique, and each of the plurality of medical condition terms includes at least one word. In various embodiments, a new alias mapping pair that is not included in the plurality of alias mapping pairs is received; and an updated medical report natural model is generated based on the new alias mapping pair.

In various embodiments, generating the medical report natural language model includes generating a plurality of alias mapping pairs, where each of plurality of alias mapping pairs includes a one of a plurality of medical condition terms and a corresponding one of a plurality of medical codes. Each of the plurality of medical condition terms in the plurality of alias mapping pairs are unique, and each of the plurality of medical condition terms includes at least one word. In various embodiments, a second medical report that is not included in the selected set is received via the network. A first medical condition term is identified in the second medical report. A first alias mapping pair of the plurality of alias mapping pairs is identified by determining a second medical condition term of the plurality of medical condition terms that corresponds to the first alias mapping pair compares favorably to the first medical condition term. A second medical code of the plurality of medical codes that corresponds to the first alias mapping pair is mapped to a second medical scan corresponding to the second medical report.

In various embodiments, the first medical code is a SNOMED code, CPT code, an ICD-9 code, or an ICD-10 code. In various embodiments, the medical report natural language model is a neural network. In various embodiments, generating the medical report natural language model includes utilizing a forward propagation algorithm on the plurality of medical reports to generate a preliminary set of neural network parameters, and by utilizing a back propagation algorithm to generate an updated set of neural network parameters based on a calculated set of parameter errors and the preliminary set of neural network parameters. Determining the first medical code includes utilizing the forward propagation algorithm on the first medical report based on the updated set of neural network parameters.

In various embodiments, utilizing the medical report natural language model to determine the first medical code includes identifying a relevant medical term in the first medical report. The relevant medical term and the first medical code are transmitted to a client device via the network for display by a display device in conjunction with the first medical report. The relevant medical term is identified in the natural language text data of the first medical report in conjunction with displaying the first medical code.

In various embodiments, a second plurality of medical reports that are not included in the selected set are received via a network. At least one second medical code for each of the second plurality of medical reports is determined by utilizing the medical report natural language model on the second plurality of medical reports. A training set that includes a second plurality of medical scans corresponding to the second plurality of medical reports is generated. A medical scan image analysis model is generated based on the training set and the at least one second medical code corresponding to each of the second plurality of medical reports by applying computer vision techniques to the second plurality of medical scans. A third medical scan is received via the network. A third medical code of the plurality of medical codes is determined by utilizing the medical scan image analysis model on the third medical scan. The third medical code is mapped to a third medical scan.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may further be used herein, the term "associated with", includes direct and/or indirect coupling of separate items and/or one item being embedded within another item. As may still further be used herein, the term "automatically" refers to an action caused directly by a processor of a computer network in response to a triggering event and particularly without human interaction.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", "processing device" and/or "processing unit" may be a single processing device or a plurality of processing devices. Such a processing device may be a microprocessor, micro-controller, digital signal processor, graphics processing unit, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random or psuedo-random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures and/or described herein. Such a memory device or memory element can be included in an article of manufacture. While the processing module, module, processing circuit, and/or processing unit device may be a general purpose computing device, the execution of the hard coded and/or operational instructions by the processing module, module, processing circuit, and/or processing unit configures such a general purpose computing device as a special purpose computing device to implement the corresponding steps and/or functions illustrated in one or more of the Figures and/or described herein. In particular, the hard coded and/or operational instructions by the processing module, module, processing circuit, and/or processing unit implement acts and algorithms performed by the processing module, module, processing circuit, and/or processing unit. Such acts and algorithms can be identified by name, can be illustrated via flowchart and/or described in words.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The term "system" is used in the description of one or more of the embodiments. A system implements one or more functions via a device such as a processor or other processing device or other hardware that may include or operate in association with a memory that stores operational instructions. A system may operate independently and/or in conjunction with software and/or firmware. As also used herein, a system may contain one or more sub-system, each of which may be one or more systems.

As may further be used herein, a computer readable memory includes one or more memory elements. A memory element may be a separate memory device, multiple memory devices, or a set of memory locations within a memory device. Such a memory device may be a read-only memory, random or psuedo-random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A medical scan diagnosing system, comprising:
a processing system that includes a processor; and
a memory that stores executable instructions that, when executed by the processing system, facilitate performance of operations that include:
receiving, via a network, a first medical scan;
generating first diagnosis data of the first medical scan by performing a first medical scan inference function that utilizes a computer vision model on the first medical scan;
transmitting, via the network, the first diagnosis data to a first client device, and wherein the first diagnosis data is displayed to a first user in conjunction with the first medical scan via an interactive interface displayed by a first display device associated with the first client device;
generating a plurality of other diagnosis data, wherein each of the plurality of other diagnosis data is generated by performing the first medical scan inference function on a corresponding one of a plurality of medical scans, wherein the plurality of medical scans includes the first medical scan;
determining a subset of the plurality of other diagnosis data is incorrect; and
automatically generating an updated first medical scan inference function, based on determining a size of the subset exceeds a predetermined threshold, by training the updated first medical scan inference function on a training set.

2. The medical scan diagnosing system of claim 1, wherein the operations further include:
receiving, via a network, a second medical scan;
generating second diagnosis data of the second medical scan by performing the updated first medical scan inference function on the second medical scan; and
transmitting, via the network, the second medical scan to the first client device associated with the first user of the medical scan diagnosing system, wherein the second medical scan is displayed to the first user via the interactive interface displayed by the first display device corresponding to the first client device.

3. The medical scan diagnosing system of claim 2, wherein the operations further include:
receiving, via the network, second review data from the first client device, wherein the second review data is generated by the first client device in response to a second prompt displayed by the first display device via the interactive interface to provide the second review data;
generating updated second diagnosis data based on the second review data; and
transmitting, via the network, the updated second diagnosis data to a second client device associated with a requesting entity.

4. The medical scan diagnosing system of claim 1, further comprising a user database that includes a plurality of registered entities that includes a requesting entity, wherein the first medical scan is received from a second client device associated with the requesting entity, and wherein the operations further include:
   retrieving usage data corresponding to the requesting entity from the user database in response to receiving the first medical scan; and
   generating the first diagnosis data in response to determining the usage data compares favorably to a usage quota.

5. The medical scan diagnosing system of claim 1, wherein the operations further include:
   receiving, via the network, first review data from the first client device, wherein the first review data is generated by the first client device in response to a first prompt displayed by the first display device via the interactive interface to provide the first review data; and
   determining that the first review data indicates that the first diagnosis data is incorrect.

6. The medical scan diagnosing system of claim 5, wherein the first review data includes second diagnosis data, wherein the second diagnosis data is generated by the first user that differs from the first diagnosis data.

7. The medical scan diagnosing system of claim 1, wherein the operations further include:
   selecting the first medical scan inference function from a plurality of medical scan inference functions based on a first medical scan classifier corresponding to the first medical scan.

8. The medical scan diagnosing system of claim 7, wherein the operations further include:
   generating a new medical scan classifier by performing a medical scan classifier function on the first medical scan;
   wherein the first medical scan inference function is selected based on the new medical scan classifier in response to determining that the first medical scan classifier compares unfavorably to the new medical scan classifier.

9. The medical scan diagnosing system of claim 8, wherein the first medical scan classifier is indicated in metadata of the first medical scan, retrieved from a medical scan database, and wherein the operations further include:
   generating updated metadata corresponding to the first medical scan based on the new medical scan classifier; and
   mapping the updated metadata to the first medical scan in the medical scan database.

10. The medical scan diagnosing system of claim 7, wherein the operations further include:
    determining to split a scan category associated with the first medical scan classifier into multiple subcategories; and
    generating the updated first medical scan inference function and a second updated first medical scan inference function based on determining to split the scan category, wherein the updated first medical scan inference function corresponds to a first one of the multiple subcategories, and wherein the second updated first medical scan inference function corresponds to a second one of the multiple subcategories.

11. A method for execution by a medical scan diagnosing system that includes a processor, the method comprising:
    receiving, via a network, a first medical scan;
    generating first diagnosis data of the first medical scan by performing a first medical scan inference function that utilizes a computer vision model on the first medical scan;
    transmitting, via the network, the first diagnosis data to a first client device, and wherein the first diagnosis data is displayed to a first user in conjunction with the first medical scan via an interactive interface displayed by a first display device associated with the first client device;
    generating a plurality of other diagnosis data, wherein each of the plurality of other diagnosis data is generated by performing the first medical scan inference function on a corresponding one of a plurality of medical scans, wherein the plurality of medical scans includes the first medical scan;
    determining a subset of the plurality of other diagnosis data is incorrect; and
    automatically generating an updated first medical scan inference function, based on determining a size of the subset exceeds a predetermined threshold, by training the updated first medical scan inference function on a training set.

12. The method of claim 11, further comprising:
    receiving, via a network, a second medical scan;
    generating second diagnosis data of the second medical scan by performing the updated first medical scan inference function on the second medical scan; and
    transmitting, via the network, the second medical scan to the first client device associated with the first user of the medical scan diagnosing system, wherein the second medical scan is displayed to the first user via the interactive interface displayed by the first display device corresponding to the first client device.

13. The method of claim 12, further comprising:
    receiving, via the network, second review data from the first client device, wherein the second review data is generated by the first client device in response to a second prompt displayed by the first display device via the interactive interface to provide the second review data;
    generating updated second diagnosis data based on the second review data; and
    transmitting, via the network, the updated second diagnosis data to a second client device associated with a requesting entity.

14. The method of claim 11, wherein a user database that includes a plurality of registered entities that includes a requesting entity, wherein the first medical scan is received from a second client device associated with the requesting entity, and wherein the method further comprises:
    retrieving usage data corresponding to the requesting entity from the user database in response to receiving the first medical scan; and
    generating the first diagnosis data in response to determining the usage data compares favorably to a usage quota.

15. The method of claim 11, further comprising:
    receiving, via the network, first review data from the first client device, wherein the first review data is generated by the first client device in response to a first prompt displayed by the first display device via the interactive interface to provide the first review data; and
    determining that the first review data indicates that the first diagnosis data is incorrect.

16. The method of claim 15, wherein the first review data includes second diagnosis data, wherein the second diagnosis data is generated by the first user that differs from the first diagnosis data.

17. The method of claim 11, further comprising:
selecting the first medical scan inference function from a plurality of medical scan inference functions based on a first medical scan classifier corresponding to the first medical scan.

18. The method of claim 17, further comprising:
generating a new medical scan classifier by performing a medical scan classifier function on the first medical scan;
wherein the first medical scan inference function is selected based on the new medical scan classifier in response to determining that the first medical scan classifier compares unfavorably to the new medical scan classifier.

19. The method of claim 18, wherein the first medical scan classifier is indicated in metadata of the first medical scan, retrieved from a medical scan database, and wherein the method further comprises:
generating updated metadata corresponding to the first medical scan based on the new medical scan classifier; and
mapping the updated metadata to the first medical scan in the medical scan database.

20. The method of claim 17, further comprising:
determining to split a scan category associated with the first medical scan classifier into multiple subcategories; and
generating the updated first medical scan inference function and a second updated first medical scan inference function based on determining to split the scan category, wherein the updated first medical scan inference function corresponds to a first one of the multiple subcategories, and wherein the second updated first medical scan inference function corresponds to a second one of the multiple subcategories.

* * * * *